US009688989B2

(12) United States Patent
Wersinger

(10) Patent No.: US 9,688,989 B2
(45) Date of Patent: Jun. 27, 2017

(54) H4 RECEPTOR INHIBITORS FOR TREATING TINNITUS

(71) Applicant: SENSORION, Montpellier (FR)

(72) Inventor: Éric Wersinger, Montpellier (FR)

(73) Assignee: SENSORION (FR)

( * ) Notice: Subject to any disclaimer, the term of this patent is extended or adjusted under 35 U.S.C. 154(b) by 1 day.

(21) Appl. No.: 14/405,776

(22) PCT Filed: Jun. 10, 2013

(86) PCT No.: PCT/EP2013/061936
§ 371 (c)(1),
(2) Date: Dec. 4, 2014

(87) PCT Pub. No.: WO2013/182711
PCT Pub. Date: Dec. 12, 2013

(65) Prior Publication Data
US 2015/0176010 A1    Jun. 25, 2015

Related U.S. Application Data

(60) Provisional application No. 61/657,460, filed on Jun. 8, 2012.

(51) Int. Cl.
| A61K 31/497 | (2006.01) |
| C12N 15/113 | (2010.01) |
| A61K 31/454 | (2006.01) |
| A61K 31/47 | (2006.01) |
| A61K 31/496 | (2006.01) |
| A61K 31/506 | (2006.01) |
| A61K 31/519 | (2006.01) |
| A61K 31/7105 | (2006.01) |
| A61K 31/713 | (2006.01) |

(52) U.S. Cl.
CPC ........ *C12N 15/1138* (2013.01); *A61K 31/454* (2013.01); *A61K 31/47* (2013.01); *A61K 31/496* (2013.01); *A61K 31/506* (2013.01); *A61K 31/519* (2013.01); *A61K 31/713* (2013.01); *A61K 31/7105* (2013.01); *C12N 2310/10* (2013.01)

(58) Field of Classification Search
USPC .............. 514/254.06, 267, 252.16
See application file for complete search history.

(56) References Cited

U.S. PATENT DOCUMENTS

| 6,093,417 | A | 7/2000 | Petrus | |
| 6,803,362 | B2 * | 10/2004 | Carruthers | A61K 31/496 514/183 |
| 2004/0048878 | A1 | 3/2004 | Cai | |
| 2004/0058934 | A1 | 3/2004 | Carruthers | |
| 2004/0105856 | A1 | 6/2004 | Thurmond | |
| 2004/0127395 | A1 | 7/2004 | Desai | |
| 2004/0132715 | A1 | 7/2004 | Dunford | |
| 2005/0070527 | A1 | 3/2005 | Edwards | |
| 2005/0070550 | A1 | 3/2005 | Arienti | |
| 2005/0261309 | A1 | 11/2005 | Buzard | |
| 2007/0238771 | A1 | 10/2007 | Edwards | |
| 2008/0188452 | A1 | 8/2008 | Altenbach | |
| 2008/0261946 | A1 | 10/2008 | Dyke | |
| 2008/0269239 | A1 | 10/2008 | Harris | |
| 2009/0275748 | A1 | 11/2009 | Edwards | |
| 2012/0039913 | A1 * | 2/2012 | Desmadryl | A61K 31/496 424/173.1 |

FOREIGN PATENT DOCUMENTS

| EP | 2491930 | 8/2012 |
| WO | 02/056871 | 7/2002 |
| WO | 2002/072548 | 9/2002 |
| WO | 2004/066960 | 8/2004 |
| WO | 2005/014556 | 2/2005 |
| WO | 2005/014579 | 2/2005 |
| WO | 2005/054239 | 6/2005 |
| WO | 2006/050965 | 5/2006 |
| WO | 2006/056848 | 6/2006 |
| WO | 2007/031529 | 3/2007 |
| WO | 2007/039467 | 4/2007 |
| WO | 2007/072163 | 6/2007 |
| WO | 2007/090852 | 8/2007 |
| WO | 2007/090853 | 8/2007 |
| WO | 2007/090854 | 8/2007 |
| WO | 2007/117399 | 10/2007 |
| WO | 2007/120690 | 10/2007 |
| WO | 2008/003702 | 1/2008 |
| WO | 2008/008359 | 1/2008 |
| WO | 2008/031556 | 3/2008 |
| WO | 2008/060767 | 5/2008 |
| WO | 2008/074445 | 6/2008 |
| WO | 2008/100565 | 8/2008 |
| WO | 2008/122378 | 10/2008 |
| WO | 2009/022551 | 2/2009 |
| WO | 2009/038673 | 3/2009 |

(Continued)

OTHER PUBLICATIONS

Zun-Li Mo and Robin Davis, 1997. Endogenous firing patterns of murine spiral ganglion neurons. J Neurophysiol. 77 (3):1294-305.
Eatock et al., Ion channels in mammalian vestibular afferents may set regularity of firing. J Exp Biol. Jun. 2008;211(Pt 11):1764-74.
Kharkovets T. et al., Mice with altered KCNQ4 K+ channels implicate sensory outer hair cells in human progressive deafness. 2006 EMBO J. 25(3):642-652.
Spitzmaul G et al., Vestibular role of KCNQ4 and KCNQ5 K+ channels revealed by mouse models. J Biol Chem. Mar. 29, 2013;288(13):9334-44.
Marzo SJ et al Intratympanic therapy for sensorineural hearing loss and vertigo Audiology meeting, Chicago, Jan. 24, 2002.
Venable JD "Preparation and biological evaluation of indole, benzimidazole, and thienopyrrole piperazine carboxamides: potent human histamine h(4) antagonists." Med Chem Dec. 2005; vol. 48 No. 26 pp. 8289-8298.

(Continued)

*Primary Examiner* — Rei-Tsang Shiao
(74) *Attorney, Agent, or Firm* — One3 IP Management, P.C.; Annette S. Parent; Peter D. Weinstein

(57) ABSTRACT

The invention relates to Histamine type 4 receptor (H4R) inhibitors for treating tinnitus.

5 Claims, 3 Drawing Sheets

(56) References Cited

FOREIGN PATENT DOCUMENTS

| | | |
|---|---|---|
| WO | 2009/047255 | 4/2009 |
| WO | 2009/056551 | 5/2009 |
| WO | 2009/068512 | 6/2009 |
| WO | 2009/071625 | 6/2009 |
| WO | 2009/077608 | 6/2009 |
| WO | 2009/079001 | 6/2009 |
| WO | 2009/080721 | 7/2009 |
| WO | 2009/083608 | 7/2009 |
| WO | 2009/107767 | 9/2009 |
| WO | 2009/114575 | 9/2009 |
| WO | 2009/115496 | 9/2009 |
| WO | 2009/123967 | 10/2009 |
| WO | 2009/134726 | 11/2009 |
| WO | 2009/137492 | 11/2009 |
| WO | 2010/072829 | 7/2010 |
| WO | 2010/113109 | 10/2010 |
| WO | 2010/146173 | 12/2010 |
| WO | 2012/041860 | 4/2012 |
| WO | 2012/042314 | 4/2012 |

OTHER PUBLICATIONS

Lovenberg et al. Cloning and functional expression of the human histamine H3 receptor. Mol Pharmacol. Jun. 1999;55 (6):1101-7.
Liu C "Cloning and pharmacological characterization of a fourth histamine receptor (H(4)) expressed in bone marrow" Mol Pharmacol Mar. 2001; vol. 59 No. 3 pp. 420-426.
Liu C "Comparison of human, mouse, rat, and guinea pig histamine H4 receptors reveals substantial pharmacological species variation" J Pharmacol Exp Ther Oct. 2001; vol. 299 No. 1 pp. 121-130.
Thurmond RL, et al. A Potent and Selective Histamine H4 Receptor Antagonist with Anti-Inflammatory Properties Journal of Pharmacology and Experimental Therapeutics,JPET 309:404-413, 2004.
Jablonowski JA, et al. The first potent and selective non-imidazole human Histamine H4 receptor antagonists. J Med Chem. Sep. 11, 2003;46(19):3957-60.
Herman et al. "Evaluation of Histamine H1-, H2-, and H3-Receptor Ligands at the Human Histamine H4 Receptor: Identification of 4-Methylhistamine as the First Potent and Selective H4 Receptor Agonist" Journal of Pharmacology and Experimental Therapeutics Sep. 2005; vol. 314 No. 3 pp. 1310-1321.
Cowart MD "Rotationally constrained 2,4-diamino-5,6-disubstituted pyrimidines: a new class of histamine H4 receptor antagonists with improved druglikeness and in vivo efficacy in pain and inflammation models" J Med Chem Oct. 23, 2008; vol. 51 No. 20 pp. 6547-6557.
Liu H, et al. cis-4-(Piperazin-1-yl)-5,6,7a,8,9,10,11,11a-octahydrobenzofuro[2,3-h]quinazolin-2-amine (A-987306), A New Histamine Histamine H4 antagonist that Blocks Pain Responses against Carrageenan-Induced Hyperalgesia. J Med Chem., 2008, 51(22):7094-7098.
Zhang M "The histamine H(4) receptor: a novel modulator of inflammatory and immune disorders" Phamacol Ther Mar. 2007; vol. 113 No. 3 pp. 594-606.
Cote RJ, et al. Generation of human monoclonal antibodies reactive with cellular antigens. Proc Natl Acad Sci U S A. Apr. 1983; vol. 80 No. 7 pp. 2026-2030.
Tuschl, T. et al. "Targeted mRNA degradation by double-stranded RNA in vitro." Genes Dev. Dec. 1999; vol. 13 No. 24 pp. 3191-3197.
Tuerk C. and Gold L "Systematic evolution of ligands by exponential enrichment: RNA ligands to bacteriophage T4 DNA polymerase." Science. Aug. 3, 1990; vol. 249 No. 4968 pp. 505-510.
Jayasena S.D. "Aptamers: an emerging class of molecules that rival antibodies in diagnostics." Clin Chem. Sep. 1999; vol. 45 No. 9 pp. 1628-1650.
Colas P, et al. "Genetic selection of peptide aptamers that recognize and inhibit cyclin-dependent kinase 2." Nature. Apr. 11, 1996; vol. 380 No. 6574 pp. 548-550.
Hannon, GJ. "RNA interference" Nature Jul. 11, 2002; vol. 418 No. 6894 pp. 244-251.
McManus, MT. et al. "Gene silencing in mammals by small interfering RNAs" Nat Rev Genet Oct. 2002; vol. 3 No. 10 pp. 737-747.
Brummelkamp TR, et al. A system for stable expression of short interfering RNAs in mammalian cells. Science. Apr. 19, 2002; vol. 296 No. 5567 pp. 550-553.
Coruzzi et al "Anti-inflammatory and anti-nociceptive effects of the selective histamine H4 receptor antagonist JNJ7777120 and VUF6002 in a rat model of carrageenan-induced acute inflammation" Feb. 2007 Eur J Pharma vol. 563 pp. 240-244.
Elbashir SM, et al. Duplexes of 21-nucleotide RNAs mediate RNA interference in cultured mammalian cells. Nature. May 24, 2001; vol. 411 No. 6836 pp. 494-498.
Robert Kiss et al. Histamine H4 receptor ligands and their potential therapeutic applications: an update. Expert Opin Ther Pat. Mar. 2012;22(3):205-21.
Desmadryl et al. Histamine H4 receptor antagonists as potent modulators of mammalian vestibular primary neuron excitability May 2012 Br . J. Pharm vol. 167 No. 4 pp. 905-916.
Press release Sensorion Palau pharma (Jul. 30, 2012) Palau Pharma signs an exclusive option agreement with Sensorion Pharmaceuticals for the development of Palau's histamine-4 receptor antagonist, UR-63325, for the treatment of vestibular disorders.
Tighilet B, et al., Histaminergic ligands improve vestibular compensation in the cat: behavioral, neurochemical and molecular evidence, European Journal of Pharmacology, 2007, 568(1-3):149-163.
Chávez H, et al. (2005) Histamine (H3) receptors modulate the excitatory amino acid receptor response of the vestibular afferents. Brain Res. 1064:1-9.
Gbahou F, et al. (2006) Compared pharmacology of human histamine H3 and H4 receptors: structure-activity relationships of histamine derivatives. Br J Pharmacol. 147:744-54.
Stark H, Expert opinion on therapeutic patents, informa healthcare, 2003, 13(6):852-858.
Parsons Mike E et al., Histamine and its receptors British Journal of Pharmacology, 2006, 147(1):S127-S135.
Godot et al., "H4 histamine receptor mediates optimal migration of mast cell precursors to CXCL12" 2007 Journal of allergy and clinical immunology, 120(4):827-834.
Piratello A C et al: "Thioperamide delays vestibular compensation in goldfish", Neuroscience Letters, Limerick, IE, vol. 415, No. 2, Mar. 26, 2007 (Mar. 26, 2007), pp. 146-148.
Yabe et al "Medial vestibular nucleus in the guinea-pig: histaminergic receptors II. An in vivo study" Exp Brain Res 1993 vol. 93 pp. 249-258.
Ling et al "Histamine H4 receptor mediates eosinophil chemotaxis with cell shape change and adhesion molecule upregulation" British J Pharmacology May 2004, vol. 142 No. 1 pp. 161-171.
Tian et al, "Advances in Ligands of Histamine H4 Receptor" Journal of Anhui Health Vocational & Technical College, 2008 vol. 7 No. 2 pp. 80-81 (chinese + english translation).
Hotson et al, "Acute Vestibular Syndrome" NEJM Sep. 1998, vol. 339 No. 10 pp. 680-685.
Botta et al., "Effects of Betahistine on Vestibular Receptors of the Frog" Acta Otolaryngol, 1998, vol. 118 pp. 519-523.
Dijkstra D et al "Human Inflammatory Dendritic Epidermal Cells Express a Functional Histamine H4 Receptor" J Invest Dermatol. Jul. 2008; vol. 128 No. 7 pp. 1696-1703.
WO2009/022551 (english translation).
ISR of WO2013/182711.
Engelhardt et al. Detailed structure-activity relationship of indolecarboxamides as H4 receptor ligands. Eur J Med Chem. Aug. 2012;54:660-8.
Andaloussi et al. A novel series of histamine H4 receptor antagonists based on the pyrido[3,2-d]pyrimidine scaffold: comparison of hERG binding and target residence time with PF-3893787. 2013 Bioorg Med Chem Lett. May 1, 2013;23 (9):2663-70.
Sander K et al. Lead identification and optimization of diaminopyrimidines as histamine H4 receptor ligands. Inflamm. Res. (2010) 59 (Suppl 2):S249-S251.

(56) References Cited

OTHER PUBLICATIONS

Gao LJ et al. Synthesis and evaluation of novel ligands for the histamine $H_4$ receptor based on a pyrrolo[2,3-d] pyrimidine scaffold. Bioorganic & Medicinal Chemistry Letters 23 (2013) 132-137.
Werner et al. In silico characterization of ligand binding modes in the human histamine H4 receptor and their impact on receptor activation. Chembiochem. Sep. 3, 2010;11(13):1850-5.
Wijtmans et al. Triazole ligands reveal distinct molecular features that induce histamine H4 receptor affinity and subtly govern H4/H3 subtype selectivity. J Med Chem. Mar. 24, 2011;54(6):1693-703.
De Lean et al. Multi-subsite receptors for multivalent ligands. Application to drugs, hormones, and neurotransmitters. Mol Pharmacol. Jan. 1979;15(1):60-70.
Turner et al. Gap detection deficits in rats with tinnitus: a potential novel screening tool. Behav Neurosci. Feb. 2006;120(1):188-95.
Cheng and Prusoff Relationship between the inhibition constant (K1) and the concentration of inhibitor which causes 50 per cent inhibition (I50) of an enzymatic reaction. Biochem Pharmacol. Dec. 1, 1973;22(23):3099-108.
Turner et al. Gap detection methods for assessing salicylate-induced tinnitus and hyperacusis in rats. Am J Audiol. Dec. 2008:17(2):S185-92.

\* cited by examiner

H4 RECEPTOR INHIBITORS FOR TREATING TINNITUS

FIELD OF INVENTION

The invention relates to Histamine type 4 receptor (H4R) antagonists or inhibitors of Histamine H4 receptor gene expression for treating tinnitus.

BACKGROUND OF INVENTION

The inner ear is the innermost part of the vertebrate ear where two sensory organs are hosted in the temporal bone:
The cochlea, dedicated to the auditory function, converting sound pressure patterns from the outer ear into electrochemical impulses which are passed on to the brain via the auditory nerve. The cochlea constitutes the ventral region of the inner ear and it contains the organ of Corti that comprises mechanosensory hair cells and supporting cells.
The vestibular system, dedicated to balance, acceleration, and gravity. This organ has a totally different function from cochlea, said function consisting in the detection of linear and angular accelerations of the head in order to transmit to the brain information on movements to achieve the equilibration function in collaboration with visual and proprioceptive information. It is also constituted of mechanosensory hair cells that convert mechanical actions into electrical potentials, and supporting cells.

Although these two organs have sensory hair cells responsible of the receptor potential and the subsequent action potentials, their distinct morphology, synaptic connections and overall function imply differences in molecular and cellular mechanisms underlying their action.

The vestibular system and the cochlea exhibit organ-dependent differences. Indeed, numbers of ion channels and neurotransmitter-gated receptors are differently expressed in those sensory organs. This is particularly true for ions channels involved in nerve cells excitability. As such, endogenous heterogeneity is for example responsible for very strong differences in action potential discharge patterns between the cochlea and the vestibule (Zun-Li M O and Robin Davis, 1997. J Neurophysiol. 77(3):1294-305; Eatock et al., 2008 J. Exp Biol. 211(Pt 11):1764-74). Therefore, impairing/modulating the expression or function of ions channels or receptor, either pharmacologically or genetically can have significantly different consequences on hearing and balance functions. Similarly, when receptors or ion channels expressed in one organ have unknown mechanisms, their likely effectors or molecular partners in the other inner ear organ are hard to foretell, and hence the outcome of their modulation/mutation is unpredictable itself.

In a more specific example, Kv7. Potassium channels family associated with neurons excitability are expressed in both tissue neurons, their modulation or mutation have very distinct functional consequences on the two sensory modalities: a progressive and severe deafness (Kharkovets T. et al., 2006 EMBO J. 25(3):642-652) but normal balance function (Spitzmaul G et al., 2013 J Biol Chem. 288(13):9334-44).

In summary, such structural, functional and pathological differences between the cochlea and the vestibule lead the search for cochlear therapeutic treatment as being highly specific to this peculiar sensory organ.

Tinnitus is a phantom sensation of hearing in the absence of external sounds. It refers to objective tinnitus, which is caused by sound generated somewhere in the body and subjective tinnitus which is the perception of meaningless sounds without any physical sound being present. Tinnitus affects approximately 10% of the population. Approximately 50 million US adults reported having any tinnitus, and 16 million US adults reported having frequent tinnitus in the past year. The prevalence of frequent tinnitus increases with age, peaking at 14.3% between 60 and 69 years old. Tinnitus may significantly impair quality of life as it causes irritability, agitation, stress, insomnia, anxiety and depression. In fact, for one in 100 adults, tinnitus affects their ability to lead a normal day-to-day life.

Subjective tinnitus is the perception of sound without any auditory stimulus. Many people experience transient tinnitus lasting seconds or minutes after exposure to loud noise. The sounds associated with subjective tinnitus have been described as ringing, hissing, water running, humming, crickets, cicadas, whistling, wind blowing. Most patients experience a high pitch noise typically above 3,000 Hz. Although there is no consensus on a single and common pathomechanisms to tinnitus, there is currently cumulative evidence for a main peripheral auditory system theory of subjective tinnitus. Spontaneous otoacoustic emissions, increased spontaneous activity in the cochlear area such as aberrant firing of the auditory nerve and discordant dysfunction of damaged outer hair cells and intact inner hair cells have been postulated as putative cause for tinnitus.

Due to the lack of pathophysiological bases, the rationale behind pharmacological treatments for tinnitus is to treat the co-morbidities that come along with tinnitus, like depression and anxiety. Others treatments use drugs which are effective in disorders thought to share some commonalities with tinnitus, like anticonvulsants used in epilepsy and the calcium antagonist gabapentin used in neuropathic pain. Although a wide variety of compounds is used off-label to treat tinnitus patients, there is still no US Food and Drug Administration (FDA) or European Medicines Agency (EMA) approved drug on the market. The list of used compounds includes anticonvulsants, anxiolytic, antidepressants, NMDA antagonists, cholinergic antagonists, antihistamines, vasodilators, antipsychotics, and calcium antagonists. For example, WO2010113109 and WO2012/042314 described the use of cyclobenzaprine for treating tinnitus.

However, most drugs have not proven sufficient effectiveness in randomized controlled clinical trials in order to be approved and marketed specifically for tinnitus.

The present invention aims to provide a new method for treating tinnitus.

SUMMARY

One object of the invention is an inhibitor of Histamine type 4 receptor (H4R) for use in the treatment of tinnitus.

In one embodiment, said inhibitor inhibits H4R protein expression and/or activity and/or gene expression.

In another embodiment, said inhibitor of protein expression and/or activity of H4R is an antagonist selected from the group consisting of small molecules, antibodies, aptamers, and ribozymes.

In another embodiment, said inhibitor is a selective inhibitor of H4R.

In another embodiment, said inhibitor is a dual antagonist for H1R and H4R or H3R and H4R.

In another embodiment, said inhibitor is an antagonist selected from 2-aminopyrimidine derivatives compound, pyrimidine derivatives compound, quinazoline derivatives compound, quinazoline sulfonamide compound, bicyclic heteroaryl-substituted imidazole compound, thieno-pyrimidine compound, furo-pyrimidine compound and mequitazine compound.

In another embodiment, said inhibitor is 1-[(5-chloro-1H-indol-2-yl)carbonyl]-4-methylpiperazine or 4-((3R)-3-Aminopyrrolidin-1-yl)-6,7-dihydro-5H-benzo[6,7]cyclohepta[1,2-d]pyrimidin-2-ylamine or cis-4-(Piperazin-1-yl)-5,6,7a,8,9,10,11,11a-octahydrobenzofuro[2,3-h]quinazolin-2-amine or 7-(furan-2-yl)-4-(piperazin-1-yl)quinazolin-2-amine or 1-(7-(2-amino-6-(4-methylpiperazin-1-yl)pyrimidin-4-yl)-3,4-dihdroisoquinolin-2(1H)-yl)-2-cyclopentylethanone or 1-[(5-Chloro-1H-benzimidazol-2-yl)carbonyl]-4-methylpiperazine maleate or PF-3893787 or PF-3893787-18 or JNJ39758979 or UR-63325.

In another embodiment, said inhibitor inhibits H4R gene expression wherein said inhibitor of H4R gene expression is selected from the group consisting of antisense RNA or DNA molecules, small inhibitory RNAs (siRNAs), short hairpin RNA, micro RNA, DNAzymes, modified or synthetic DNA or RNA degradation-resistant polynucleoside amides, peptide nucleic acids (PNAs), locked nucleic acids (LNAs) and other nucleobase-containing polymers.

Another object of the invention is a pharmaceutical composition comprising an inhibitor of H4R according to anyone of claims 1 to 7 for use in the treatment of tinnitus.

DEFINITIONS

The term "Histamine H4 receptor" has its general meaning in the art. The term may include naturally occurring Histamine H4 receptors and variants and modified forms thereof. The Histamine H4 receptor can be from any source, but typically is a mammalian (e.g., human and non-human primate) Histamine H4 receptor, particularly a human Histamine H4 receptor. Sequences for Histamine H4 receptor have been published under the references NM_021624 (*Homo sapiens*), NM_153087 (*Mus musculus*) and NM_131909 (*Rattus norvegicus*).

An "inhibitor of gene expression" refers to a natural or synthetic compound that has a biological effect to inhibit or significantly reduce the expression of a gene. Consequently an "inhibitor of Histamine H4 receptor gene expression" refers to a natural or synthetic compound that has a biological effect to inhibit or significantly reduce the expression of the gene encoding for the Histamine H4 receptor.

The term "receptor antagonist" is used indifferently to denote a "true" antagonist and an inverse agonist of a receptor. A "true" receptor antagonist is a compound which binds the receptor and blocks the biological activation of the receptor, and thereby the action of the receptor agonist, for example, by competing with the agonist for said receptor. An inverse agonist is a compound which binds to the same receptor as the agonist but exerts the opposite effect. Inverse agonists have the ability to decrease the constitutive level of receptor activation in the absence of an agonist.

The term "Histamine H4 receptor antagonist" includes any chemical entity that, upon administration to a patient, results in inhibition or down-regulation of a biological activity associated with activation of the Histamine H4 receptor in the patient, including any of the downstream biological effects otherwise resulting from the binding to Histamine H4 receptor of its natural ligand. Such Histamine H4 receptor antagonists include any agent that can block Histamine H4 receptor activation or any of the downstream biological effects of Histamine H4 receptor activation. For example, such Histamine H4 receptor antagonists can act by occupying the ligand binding site or a portion thereof of the Histamine H4 receptor, thereby making the receptor inaccessible to its natural ligand so that its normal biological activity is prevented or reduced. In the context of the present invention, Histamine H4 receptor antagonists are selective for the Histamine H4 receptor as compared with the other histamine receptors, such as histamine H1 receptor, histamine H2 receptor, and histamine H3 receptor. By "selective" it is meant that the affinity of the antagonist for the human Histamine H4 receptor is at least 10-fold, preferably 25-fold, more preferably 100-fold, still preferably 500-fold higher than the affinity for the other human histamine receptor (H1, H2 and H3).

The affinity of an antagonist for Histamine H4 receptor may be quantified by measuring the activity of Histamine H4 receptor or the biological effect resulting from antagonism of the receptor in the presence of a range of concentrations of said antagonist in order to establish a dose-response curve. From that dose response curve, an $IC_{50}$ value may be deduced which represents the concentration of antagonist necessary to inhibit 50% of a biological activity induced by an agonist in defined concentration. The $IC_{50}$ value may be readily determined by the one skilled in the art by fitting the dose-response plots with a dose-response equation as described by De Lean et al. (1979). $IC_{50}$ values can be converted into affinity constant (Ki) using the assumptions of Cheng and Prusoff (1973).

Accordingly, a selective Histamine H4 receptor antagonist is a compound for which at least one of the ratios (i) $K_i$ H3:$K_i$ H4, and (ii) $IC_{50}$ H3:$IC_{50}$ H4, is above 10:1, preferably 25:1, more preferably 100:1, still preferably 1000:1.

The antagonistic activity of compounds towards the Histamine H4 receptors may be determined using various methods, such as those described in Thurmond R L et al. (2004) or Venable J D. et al. (2005).

The term "small organic molecule" refers to a molecule of a size comparable to those organic molecules generally used in pharmaceuticals. The term excludes biological macromolecules (e. g., proteins, nucleic acids, etc.). Preferred small organic molecules range in size up to about 5000 Da, more preferably up to 2000 Da, and most preferably up to about 1000 Da.

As used herein, the term "subject" denotes a mammal, such as a rodent, a feline, a canine, and a primate. Preferably, a subject according to the invention is a human.

The term "treating" refers to preventing (i.e. keeping from happening), reducing or alleviating at least one adverse effect or symptom of a disease, disorder or condition associated with a deficiency in or absence of an organ, tissue or cell function. Accordingly the aim of the invention is to provide an ending of the tinnitus, a decrease of tinnitus loudness or an amelioration of the subject's condition by protecting or restoring the functionality or part of the functionality of the cochlea.

DETAILED DESCRIPTION

The present invention relates to H4 receptor antagonists for treating or for use in treating tinnitus.

The tinnitus to be treated may be provoked by acoustic trauma, presbycusis, fluctuation in the blood supply to the cochlea leading to ischemia, anoxia treatments with ototoxic medications, sudden deafness, or other cochlear excitotoxic-inducing occurrence.

Tinnitus is thought to arise from neural hyperactivity. Without willing to be bound to a theory, the inventors suggest that efficient and selective pharmacological control of the primary auditory neurons excitability is a solution to attenuate tinnitus. Indeed, as histamine type 4 receptor (H4R) is found to be expressed in spiral ganglion neuron, H4R selective antagonists may efficiently modulate the electrical activity of mammal cochlear primary neurons.

In one embodiment, said H4 receptor antagonist is a selective H4 receptor antagonist.

In one embodiment, the selective Histamine H4 receptor antagonists may be low molecular weight antagonists, e. g. a small organic molecule.

According to one embodiment of the invention, a selective H4 receptor antagonist refers to a molecule that has an affinity for H4 receptor at least 10 fold, preferably 25 fold, preferably 50 fold, more preferably 100 fold, and even more preferably 500 fold higher than its affinity for any one of H1, H2 or H3 receptor.

According to another embodiment of the invention, a selective H4 receptor antagonist is a molecule for which one of the ratios Ki H3:Ki H4 and (ii) IC50 H3:IC50 H4 is above 10:1, preferably 25:1, preferably 50:1, more preferably 100:1 and even more preferably between 500:1 to 1000:1.

The affinity for H4 receptor and others (H1, H2 and H3) receptors may be characterized by any conventional technique known in the art. For example, it can be determined by binding assays. Said assays use cells pellets from cells such as SK-N-MC or HEK293 T, cells transfected with human, rat or mouse H4, H3, H2 or H1 receptor (Lovenberg et al. 1999, Liu et al. 2001a,b, Thurmond et al. 2004). Cells can be homogenized in 50 mM Tris pH 7.5 containing 5 mM EDTA, and supernatants from an 800 g spin are collected and recentrifugated at 30 000 g for 30 min. Pellets are then homogenized in 50 mM Tris pH 7.5 containing 5 mM EDTA. For H4 competition binding studies, human, mouse or rat cells are incubated using different concentrations of [$^3$H] histamine (specific for each species, for example 10, 40 and 50 nM respectively), in the presence or absence of the molecule to be tested, for about 45 min at 25° C. The non-specific binding is defined using 100 µM unlabeled histamine or using $10^{-6}$ M of specific or selective H4 receptor antagonist such as JNJ-7777120 or JNJ-10191584. The Kd values for the human, mouse and rat H4 receptor were determined with this method to be 5, 42 and 178 nM respectively, and the Bmax values were determined to be 1.12, 1.7 and 0.68 pmol/mg protein, respectively. Similarly, the ligand used for the H3 receptor binding assays is for example [$^3$H]N-a-methyl histamine, and the non-specific binding is defined using 100 µM unlabeled histamine. The Kd value for human H3 receptor was determined with this method to be 1 nM and the Bmax value 2.13 pmol/mg protein. The ligand used for the H1 receptor binding was [$^3$H]pyrilamine and the non-specific activity is defined using 10 µM unlabeled diphenhydramine. The Kd value for human H1 receptor was determined with this method to be 1 nM and the Bmax value 2.68 pmol/mg protein. In these assays, the cells are typically incubated with different concentration of such as $10^{-11}$ to $10^{-4}$ M of molecule to be tested.

The person skilled in the art willing to verify or determine the antagonist activity of the molecule to be tested may use any method known in the art and for example a cell-based cAMP assay. Said assay use SK-n-MC cell lines transfected with H4, H3, H2 or H1 receptor and a reporter gene construct such as b-galactosidase under the control of cyclic AMP-responsive elements. Cells are plated overnight before the assay. Histamine is used as the agonist molecule. For determination of antagonist activity, molecules to be tested are added 10 min prior to the addition of agonist. Forskolin (5 µM final concentration) is added 10 min after the addition of histamine. Cells are then maintained at 37° C. for 6 hours, and then after washing lysed with about 25 µl of 0.1× assay buffer (10 mM sodium phosphate, pH 8, 0.2 mM MgSO$_4$ and 0.01 mM MnCl$_2$) and incubated at room temperature for 10 min. Cells are then incubated for 10 min with about 100 µl of 1× assay buffer containing 0.5% (v/v) Triton X-100 and 40 mM β-mercaptoethanol. Color can be developed using 25 µl of 1 mg/ml substrate solution such as chlorophenol red b-D-galactopyranoside, and quantified by measuring the absorbance at 570 nm. The data obtained for each concentration-response curve can be fitted to a sigmoidal curve to obtain the maximum response, Hill coefficient and EC$_{50}$.

Histamine H4 antagonists and Selective Histamine H4 antagonists that are contemplated by the invention belong to the following classes of compounds: indoles, benzimidazoles, quinoxalines, quinazoline sulfonamide, aminopyrimidines or annelated pyrimidines.

Exemplary Histamine H4 antagonists and selective Histamine H4 antagonists that are contemplated by the invention include but are not limited to those described in U.S. Pat. No. 6,803,362; US Patent Application Publication Nos. 2004/0105856, 2004/0127395, 2004/0132715, 2004/0048878, 2004/0058934, 2005/0070527, 2005/0070550, 2005/0261309, 2007/0238771, 2008/0269239, 2008/0261946, 2008/0188452, 2009/275748, and International Patent Application Nos WO2005/054239, WO2005/014556, WO2007/031529, WO2007/072163, WO2007/090852, WO2007/117399, WO2007/120690, WO2008/074445, WO2008/008359, WO2008/031556, WO2008/100565, WO2008/003702, WO2009/134726, WO2009/115496, WO2009/114575, WO2009/080721, WO2009/083608, WO2009/077608, WO2009/071625, WO2009/068512, WO2009/056551, WO2009/038673, WO2009/077608, WO2009/079001 and WO2009/047255, which are incorporated herein by reference.

Other exemplary selective Histamine H4 antagonists that are contemplated by the invention include but are not limited to those described in Jablonowski J A et al. (2003), Venable J D. et al. (2005), Thurmond R L. et al. (2004), Herman D. et al. (2005) Robin L. et al. (2004), Cowart M D. et al. (2008) and Liu H. et al. (2008).

Typically, compounds that may be contemplated by the invention are 2-aminopyrimidine derivatives, such as described in WO2005/054239 or WO2005/014556, or quinazoline derivatives such as described in WO2008/003702.

In one embodiment of the invention, the Histamine H4 antagonist or selective H4 antagonist is selected among bicyclic heteroaryl-substituted imidazole compounds, such as the ones described in WO2009/079001 and WO2007/120690; thieno- and furo-pyrimidine compounds such as the ones described in WO2009/038673; 2-Aminopyrimidine compounds such as the ones described in WO2008/100565, WO2009077608, WO2009/068512, WO2005/054239, WO2008/031556, WO2008122378 and WO2005/014556; benzofuro- and benzothienopyrimidine compounds such as the ones described in WO2008/008359; Furo[3,2-d]pyrimidine derivatives such as the ones described in WO2009/056551 and WO2009/115496; 4-Amino-pyrimidine derivatives such as the ones described in WO2009/080721; amino pyrimidine compounds such as the ones described in WO2007/090852; enantiomers of amino pyrimidine compounds such as the ones described in WO2007/090853; azetidine amino pyrimidine compounds, such, as the ones described in WO2007/090854; pyrimidine compounds such as the ones described in WO2007/039467, WO2006/050965 and WO2007/072163; mequitazine, such as the ones described in WO2009/071625; substituted pyrimidine derivatives, particularly macrocyclic fused substituted pyrimidine derivatives, such as the ones described in WO2009/134726; macrocyclic spiro pyrimidine compounds, particularly tricyclic spiro pyrimidine compounds, such as the ones described in WO2009/114575; macrocyclic benzofused pyrimidine compounds, such as the ones described in WO2008/060767; heteroaryl-fused macrocylciv pyrimidine derivatives, particularly heteroaryl-fused macrocyclic 2,4-diaminopyrimidine compounds, such as the ones described in WO2009137492; 5,6,7,8-tetrahydroquinazolin-2-amine derivatives, such as the ones described in WO2009123967; octahydropyrrolo[3,4-c]pyrrole derivatives, such as the ones described in WO2006056848; tricyclic and heterotricyclic derivatives, such as the ones described in WO2008/074445; heterobicyclic compounds such as the ones described in WO2009047255; quinazolines and related heterocyclic compounds, such as the ones described in WO2008/003702; imidazole derivatives of piperidine, such as the ones described in WO2005/014579; bicyclic pyrimidine compound, such as the ones described in WO2009107767 (all references being incorporated by reference).

In a particular embodiment, the Histamine H4 antagonist or selective Histamine H4 antagonists are selected from those described in the international Patent Application WO2007/120690:(1H-Benzoimidazol-2-yl)-(4-methyl-piperazin-1-yl)-methanone; (1H-Benzoimidazol-2-yl)-(4-ethyl-piperazin-1-yl)-methanone; (1H-Benzoimidazol-2-yl)-(3-methyl-piperazin-1-yl)-methanone; (1H-Benzoimidazol-2-yl)-(4-methyl-[1,4]diazepan-1-yl)-methanone; 1H-Benzoimidazole-2-carboxylic acid (8-methyl-8-aza-bicyclo[3.2.1]oct-3-yl)-amide; (5-Chloro-1H-benzoimidazol-2-yl)-(4-methyl-piperazin-1-yl)-methanone; (5-Chloro-1H-benzoimidazol-2-yl)-piperazin-1-yl-methanone; (5-Chloro-1H-benzoimidazol-2-yl)-(3-methyl-piperazin-1-yl)-methanone; (5,6-Difluoro-1H-benzoimidazol-2-yl)-(4-methyl-piperazin-1-yl)-methanone; (5,6-Difluoro-1H-benzoimidazol-2-yl)-(4-ethyl-piperazin-1-yl)-methanone; (5,6-Difluoro-1H-benzoimidazol-2-yl)-(3-methyl-piperazin-1-yl)-methanone; (5,6-Difluoro-1H-benzoimidazol-2-yl)-(4-methyl-[1,4]diazepan-1-yl)-methanone; 5,6-Difluoro-1H-benzoimidazole-2-carboxylic acid (8-methyl-8-aza-bicyclo[3.2.1]oct-3-yl)-amide; (6-Chloro-5-fluoro-1H-benzoimidazol-2-yl)-(4-methyl-piperazin-1-yl)-methanone; (6-Chloro-5-fluoro-1H-benzoimidazol-2-yl)-(4-methyl-[1,4]diazepan-1-yl)-methanone; 6-Chloro-5-fluoro-1H-benzoimidazole-2-carboxylic acid (8-methyl-8-aza-bicyclo[3.2.1]oct-3-yl)-amide; (5-Chloro-6-methyl-1H-benzoimidazol-2-yl)-(4-methyl-piperazin-1-yl)-methanone; (5-Chloro-6-methyl-1H-benzoimidazol-2-yl)-piperazin-1-yl-methanone; (4-Methyl-1H-benzoimidazol-2-yl)-(3-methyl-piperazin-1-yl)-methanone; (4-Ethyl-piperazin-1-yl)-(4-methyl-1H-benzoimidazol-2-yl)-methanone; (4-Methyl-1H-benzoimidazol-2-yl)-(4-methyl-piperazin-1-yl)-methanone; (4-Methyl-1H-benzoimidazol-2-yl)-piperazin-1-yl-methanone; 4-Methyl-1H-benzoimidazole-2-carboxylic acid (8-methyl-8-aza-bicyclo[3.2.1]oct-3-yl)-amide; 5-Methyl-1H-benzoimidazole-2-carboxylic acid (8-methyl-8-aza-bicyclo[3.2.1]oct-3-yl)-amide; (5-Methyl-1H-benzoimidazol-2-yl)-(4-methyl-piperazin-1-yl)-methanone; (4-Methyl-piperazin-1-yl)-(5-trifluoromethyl-1H-benzoimidazol-2-yl)-methanone; Piperazin-1-yl-(5-trifluoromethyl-1H-benzoimidazol-2-yl)-methanone; (5-Fluoro-1H-benzoimidazol-2-yl)-(4-methyl-piperazin-1-yl)-methanone; (4-Ethyl-piperazin-1-yl)-(5-fluoro-1H-benzoimidazol-2-yl)-methanone; (5-Fluoro-1H-benzoimidazol-2-yl)-piperazin-1-yl-methanone; (5-Fluoro-1H-benzoimidazol-2-yl)-(3-methyl-piperazin-1-yl)-methanone; 5-Fluoro-1H-benzoimidazole-carboxylic acid (8-methyl-8-aza-bicyclo[3.2.1]oct-3-yl)-amide; Benzooxazol-2-yl-(4-methyl-piperazin-1-yl)-methanone; (7-Methyl-benzooxazol-2-yl)-(4-methyl-piperazin-1-yl)-methanone; (5-Methyl-benzooxazol-2-yl)-(4-methyl-piperazin-1-yl)-methanone; (4-Methyl-benzooxazol-2-yl)-(4-methyl-piperazin-1-yl)-methanone; Benzothiazol-2-yl-(4-methyl-piperazin-1-yl)-methanone; (5-Benzoyl-1H-benzoimidazol-2-yl)-(4-methyl-piperazin-1-yl)-methanone; (4-Chloro-1H-benzoimidazol-2-yl)-(4-methyl-piperazin-1-yl)-methanone; (4-Methyl-piperazin-1-yl)-(4-nitro-1H-benzoimidazol-2-yl)-methanone; (4-Amino-1H-benzoimidazol-2-yl)-(4-methyl-piperazin-1-yl)-methanone; (4-Isopropylamino-1H-benzoimidazol-2-yl)-(4-methyl-piperazin-1-yl)-methanone; C-(5-Chloro-1H-benzoimidazol-2-yl)-C-(4-methyl-piperazin-1-yl)-methyleneamine; (4,6-Difluoro-1H-benzoimidazol-2-yl)-(4-methyl-piperazin-1-yl)-methanone; (4-Methyl-piperazin-1-yl)-(5-nitro-1H-benzoimidazol-2-yl)-methanone; (5-Fluoro-4-methyl-1H-benzoimidazol-2-yl)-(4-methyl-piperazin-1-yl)-methanone; (5-Bromo-1H-benzoimidazol-2-yl)-(4-methyl-piperazin-1-yl)-methanone; (5,6-Dichloro-1H-benzoimidazol-2-yl)-(4-methyl-piperazin-1-yl)-methanone; (4,5-Dimethyl-1H-benzoimidazol-2-yl)-(4-methyl-piperazin-1-yl)-methanone; (5,6-Dimethyl-1H-benzoimidazol-2-yl)-(4-methyl-pipera2in-1-yl)-methanone; (5-Methoxy-1H-benzoimidazol-2-yl)-(4-methyl-piperazin-1-yl)-methanone; (5-Chloro-benzooxazol-2-yl)-(4-methyl-piperazin-1-yl)-methanone; (5-Fluoro-benzooxazol-2-yl)-(4-methyl-piperazin-1-yl)-methanone; (6-Fluoro-benzooxazol-2-yl)-(4-methyl-piperazin-1-yl)-methanone; (5,7-Difluoro-benzooxazol-2-yl)-(4-methyl-piperazin-1-yl)-methanone; (4-Methyl-piperazin-1-yl)-(5-trifluoromethoxy-benzooxazol-2-yl)-methanone; (5-Chloro-benzothiazol-2-yl)-(4-methyl-piperazin-1-yl)-methanone; (4-Methyl-piperazin-1-yl)-(5-trifluoromethyl-benzothiazol-2-yl)-methanone; (4-Methyl-piperazin-1-yl)-(6H-thieno[2,3-b]pyrrol-5-yl)-methanone; (Hexahydro-pyrrolo[1,2-a]pyrazin-2-yl)-(6H-thieno[2,3-b]pyrrol-5-yl)-methanone; (2-Chloro-6H-thieno[2,3-b]pyrrol-5-yl)-(4-methyl-piperazin-1-yl)-methanone; (2-Chloro-6H-thieno[2,3-b]pyrrol-5-yl)-(hexahydro-pyrrolo[1,2-a]pyrazin-2-yl)-methanone; (2-Chloro-6H-thieno[2,3-b]pyrrol-5-yl)-piperazin-1-yl-methanone; (4H-Furo[3,2-b]pyrrol-5-yl)-(4-methyl-piperazin-1-yl)-methanone; (4-Methyl-piperazin-1-yl)-(4H-thieno[3,2-b]pyrrol-5-yl)-methanone; Piperazin-1-yl-(4H-thieno[3,2-b]pyrrol-5-yl)-methanone; (3-Methyl-piperazin-1-yl)-(4H-thieno[3,2-b]pyrrol-5-yl)-methanone; (2-Chloro-4H-thieno[3,2-b]pyrrol-5-yl)-(4-methyl-piperazin-1-yl)-methanone; (2-Chloro-4H-thieno[3,2-b]pyrrol-5-yl)-(hexahydro-pyrrolo[1,2-a]pyrazin-2-yl)-methanone; (3-Bromo-4H-thieno[3,2-b]pyrrol-5-yl)-(4-methyl-piperazin-1-yl)-methanone; 4-Methyl-piperazin-1-yl)-(3-methyl-4H-thieno[3,2-b]pyrrol-5-yl)-methanone; (2-Methyl-4H-furo[3,2-b]pyrrol-5-yl)-(4-methyl-piperazin-1-yl)-methanone; (2,3-Dimethyl-4H-furo[3,2-b]pyrrol-5-yl)-(4-methyl-piperazin-1-yl)-methanone; (2.3-Dimethyl-4H-thieno[3,2-b]pyrrol-5-yl)-(4-methyl-piperazin-1-yl)-methanone; (2,3-Dichloro-6H-thieno[2,3-b]pyrrol-5-yl)-(4-methyl-piperazin-1-yl)-methanone; (2-Methyl-4H-furo[3,2-b]pyrrol-5-yl)-piperazin-1-yl-methanone; (3-Bromo-4H-thieno[3,2-b]pyrrol-5-yl)-piperazin-1-yl-methanone; (3-Bromo-4H-thieno[3,2-b]pyianol-5-yl)-(3-methyl-piperazin-1-yl)-methanone; (3-Methyl-4H-thieno[3,2-b]pyrrol-5-yl)-piperazin-1-yl-methanone; (3-Methyl-piperazin-1-yl)-(3-methyl-4H-thieno[3,2-b]pyrrol-5-yl)-methanone; (2-Chloro-3-methyl-4H-thieno[3,2-b]pyrrol-5-yl)-(4-methyl-piperazin-1-yl)-methanone; (2-Chloro-3-methyl-4H-thieno[3,2-b]pyrrol-5-yl)-piperazin-1-yl-methanone;

(2,3-Dichloro-4H-thieno[3,2-b]pyrrol-5-yl)-(4-methyl-piperazin-1-yl)-methanone; (2,3-Dimethyl-6H-thieno[2,3-b]pyrrol-5-yl)-(4-methyl-piperazin-1-yl)-methanone; (2-Chloro-3-methyl-6H-thieno[2,3-b]pyrrol-5-yl)-(4-methyl-piperazin-1-yl)-methanone; (3-Chloro-2-methyl-6H-thieno[2,3-b]pyrrol-5-yl)-(4-methyl-piperazin-1-yl)-methanone; (2-Bromo-6H-thieno[2,3-b]pyranol-5-yl)-(4-methyl-piperazin-1-yl)-methanone; (3-Bromo-6H-thieno[2,3-b]pyrrol-5-yl)-(4-methyl-piperazin-1-yl)-methanone; (4-Methyl-piperazin-1-yl)-(2-phenyl-6H-thieno[2,3-b]pyrrol-5-yl)-methanone; [2-(4-Chloro-phenyl)-6H-thieno[2,3-b]pyrrol-5-yl]-(4-methyl-piperazin-1-yl)-methanone; (3-Bromo-4H-thieno[3,2-b]pyranol-5-yl)-(3,4-dimethyl-piperazin-1-yl)-methanone; (3,4-Dimethyl-piperazin-1-yl)-(3-methyl-4H-thieno[3,2-b]pyrrol-5-yl)-methanone; (2-Bromo-3-methyl-4H-thieno[3,2-b]pyrrol-5-yl)-(4-methyl-piperazin-1-yl)-methanone; (3-Bromo-2-chloro-4H-thieno[3,2-b]pyrrol-5-yl)-(4-methyl-piperazin-1-yl)-methanone; (2,3-Dichloro-4H-thieno[3,2-b]pyrrol-5-yl)-(3-methyl-piperazin-1-yl)-methanone; (4-Methyl-piperazin-1-yl)-(2-phenyl-4H-thieno[3,2-b]pyrrol-5-yl)-methanone; (4-Methyl-piperazin-1-yl)-[2-(4-trifluoromethyl-phenyl)-4H-thieno[3,2-b]-pyrrol-5-yl]-methanone; 8-Methyl-3-(4-methyl-piperazin-1-yl)-1H-quinoxalin-2-one; 8-Methyl-3-piperazin-1-yl-1H-quinoxalin-2-one; 8-Nitro-3-piperazin-1-yl-1H-quinoxalin-2-one; 7,8-Difluoro-3-piperazin-1-yl-1H-quinoxalin-2-one; 8-Methyl-3-(3-methyl-piperazin-1-yl)-1H-quinoxalin-2-one; 3-(3-Methyl-piperazin-1-yl)-1H-quinoxalin-2-one; 3-[4-(2-Hydroxy-ethyl)-piperazin-1-yl]-8-methyl-1H-quinoxalin-2-one; 6-Chloro-3-(4-methyl-piperazin-1-yl)-1H-quinoxalin-2-one; 7-Chloro-3-(4-methyl-piperazin-1-yl)-1H-quinoxalin-2-one; 3-(4-Methyl-piperazin-1-yl)-6-trifluoromethyl-1H-quinoxalin-2-one; 3-(4-Methyl-piperazin-1-yl)-7-trifluoromethyl-1H-quinoxalin-2-one; 6,7-Dichloro-3-(4-methyl-piperazin-1-yl)-1H-quinoxalin-2-one; 6,7-Dichloro-3-piperazin-1-yl-1H-quinoxalin-2-one; 6,7-Dichloro-3-(4-methyl-[1,4]diazepan-1-yl)-1H-quinoxalin-2-one; 6,7-Difluoro-3-(4-methyl-piperazin-1-yl)-1H-quinoxalin-2-one; 7-Chloro-6-methyl-3-(4-methyl-piperazin-1-yl)-1H-quinoxalin-2-one; 6-Chloro-7-methyl-3-(4-methyl-piperazin-1-yl)-1H-quinoxalin-2-one; 6-Fluoro-3-(4-methyl-piperazin-1-yl)-1H-quinoxalin-2-one; 7,8-Difluoro-3-(4-methyl-piperazin-1-yl)-1H-quinoxalin-2-one; 8-Chloro-3-(4-methyl-piperazin-1-yl)-6-trifluoromethyl-1H-quinoxalin-2-one; 3-Piperazin-1-yl-6-trifluoromethyl-1H-quinoxalin-2-one; 3-Piperazin-1-yl-7-trifluoromethyl-1H-quinoxalin-2-one; 6-Chloro-7-fluoro-3-(4-methyl-piperazin-1-yl)-1H-quinoxalin-2-one; 7-Chloro-6-fluoro-3-(4-methyl-piperazin-1-yl)-1H-quinoxalin-2-one; 7-Chloro-3-piperazin-1-yl-1H-quinoxalin-2-one; 6-Chloro-3-piperazin-1-yl-1H-quinoxalin-2-one; 6-Chloro-3-(3-methyl-piperazin-1-yl)-1H-quinoxalin-2-one; 7-Chloro-3-(3-methyl-piperazin-1-yl)-1H-quinoxalin-2-one; 3-(3-Methyl-piperazin-1-yl)-6-trifluoromethyl-1H-quinoxalin-2-one; 3-(3-Methyl-piperazin-1-yl)-7-trifluoromethyl-1H-quinoxalin-2-one; 2-{2-Chloro-4-[3-(4-methyl-piperazin-1-yl)-propoxy]-phenyl}-4,5-dimethyl-1H-benzoimidazole; 2-{2-Chloro-4-[3-(1-methyl-piperidin-4-yl)-propoxy]-phenyl}-4-methyl-1H-benzoimidazole; 2-{2-Chloro-4-[3-(4-methyl-piperazin-1-yl)-propoxy]-phenyl}-5-trifluoromethoxy-1H-benzoimidazole; 5-tert-Butyl-2-{3-chloro-4-[3-(4-methyl-[1,4]diazepan-1-yl)-propoxy]-phenyl}-1H-benzoimidazole; 5-tert-Butyl-2-{3-chloro-4-[3-(4-methyl-piperazin-1-yl)-propoxy]-phenyl}-1H-benzoimidazole; 4,5-Dimethyl-2-{3-methyl-4-[3-(4-methyl-piperazin-1-yl)-propoxy]-phenyl}-1H-benzoimidazole; 5-tert-Butyl-2-{3-[4-(4-methyl-piperazin-1-yl)-butoxy]-phenyl}-1H-benzoimidazole; 5-tert-Butyl-2-{3-[4-(4-methyl-[1,4]diazepan-1-yl)-butoxy]-phenyl}-1H-benzoimidazole; (1-{3-[4-(5-tert-Butyl-1H-benzoimidazol-2-yl)-2-chloro-phenoxy]-propyl}-pyrrolidin-3-yl)-dimethylamine; 2-{3-Fluoro-4-[3-(4-methyl-piperazin-1-yl)-propoxy]-phenyl}-4-methyl-1H-benzoimidazole; 5-Methyl-2-{4-[3-(4-methyl-piperazin-1-yl)-propoxy]-naphthalen-1-yl}-1H-benzoimidazole; 4-[3-(5-tert-Butyl-1H-benzoimidazol-2-yl)-phenoxy]-1-(4-methyl-piperazin-1-yl)-butan-1-one; 5-Chloro-2-[3-chloro-4-(3-piperazin-1-yl-propoxy)-phenyl]-6-fluoro-1H-benzoimidazole; 5-tert-Butyl-2-{3-methyl-4-[3-(4-methyl-piperazin-1-yl)-propoxy]-phenyl}-1H-benzoimidazole; 2-{2-Chloro-4-[3-(1-methyl-piperidin-4-yl)-propoxy]-phenyl}-4,6-dimethyl-1H-benzoimidazole; 2-{2-Chloro-4-[2-methyl-3-(4-methyl-piperazin-1-yl)-propoxy]-phenyl}-4-methyl-1H-benzoimidazole; 5-Chloro-2-{3-chloro-4-[3-(4-methyl-piperazin-1-yl)-propoxy]-phenyl}-6-methyl-1H-benzoimidazole; 6-Chloro-2-{2-chloro-4-[3-(4-methyl-piperazin-1-yl)-propoxy]-phenyl}-4-ethyl-1H-benzoimidazole; 5-tert-Butyl-2-{3-chloro-4-[3-(4-methyl-piperazin-1-yl)-propoxy]-phenyl}-1H-benzoimidazole; 5-Chloro-2-{3-fluoro-4-[3-(4-methyl-piperazin-1-yl)-propoxy]-phenyl}-1H-benzoimidazole; 2-{2-Chloro-4-[3-(4-methyl-[1,4]diazepan-1-yl)-propoxy]-phenyl}-4,6-dimethyl-1H-benzoimidazole; 5-Chloro-6-methyl-2-{3-[4-(4-methyl-piperazin-1-yl)-butoxy]-phenyl}-1H-benzoimidazole; 2-{3-Fluoro-4-[3-(4-methyl-piperazin-1-yl)-propoxy]-phenyl}-5-methyl-1H-benzoimidazole; 5,6-Difluoro-2-{3-fluoro-4-[3-(4-methyl-piperazin-1-yl)-propoxy]-phenyl}-1H-benzoimidazole; 2-{3-Fluoro-4-[3-(4-methyl-piperazin-1-yl)-propoxy]-phenyl}-1H-benzoimidazole; 2-{2-Chloro-4-[3-(4-methyl-[1,4]diazepan-1-yl)-propoxy]-phenyl}-4,5-dimethyl-1H-benzoimidazole; 5,6-Dimethyl-2-{3-[4-(4-methyl-piperazin-1-yl)-butoxy]-phenyl}-1H-benzoimidazole; 2-{2-Chloro-4-[3-(4-methyl-piperazin-1-yl)-propoxy]-phenyl}-4,6-dimethyl-1H-benzoimidazole; 2-{2-Chloro-4-[3-(4-methyl-[1,4]diazepan-1-yl)-propoxy]-phenyl}-4-methyl-1H-benzoimidazole; 5-tert-Butyl-2-{2-chloro-4-[3-(4-methyl-piperazin-1-yl)-propoxy]-phenyl}-1H-benzoimidazole; 2-{3-Methoxy-4-[3-(4-methyl-piperazin-1-yl)-propoxy3-phenyl}-5-trifluoromethyl-1H-benzoimidazole; 5-Chloro-2-{3-chloro-4-[3-(4-methyl-piperazin-1-yl)-propoxy]-phenyl}-6-fluoro-1H-benzoimidazole; 5,6-Dichloro-2-{2-chloro-4-[3-(4-methyl-piperazin-1-yl)-propoxy]-phenyl}-1H-benzoimidazole; 5-Chloro-2-{2-chloro-4-[3-(4-methyl-piperazin-1-yl)-propoxy]-phenyl}-1H-benzoimidazole; 5-Chloro-2-{2-chloro-4-[3-(4-methyl-piperazin-1-yl)-propoxy]-phenyl}-6-fluoro-1H-benzoimidazole; 5-Chloro-2-{3-methyl-4-[3-(4-methyl-piperazin-1-yl)-propoxy]-phenyl}-1H-benzoimidazole; 2-{3-Chloro-4-[3-(4-methyl-piperazin-1-yl)-propoxy]-phenyl}-5-methyl-1H-benzoimidazole; 5,6-Dichloro-2-{3-chloro-4-[3-(4-methyl-piperazin-1-yl)-propoxy]-phenyl}-1H-benzoimidazole; 5-Chloro-6-methyl-2-{3-methyl-4-[3-(4-methyl-piperazin-1-yl)-propoxy]-phenyl}-1H-benzoimidazole; 2-{2-Chloro-4-[3-(4-methyl-piperazin-1-yl)-propoxy]-phenyl}-5-methyl-1H-benzoimidazole; 5-Chloro-2-{3-chloro-4-[3-(4-methyl-piperazin-1-yl)-propoxy]-phenyl}-1H-benzoimidazole; 2-{3-Chloro-4-[3-(4-methyl-piperazin-1-yl)-propoxy]-phenyl}-5-trifluoromethyl-1H-benzoimidazole; 5-Chloro-6-fluoro-2-{3-methyl-4-[3-(4-methyl-piperazin-1-yl)-propoxy]-phenyl}-1H-benzoimidazole; 5-Methyl-2-{3-methyl-4-[3-(4-methyl-piperazin-1-yl)-propoxy]-phenyl}-1H-benzoimidazole; 2-{3-Chloro-4-[3-(4-methyl-piperazin-1-yl)-propoxy]-phenyl}-1H-benzoimidazole; 2-{3-Methyl- 4-[3-(4-methyl-piperazin-1-yl)-propoxy]-phenyl}-1H-benzoimidazole; 2-{2-Chloro-4-[3-(4-methyl-piperazin-1-yl)-propoxy]-phenyl}-1H-benzoimidazole; 5-Chloro-6-fluoro-2-{3-methoxy-4-[3-(4-methyl-piperazin-1-yl)-propoxy]-phenyl}-1H-benzoimidazole; 2-{3-Chloro-4-[3-(4-methyl-piperazin-1-yl)-propoxy]-phenyl}-5-methoxy-1H-benzoimidazole; 5-tert-Butyl-2-{3,5-dibromo-4-[3-(4-methyl-piperazin-1-yl)-propoxy]-phenyl}-1H-benzoimidazole; 2-{2-Methoxy-4-[3-(4-methyl-piperazin-1-yl)-propoxy]-phenyl}-5-trifluoromethyl-1H-benzoimidazole; 2-{2-Chloro-4-[3-(4-methyl-piperazin-1-yl)-propoxy]-phenyl}-5-trifluoromethyl-1H-benzoimidazole; 2-{3-[3-(4-Methyl-piperazin-1-yl)-propoxy]-phenyl}-1H-benzoimidazole; (2-{3-[4-(4-Methyl-piperazin-1-yl)-butoxy]-phenyl}-1H-benzoimidazol-5-yl)-phenyl-methanone; 6-Chloro-2-{2-chloro-4-[3-(1-methyl-piperidin-4-yl)-propoxy]-phenyl}-4-methyl-1H-benzoimidazole; 5-tert-Butyl-2-{3-chloro-4-[3-(1-methyl-piperidin-4-yl)-propoxy]-phenyl}-1H-benzoimidazole; 2-{2-Chloro-4-[3-(1-methyl-piperidin-4-yl)-propoxy]-phenyl}-4,5-dimethyl-1H-benzoimidazole; 5-Chloro-6-methyl-2-{4-[3-(1-methyl-piperidin-4-yl)-propoxy]-phenyl}-1H-benzoimidazole; 5-Chloro-2-{4-[3-(1-methyl-piperidin-4-yl)-propoxy]-phenyl}-1H-benzoimidazole; 5-Chloro-6-fluoro-2-{4-[3-(1-methyl-piperidin-4-yl)-propoxy]-phenyl}-1H-benzoimidazole; 5-tert-Butyl-2-{4-[3-(1-methyl-piperidin-4-yl)-propoxy]-phenyl}-1H-benzoimidazole; 5-Methyl-2-{4-[3-(1-methyl-piperidin-4-yl)-propoxy]-phenyl}-1H-benzoimidazole; 2-{4-[3-(1-Methyl-piperidin-4-yl)-propoxy]-phenyl}-1H-benzoimidazole; 6-Chloro-2-{2-fluoro-4-[3-(1-methyl-piperidin-4-yl)-propoxy]-phenyl}-4-methyl-1H-benzoimidazole; 5-Fluoro-2-{2-methyl-4-[3-(1-methyl-piperidin-4-yl)-propoxy]-phenyl}-1H-benzoimidazole; 4-Chloro-2-{2-methyl-4-[3-(1-methyl-piperidin-4-yl)-propoxy]-phenyl}-1H-benzoimidazole; 6-Chloro-4-methyl-2-{2-methyl-4-[3-(1-methyl-piperidin-4-yl)-propoxy]-phenyl}-1H-benzoimidazole; 2-{2-Chloro-4-[3-(1-methyl-piperidin-4-yl)-propoxy]-phenyl}-3H-naphtho[1,2-d]imidazole; 4,6-Dimethyl-2-{2-methyl-4-[3-(4-methyl-piperazin-1-yl)-propoxy]-phenyl}-1H-benzoimidazole; 2-{2-Chloro-4-[3-(4-methyl-piperazin-1-yl)-propoxy]-phenyl}-4-methyl-1H-benzoimidazole; 2-{2-Chloro-4-[3-(4-methyl-piperazin-1-yl)-propoxy]-phenyl}-5-fluoro-4-methyl-1H-benzoimidazole; 2-{2-Chloro-4-[3-(4-methyl-piperazin-1-yl)-propoxy]-phenyl}-3H-naphtho[1,2-d]imidazole; 6-Chloro-2-{2-chloro-4-[3-(4-methyl-[1,4]diazepan-1-yl)-propoxy]-phenyl}-4-methyl-1H-benzoimidazole; 2-{3-Chloro-4-[3-(4-methyl-[1,4]diazepan-1-yl)-propoxy]-phenyl}-4-methyl-1H-benzoimidazole; 4,6-Dimethyl-2-{3-[4-(4-methyl-[1,4]diazepan-1-yl)-butoxy]-phenyl}-1H-benzoimidazole; 5-Chloro-2-{4-[3-(4-methyl-piperazin-1-yl)-propoxy]-phenyl}-1H-benzoimidazole; 2-{4-[3-(4-Methyl-piperazin-1-yl)-propoxy]-phenyl}-1H-benzoimidazole; {2-(6-Chloro-4-methyl-1H-benzoimidazol-2-yl)-5-[3-(1-methyl-piperidin-4-yl)-propoxy]-benzyl}-dimethyl-amine; {2-(5-Fluoro-4-methyl-1H-benzoimidazol-2-yl)-5-[3-(1-methyl-piperidin-4-yl)-propoxy]-benzyl}-dimethyl-amine; 4-{3-[4-(6-Chloro-4-methyl-1H-benzoimidazol-2-yl)-3-methyl-phenoxy]-propyl}-[1,4]diazepan-5-one; 4-{3-[4-(5-tert-Butyl-1H-benzoimidazol-2-yl)-3-methyl-phenoxy]-propyl}-1-methyl-[1,4]diazepan-5-one; 5-tert-Butyl-2-{2-methyl-4-[3-(2-methyl-piperazin-1-yl)-propoxy]-phenyl}-1H-benzoimidazole; 5-tert-Butyl-2-{2-methyl-4-[3-(2-methyl-piperazin-1-yl)-propoxy]-phenyl}-1H-benzoimidazole; 6-Chloro-4-methyl-2-[2-methyl-4-(3-piperidin-4-yl-propoxy)-phenyl]-1H-benzoimidazole; 5-Fluoro-4-methyl-2-[2-methyl-4-(3-piperidin-4-yl-propoxy)-phenyl]-1H-benzoimidazole; 6-Chloro-2-{4-[3-(1-ethyl-piperidin-4-yl)-propoxy]-2-methyl-phenyl}-4-methyl-1H-benzoimidazole; {2-[3-Chloro-4-(4-methyl-1H-benzoimidazol-2-yl)-phenoxy]-ethyl}-methyl-(1-methyl-piperidin-4-yl)-amine; 6-Chloro-4-methyl-2-{2-methyl-4-[2-(1-methyl-piperidin-4-yloxy)-ethoxy]-phenyl}-1H-benzoimidazole; 6-Chloro-4-methyl-2-{2-methyl-4-[3-(1-methyl-1,2-6-tetrahydro-pyridin-4-yl)-propoxy]-phenyl}-1H-benzoimidazole; 5-Fluoro-4-methyl-2-{2-methyl-4-[3-(1-methyl-1,2,3,6-tetrahydro-pyridin-4-yl)-propoxy]-phenyl}-1H-benzoimidazole; 6-Fluoro-7-methyl-2-{3-[4-(1-methyl-piperidin-4-yl)-butoxy]-phenyl}-1H-benzoimidazole; 7-Methyl-2-{3-[4-(1-methyl-piperidin-4-yl)-butoxy]-phenyl}-1H-benzoimidazole; 6,7-Dimethyl-2-{3-[4-(1-methyl-pipericlin-4-yl)-butoxy]-phenyl}-1H-benzoimidazole; (5-Chloro-1H-indol-2-yl)-(4-methyl-piperazin-1-yl)-methanone; (5-Fluoro-1H-indol-2-yl)-(4-methyl-piperazin-1-yl)-methanone; (5-Bromo-1H-indol-2-yl)-(4-methyl-piperazin-1-yl)-methanone; (1H-indol-2-yl)-(4-methyl-piperazin-1-yl)-methanone; (5-Benzyloxy-1H-indol-2-yl)-(4-methyl-piperazin-1-yl)-methanone; (5-Methyl-1H-indol-2-yl)-(4-methyl-piperazin-1-yl)-methanone; (5,6-Dimethoxy-1H-indol-2-yl)-(4-methyl-piperazin-1-yl)-methanone; (4-Methyl-piperazin-1-yl)-(7-nitro-1H-indol-2-yl)-methanone; (4-Methyl-piperazin-1-yl)-(5-nitro-3-phenyl-1H-indol-2-yl)-methanone; (4-Methyl-piperazin-1-yl)-(5-trifluoromethoxy-1H-indol-2-yl)-methanone; (6-Chloro-1H-indol-2-yl)-(4-methyl-piperazin-1-yl)-methanone; (5,7-Difluoro-1H-indol-2-yl)-(4-methyl-piperazin-1-yl)-methanone; (6-Fluoro-1H-indol-2-yl)-(4-methyl-piperazin-1-yl)-methanone; (4,6-Dichloro-1H-indol-2-yl)-(4-methyl-piperazin-1-yl)-methanone; (1H-indol-2-yl)-(4-octyl-piperazin-1-yl)-methanone; (4-Ethyl-piperazin-1-yl)-(1H-indol-2-yl)-methanone; (1H-indol-2-yl)-(4-isopropyl-piperazin-1-yl)-methanone; [4-(3-Dimethylamino-propyl)-piperazin-1-yl]-(1H-indol-2-yl)-methanone; (4-Butyl-piperazin-1-yl)-(1H-indol-2-yl)-methanone; (4-Cyclopentyl-piperazin-1-yl)-(1H-indol-2-yl)-methanone; (1H-indol-2-yl)-(4-phenethyl-piperazin-1-yl)-methanone; (1H-indol-2-yl)-[4-(2-piperidin-1-yl-ethyl)-piperazin-1-yl]-methanone; [4-(2-Ethoxy-ethyl)-piperazin-1-yl]-(1H-indol-2-yl)-methanone; (4-sec-Butyl-piperazin-1-yl)-(1H-indol-2-yl)-methanone; [4-(1-Ethyl-propyl)-piperazin-1-yl]-(1H-indol-2-yl)-methanone; (1H-indol-2-yl)-[4-(3-phenyl-propyl)-piperazin-1-yl]-methanone; (1H-indol-2-yl)-[4-(1-methyl-piperidin-4-yl)-piperazin-1-yl]-methanone; [4-(2-Dipropylamino-ethyl)-piperazin-1-yl]-1H-indol-2-yl)-methanone; (1H-indol-2-yl)-[4-(3-phenyl-allyl)-piperazin-1-yl]-methanone; (1H-indol-2-yl)-(4-pentyl-piperazin-1-yl)-methanone; (4-Heptyl-piperazin-1-yl)-(1H-indol-2-yl)-methanone; [4-(2-Diethylamino-ethyl)-piperazin-1-yl]-(1H-indol-2-yl)-methanone; (1H-indol-2-yl)-[4-(4-methoxy-butyl)-pyperazin-1-yl]-methanone; 5-Chloro-7-methyl-2-{3-[4-(1-methyl-piperidin-4-yl)-butoxy]-phenyl}-1H-benzoimidazole; 5,7-Dimethyl-2-{2-methyl-3-[4-(1-methyl-piperidin-4-yl)-butoxy]-phenyl}-1H-benzoimidazole; 5-Chloro-7-methyl-2-{2-methyl-3-[4-(1-methyl-piperidin-4-yl)-butoxy]-phenyl}-1H-benzoimidazole; 6-Fluoro-7-methyl-2-{2-methyl-3-[4-(1-methyl-piperidin-4-yl)-butoxy]-phenyl}-1H-benzoimidazole; 6-Fluoro-7-methyl-2-{3-[3-(1-methyl-piperidin-4-yloxy)-propoxy]-phenyl}-1H-benzoimidazole; {2-(5-Fluoro-4-methyl-1H-benzoimidazol-2-yl)-5-[3-(1-methyl-piperidin-4-yl)-propoxy]-phenyl}-methanol; 6-Chloro-4-methyl-2-{6-[3-(4-methyl-piperazin-1-yl)- propoxy]-pyridin-3-yl}-1H-benzoimidazole; 4-Methyl-2-{6-[3-(4-methyl-piperazin-1-yl)-propoxy]-pyridin-3-yl}-1H-benzoimidazole; 5-Fluoro-4-methyl-2-{6-[3-(4-methyl-piperazin-1-yl)-propoxy]-pyridin-3-yl}-1H-benzoimidazole; 4-Methyl-2-{6-[3-(1-methyl-piperidin-4-yl)-propoxy]-pyridin-3-yl}-1H-benzoimidazole; 4,5-Dimethyl-2-{6-[3-(1-methyl-piperidin-4-yl)-propoxy]-pyridin-3-yl}-1H-benzoimidazole; 4-Chloro-2-{6-[3-(1-methyl-piperidin-4-yl)-propoxy]-pyridin-3-yl}-1H-benzoimidazole; 5-Fluoro-4-methyl-2-{4-methyl-6-[3-(1-methyl-piperidin-4-yl)-propoxy]-pyridin-3-yl}-1H-benzoimidazole; 4,5-Dimethyl-2-{4-methyl-6-[3-(1-methyl-piperidin-4-yl)-propoxy]-pyridin-3-yl}-1H-benzoimidazole; 4,6-Dimethyl-2-{4-methyl-6-[3-(1-methyl-piperidin-4-yl)-propoxy]-pyridin-3-yl}-1H-benzoimidazole; 4-Chloro-2-{4-methyl-6-[3-(1-methyl-piperidin-4-yl)-propoxy]-pyridin-3-yl}-1H-benzoimidazole; 2-{4-Chloro-6-[3-(1-methyl-piperidin-4-yl)-propoxy]-pyridin-3-yl}-5-fluoro-4-methyl-1H-benzoimidazole; 2-{4-Chloro-6-[3-(1-methyl-piperidin-4-yl)-propoxy]-pyridin-3-yl}-4-methyl-1H-benzoimidazole; 6-Chloro-2-{4-chloro-6-[3-(1-methyl-piperidin-4-yl)-propoxy]-pyridin-3-yl}-4-methyl-1H-benzoimidazole; 2-{4-Chloro-6-[3-(1-methyl-piperidin-4-yl)-propoxy]-pyridin-3-yl}-4,6-dimethyl-1H-benzoimidazole; 2-{4-Methoxy-6-[3-(1-methyl-piperidin-4-yl)-propoxy]-pyridin-3-yl}-4-methyl-1H-benzoimidazole; 5-Fluoro-2-{4-methoxy-6-[3-(1-methyl-piperidin-4-yl)-propoxy]-pyridin-3-yl}-4-methyl-1H-benzoimidazole; 5-Fluoro-4-methyl-2-{6-[3-(1-methyl-1,2,3,6-tetrahydro-pyridin-4-yl)-propoxy]-pyridin-3-yl}-1H-benzoimidazole; 4-Methyl-2-{6-[3-(1-methyl-1,2,3,6-tetrahydro-pyridin-4-yl)-propoxy]-pyridin-3-yl}-1H-benzoimidazole; 6-Chloro-4-methyl-2-{6-[3-(1-methyl-1,2,3,6-tetrahydro-pyridin-4-yl)-propoxy]-pyridin-3-yl}-1H-benzoimidazole; 4,5-Dimethyl-2-{6-[3-(1-methyl-1,2,3,6-tetrahydro-pyridin-4-yl)-propoxy]-pyridin-3-yl}-1H-benzoimidazole; 4,6-Dimethyl-2-{6-[3-(1-methyl-1,2,3,6-tetrahydro-pyridin-4-yl)-propoxy]-pyridin-3-yl}-1H-benzoimidazole; 5-Chloro-4-methyl-2-{6-[3-(1-methyl-1,2,3,6-tetrahydro-pyridin-4-yl)-propoxy]-pyridin-3-yl}-1H-benzoimidazole; 5-Fluoro-4-methyl-2-{6-[3-(1-methyl-piperidin-4-yl)-propoxy]-4-pyrrolidin-1-ylmethyl-pyridin-3-yl}-1H-benzoimidazole; 2-{5-Bromo-2-[4-(1-methyl-piperidin-4-yl)-butoxy]-pyridin-4-yl}-4-methyl-1H-benzoimidazole; 2-{5-Bromo-2-[4-(1-methyl-piperidin-4-yl)-butoxy]-pyridin-4-yl}-5-fluoro-4-methyl-1H-benzoimidazole; 2-{5-Bromo-2-[4-(1-methyl-piperidin-4-yl)-butoxy]-pyridin-4-yl}-6-chloro-4-methyl-1H-benzoimidazole; 2-{5-Bromo-2-[4-(1-methyl-piperidin-4-yl)-butoxy]-pyridin-4-yl}-4,6-dimethyl-1H-benzoimidazole; 2-{5-Bromo-2-[4-(1-methyl-piperidin-4-yl)-butoxy]-pyridin-4-yl}-4,5-dimethyl-1H-benzoimidazole; 2-{5-Bromo-2-[4-(1-methyl-piperidin-4-yl)-butoxy]-pyridin-4-yl}-5-chloro-4-methyl-1H-benzoimidazole; 2-{5-Bromo-2-[4-(1-methyl-piperidin-4-yl)-butoxy]-pyridin-4-yl}-5-tert-butyl-1H-benzoimidazole; 5-tert-Butyl-2-{2-[4-(1-methyl-piperidin-4-yl)-butoxy]-pyridin-4-yl}-1H-benzoimidazole; 2-{5-Chloro-2-[4-(1-methyl-piperidin-4-yl)-butoxy]-pyridin-4-yl}-5-fluoro-4-methyl-1H-benzoimidazole; 2-{5-Chloro-2-[4-(1-methyl-piperidin-4-yl)-butoxy]-pyridin-4-yl}-4,5-dimethyl-1H-benzoimidazole; 4,6-Dimethyl-2-{2-[4-(4-methyl-piperazin-1-yl)-butoxy]-pyridin-4-yl}-1H-benzoimidazole; 4-Methyl-2-{2-[4-(4-methyl-piperazin-1-yl)-butoxy]-pyridin-4-yl}-1H-benzoimidazole; 4,5-Dimethyl-2-{2-[4-(4-methyl-piperazin-1-yl)-butoxy]-pyridin-4-yl}-1H-benzoimidazole; 5-Fluoro-4-methyl-2-{2-[4-(4-methyl-piperazin-1-yl)-butoxy]-pyridin-4-yl}-1H-benzoimidazole; 6-Chloro-4-methyl-2-{2-[4-(4-methyl-piperazin-1-yl)-butoxy]-pyridin-4-yl}-1H-benzoimidazole; 5-Fluoro-4-methyl-2-{2-[4-(4-methyl-[1,4]diazepan-1-yl)-butoxy]-pyridin-4-yl}-1H-benzoimidazole; 4,5-Dimethyl-2-{2-[4-(4-methyl-[1,4]diazepan-1-yl)-butoxy]-pyridin-4-yl}-1H-benzoimidazole; 4,6-Dimethyl-2-{2-[4-(1-methyl-piperidin-4-yl)-butoxy]-pyridin-4-yl}-1H-benzoimidazole; 4-Methyl-2-{2-[4-(1-methyl-piperidin-4-yl)-butoxy]-pyridin-4-yl}-1H-benzoimidazole; 5-Fluoro-4-methyl-2-{2-[4-(1-methyl-piperidin-4-yl)-butoxy]-pyridin-4-yl}-1H-benzoimidazole; 4-Chloro-2-{2-[4-(1-methyl-piperidin-4-yl)-butoxy]-pyridin-4-yl}-1H-benzoimidazole; 4,5-Dimethyl-2-{2-[4-(1-methyl-piperidin-4-yl)-butoxy]-pyridin-4-yl}-1H-benzoimidazole; 6-Chloro-4-methyl-2-{2-[4-(1-methyl-piperidin-4-yl)-butoxy]-pyridin-4-yl}-1H-benzoimidazole; 5-tert-Butyl-2-[2-(4-piperidin-4-yl-butoxy)-pyridin-4-yl]-1H-benzoimidazole; 4,6-Dimethyl-2-[2-(4-piperidin-4-yl-butoxy)-pyridin-4-yl]-1H-benzoimidazole; 2-{2-[4-(1-Ethyl-piperidin-4-yl)-butoxy]-pyridin-4-yl}-4,5-dimethyl-1H-benzoimidazole; 4,6-Dimethyl-2-{3-methyl-2-[4-(1-methyl-piperidin-4-yl)-butoxy]-pyridin-4-yl}-1H-benzoimidazole; 4-Methyl-2-{3-methyl-2-[4-(1-methyl-piperidin-4-yl)-butoxy]-pyridin-4-yl}-1H-benzoimidazole; 6-Chloro-4-methyl-2-{3-methyl-2-[4-(1-methyl-piperidin-4-yl)-butoxy]-pyridin-4-yl}-1H-benzoimidazole; 2-{3-Chloro-2-[4-(1-methyl-piperidin-4-yl)-butoxy]-pyridin-4-yl}-4-methyl-1H-benzoimidazole; 2-{3-Chloro-2-[4-(1-methyl-piperidin-4-yl)-butoxy]-pyridin-4-yl}-4,5-dimethyl-1H-benzoimidazole; 4-Chloro-2-{3-chloro-2-[4-(1-methyl-piperidin-4-yl)-butoxy]-pyridin-4-yl}-1H-benzoimidazole; 2-{3-Chloro-2-[4-(1-methyl-piperidin-4-yl)-butoxy]-pyridin-4-yl}-5-fluoro-4-methyl-1H-benzoimidazole; 2-{3-Chloro-2-[4-(1-methyl-piperidin-4-yl)-butoxy]-pyridin-4-yl}-4,6-dimethyl-1H-benzoimidazole; 6-Chloro-2-{3-chloro-2-[4-(1-methyl-piperidin-4-yl)-butoxy]-pyridin-4-yl}-4-methyl-1H-benzoimidazole; 5-Fluoro-4-methyl-2-{5-methyl-2-[4-(1-methyl-piperidin-4-yl)-butoxy]-pyridin-4-yl}-1H-benzoimidazole; 5-Chloro-6-fluoro-2-{5-methyl-2-[4-(1-methyl-piperidin-4-yl)-butoxy]-pyridin-4-yl}-1H-benzoimidazole; 5-tert-Butyl-2-{5-methyl-2-[4-(1-methyl-piperidin-4-yl)-butoxy]-pyridin-4-yl}-1H-benzoimidazole; 4,5-Dimethyl-2-{5-methyl-2-[4-(1-methyl-piperidin-4-yl)-butoxy]-pyridin-4-yl}-1H-benzoimidazole; 2-{5-Chloro-2-[4-(1-methyl-piperidin-4-yl)-butoxy]-pyridin-4-yl}-4,6-dimethyl-1H-benzoimidazole; 5-tert-Butyl-2-{5-chloro-2-[4-(1-methyl-piperidin-4-yl)-butoxy]-pyridin-4-yl}-1H-benzoimidazole; 2-{5-Bromo-2-[4-(1-methyl-piperidin-4-yl)-butoxy]-pyridin-4-yl}-4-chloro-1H-benzoimidazole; 2-{5-Bromo-2-[4-(1-methyl-piperidin-4-yl)-butoxy]-pyridin-4-yl}-5-chloro-6-fluoro-1H-benzoimidazole; 2-{5-Bromo-2-[4-(1-methyl-piperidin-4-yl)-butoxy]-pyridin-4-yl}-5-chloro-1H-benzoimidazole; 1-(3-{4-[4,5-Bis-(4-bromo-phenyl)-1H-imidazol-2-yl]-3-chloro-phenoxy}-propyl)-4-methyl-piperazine; 1-{3-[3-Chloro-4-(4,5-diphenyl-1H-imidazol-2-yl)-phenoxy]-propyl}-4-methyl-piperazine; 1-(3-{4-[4,5-Bis-(4-methoxy-phenyl)-1H-imidazol-2-yl]-3-chloro-phenoxy}-propyl)-4-methyl-piperazine; 1-{3-[3-Chloro-4-(4,5-di-p-tolyl-1H-imidazol-2-yl)-phenoxy]-propyl}-4-methyl-piperazine; 1-(3-{4-[4,5-Bis-(3-methoxy-phenyl)-1H-imidazol-2-yl]-3-chloro-phenoxy}-propyl)-4-methyl-piperazine; 1-(3-{4-[4,5-Bis-(3-methoxy-phenyl)-1H-imidazol-2-yl]-2-fluoro-phenoxy}-propyl)-4-methyl-piperazine; 1-(3-{4-[4,5-Bis-(4-bromo-phenyl)-1H-imidazol-2-yl]-3-chloro-phenoxy}-propyl)-4-methyl-[1,4]diazepane; 1-(3-{4-[4,5-Bis-(3-methoxy-phenyl)-1H-imidazol-2-yl]-3-chloro-phenoxy}-propyl)-4- methyl-[1,4]diazepane; 2-{3-Chloro-4-[3-(4-methyl-[1,4]diazepan-1-yl)-propoxy]-phenyl}-4,5,6,7-tetrahydro-1H-benzoimidazole; 2-{2-Chloro-4-[3-(4-methyl-[1,4]diazepan-1-yl)-propoxy]-phenyl}-4,5,6,7-tetrahydro-1H-benzoimidazole; 1-Methyl-4-{3-[3-methyl-4-(4-phenyl-5-trifluoromethyl-1H-imidazol-2-yl)-phenoxy]-propyl}-piperidine; 4-{3-[3-Chloro-4-(4-phenyl-5-trifluoromethyl-1H-imidazol-2-yl)-phenoxy]-propyl}-1-methyl-piperidine; 4-(3-{3-Chloro-4-[5-methyl-4-(3-trifluoromethyl-phenyl)-1H-imidazol-2-yl]-phenoxy}-propyl)-1-methyl-piperidine; 4-(3-{3-Chloro-4-[4-(3,5-dichloro-phenyl)-5-methyl-1H-imidazol-2-yl]-phenoxy}-propyl)-1-methyl-piperidine; 4-(3-{4-[4-(3,5-Dichloro-phenyl)-5-methyl-1H-imidazol-2-yl]-3-methyl-phenoxy}-propyl)-1-methyl-piperidine; 4-(3-{3-Chloro-4-[4-(4-chloro-phenyl)-5-methyl-1H-imidazol-2-yl]-phenoxy}-propyl)-1-methyl-piperidine; 4-(3-{4-[4,5-Bis-(4-fluoro-phenyl)-1H-imidazol-2-yl]-3-chloro-phenoxy}-propyl)-1-methyl-piperidine; 4-(3-{4-[4,5-Bis-(3-methoxy-phenyl)-1H-imidazol-2-yl]-3-chloro-phenoxy}-propyl)-1-methyl-piperidine; 4-(3-{3-Chloro-4-[4-(4-chloro-phenyl)-5-p-tolyl-1H-imidazol-2-yl]-phenoxy}-propyl)-1-methyl-piperidine; 2-{2-Chloro-4-[3-(1-methyl-piperidin-4-yl)-propoxy]-phenyl}-4,5,6,7-tetrahydro-1H-benzoimidazole; 4-{3-[3-Chloro-4-(4-methyl-5-propyl-1H-imidazol-2-yl)-phenoxy]-propyl}-1-methyl-piperidine; 4-{3-[3-Chloro-4-(5-ethyl-4-methyl-1H-imidazol-2-yl)-phenoxy]-propyl}-1-methylpiperidine; 1-Methyl-4-(2-{3-methyl-4-[5-methyl-4-(3-trifluoromethyl-phenyl)-1H-imidazol-2-yl]-phenoxy}-ethoxy)-piperidine; 5-[4-(4-Chloro-phenyl)-5-methyl-1H-imidazol-2-yl]-2-[3-(1-methyl-piperidin-4-yl)-propoxy]-pyridine; 2-[3-(1-Methyl-piperidin-4-yl)-propoxy]-5-[5-methyl-4-(3-trifluoromethyl-phenyl)-1H-imidazol-2-yl]-pyridine; 2-[3-(1-Methyl-piperidin-4-yl)-propoxy]-5-[5-methyl-4-(4-trifluoromethyl-phenyl)-1H-imidazol-2-yl]-pyridine; 2-[3-(1-Methyl-piperidin-4-yl)-propoxy]-5-(4-phenyl-5-trifluoromethyl-1H-imidazol-2-yl)-pyridine; 1-Methyl-4-(3-{5-[5-methyl-4-(4-trifluoromethyl-phenyl)-1H-imidazol-2-yl]-pyridin-2-yloxy}-propyl)-piperazine; 1-Methyl-4-(3-{5-[5-methyl-4-(3-trifluoromethyl-phenyl)-1H-imidazol-2-yl]-pyridin-2-yloxy}-propyl)-piperazine; 4-(4-{3-[4-(4-Chloro-phenyl)-5-methyl-1H-imidazol-2-yl]-phenoxy}-butyl)-1-methyl-piperidine; 1-Methyl-4-{4-[3-(4-phenyl-5-trifluoromethyl-1H-imidazol-2-yl)-phenoxy]-butyl}-piperidine; 2-[4-(1-Methyl-piperidin-4-yl)-butoxy]-4-(4-phenyl-5-trifluoromethyl-1H-imidazol-2-yl)-pyridine; 2-[4-(1-Methyl-piperidin-4-yl)-butoxy]-4-[5-methyl-4-(3-trifluoromethyl-phenyl)-1H-imidazol-2-yl]-pyridine; 4-{3-[4-(5-isobutyl-4-methyl-1H-imidazol-2-yl)-3-methyl-phenoxy]-propyl}-1-methyl-piperidine; 4-[4-(4-Chloro-phenyl)-5-methyl-1H-imidazol-2-yl]-2-[4-(1-methyl-piperidin-4-yl)-butoxy]-pyridine; 4-{3-[3-Chloro-4-(5-isobutyl-4-methyl-1H-imidazol-2-yl)-phenoxy]-propyl}-1-methyl-piperidine; 1-Methyl-4-(4-{3-[5-methyl-4-(4-trifluoromethyl-phenyl)-1H-imidazol-2-yl]-phenoxy}-butyl)-piperidine; 1-{3-[2-Chloro-4-(1H-imidazol-2-yl)-phenoxy]-propyl}-4-methyl-piperazine; 1-{3-[3-Chloro-4-(4,5-dimethyl-1H-imidazol-2-yl)-phenoxy]-propyl}-4-methyl-piperazine; 1-{3-[3-Chloro-4-(4-phenyl-5-trifluoromethyl-1H-imidazol-2-yl)-phenoxy]-propyl}-4-methyl-piperazine; 1-{3-[2-Chloro-4-(4-phenyl-5-trifluoromethyl-1H-imidazol-2-yl)-phenoxy]-propyl}-4-methyl-[1,4]diazepane; 1-Methyl-4-(3-{3-methyl-4-[5-methyl-4-(3-tri1luoromethyl-phenyl)-1H-imidazol-2-yl]-phenoxy}-propyl)-piperidine; 4-(3-{4-[4-(4-Chloro-phenyl)-5-methyl-1H-imidazol-2-yl]-3-methyl-phenoxy}-propyl)-1-methyl-piperidine; 4-(2-{4-[4-(4-Chloro-phenyl)-5-methyl-1H-imidazol-2-yl]-3-methyl-phenoxy}-ethoxy)-1-methyl-piperidine; 1-(3-{4-[4-(4-Chloro-phenyl)-5-methyl-1H-imidazol-2-yl]-3-methyl-phenoxy}-2-methyl-propyl)-4-methyl-piperazine; 2-[4-(4-Chloro-phenyl)-5-methyl-1H-imidazol-2-yl]-6-[4-(1-methyl-piperidin-4-yl)-butoxy]-pyridine; 4-Methyl-2-[3-(1-methyl-piperidin-4-yl)-propoxy]-5-[5-methyl-4-(3-trifluoromethyl-phenyl)-1H-imidazol-2-yl]-pyridine; 5-Bromo-4-[4-(4-chloro-phenyl)-5-methyl-1H-imidazol-2-yl]-2-[4-(1-methyl-piperidin-4-yl)-butoxy]-pyridine; 2,4-Dimethyl-1-{3-[4-(4-phenyl-5-trifluoromethyl-1H-imidazol-2-yl)-phenoxy]-propyl}-piperazine; 1,2-Dimethyl-4-{3-[4-(4-phenyl-5-trifluoromethyl-1H-imidazol-2-yl)-phenoxy]-propyl}-piperazine; 3-Chloro-2-[4-(1-methyl-piperidin-4-yl)-butoxy]-4-(4-phenyl-5-trifluoromethyl-1H-imidazol-2-yl)-pyridine; 1-Methyl-4-(4-{4-[5-methyl-4-(3-trifluoromethyl-phenyl)-1H-imidazol-2-yl]-pyridin-2-yloxy}-butyl)-[1,4]diazepane; 5-Bromo-2-[4-(1-methyl-piperidin-4-yl)-butoxy]-4-[5-methyl-4-(3-trifluoromethyl-phenyl)-1H-imidazol-2-yl]-pyridine; 4-[4-(4-Chloro-phenyl)-5-trifluoromethyl-1H-imidazol-2-yl]-2-[4-(1-methyl-piperidin-4-yl)-butoxy]-pyrimidine; 4-(3-{4-[5-Cyclopropylmethyl-4-(3-trifluoromethyl-phenyl)-1H-imidazol-2-yl]-3-methyl-phenoxy}~propyl)-1-methyl-piperidine; 1-{4-[4-(4-Chloro-phenyl)-5-methyl-1H-imidazol-2-yl]-3-methyl-phenoxy}-3-(4-methyl-piperazin-1-yl)-propan-2-ol; 4-(3-{3-Chloro-4-[4-(4-chloro-phenyl)-5-methyl-1H-imidazol-2-yl]-phenoxy}-propyl)-piperidine; 4-(3-{3-Chloro-4-[4-(4-chloro-phenyl)-5-methyl-1H-imidazol-2-yl]-phenoxy}-propyl)-1-ethyl-piperidine; 4-(3-{3-Chloro-4-[4-(4-chloro-phenyl)-5-methyl-1H-imidazol-2-yl]-phenoxy}-propyl)-1-isopropyl-piperidine; 1-Methyl-4-{3-[4-(4-phenyl-5-trifluoromethyl-1H-imidazol-2-yl)-naphthalen-1-yloxy]-propyl}-piperidine; 1-(4-Methyl-piperazin-1-yl)-3-{5-[5-methyl-4-(4-trifluoromethyl-phenyl)-1H-imidazol-2-yl]-pyridin-2-yloxy}-propan-1-one; 6-[4-(4-Chloro-phenyl)-5-methyl-1H-imidazol-2-yl]-3-fluoro-2-[4-(1-methyl-piperidin-4-yl)-butoxy]-pyridine; 1-Methyl-4-(4-{3-methyl-6-[5-methyl-4-(3-trifluoromethyl-phenyl)-1H-imidazol-2-yl]-pyridin-2-yloxy}-butyl)-piperazine; 1-Methyl-4-{3-[4-(5-methyl-4-thiophen-2-yl-1H-imidazol-2-yl)-phenoxy]-propyl}-piperidine; 2-{3-[4-(1-Methyl-piperidin-4-yl)-butoxy]-phenyl}-3H-imidazo[4,5-b]pyridine; (5-Chloro-1H-indol-2-yl)-(4-methyl-piperazin-1-yl)-methanone; (5-Fluoro-1H-indol-2-yl)-(4-methyl-piperazin-1-yl)-methanone; (5-Bromo-1H-indol-2-yl)-(4-methyl-piperazin-1-yl)-methanone; (5-Methyl-1H-indol-2-yl)-(4-methyl-piperazin-1-yl)-methanone; (5,7-Difluoro-1H-indol-2-yl)-(4-methyl-piperazin-1-yl)-methanone; (7-Chloro-1H-indol-2-yl)-(4-methyl-piperazin-1-yl)-methanone; (5,7-Dichloro-1H-indol-2-yl)-(4-methyl-piperazin-1-yl)-methanone; (3,5-Dichloro-1H-indol-2-yl)-(4-methyl-piperazin-1-yl)-methanone; (6-Chloro-1H-indol-2-yl)-(4-methyl-piperazin-1-yl)-methanone; (1H-indol-2-yl)-(3-methyl-piperazin-1-yl)-methanone; (7-Bromo-1H-indol-2-yl)-(4-methyl-piperazin-1-yl)-methanone; (5-Bromo-benzofuran-2-yl)-(4-methyl-piperazin-1-yl)-methanone; (1H-indol-2-yl)-(4-methyl-piperazin-1-yl)-methanethione; [5-(5-Fluoro-4-methyl-1H-benzoimidazol-2-yl)-4-methyl-pyrimidin-2-yl]-[3-(1-methyl-piperidin-4-yl)-propyl]-amine; and [5-(4,6-Dimethyl-1H-benzoimidazol-2-yl)-4-methyl-pyrimidin-2-yl]-[3-(1-methyl-piperidin-4-yl)-propyl]-amine and pharmaceutically acceptable salts thereof.

In another embodiment, selective Histamine H4 antagonists are selected from those described in the international Patent Application WO2009/079001: 5-Fluoro-4-methyl-2-

{4-methyl-1-[3-(1-methyl-piperidin-4-yl)-propyl]-2,3-dihydro-1H-indol-5-yl}-1H-benzoimidazole; 4,5-Dimethyl-2-{4-methyl-1-[3-(1-methyl-piperidin-4-yl)-propyl]-2,3-dihydro-1H-indol-5-yl}-1H-benzoimidazole; 2-{4-Chloro-1-[3-(1-methyl-piperidin-4-yl)-propyl]-2,3-dihydro-1H-indol-5-yl}-4,6-dimethyl-1H-benzoimidazole; 2-{4-Chloro-1-[3-(1-methyl-piperidin-4-yl)-propyl]-2,3-dihydro-1H-indol-5-yl}-5-fluoro-4-methyl-1H-benzoimidazole; 2-{4-Chloro-1-[3-(1-methyl-piperidin-4-yl)-propyl]-2,3-dihydro-1H-indol-5-yl}-1H-benzoimidazole-5-carboxylic acid methyl ester; 5-Fluoro-2-{4-fluoro-1-[3-(1-methyl-piperidin-4-yl)-propyl]-2,3-dihydro-1H-indol-5-yl}-4-methyl-1H-benzoimidazole; 5-Fluoro-4-methyl-2-{4-methyl-1-[3-(1-methyl-piperidin-4-yl)-propyl]-1H-indol-5-yl}-1H-benzoimidazole; 2-{4-Chloro-1-[3-(1-methyl-piperidin-4-yl)-propyl]-1H-indol-5-yl}-5-fluoro-4-methyl-1H-benzoimidazole; 2-{4-Chloro-1-[3-(1-methyl-piperidin-4-yl)-propyl]-1H-indol-5-yl}-4,6-dimethyl-1H-benzoimidazole; 5-Chloro-2-{4-methyl-1-[3-(1-methyl-piperidin-4-yl)-propyl]-1H-indol-5-yl}-1H-benzoimidazole; 5-Fluoro-4-methyl-2-{1-[3-(1-methyl-piperidin-4-yl)-propyl]-1H-indol-5-yl}-1H-benzoimidazole; 4-Methyl-2-{1-[3-(1-methyl-piperidin-4-yl)-propyl]-1H-indol-5-yl}-1H-benzoimidazole; 5-Fluoro-4-methyl-2-{1-[3-(4-methyl-piperazin-1-yl)-propyl]-1H-indol-5-yl}-1H-benzoimidazole; 2-{2,3-Dimethyl-1-[3-(1-methyl-piperidin-4-yl)-propyl]-1H-indol-5-yl}-4,6-dimethyl-1H-benzoimidazole; 2-{2,3-Dimethyl-1-[3-(1-methyl-piperidin-4-yl)-propyl]-1H-indol-5-yl}-5-fluoro-4-methyl-1H-benzoimidazole; 5-Fluoro-4-methyl-2-{1-[4-(1-methyl-piperidin-4-yl)-butyl]-1H-indol-4-yl}-1H-benzoimidazole; 4-Chloro-2-{1-[4-(1-methyl-piperidin-4-yl)-butyl]-1H-indol-4-yl}-1H-benzoimidazole; 2-{1-[4-(1-Methyl-piperidin-4-yl)-butyl]-1H-indol-4-yl}-5-trifluoromethyl-1H-benzoimidazole; 6-{1-[4-(1-Methyl-piperidin-4-yl)-butyl]-1H-indol-4-yl}-5H-[1,3]dioxolo[4',5':4,5]benzo[1,2-d]-imidazole; (2-{1-[4-(1-Methyl-piperidin-4-yl)-butyl]-1H-indol-4-yl}-1H-benzoimidazol-5-yl)-phenyl-methanone; 2-{1-[4-(1-Methyl-piperidin-4-yl)-butyl]-1H-indol-4-yl}-1H-naphtho[2,3-d]imidazole; 6-Chloro-4-methyl-2-{1-[4-(1-methyl-piperidin-4-yl)-butyl]-1H-indol-4-yl}-1H-benzoimidazole; 4-Methyl-2-{1-[4-(1-methyl-piperidin-4-yl)-butyl]-1H-indol-4-yl}-1H-benzoimidazole; 5-tert-Butyl-2-{1-[4-(1-methyl-piperidin-4-yl)-butyl]-1H-indol-4-yl}-1H-benzoimidazole; 4,6-Dimethyl-2-{1-[4-(1-methyl-piperidin-4-yl)-butyl]-1H-indol-6-yl}-1H-benzoimidazole; 5-Fluoro-4-methyl-2-{1-[4-(1-methyl-piperidin-4-yl)-butyl]-1H-indol-6-yl}-1H-benzoimidazole; 4-Methyl-2-{1-[4-(1-methyl-piperidin-4-yl)-butyl]-1H-indol-6-yl}-1H-benzoimidazole; 5-tert-Butyl-2-{3-chloro-1-[3-(1-methyl-piperidin-4-yl)-propyl]-1H-indol-5-yl}-1H-benzoimidazole; 6-Chloro-2-{3-chloro-1-[3-(1-methyl-piperidin-4-yl)-propyl]-1H-indol-5-yl}-4-methyl-1H-benzoimidazole; 2-{3-Chloro-1-[4-(1-methyl-piperidin-4-yl)-butyl]-1H-indol-4-yl}-5-trifluoromethyl-1H-benzoimidazole; 2-{3-Chloro-1-[4-(1-methyl-piperidin-4-yl)-butyl]-1H-indol-4-yl}-5-fluoro-4-methyl-1H-benzoimidazole; 2-{3-Chloro-1-[4-(1-methyl-piperidin-4-yl)-butyl]-1H-indol-4-yl}-5,6-difluoro-1H-benzoimidazole; 5-Fluoro-4-methyl-2-[1-(3-piperazin-1-yl-propyl)-1H-indol-5-yl]-1H-benzoimidazole; 5-tert-Butyl-2-[3-chloro-1-(3-piperidin-4-yl-propyl)-1H-indol-5-yl]-1H-benzoimidazole; 5-Fluoro-4-methyl-2-[1-(4-piperidin-4-yl-butyl)-1H-indol-4-yl]-1H-benzoimidazole; 4-Chloro-2-[1-(4-piperidin-4-yl-butyl)-1H-indol-4-yl]-1H-benzoimidazole; 4,6-Dimethyl-2-[1-(4-piperidin-4-yl-butyl)-1H-indol-6-yl]-1H-benzoimidazole; 5-Fluoro-4-methyl-2-[1-(4-piperidin-4-yl-butyl)-1H-indol-6-yl]-1H-benzoimidazole; [5-(5-ten-Butyl-1H-benzoimidazol-2-yl)-1-(4-piperidin-4-yl-butyl)-1H-indol-3-ylmethyl]-dimethyl-amine; 5-Fluoro-4-methyl-1'-[3-(1-methyl-piperidin-4-yl)-propyl]-1H,1'H-[2,5']bibenzoimidazolyl; 5-Fluoro-4-methyl-3'-[3-(1-methyl-piperidin-4-yl)-propyl]-1H,3'H-[2,5']bibenzoimidazolyl; 4-Methyl-1'-[4-(1-methyl-piperidin-4-yl)-butyl]-1H,1'H-[2,5']bibenzoimidazolyl; 4-Methyl-31-[4-(1-methyl-piperidin-4-yl)-butyl]-1H,3'H-[2,5']bibenzoimidazolyl; 5-Fluoro-4-methyl-1'-[4-(1-methyl-piperidin-4-yl)-butyl]-1H,1'H-[2,5']bibenzoimidazolyl; 5-Fluoro-4-methyl-3'-[4-(1-methyl-piperidin-4-yl)-butyl]-1H,3'H-[2,5']bibenzoimidazolyl; 5-Fluoro-4-methyl-2-{1-[3-(1-methyl-piperidin-4-yl)-propyl]-1H-pyrrolo[2,3-b]pyridin-5-yl}-1H-benzoimidazole; 4,5-Dimethyl-2-{1-[3-(1-methyl-piperidin-4-yl)-propyl]-1H-pyrrolo[2,3-b]pyridin-5-yl}-1H-benzoimidazole; 2-{6-Chloro-1-[3-(1-methyl-piperidin-4-yl)-propyl]-1H-indol-5-yl}-4,6-difluoro-1H-benzoimidazole; 2-[6-Chloro-1-(3-piperidin-4-yl-propyl)-1H-indol-5-yl]-5-fluoro-4-methyl-1H-benzoimidazole; 2-{6-Chloro-1-[3-(1-methyl-piperidin-4-yl)-propyl]-1H-indol-5-yl}-5-fluoro-4-methyl-1H-benzoimidazole; 5-Fluoro-4,4'-dimethyl-1'-[3-(1-methyl-piperidin-4-yl)-propyl]-1H,1'H-[2,5']bibenzoimidazolyl; 5,4'-Trimethyl-1'[3-(1-methyl-piperidin-4-yl)-propyl]-1H,1'H-[2,5']bibenzoimidazolyl; 4,4'-Dimethyl-1'-[3-(1-methyl-piperidin-4-yl)-propyl]-1H,1'H-[2,5']bibenzoimidazolyl; 5-Chloro-4,4'-dimethyl-1'-[3-(1-methyl-piperidin-4-yl)-propyl]-1H,1'H-[2,5']bibenzoimidazolyl; 6-Fluoro-4,4'-dimethyl-1'-[3-(1-methyl-piperidin-4-yl)-propyl]-1H,1'H-[2,5']bibenzoimidazolyl; 4,5-Dimethyl-2-[1-(3-piperidin-4-yl-propyl)-2,3-dihydro-1H-indol-5-yl]-1H-benzoimidazole; 4,6-Dimethyl-2-{4-methyl-1-[3-(1-methyl-piperidin-4-yl)-propyl]-2,3-dihydro-1H-indol-5-yl}-1H-benzoimidazole; 5-Chloro-2-{4-methyl-1-[3-(1-methyl-piperidin-4-yl)-propyl]-2,3-dihydro-1H-indol-5-yl}-1H-benzoimidazole; 6-Fluoro-4-methyl-2-{4-methyl-1-[3-(1-methyl-piperidin-4-yl)-propyl]-2,3-dihydro-1H-indol-5-yl}-1H-benzoimidazole; 2-Methyl-7-{4-methyl-1-[3-(1-methyl-piperidin-4-yl)-propyl]-2,3-dihydro-1H-indol-5-yl}-6H-imidazo {4',5':3,4}benzo[2,1-d]thiazole; 4,6-Dimethyl-2-{4-methyl-1-[3-(1-methyl-piperidin-4-yl)-propyl]-1H-indol-5-yl}-1H-benzoimidazole; 4,5-Dimethyl-2-[1-(3-piperazin-1-yl-propyl)-1H-indol-5-yl]-1H-benzoimidazole; 5-tert-Butyl-2-[1-(3-piperazin-1-yl-propyl)-1H-indol-5-yl]-1H-benzoimidazole; 5-Chloro-2-[1-(3-piperazin-1-yl-propyl)-1H-indol-5-yl]-1H-benzoimidazole; 5-Chloro-2-{1-[3-(4-methyl-piperazin-1-yl)-propyl]-1H-indol-5-yl}-1H-benzoimidazole; 4-Methyl-2-[1-(4-piperidin-4-yl-butyl)-1H-indol-4-yl]-1H-benzoimidazole; 5,6-Difluoro-2-{1-[4-(1-methyl-piperidin-4-yl)-butyl]-1H-indol-4-yl}-1H-benzoimidazole; 5-Chloro-2-{1-[4-(1-methyl-piperidin-4-yl)-butyl]-1H-indol-4-yl}-1H-benzoimidazole; 5-Fluoro-2-{1-[4-(1-methyl-piperidin-4-yl)-butyl]-1H-indol-4-yl}-1H-benzoimidazole; 4,6-Difluoro-2-{1-[4-(1-methyl-piperidin-4-yl)-butyl]-1H-indol-4-yl}-1H-benzoimidazole; 2-{1-[4-(1-Methyl-piperidin-4-yl)-butyl]-1H-indol-4-yl}-1H-naphtho[1,2-d]imidazole; (2-{3-Chloro-1-[4-(1-methyl-piperidin-4-yl)-butyl]-1H-indol-4-yl}-3H-benzoimidazol-4-yl)-phenyl-methanone; 2-[3-Chloro-1-(4-piperidin-4-yl-butyl)-1H-indol-4-yl]-4,5-dimethyl-1H-benzoimidazole; 2-{3-Chloro-1-[4-(1-methyl-piperidin-4-yl)-butyl]-1H-indol-4-yl}-4,5-dimethyl-1H-benzoimidazole; 2-{3-Chloro-1-[4-(1-methyl-piperidin-4-yl)-butyl]-1H-indol-4-yl}-4,5-difluoro-1H-benzoimidazole; 6-[1-(4-Piperidin-4-yl-butyl)-1H-indol-4-yl]-5H-[1.3dioxolo[4',5':4,5]-benzo[1,2-d]imidazole; Phenyl-{2-[1-(4-piperidin-4-yl-butyl)-1H-indol-4-yl]-1H-benzoimidazol-5-yl}-methanone; 4,5-Dimethyl-2-

{1-[4-(1-methyl-piperidin-4-yl)-butyl]-1H-indol-4-yl}-1H-benzoimidazole; 1-[3-(4-Methyl-piperazin-1-yl)-propyl]-5-[5-methyl-4-(3-trifluoromethyl-phenyl)-1H-imidazol-2-yl]-1H-indole; 5-[4-(4-Chloro-phenyl)-5-methyl-1H-imidazol-2-yl]-1-[3-(4-methyl-piperazin-1-yl)-propyl]-1H-indole; 4-Methyl-1-[3-(1-methyl-piperidin-4-yl)-propyl]-5-(4-methyl-5-propyl-1H-imidazol-2-yl)-1H-benzoimidazole; 4-Methyl-1-[3-(1-methyl-piperidin-4-yl)-propyl]-5-[4-methyl-5-(4-trifluoromethyl-phenyl)-1H-imidazol-2-yl]-1H-benzoimidazole; 5-[5-(3,5-Dichloro-phenyl)-4-methyl-1H-imidazol-2-yl]-4-methyl-1-[3-(1-methyl-piperidin-4-yl)-propyl]-1H-benzoimidazole; 4-Methyl-1-[3-(1-methyl-piperidin-4-yl)-propyl]-5-(5-phenyl-4-trifluoromethyl-1H-imidazol-2-yl)-1H-benzoimidazole; 5-[5-(4-Chloro-phenyl)-4-p-tolyl-1H-imidazol-2-yl]-4-methyl-1-[3-(1-methyl-piperidin-4-yl)-propyl]-1H-benzoimidazole; {5-(5-Fluoro-4-methyl-1H-benzoimidazol-2-yl)-1-[3-(1-methyl-piperidin-4-yl)-propyl]-1H-indol-3-ylmethyl}-dimethyl-amine; 2-[3-Chloro-1-(3-piperidin-4-yl-propyl)-1H-indol-5-yl]-5-fluoro-4-methyl-1H-benzoimidazole; 2-{3-Chloro-1-[3-(1-methyl-piperidin-4-yl)-propyl]-1H-indol-5-yl}-5-fluoro-4-methyl-1H-benzoimidazole; 2-[2,3-Dimethyl-1-(3-piperidin-4-yl-propyl)-1H-indol-5-yl]-4,6-dimethyl-1H-benzoimidazole; 2-[2,3-Dimethyl-1-(3-piperidin-4-yl-propyl)-1H-indol-5-yl]-5-fluoro-4-methyl-1H-benzoimidazole; 5-Fluoro-4-methyl-2-[1-(3-piperidin-4-yl-propyl)-1H-pyrrolo[2,3-b]pyridin-5-yl]-1H-benzoimidazole; 5-tert-Butyl-2-{1-[3-(1-methyl-piperidin-4-yl)-propyl]-1H-pyrrolo[2,3-b]pyridin-5-yl}-1H-benzoimidazole; 5-Fluoro-4-methyl-2-[1-(3-piperidin-4-yl-propyl)-2,3-dihydro-1H-indol-5-yl]-1H-benzoimidazole; 5-Chloro-2-[1-(3-piperidin-4-yl-propyl)-2,3-dihydro-1H-indol-5-yl]-1H-benzoimidazole; 4-Methyl-2-[1-(3-piperidin-4-yl-propyl)-2,3-dihydro-1H-indol-5-yl]-1H-benzoimidazole; 5-Fluoro-4-methyl-2-{1-[3-(1-methyl-piperidin-4-yl)-propyl]-2,3-dihydro-1H-indol-5-yl}-1H-benzoimidazole; 5-Chloro-2-{1-[3-(1-methyl-piperidin-4-yl)-propyl]-2,3-dihydro-1H-indol-5-yl}-1H-benzoimidazole; 4-Methyl-2-{1-[3-(1-methyl-piperidin-4-yl)-propyl]-2,3-dihydro-1H-indol-5-yl}-1H-benzoimidazole; 2-[6-Chloro-1-(3-piperidin-4-yl-propyl)-1H-indol-5-yl]-4,6-difluoro-1H-benzoimidazole; 2-[6-Chloro-1-(3-piperidin-4-yl-propyl)-1H-indol-5-yl]-4,5-dimethyl-1H-benzoimidazole; 5-Chloro-2-[6-chloro-1-(3-piperidin-4-yl-propyl)-1H-indol-5-yl]-1H-benzoimidazole; 5-Chloro-2-{6-chloro-1-[3-(1-methyl-piperidin-4-yl)-propyl]-1H-indol-5-yl}-1H-benzoimidazole; 2-{6-Chloro-1-[3-(1-methyl-piperidin-4-yl)-propyl]-1H-indol-5-yl}-4,5-dimethyl-1H-benzoimidazole; 6-Chloro-4-methyl-2-[1-(4-piperidin-4-yl-butyl)-1H-indol-4-yl]-1H-benzoimidazole; 5-tert-Butyl-2-[1-(4-piperidin-4-yl-butyl)-1H-indol-4-yl]-1H-benzoimidazole; 6,7-Dimethyl-2-[1-(4-piperidin-4-yl-butyl)-1H-indol-4-yl]-1H-benzoimidazole; 4-Methyl-2-[1-(4-piperidin-4-yl-butyl)-1H-indol-6-yl]-1H-benzoimidazole; 6-Chloro-4-methyl-2-[1-(4-piperidin-4-yl-butyl)-1H-indol-6-yl]-1H-benzoimidazole; 5-tert-Butyl-2-[1-(4-piperidin-4-yl-butyl)-1H-indol-6-yl]-1H-benzoimidazole; 4,5-Difluoro-2-[1-(4-piperidin-4-yl-butyl)-1H-indol-4-yl]-1H-benzoimidazole; 4,4'-Dimethyl-1'-(3-piperidin-4-yl-propyl)-1H,1'H-[2,5']bibenzoimidazolyl; 6-Fluoro-4,4'-dimethyl-1'-(3-piperidin-4-yl-propyl)-1H,1'H-[2,5']bibenzoimidazolyl; 5-Chloro-4,4'-dimethyl-1'-(3-piperidin-4-yl-propyl)-1H,1'H-[2,5']bibenzoimidazolyl; 5-Fluoro-4,4'-dimethyl-1'-(3-piperidin-4-yl-propyl)-1H,1'H-[2,5']bibenzoimidazolyl; 5-Fluoro-2-[1-(4-piperidin-4-yl-butyl)-1H-indol-4-yl]-1H-benzoimidazole; 4,6-Difluoro-2-[1-(4-piperidin-4-yl-butyl)-1H-indol-4-yl]-1H-benzoimidazole; 4-Methyl-1'-(4-piperidin-4-yl-butyl)-1H,1'H-[2,5']bibenzoimidazolyl; 4,5-Dimethyl-1'-(4-piperidin-4-yl-butyl)-1H,1'H-[2,5']bibenzoimidazolyl; 5-Fluoro-1'-(4-piperidin-4-yl-butyl)-1H,1'H-[2,4']bibenzoimidazolyl; 5-Fluoro-1'-[4-(1-methyl-piperidin-4-yl)-butyl]-1H,1'H-[2,4]bibenzoimidazolyl; 4,5-Dimethyl-1'-[4-(1-methyl-piperidin-4-yl)-butyl]-1H,1'H-[2,5']bibenzoimidazolyl; 4-Methyl-3'-(4-piperidin-4-yl-butyl)-1H,3H-[2,5']bibenzoimidazolyl; 4,5-Dimethyl-3'-(4-piperidin-4-yl-butyl)-1H,3H-[2,5']bibenzoimidazolyl; 5-Fluoro-3'-(4-piperidin-4-yl-butyl)-1H,3H-[2,5']bibenzoimidazolyl; 4,5-Dimethyl-3'-[4-(1-methyl-piperidin-4-yl)-butyl]-1H,3H-[2,5']bibenzoimidazolyl; 5-Fluoro-3'-[4-(1-methyl-piperidin-4-yl)-butyl]-1H,3'H[2,5']bibenzoimidazolyl; 2-[1-(4-Piperidin-4-yl-butyl)-1H-indol-4-yl]-1H-naphtho[2,3-d]imidazole; 2-[1-(4-Piperidin-4-yl-butyl)-1H-indol-4-yl]-1H-naphtho[1,2-d]imidazole; {2-[3-Chloro-1-(4-piperidin-4-yl-butyl)-1H-indol-4-yl]-1H-benzoimidazol-5-yl}-phenyl-methanone; 2-[3-Chloro-1-(4-piperidin-4-yl-butyl)-1H-indol-4-yl]-5-trifluoromethyl-1H-benzoimidazole; 2-[3-Chloro-1-(4-piperidin-4-yl-butyl)-1H-indol-4-yl]-5,6-difluoro-1H-benzoimidazole; 2-[3-Chloro-1-(4-piperidin-4-yl-butyl)-1H-indol-4-yl]-4,5-difluoro-1H-benzoimidazole; 2-[3-Chloro-1-(4-piperidin-4-yl-butyl)-1H-indol-4-yl]-5-fluoro-4-methyl-1H-benzoimidazole; 7-[3-Chloro-1-(4-piperidin-4-yl-butyl)-1H-indol-4-yl]-2-methyl-8H-2-[3-Chloro-1-(4-piperidin-4-yl-butyl)-1H-indol-4-yl]-3H-benzoimidazole-5-carboxylic acid methyl ester; 2-{3-Chloro-1-[4-(1-methyl-piperidin-4-yl)-butyl]-1H-indol-4-yl}-3H-benzoimidazole-5-carboxylic acid methyl ester; 4,5,4'-Trimethyl-1'-(3-piperidin-4-yl-propyl)-1'H,1H-[2,5']bibenzoimidazolyl; 4,6-Dimethyl-2-[1-(4-piperidin-4-yl-butyl)-1H-indol-4-yl]-1H-benzoimidazole; 6-Chloro-2-[1-(4-piperidin-4-yl-butyl)-1H-indol-4-yl]-1H-benzoimidazole; 2-[1-(4-Piperidin-4-yl-butyl)-1H-indol-4-yl]-6-trifluoromethyl-1H-benzoimidazole; 4-Methyl-1-[3-(1-methyl-piperidin-4-yl)-propyl]-5-[4-methyl-5-(4-trifluoromethyl-phenyl)-1H-imidazol-2-yl]-1H-benzoimidazole; 5-[5-(4-Methoxy-phenyl)-4-methyl-1H-imidazol-2-yl]-4-methyl-1-[3-(1-methyl-piperidin-4-yl)-propyl]-1H-benzoimidazole; and pharmaceutically acceptable salts, prodrugs, and active metabolites thereof.

In another particular embodiment, the Histamine H4 antagonist or selective Histamine H4 antagonists are selected from those described in the international Patent Application WO2009/038673: 4-(4-Methyl-piperazin-1-yl)-thieno[3,2-d]pyrimidin-2-ylamine; 4-(4-Methyl-piperazin-1-yl)-6,7,8,9-tetrahydro-benzo[4,5]thieno[3,2-d]pyrimidin-2-ylamine; 4-Piperazin-1-yl-6,7,8,9-tetrahydro-benzo[4,5]thieno[3,2-d]pyrimidin-2-ylamine; 4-[(3aR,6aR)-Hexahydropyrrolo[3,4-b]pyrrol-5 (1H)-yl]-6,7,8,9-tetrahydro[1]benzothieno[3,2-d]pyrimidin-2-amine; 4-(4-Methyl-piperazin-1-yl)-6,7,8,9-tetrahydro-benzo[4,5]furo[3,2-d]pyrimidin-2-ylamine; 4-Piperazin-1-yl-6,7,8,9-tetrahydro-benzo[4,5]furo[3,2-d]pyrimidin-2-ylamine; 4-[(3aR,6aR)-Hexahydropyrrolo[3,4-b]pyrrol-5 (1H)-yl]-6,7,8,9-tetrahydro[1]benzofuro[3,2-d]pyrimidin-2-amine; 4-(4-Methyl-piperazin-1-yl)-6,7,8,9-tetrahydro-benzo[4,5]furo[3,2-d]pyrimidine; 4-Piperazin-1-yl-6,7,8,9-tetrahydro-benzo[4,5]furo[3,2-d]pyrimidine; 4-(4-Methyl-piperazin-1-yl)-6,7,8,9-tetrahydro-benzo[4,5]thieno[3,2-d]pyrimidine; 4-Piperazin-1-yl-6,7,8,9-tetrahydro-benzo[4,5]thieno[3,2-d]pyrimidine; 7-Methyl-4-[(3R)-3-(methylamino)pyrrolidin-1-yl]thieno[3,2-d]pyrimidin-2-amine; 7-Methyl-4-(4-methylpiperazin-1-yl)thieno[3,2-d]pyrimidin-2-amine; 7-Bromo-4-[(3R)-3-(methylamino)pyrrolidin-1-yl]thieno[3,2-d]pyrimidin-2-amine; 6-tert-Butyl-4-(4-methylpiperazin-1-yl)thieno[3,2-d]pyrimidin-2-amine; 6-tert-Butyl-4-[(3R)-3-

(methylamino)pyrrolidin-1-yl]thieno[3,2-d]pyrimidin-2-amine; 6-tert-Butyl-4-piperazin-1-ylthieno[3,2-d]pyrimidin-2-amine; 4-[(3R)-3-Aminopyrrolidin-1-yl]-6-tert-butylthieno[3,2-d]pyrimidin-2-amine; 6-tert-Butyl-4-(octahydro-6H-pyrrolo[3,4-b]pyridin-6-yl)thieno[3,2-d]pyrimidin-2-amine; 4-[(4aR,7aR)-Octahydro-6H-pyrrolo[3,4-b]pyridin-6-yl]-6,7,8,9-tetrahydro[1]benzofuro[3,2-d]pyrimidin-2-amine; 4-[(3R)-3-(Methylamino)pyrrolidin-1-yl]-6,7,8,9-tetrahydro[1]benzofuro[3,2-d]pyrimidin-2-amine; 4-(1,4-Diazepan-1-yl)-6,7,8,9-tetrahydro[1]benzofuro[3,2-d]pyrimidin-2-amine; 4-(3-Aminoazetidin-1-yl)-6,7,8,9-tetrahydro[1]benzofuro[3,2-d]pyrimidin-2-amine; 4-[(3R)-3-Aminopyrrolidin-1-yl]-6,7,8,9-tetrahydro[1]benzofuro[3,2-d]pyrimidin-2-amine; N4-(2-Aminoethyl)-6,7,8,9-tetrahydro[1]benzofuro[3,2-d]pyrimidine-2,4-diamine; 4-(3,8-Diazabicyclo[3.2.1]oct-3-yl)6,7,8,9-tetrahydro[1]benzofuro[3,2d]pyrimidin-2-amine; N-(6,7,8,9-Tetrahydro[1]benzofuro[3,2d]pyrimidin-4-yl)ethane-1,2-diamine; (3R)—N-Methyl-1-(6,7,8,9-tetrahydro[1]benzofuro[3,2-d]pyrimidin-4-yl)pyrrolidin-3-amine; N-(6,7,8,9-Tetrahydro[1]benzothieno[3,2-d]pyrimidin-4-yl)ethane-1,2-diamine; (3R)—N-Methyl-1-(6,7,8,9-tetrahydrotilbenzothieno[3,2d]pyrimidin-4-yl)pyrrolidin-3-amine; 4-[(3R)-3-(Methylamino)pyrrolidin-1-yl]-6,7,8,9-tetrahydro[1]benzothieno[3,2-d]pyrimidin-2-amine; 4-[(4aR,7aR)-Octahydro-6H-pyrrolo[3,4-b]pyridin-6-yl]-6,7,8,9-tetrahydro[1]benzothieno[3,2-d]pyrimidin-2-amine; 4-Hexahydropyrrolo[3,4-c]pyrrol-2(1H)-yl]-6,7,8,9-tetrahydro[1]benzothieno[3,2-d]pyrimidin-2-amine; 4-[(3S)-3-Aminopiperidin-1-yl]-6,7,8,9-tetrahydro[1]benzothieno[3,2-d]pyrimidin-2-amine; 4-[(1S,4S)-2,5-Diazabicyclo[2.2.1]hept-2-yl]-6,7,8,9-tetrahydro[1]benzothieno[3,2-d]pyrimidin-2-amine; 4-[(1R,4R)-2,5-Diazabicyclo[2.2.1]hept-2-yl]-6,7,8,9-tetrahydro[1]benzothieno[3,2-d]pyrimidin-2-amine; 4-(1,4-Diazepan-1-yl)-6,7,8,9-tetrahydro[1]benzothieno[3,2-d]pyrimidin-2-amine; (3S,4S)-1-(2-Amino-6,7,8,9-tetrahydro[1]benzothieno[3,2-d]pyrimidin-4-yl)-4-(methylamino)pyrrolidin-3-ol; 4-[(3R)-3-(Dimethylamino)pyrrolidin-1-yl]-6,7,8,9-tetrahydro[1]benzothieno[3,2-d]pyrimidin-2-amine; 4-[(3R)-3-(Ethylamino)pyrrolidin-1-yl]-6,7,8,9-tetrahydro[1]benzothieno[3,2-d]pyrimidin-2-amine; 4-[(3R)-3-(Aminomethyl)pyrrolidin-1-yl]-6,7,8,9-tetrahydro[1]benzothieno[3,2-d]pyrimidin-2-amine; 4-(3-Aminoazetidin-1-yl)-6,7,8,9-tetrahydro[1]benzothieno[3,2-d]pyrimidin-2-amine; 8-Methyl-4-(4-methylpiperazin-1-yl)-6,7,8,9-tetrahydro[1]benzothieno[3,2-d]pyrimidin-2-amine; 8-Methyl-4-[(3R)-3-(methylamino)pyrrolidin-1-yl]-6,7,8,9-tetrahydro[1]benzothieno[3,2-d]pyrimidin-2-amine; 8-Methyl-4-[(4aR,7aR)-octahydro-6H-pyrrolo[3,4-b]pyridin-6-yl]-6,7,8,9-tetrahydro[1]benzothieno[3,2-d]pyrimidin-2-amine; 4-(4-Methylpiperazin-1-yl)-7,8,9,10-tetrahydro-6H-cyclohepta[4,5]thieno[3,2-d]pyrimidin-2-amine; 4-[(3R)-3-(Methylamino)pyrrolidin-1-yl]-7,8,9,10-tetrahydro-6H-cyclohepta[4,5]thieno[3,2-d]pyrimidin-2-amine; 4-[(4aR,7aR)-Octahydro-6H-pyrrolo[3,4-b]pyridin-6-yl]-7,8,9,10-tetrahydro-6H-cyclohepta[4,5]thieno[3,2-d]pyrimidin-2-amine; 4-[4-(2-Aminoethyl)piperazin-1-yl]-6,7,8,9-tetrahydro[1]benzothieno[3,2-d]pyrimidin-2-amine; 4-[4-(1-Methylethyl)piperazin-1-yl]-6,7,8,9-tetrahydro[1]benzothieno[3,2-d]pyrimidin-2-amine; 4-(4-Ethylpiperazin-1-yl)-6,7,8,9-tetrahydro[1]benzothieno[3,2-d]pyrimidin-2-amine; 4-(Hexahydropyrrolo[1,2-a]pyrazin-2(1H)-yl)-6,7,8,9-tetrahydro[1]benzothieno[3,2-d]pyrimidin-2-amine; 4-(Octahydro-2H-pyrido[1,2-a]pyrazin-2-yl)-6,7,8,9-tetrahydro[1]benzothieno[3,2-d]pyrimidin-2-amine; 4-(5,6-Dihydro[1,2,4]triazolo[4,3-a]pyrazin-7(8H)-yl)-6,7,8,9-tetrahydro[1]benzothieno[3,2-d]pyrimidin-2-amine; 4-[(3S)-3-(Methylamino)pyrrolidin-1-yl]-6,7,8,9-tetrahydro[1]benzothieno[3,2-d]pyrimidin-2-amine; 4-[(3R)-3-Aminopyrrolidin-1-yl]-6,7,8,9-tetrahydro[1]benzothieno[3,2-d]pyrimidin-2-amine; 8,8-Difluoro-4-(4-methylpiperazin-1-yl)-6,7,8,9-tetrahydro[1]benzothieno[3,2-d]pyrimidin-2-amine; 8,8-Difluoro-4-piperazin-1-yl-6,7,8,9-tetrahydrotilbenzothieno[3,2d]pyrimidin-2-amine; 8,8-Difluoro-4-[(3R)-3-(methylamino)pyrrolidin-1-yl]-6,7,8,9-tetrahydro[1]benzothieno[3,2-d]pyrimidin-2-amine; 4-(3,8-Diaza-bicyclo[3.2.1]oct-3-yl)-8-methoxy-6,7,8,9-tetrahydro-benzo[4,5]thieno[3,2-d]pyrimidin-2-ylamine; 8-tert-Butyl-4-(4-methyl-piperazin-1-yl)-6,7,8,9-tetrahydro-benzo[4,5]thieno[3,2-d]pyrimidin-2-ylamine; 4-[1,4]Diazepan-1-yl-8-trifluoromethyl-6,7,8,9-tetrahydro-benzo[4,5]thieno[3,2-d]pyrimidin-2-ylamine; 4-(3 (S)-Amino-pyrrolidin-1-yl)-8-tert-butyl-6,7,8,9-tetrahydro-benzo[4,5]thieno[3,2-d]pyrimidin-2-ylamine; 4-(3,8-Diazabicyclo[3.2.1]oct-3-yl)-8-methyl-6,7,8,9-tetrahydro[1]benzofuro[3,2-d]pyrimidin-2-amine; 8-tert-Butyl-4-(3,8-diazabicyclo[3.2.1]oct-3-yl)-6,7,8,9-tetrahydro[1]benzothieno[3,2-d]pyrimidin-2-amine; 8-Methoxy-4-(4-methylpiperazin-1-yl)-6,7,8,9-tetrahydro[1]benzothieno[3,2-d]pyrimidin-2-amine; 4-[3-(Aminomethyl)azetidin-1-yl]-8-tert-butyl-6,7,8,9-tetrahydro[1]benzothieno[3,2-d]pyrimidin-2-amine; 4-(3,4-Diazabicyclo[3.2.1]oct-3-yl)-8-methyl-6,7,8,9-tetrahydro[1]benzothieno[3,2-d]pyrimidin-2-amine; 4-[(3R)-3-Aminopyrrolidin-1-yl]-8-methoxy-6,7,8,9-tetrahydro[1]benzothieno[3,2-d]pyrimidin-2-amine; 4-Piperazin-1-yl-8-(trifluoromethyl)-6,7,8,9-tetrahydro[1]benzofuro[3,2-d]pyrimidin-2-amine; 4-(4-Methylpiperazin-1-yl)-8-(trifluoromethyl)-6,7,8,9-tetrahydro[1]benzofuro[3,2-d]pyrimidin-2-amine; 8-tert-Butyl-4-(4-methylpiperazin-1-yl)-6,7,8,9-tetrahydro[1]benzofuro[3,2-d]pyrimidin-2-amine; 8-Methyl-4-piperazin-1-yl)-6,7,8,9-tetrahydro[1]benzofuro[3,2-d]pyrimidin-2-amine; 8-Methyl-4-(4-methylpiperazin-1-yl)-6,7,8,9-tetrahydro[1]benzofuro[3,2-d]pyrimidin-2-amine; 6,6-Dimethyl-4-(4-methylpiperazin-1-yl)-6,7,8,9-tetrahydro[1]benzothieno[3,2-d]pyrimidin-2-amine; 4-(1,4-Diazepan-1-yl)-8-methoxy-6,7,8,9-tetrahydro[1]benzothieno[3,2-d]pyrimidin-2-amine; 8-tert-Butyl-4-[(3R)-3-(methylamino)pyrrolidin-1-yl]-6,7,8,9-tetrahydro[1]benzofuro[3,2-d]pyrimidin-2-amine; 4-[(3R)-3-(Methylamino)pyrrolidin-1-yl]-8-(trifluoromethyl)-6,7,8,9-tetrahydro[1]benzofuro[3,2-d]pyrimidin-2-amine; 4-[(3S)-3-Aminopyrrolidin-1-yl]-8-methoxy-6,7,8,9-tetrahydro[1]benzothieno[3,2-d]pyrimidin-2-amine; 8-Methoxy-4-[(3R)-3-(methylamino)pyrrolidin-1-yl]-6,7,8,9-tetrahydro[1]benzothieno[3,2-d]pyrimidin-2-amine; 4-[(3R)-3-Aminopyrrolidin-1-yl]-8-(trifluoromethyl)-6,7,8,9-tetrahydro[1]benzothieno[3,2-d]pyrimidin-2-amine; 4-[(3R)-3-Aminopyrrolidin-1-yl]-8-(trifluoromethyl)-6,7,8,9-tetrahydro[1]benzofuro[3,2-d]pyrimidin-2-amine; 4-[(3S)-3-Aminopyrrolidin-1-yl]-8-(trifluoromethyl)-6,7,8,9-tetrahydro[1]benzofuro[3,2-d]pyrimidin-2-amine; 4-[(3R)-3-Aminopyrrolidin-1-yl]-8-methyl-6,7,8,9-tetrahydro[1]benzothieno[3,2-d]pyrimidin-2-amine; 4-[(3S)-3-Aminopyrrolidin-1-yl]-8-methyl-6,7,8,9-tetrahydro[1]benzothieno[3,2-d]pyrimidin-2-amine; 4-[3-(Aminomethyl)azetidin-1-yl]-8-methoxy-6,7,8,9-tetrahydro[1]benzothieno[3,2-d]pyrimidin-2-amine; 4-[(3S)-3-Aminopyrrolidin-1-yl]-6,6-dimethyl-6,7,8,9-tetrahydro[1]benzofuro[3,2-d]pyrimidin-2-amine; 4-[(3R)-3-Aminopyrrolidin-1-yl]-6,6-dimethyl-6,7,8,9-tetrahydro[1]benzofuro[3,2-d]pyrimidin-2-amine; 6,6-Dimethyl-4-[(3R)-3-(methylamino)pyrrolidin-1-yl]-6,7,8,9-tetrahydro[1]benzofuro[3,2-d]pyrimidin-2-amine; 4-[3-(Aminomethyl)azetidin-1-yl]-6,6-dimethyl-6,7, 8,9-tetrahydro[1]benzofuro[3,2-d]pyrimidin-2-amine; 6,6-Dimethyl-4-[(3aR,6aS)-5-methylhexahydropyrrolo[3,4-c]pyrrol-2 (1H)-yl]-6,7,8,9-tetrahydroπibenzothieno[3,2-d]pyrimidin-2-amine; 8-tert-Butyl-4-[(3aR,6aS)-5-methylhexahydropyrrolo[3,4-c]pyrrol-2(1H)-yl]-6,7,8,9-tetrahydro[1]benzothieno[3,2-d]pyrimidin-2-amine; 4-[(3aR,6aS)-5-Methylhexahydropyrrolo[3,4-c]pyrrol-2(1H)-yl]-8-(trifluoromethyl)-6,7,8,9-tetrahydro[1]benzothieno[3,2-d]pyrimidin-2-amine; tetrahydro[1]benzothieno[3,2-d]pyrimidin-2-amine; tetrahydro[1]benzofuro[3,2-d]pyrimidin-2-amine; 8-Methoxy-4-[(3aR,6aS)-5-methylhexahydropyrrolo[3,4-c]pyrrol-2(1H)-yl]-6,7,8,9-tetrahydro[1]benzothieno[3,2-d]pyrimidin-2-amine; 4-[(3aR,6aS)-5-Methylhexahydropyrrolo[3,4-c]pyrrol-2(1H)-yl]-8-(trifluoromethyl)-6,7,8,9-tetrahydro[1]benzofuro[3,2-d]pyrimidin-2-amine; 8-Methyl-4-[(3 ar,6aS)-5-methylhexahydropyrrol[3,4-c]pyrrol-2(1H)-yl]-6,7,8,9-tetrahydro[1]benzofuro[3,2-d]pyrimidin-2-amine; 4-(1,4-Diazepan-1-yl)-6,6-dimethyl-6,7,8,9-tetrahydro[1]benzofuro[3,2-d]pyrimidin-2-amine; 6,6-Dimethyl-4-piperazin-1-yl-6,7,8,9-tetrahydro[1]benzofuro[3,2-d]pyrimidin-2-amine; 6,6-Dimethyl-4-(4-methylpiperazin-1-yl)-6,7,8,9-tetrahydro[1]benzofuro[3,2-d]pyrimidin-2-amine; N4-(2-Aminoethyl)-N4,6,6-trimethyl-6,7,8,9-tetrahydro[1]benzothieno[3,2-d]pyrimidine-2,4-diamine; N4-(2-Aminoethyl)-N4,6,6-trimethyl-6,7,8,9-tetrahydro[1]benzofuro[3,2-d]pyrimidine-2,4-diamine; N4-(2-Aminoethyl)-8-methoxy-N4-methyl-6,7,8,9-tetrahydro[1]benzothieno[3,2-d]pyrimidine-2,4-diamine; N4-(2-Aminoethyl)-8-methoxy-N4-methyl-6,7,8,9-tetrahydro[1]benzofuro[3,2-d]pyrimidine-2,4-diamine; N4-(2-Aminoethyl)-8-tert-butyl-N4-methyl-6,7,8,9-tetrahydro[1]benzothieno[3,2-d]pyrimidine-2,4-diamine; N4-(2-Aminoethyl)-8-tert-butyl-N4-methyl-6,7,8,9-tetrahydro[1]benzofuro[3,2-]pyrimidine-2,4-diamine; N4-(2-Aminoethyl)-N4-methyl-8-(trifluoromethyl)-6,7,8,9-tetrahydro[1]benzothieno[3,2-d]pyrimidine-2,4-diamine; N4-(2-Aminoethyl)-N4-methyl-8-(trifluoromethyl)-6,7,8,9-tetrahydro[1]benzofuro[3,2-d]pyrimidine-2,4-diamine; N4-(2-Aminoethyl)-N4,8-dimethyl-6,7,8,9-tetrahydro[1]benzothieno[3,2-d]pyrimidine-2,4-diamine; N4-(2-Aminoethyl)-N4,8-dimethyl-6,7,8,9-tetrahydro[1]benzofuro[3,2-d]pyrimidine-2,4-diamine; 8,8-Difluoro-4-[(3S)-3-(methylamino)pyrrolidin-1-yl]-6,7,8,9-tetrahydro[1]benzothieno[3,2-d]pyrimidin-2-amine; 4-[(3R)-3-Aminopyrrolidin-1-yl]-8,8-difluoro-6,7,8,9-tetrahydro[1]benzothieno[3,2-d]pyrimidin-2-amine; 4-(1,4-Diazepan-1-yl)-8,8-difluoro-6,7,8,9-tetrahydro[1]benzothieno[3,2-d]pyrimidin-2-amine; N4-(2-Aminoethyl)-8,8-difluoro-N4-methyl-6,7,8,9-tetrahydro[1]benzothieno[3,2-d]pyrimidine-2,4-diamine; 8,8-Difluoro-4-[(3R)-3-(methylamino)pyrrolidin-1-yl]-6,7,8,9-tetrahydro[1]benzofuro[3,2-d]pyrimidin-2-amine; 4-[(3R)-3-Aminopyrrolidin-1-yl]-8,8-difluoro-6,7,8,9-tetrahydro[1]benzofuro[3,2-d]pyrimidin-2-amine; 8,8-Difluoro-4-piperazin-1-yl-6,7,8,9-tetrahydro[1]benzofuro[3,2-d]pyrimidin-2-amine; 4-[(3S)-3-Aminopyrrolidin-1-yl]-8,8-difluoro-6,7,8,9-tetrahydro[1]benzothieno[3,2-d]pyrimidin-2-amine; 4-(3-Aminoazetidin-1-yl)-8,8-difluoro-6,7,8,9-tetrahydro[1]benzothieno[3,2-d]pyrimidin-2-amine; 8,8-Difluoro-4-[(3S)-3-(methylamino)pyrrolidin-1-yl]-6,7,8,9-tetrahydro[1]benzofuro[3,2-d]pyrimidin-2-amine; 8,8-Difluoro-4-(4-methylpiperazin-1-yl)-6,7,8,9-tetrahydro[1]benzofuro[3,2-d]pyrimidin-2-amine; 4-((R,R)-octahydropyrrolo[3,4-b]pyridin-6-yl)-8,8-difluoro-6,7,8,9-tetrahydro[1]benzofuro[3,2-d]pyrimidin-2-amine; N4-(2-Aminoethyl)-8,8-difluoro-N4-methyl-6,7,8,9-tetrahydro[1]benzofuro[3,2-d]pyrimidine-2,4-diamine; 4-[(3S)-3-Aminopyrrolidin-1-yl]-8,8-difluoro-6,7,8,9-tetrahydro[1]benzofuro[3,2-d]pyrimidin-2-amine; 4-(3-Aminoazetidin-1-yl)-8,8-difluoro-6,7,8,9-tetrahydro[1]benzofuro[3,2-d]pyrimidin-2-amine; N4-(2-Aminoethyl)-8,8-difluoro-6,7,8,9-tetrahydro[1]benzothieno[3,2-d]pyrimidine-2,4-diamine; 8,8-Difluoro-4-[(3aR,6aS)-hexahydropyrrolo[3,4-c]pyrrol-2(1H)-yl]-6,7,8,9-tetrahydro[1]benzothieno[3,2-d]pyrimidin-2-amine; 4-(1,4-Diazepan-1-yl)-8,8-difluoro-6,7,8,9-tetrahydro[1]benzofuro[3,2-d]pyrimidin-2-amine; 8,8-Dimethyl-4-(4-methylpiperazin-1-yl)-6,7,8,9-tetrahydro[1]benzothieno[3,2-d]pyrimidin-2-amine; 4-(1,4-Diazepan-1-yl)-8,8-dimethyl-6,7,8,9-tetrahydro[1]benzothieno[3,2-d]pyrimidin-2-amine; N4-(2-Aminoethyl)-N4,8,8-trimethyl-6,7,8,9-tetrahydro[1]benzothieno[3,2-d]pyrimidine-2,4-diamine; 8,8-Dimethyl-4-[(3R)-3-(methylamino)pyrrolidin-1-yl]-6,7,8,9-tetrahydro[1]benzothieno[3,2-d]pyrimidin-2-amine; 8,8-Dimethyl-4-[(3S)-3-(methylamino)pyrrolidin-1-yl]-6,7,8,9-tetrahydro[1]benzothieno[3,2-d]pyrimidin-2-amine; 4-[(3R)-3-Aminopyrrolidin-1-yl]-8,8-dimethyl-6,7,8,9-tetrahydro[1]benzothieno[3,2-d]pyrimidin-2-amine; 8,8-Dimethyl-4-[(3R)-3-(methylamino)pyrrolidin-1-yl]-6,7,8,9-tetrahydro[1]benzofuro[3,2-d]pyrimidin-2-amine; 4-(4-Methylpiperazin-1-yl)-8-(trifluoromethyl)-6,7,8,9-tetrahydro[1]benzothieno[3,2-d]pyrimidin-2-amine; 4-[(3R)-3-Aminopyrrolidin-1-yl]-8-tert-butyl-6,7,8,9-tetrahydro[1]benzothieno[3,2-d]pyrimidin-2-amine; 8-Methyl-4-[(3)-3-(methylamino)pyrrolidin-1-yl]-6,7,8,9-tetrahydro[1]benzofuro[3,2-d]pyrimidin-2-amine; 4-[(3R)-3-(Methylamino)pyrrolidin-1-yl]-8-(trifluoromethyl)-6,7,8,9-tetrahydro[1]benzothieno[3,2-d]pyrimidin-2-amine; 8-tert-Butyl-4-[(3R)-3-(methylamino)pyrrolidin-1-yl]-6,7,8,9-tetrahydro[1]benzothieno[3,2-d]pyrimidin-2-amine; 4-[3-(Aminomethyl)azetidin-1-yl]-8-methyl-6,7,8,9-tetrahydro[1]benzothieno[3,2-d]pyrimidin-2-amine; 4-[(3R)-3-Aminopyrrolidin-1-yl]-8-methyl-6,7,8,9-tetrahydro[1]benzofuro[3,2-d]pyrimidin-2-amine; 4-(1,4-Diazepan-1-yl)-8-methyl-6,7,8,9-tetrahydro[1]benzofuro[3,2-d]pyrimidin-2-amine; 8-Methyl-4-piperazin-1-yl-6,7,8,9-tetrahydro[1]benzothieno[3,2-d]pyrimidin-2-amine; 4-(3,8-Diazabicyclo[3.2.1]oct-3-yl)-8-(trifluoromethyl)-6,7,8,9-tetrahydro[1]benzothieno[3,2-d]pyrimidin-2-amine; 4-Piperazin-1-yl-8-(trifluoromethyl)-6,7,8,9-tetrahydro[1]benzothieno[3,2-d]pyrimidin-2-amine; 4-(1,4-Diazepan-1-yl)-8-methyl-6,7,8,9-tetrahydro[1]benzothieno[3,2-d]pyrimidin-2-amine; 8-Methoxy-4-piperazin-1-yl-6,7,8,9-tetrahydro[1]benzothieno[3,2-d]pyrimidin-2-amine; 4-(3,8-Diazabicyclo[3.2.1]oct-3-yl)-6,6-dimethyl-6,7,8,9-tetrahydro[1]benzofuro[3,2-d]pyrimidin-2-amine; and pharmaceutically acceptable salts, prodrugs, and active metabolites thereof.

In another embodiment, the Histamine H4 antagonist or selective Histamine H4 antagonists are selected from those described in the international Patent Application WO2008/100565: 4-Cyclopentyl-6-(4-methyl-piperazin-1-yl)-pyrimidin-2-ylamine; 4-Cyclopentyl-6-(4-methyl-piperazin-1-yl)-pyrimidin-2-ylamine; (R)-4-(3-Amino-piperidin-1-yl)-6-cyclopentyl-pyrimidin-2-ylamine; (R)-4-Cyclopentyl-6-(3-methylamino-pyrrolidin-1-yl)-pyrimidin-2-ylamine; trans-1-(2-Amino-6-cyclopentyl-pyrimidin-4-yl)-4-methylamino-pyrrolidin-3-ol; 4-Cyclopentyl-6-(cis-hexahydro-pyrrolo[3,4-b]pyrrol-5-yl)-pyrimidin-2-ylamine; 4-Cyclopentyl-6-(cis-octahydro-pyrrolo[3,4-b]pyridin-6-yl)-pyrimidin-2-ylamine; 4-Isopropyl-6-piperazin-1-yl-pyrimidin-2-ylamine; (R)-4-(3-Amino-piperidin-1-yl)-6-isopropyl-pyrimidin-2-ylamine; (S)-4-(3-Amino-piperidin-1-yl)-6-isopropyl-pyrimidin-2-ylamine; (R)-4-Isopropyl-6-(3-methylamino-pyrrolidin-1-yl)-pyrimidin-2-ylamine; (R)-4-(3-Amino-pyrrolidin-1-yl)-6-isopropyl-pyrimidin-2- ylamine; trans-1-(2-Amino-6-isopropyl-pyrimidin-4-yl)-4-methylamino-pyrrolidin-3-ol; (S,S)-4-(2,5-Diaza-bicyclo[2.2.1]hept-2-yl)-6-isopropyl-pyrimidin-2-ylamine; (R;R)-4-(2,5-Diaza-bicyclo[2.2.1]hept-2-yl)-6-isopropyl-pyrimidin-2-ylamine; 4-(cis-Hexahydro-pyrrolo[3,4-b]pyrrol-5-yl)-6-isopropyl-pyrimidin-2-ylamine; (R,R)-4-(Hexahydro-pyrrolo[3,4-b]pyrrol-5-yl)-6-isopropyl-pyrimidin-2-ylamine; 4-Isopropyl-6-(cis-5-methyl-hexahydro-pyrrolo[3,4-c]pyrrol-2-yl)-pyrimidin-2-ylamine; 4-Isopropyl-6-(cis-octahydro-pyrrolo[3,4-b]pyridin-6-yl)-pyrimidin-2-ylamine; (R,R)-4-Isopropyl-6-(cis-octahydro-pyrrolo[3,4-b]pyridin-6-yl)-pyrimidin-2-ylamine; (R)-4-Methyl-6-(3-methylamino-pyrrolidin-1-yl)-pyrimidin-2-ylamine; 4-Methyl-6-(cis-octahydro-pyrrolo[3,4-b]pyridin-6-yl)-pyrimidin-2-ylamine; 4,5-Dimethyl-6-piperazin-1-yl-pyrimidin-2-ylamine; 4,5-Dimethyl-6-(4-methyl-piperazin-1-yl)-pyrimidin-2-ylamine; (R)-4-(3-Amino-pyrrolidin-1-yl)-5,6-dimethyl-pyrimidin-2-ylamine; (R)-4,5-Dimethyl-6-(3-methylamino-pyrrolidin-1-yl)-pyrimidin-2-ylamine; 4-(cis-Hexahydro-pyrrolo[3,4-b]pyrrol-5-yl)-5,6-dimethyl-pyrimidin-2-ylamine; 4,5-Dimethyl-6-(cis-5-methyl-hexahydro-pyrrolo[3,4-c]pyrrol-2-yl)-pyrimidin-2-ylamine; 4,5-Dimethyl-6-(cis-octahydro-pyrrolo[3,4-b]pyridin-6-yl)-pyrimidin-2-ylamine; (S,S)-4-(2,5-Diaza-bicyclo[2.2.1]hept-2-yl)-5,6-dimethyl-pyrimidin-2-ylamine; (R)-4-(3-Amino-pyrrolidin-1-yl)-6-ethyl-pyrimidin-2-ylamine; (R)-4-Ethyl-6-(3-methylamino-pyrrolidin-1-yl)-pyrimidin-2-ylamine; (R,R)-(4-Ethyl-6-hexahydro-pyrrolo[3,4-b]pyrrol-5-yl)-pyrimidin-2-ylamine; 4-Ethyl-6-(c/s-hexahydro-pyrrolo[3,4-c]pyrrol-2-yl)-pyrimidin-2-ylamine; (R,R)-(4-Ethyl-6-octahydro-pyrrolo[3,4-b]pyridin-6-yl)-pyrimidin-2-ylamine; 4-Cyclopropyl-6-(4-methyl-piperazin-1-yl)-pyrimidin-2-ylamine; (R)-4-Cyclopropyl-6-3-methylamino-pyrrolidin-1-yl)-pyrimidin-2-ylamine; 4-Cyclopropyl-6-(cis-octahydro-pyrrolo[3,4-b]pyridin-6-yl)-pyrimidin-2-ylamine; 4-Cyclobutyl-6-piperazin-1-yl-pyrimidin-2-ylamine; 4-Cyclobutyl-6-(4-methyl-piperazin-1-yl)-pyrimidin-2-ylamine; (R)-4-(3-Amino-piperidin-1-yl)-6-cyclobutyl-pyrimidin-2-ylamine; (R)-4-Cyclobutyl-6-(3-methylamino-pyrrolidin-1-yl)-pyrimidin-2-ylamine; 4-Cyclobutyl-6-(cis-hexahydro-pyrrolo[3,4-b]pyrrol-5-yl)-pyrimidin-2-ylamine; 4-Cyclobutyl-6-(cis-hexahydro-pyrrolo[3,4-c]pyrrol-2-yl)-pyrimidin-2-ylamine; 4-Cyclobutyl-6-(cis-5-methyl-hexahydro-pyrrolo[3,4-c]pyrrol-2-yl)-pyrimidin-2-ylamine; 4-Cyclobutyl-6-(cis-octahydro-pyrrolo[3,4-b]pyridin-6-yl)-pyrimidin-2-ylamine; (R,R)-(4-Cyclobutyl-6-cis-octahydro-pyrrolo[3,4-b]pyridin-6-yl)-pyrimidin-2-ylamine; 4-Cyclohexyl-6-(4-methyl-piperazin-1-yl)-pyrimidin-2-ylamine; (R)-(4-Cyclohexyl-6-3-methylamino-pyrrolidin-1-yl)-pyrimidin-2-ylamine; 4-Cyclohexyl-6-(cis-hexahydro-pyrrolo[3,4-b]pyrrol-5-yl)-pyrimidin-2-ylamine; (R,R)-4-Cyclohexyl-6-(octahydro-pyrrolo[3,4-b]pyridin-6-yl)-pyrimidin-2-ylamine; 4-Piperazin-1-yl-6-(tetrahydro-furan-3-yl)-pyrimidin-2-ylamine; 4-(4-Methyl-piperazin-1-yl)-6-(tetrahydro-furan-3-yl)-pyrimidin-2-ylamine; 4-Piperazin-1-yl-6-(tetrahydro-pyran-4-yl)-pyrimidin-2-ylamine; 4-(4-Methyl-piperazin-1-yl)-6-(tetrahydro-pyran-4-yl)-pyrimidin-2-ylamine; (R)-4-(3-Methylamino-pyrrolidin-1-yl)-6-(tetrahydro-pyran-4-yl)-pyrimidin-2-ylamine; (R,R)-4-(Octahydro-pyrrolo[3,4-b]pyridin-6-yl)-6-(tetrahydro-pyran-4-yl)-pyrimidin-2-ylamine; 4-Benzyl-6-piperazin-1-yl-pyrimidin-2-ylamine; 4-Benzyl-6-(4-methyl-piperazin-1-yl)-pyrimidin-2-ylamine; (R)-Benzyl-6-(3-methylamino-pyrrolidin-1-yl)-pyrimidin-2-ylamine; (R,R)-4-Benzyl-6-(octahydro-pyrrolo[3,4-b]pyridin-6-yl)-pyrimidin-2-ylamine; 4-(4-Methyl-piperazin-1-yl)-5,6,7,8-tetrahydro-quinazolin-2-ylamine; 4-(4-Piperazin-1-yl)-5,6,7,8-tetrahydro-quinazolin-2-ylamine; (R)-4-(3-Amino-pyrrolidin-1-yl)-5,6,7,8-tetrahydro-quinazolin-2-ylamine; (R)-4-(3-Methylamino-pyrrolidin-1-yl)-5,6,7,8-tetrahydro-quinazolin-2-ylamine; (R,R)-4-(Hexahydro-pyrrolo[3,4-b]pyrrol-5-yl)-5A7,8-tetrahydro-quinazolin-2-ylamine; 4-(cis-Octahydro-pyrrolo[3,4-b]pyridin-6-yl)-5,6,7,8-tetrahydro-quinazolin-2-ylamine; (R,R)-4-(Octahydro-pyrrolo[3,4-b]pyridin-6-yl)-5,6,7,8-tetrahydro-quinazolin-2-ylamine; (S,S)-4-(2,5-Diaza-bicyclo[2.2.1]hept-2-yl)-5,6,7,8-tetrahydro-quinazolin-2-ylamine; 4-(4-Methyl-piperazin-1-yl)-6,7-dihydro-5H-cyclopentapyrimidin-2-ylamine; (R,R)-4-(4-Methylamino-pyrrolidin-1-yl-6,7-dihydro-5H-cyclopentapyrimidin-2-ylamine; 4-tert-Butyl-6-piperazin-1-yl-pyrimidin-2-ylamine; 4-tert-Butyl-6-(4-methyl-piperazin-1-yl)-pyrimidin-2-ylamine; (R)-4-tert-Butyl-6-(3-methylamino-pyrrolidin-1-yl)-pyrimidin-2-ylannine; (R,R)-4-tert-Butyl-6-(octahydro-pyrrolo[3,4-b]pyridin-6-yl)-pyrimidin-2-ylamine; (R)-4-(3-Amino-pyrrolidin-1-yl)-6-cyclopentyl-pyrimidin-2-ylamine; (R,R)-4-Cyclopentyl-6-(octahydro-pyrrolo[3,4-b]pyridin-6-yl)-pyrimidin-2-ylamine; 4-Cyclopentyl-6-(cis-5-methyl-hexahydro-pyrrolo[3,4-c]pyrrol-2-yl)-pyrimidin-2-ylamine; (R,R)-4-Cyclopentyl-6-(hexahydro-pyrrolo[3,4-b]pyrrol-5-yl)-pyrimidin-2-ylamine; 4-Cyclopentyl-6-(cis-1,7-diaza-spiro[4.4]non-7-yl)-pyrimidin-2-ylamine; 4-(3-Amino-azetidin-1-yl)-6-cyclopentyl-pyrimidin-2-ylamine; 4-Cyclopentyl-6-(trans-hexahydro-pyrrolo[3,4-b][1,4]oxazin-6-yl)-pyrimidin-2-ylamine; 4-Cyclopentyl-6-(hexahydro-pyrrolo[3,4-c]pyrrol-2-yl)-pyrimidin-2-ylamine; 4-Cyclopentyl-6-(cis-hexahydro-pyrrolo[3,4-b][1,4]oxazin-6-yl)-pyrimidin-2-ylamine; (2-Amino-ethyl)-6-isopropyl-pyrimidine-2,4-diamine; 4-(3-Amino-azetidin-1-yl)-6-isopropyl-pyrimidin-2-ylamine; 4-(1,7-Diaza-spiro[4.4]non-7-yl)-6-isopropyl-pyrimidin-2-ylamine; N4-(2-Amino-ethyl)-6-isopropyl-N4-methyl-pyrimidine-2,4-diamine; 4-(cis-Hexahydro-pyrrolo[3,4-b][1,4]oxazin-6-yl)-6-isopropyl-pyrimidin-2-ylamine; 4-(trans-Hexahydro-pyrrolo[3,4-b][1,4]oxazin-6-yl)-6-isopropyl-pyrimidin-2-ylamine; 4-Isopropyl-6-(4-methyl-piperazin-1-yl)-pyrimidin-2-ylamine; 4-(4-Methyl-piperazin-1-yl)-7,8-dihydro-5H-pyrano[4,3-d]pyrimidin-2-ylamine; (R,R)-4-(Octahydro-pyrrolo[3,4-b]pyridin-6-yl)-7,8-dihydro-5H-pyrano[4,3-d]pyrimidin-2-ylamine; (R)-4-(3-Amino-pyrrolidin-1-yl)-7,8-dihydro-5H-pyrano[4,3-d]pyrimidin-2-ylamine; (R)-4-(3-Methylamino-pyrrolidin-1-yl)-7,8-dihydro-5H-pyrano[4,3-d]pyrimidin-2-ylamine; 4-Piperazin-1-yl-7,8-dihydro-5H-pyrano[4,3-d]pyrimidin-2-ylamine; 4-Butyl-5-methoxy-6-piperazin-1-yl-pyrimidin-2-ylamine; 4-Butyl-6-[1,4]diazepan-1-yl-5-methoxy-pyrimidin-2-ylamine; 4-(3-Amino-azetidin-1-yl)-6-butyl-5-methoxy-pyrimidin-2-ylamine; (R)-4-(3-Amino-pyrrolidin-1-yl)-6-butyl-5-methoxy-pyrimidin-2-ylamine; (S)-4-(3-Amino-pyrrolidin-1-yl)-6-butyl-5-methoxy-pyrimidin-2-ylamine; (R)-4-Butyl-5-methoxy-6-(3-methylamino-pyrrolidin-1-yl)-pyrimidin-2-ylamine; (S)-4-Butyl-5-methoxy-6-(3-methylamino-pyrrolidin-1-yl)-pyrimidin-2-ylamine; 4-Butyl-5-methoxy-6-(4-methyl-piperazin-1-yl)-pyrimidin-2-ylamine; $N^4$-(2-Amino-ethyl)-6-butyl-5-methoxy-N4-methyl-pyrimidine-2,4-diamine; $N^4$-(2-Amino-ethyl)-6-butyl-5-methoxy-pyrimidine-2,4-diamine; 4-(3-Amino-azetidin-1-yl)-6-cyclopentyl-5-methoxy-pyrimidin-2-ylamine; 4-Cyclopentyl-6-[1,4]diazepan-1-yl-5-methoxy-pyrimidin-2-ylamine; (R)-4-(3-Amino-pyrrolidin-1-yl)-6-cyclopentyl-5-methoxy-pyrimidin-2-ylamine; (S)-4-Cyclopentyl-5-methoxy-6-(3-methylamino-pyrrolidin-1-yl)-pyrimidin-2-ylamine; $N^4$-(2-Amino-ethyl)-6-cyclopentyl-5-methoxy-$N^4$-methyl-pyrimidine-2,4-diamine; $N^4$-(2-Amino-ethyl)-6-cyclopentyl-5-methoxypyrimidine-2I4-diamine; 4-[1,4]Diazepan-1-yl)-6-methoxymethyl-pyrimidin-2-ylamine; (S)-4-(3-Amino-pyrrolidin-1-yl)-6-methoxymethyl-pyrimidin-2-ylamine; (S)-4-Methoxymethyl-6-(3-methylamino-pyrrolidin-1-yl)-pyrimidin-2-ylamine; 4-Cyclopropyl-6-(cis-5-methyl-hexahydro-pyrrolo[3,4-c]pyrrol-2-yl)-pyrimidin-2-ylamine; 4-Cyclopropyl-6-piperazin-1-yl-pyrimidin-2-ylamine; 4-(3-Amino-azetidin-1-yl)-6-cyclopropyl-pyrimidin-2-ylamine; (R)-4-(3-Amino-pyrrolidin-1-yl)-6-cyclopropyl-pyrimidin-2-ylamine; 4-Cyclopropyl-6-(cis-hexahydro-pyrrolo[3,4-c]pyrrol-2-yl)-pyrimidin-2-ylamine; (S)-4-isopropyl-6-(3-methylamino-pyrrolidin-1-yl)-pyrimidin-2-ylamine; (S)-4-(3-Amino-pyrrolidin-1-yl)-6-isopropyl-pyrimidin-2-ylamine; (R)-4-(3-Amino-pyrrolidin-1-yl)-6-tert-butyl-pyrimidin-2-ylamine; 4-tert-Butyl-6-(cis-5-methyl-hexahydro-pyrrolo[3,4-c]pyrrol-2-yl)-pyrimidin-2-ylamine; (S)-4-(3-Amino-pyrrolidin-1-yl)-6-tert-butyl-pyrimidin-2-ylamine; (S)-4-tert-Butyl-6-(3-methylamino-pyrrolidin-1-yl)-pyrimidin-2-ylamine; N4-(2-Amino-ethyl)-6-tert-butyl-N4-methyl-pyrimidine-2,4-diamine; 4-tert-Butyl-6-(cis-hexahydro-pyrrolo[3,4-c]pyrrol-2-yl)-pyrimidin-2-ylamine; 4-(3-Amino-azetidin-1-yl)-6-tert-butyl-pyrimidin-2-ylamine; 4-tert-Butyl-6-(3,8-diaza-bicyclo[3.2.1]oct-3-yl)-pyrimidin-2-ylamine; (R)-4-(3-Amino-pyrrolidin-1-yl)-6-butyl-pyrimidin-2-ylamine; 4-Butyl-6-(4-methyl-piperazin-1-yl)-pyrimidin-2-ylamine; (R)-4-Butyl-6-(3-methylamino-pyrrolidin-1-yl)-pyrimidin-2-ylamine; N4-(2-Amino-ethyl)-6-butyl-N$^4$-methyl-pyrimidine-2,4-diamine; 4-Butyl-6-(cis-5-methyl-hexahydro-pyrrolo[3,4-c]pyrrol-2-yl)-pyrimidin-2-ylamine; 4-Butyl-6-(cis-hexahydro-pyrrolo[3,4-c]pyrrol-2-yl)-pyrimidin-2-ylamine; 4-Butyl-6-(cis-octahydro-pyrrolo[3,4-b]pyridin-6-yl)-pyrimidin-2-ylamine; 4-Butyl-6-piperazin-1-yl-pyrimidin-2-ylamine; 4-Butyl-6-(3,8-diaza-bicyclo[3.2.1]oct-3-yl)-pyrimidin-2-ylamine; 4-(4-Methyl-piperazin-1-yl)-6-propyl-pyrimidin-2-ylamine; 4-(cis-5-Methyl-hexahydro-pyrrolo[3,4-c]pyrrol-2-yl)-6-propyl-pyrimidin-2-ylamine; 4-Isobutyl-6-(4-methyl-piperazin-1-yl)-pyrimidin-2-ylamine; 4-Isobutyl-6-piperazin-1-yl-pyrimidin-2-ylamine; (R)-4-isobutyl-6-(3-methylamino-pyrrolidin-1-yl)-pyrimidin-2-ylamine; (R)-4-(3-Amino-pyrrolidin-1-yl)-6-isobutyl-pyrimidin-2-ylamine; (S)-4-Ethyl-6-(3-methylamino-pyrrolidin-1-yl)-pyrimidin-2-ylamine; (R)-4-Adamantan-1-yl-6-(3-methylamino-pyrrolidin-1-yl)-pyrimidin-2-ylamine; 4-Adamantan-1-yl-6-(4-methyl-piperazin-1-yl)-pyrimidin-2-ylamine; 4-(4-Methyl-tetrahydro-pyran-4-yl)-6-piperazin-1-yl-pyrimidin-2-ylamine; 4-(4-Methyl-piperazin-1-yl)-6-(4-methyl-tetrahydro-pyran-4-yl)-pyrimidin-2-ylamine; (R)-4-(3-Methylamino-pyrrolidin-1-yl)-6-(4-methyl-tetrahydro-pyran-4-yl)-pyrimidin-2-ylamine; 4-(trans-2-Phenyl-cyclopropyl)-6-piperazin-1-yl-pyrimidin-2-ylamine; (R)-4-(3-Amino-pyrrolidin-1-yl)-6-(trans-2-phenyl-cyclopropyl)-pyrimidin-2-ylamine; 4-(4-Methyl-piperazin-1-yl)-6-(trans-2-phenyl-cyclopropyl)-pyrimidin-2-ylamine; N4-(2-Amino-ethyl)-6-(trans-2-phenyl-cyclopropyl)-pyrimidine-2,4-diamine; (R)-4-(3-Methylamino-pyrrolidin-1-yl)-6-(trans-2-phenyl-cyclopropyl)-pyrimidin-2-ylamine; 4-(3-Amino-azetidin-1-yl)-6-indan-2-yl-pyrimidin-2-ylamine; (R)-4-(3-Amino-pyrrolidin-1-yl)-6-indan-2-yl-pyrimidin-2-ylamine; 4-Indan-2-yl-6-(4-methyl-piperazin-1-yl)-pyrimidin-2-ylamine; (R)-4-Indan-2-yl-6-(3-methylamino-pyrrolidin-1-yl)-pyrimidin-2-ylamine; 4-Indan-2-yl-6-piperazin-1-yl-pyrimidin-2-ylamine; 4-(3-Amino-azetidin-1-yl)-6-benzyl-pyrimidin-2-ylannine; (R)-4-(3-Amino-pyrrolidin-1-yl)-6-benzyl-pyrimidin-2-ylamine; N4-(2-Amino-ethyl)-6-indan-2-yl-pyrimidine-2,4-diamine; (R)-4-(2,3-Dihydro-benzofuran-2-yl)-6-(3-methylamino-pyrrolidin-1-yl)-pyrimidin-2-ylamine; 4-(cis-Hexahydro-pyrrolo[3,4-c]pyrrol-2-yl)-6-(4-methyl-tetrahydro-pyran-4-yl)-pyrimidin-2-ylamine; 4-(2,3-Dihydro-benzofuran-2-yl)-6-piperazin-1-yl-pyrimidin-2-ylamine; 4-(3-Amino-azetidin-1-yl)-6-(2,3-dihydro-benzofuran-2-yl)-pyrimidin-2-ylamine; 4-(cis-Hexahydro-pyrrolo[3,4-c]pyrrol-2-yl)-6-indan-2-yl-pyrimidin-2-ylamine; (R)-4-(3-Amino-pyrrolidin-1-yl)-6-(4-methyl-tetrahydro-pyran-4-yl)-pyrimidin-2-ylamine; (R)-4-(3-Amino-pyrrolidin-1-yl)-6-(tetrahydro-pyran-4-yl)-pyrimidin-2-ylamine; N4-(2-Amino-ethyl)-6-(tetrahydro-pyran-4-yl)-pyrimidine-2,4-diamine; N4-(2-Amino-ethyl)-N4-methyl-6-(tetrahydro-pyran-4-yl)-pyrimidine-2,4-diamine; (R)-4-(3-Amino-pyrrolidin-1-yl)-6-phenethyl-pyrimidin-2-ylamine; 4-(4-Methyl-piperazin-1-yl)-6-phenethyl-pyrimidin-2-ylamine; (R)-4-(3-Methylamino-pyrrolidin-1-yl)-6-phenethyl-pyrimidin-2-ylamine; 4-(4-Methyl-piperazin-1-yl)-6-(3,3,3-trifluoro-propyl)-pyrimidin-2-ylamine; 4-Piperazin-1-yl-6-(3,3,3-trifluoro-propyl)-pyrimidin-2-ylamine; (R)-4-(3-Methylamino-pyrrolidin-1-yl)-6-(3,3,3-trifluoro-propyl)-pyrimidin-2-ylamine; (R)-4-(3-Amino-pyrrolidin-1-yl)-6-(3,3,3-trifluoro-propyl)-pyrimidin-2-ylamine; 4-Cyclopentyl-5-methoxy-6-(4-methyl-piperazin-1-yl)-pyrimidin-2-ylamine; 4-Cyclopentyl-5-methoxy-6-piperazin-1-yl-pyrimidin-2-ylamine; (R)-4-Cyclopentyl-5-methoxy-6-(3-methylamino-pyrrolidin-1-yl)-pyrimidin-2-ylamine; (R,R)-4-Cyclopentyl-5-methoxy-6-(octahydro-pyrrolo[3,4-b]pyridin-6-yl)-pyrimidin-2-ylamine; N4-(2-Amino-ethyl)-N4-methyl-6-(tetrahydro-furan-3-yl)-pyrimidine-2,4-diamine; 4-(cis-Octahydro-pyrrolo[3,4-b]pyridin-6-yl)-6-(tetrahydro-furan-3-yl)-pyrimidin-2-ylamine; (R)-4-(3-Methylamino-pyrrolidin-1-yl)-6-(tetrahydro-furan-3-yl)-pyrimidin-2-ylamine; 4-[1,4]Diazepan-1-yl-6-(tetrahydro-furan-3-yl)-pyrimidin-2-ylamine; (−)-4-Piperazin-1-yl-6-(tetrahydro-furan-3-yl)-pyrimidin-2-ylamine; (+)-4-Piperazin-1-yl-6-(tetrahydro-furan-3-yl)-pyrimidin-2-ylamine; N4-(2-Amino-ethyl)-6-(tetrahydro-furan-3-yl)-pyrimidine-2,4-diamine; N4-(3-Amino-propyl)-6-(tetrahydro-furan-3-yl)-pyrimidine-2,4-diamine; N4-Methyl-N4-(2-methylamino-ethyl)-6-(tetrahydro-furan-3-yl)-pyrimidine-2,4-diamine; N4-(2-Methylamino-ethyl)-6-(tetrahydro-furan-3-yl)-pyrimidine-2,4-diamine; 5-Fluoro-4-methyl-6-(4-methyl-piperazin-1-yl)-pyrimidin-2-ylamine; 5-Fluoro-4-methyl-6-(octahydro-pyrrolo[3,4-b]pyridin-6-yl)-pyrimidin-2-ylamine; 5-Fluoro-4-methyl-6-piperazin-1-yl-pyrimidin-2-ylamine; (R)-5-Fluoro-4-methyl-6-(3-methylarnino-pyrrolidin-1-yl)-pyrimidin-2-ylamine; N4-(2-Amino-ethyl)-5-fluoro-6,N4-dimethyl-pyrimidine-2,4-diamine; 4-Piperazin-1-yl-6-pyridin-4-ylmethyl-pyrimidin-2-ylamine; (R)-4-(3-Methylamino-pyrrolidin-1-yl)-6-pyridin-4-ylmethyl-pyrimidin-2-ylamine; 4-(4-Methyl-piperazin-1-yl)-6-pyridin-4-ylmethyl-pyrimidin-2-ylamine; 4-(4-Methyl-piperazin-1-yl)-6-thiophen-3-ylmethyl-pyrimidin-2-ylamine; (R)-4-(3-Methylamino-pyrrolidin-1-yl)-6-thiophen-3-ylmethyl-pyrimidin-2-ylamine; 4-Piperazin-1-yl-6-thiophen-3-ylmethyl-pyrimidin-2-ylamine; (R)-4-(3-Amino-pyrrolidin-1-yl)-6-thiophen-3-ylmethyl-pyrimidin-2-ylamine; 4-(cis-Octahydro-pyrrolo[3,4-b]pyridin-6-yl)-6-thiophen-3-ylmethyl-pyrimidin-2-ylamine; N$^4$-(2-Amino-ethyl)-6-thiophen-3-ylmethyl-pyrimidine-2,4-diamine; 4-(4-Methyl-piperazin-1-yl)-6-thiophen-2-ylmethyl-pyrimidin-2-ylamine; (R)-4-(3-Methylamino-pyrrolidin-1-yl)-6-thiophen-2-ylmethyl-pyrimidin-2-ylamine; 4-Piperazin-1-yl-6-thiophen-2-ylmethyl-pyrimidin-2-ylamine; (R)-4-(3-Amino-pyrrolidin-1-yl)-6-thiophen-2-ylmethyl-pyrimidin-2-ylamine; 4-(cis-Octahydro-pyrrolo[3,4-b]pyridin-6-yl)-6-thiophen-2-ylmethyl-pyrimidin-2-ylamine; N$^4$-(2-Aminoethyl)-6-thiophen-2-ylmethyl-pyrimidine-2,4-diamine; N⁴-(2-Amino-ethyl)-6-methoxymethyl-pyrimidine-2,4-diamine; 4-(3-Amino-azetidin-1-yl)-6-methoxymethyl-pyrimidin-2-ylamine; (R)-4-Methoxymethyl-6-(3-methylamino-pyrrolidin-1-yl)-pyrimidin-2-ylamine; (R)-4-(3-Amino-pyrrolidin-1-yl)-6-methoxymethyl-pyrimidin-2-ylamine; 4-Methoxymethyl-6-(4-methyl-piperazin-1-yl)-pyrimidin-2-ylamine; 4-Methoxymethyl-6-piperazin-1-yl-pyrimidin-2-ylamine; (R)-4-(3-Amino-piperidin-1-yl)-6-methoxymethyl-pyrimidin-2-ylamine; (R,R)-4-Methoxymethyl-6-(octahydro-pyrrolo[3,4-b]pyridin-6-yl)-pyrimidin-2-ylamine; 4-(4-Methyl-piperazin-1-yl)-6-(tetrahydro-furan-2-ylmethyl)-pyrimidin-2-ylamine; (R)-4-(3-Methylamino-pyrrolidin-1-yl)-6-(tetrahydro-furan-2-ylmethyl)-pyrimidin-2-ylamine; 4-(cis-5-Methyl-hexahydro-pyrrolo[3,4-c]pyrrol-2-yl)-6-(tetrahydro-furan-2-ylmethyl)-pyrimidin-2-ylamine; 4-Piperazin-1-yl-6-(tetrahydro-furan-2-ylmethyl)-pyrimidin-2-ylamine; 4-(cis-Octahydro-pyrrolo[3,4-b]pyridin-6-yl)-6-(tetrahydro-furan-2-ylmethyl)-pyrimidin-2-ylamine; 4-(4-Chloro-benzyl)-6-(4-methyl-piperazin-1-yl)-pyrimidin-2-ylamine; 4-(4-Chloro-benzyl)-6-piperazin-1-yl-pyrimidin-2-ylamine; (R)-4-(4-Chloro-benzyl)-6-(3-methylamino-pyrrolidin-1-yl)-pyrimidin-2-ylamine; (R)-4-(3-Amino-pyrrolidin-1-yl)-6-(4-chloro-benzyl)-pyrimidin-2-ylamine; 4-(4-Chloro-benzyl)-6-(cis-5-methyl-hexahydro-pyrrolo[3,4-c]pyrrol-2-yl)-pyrimidin-2-ylamine; 4-(4-Chloro-benzyl)-6-(cis-hexahydro-pyrrolo[3,4-c]pyrrol-2-yl)-pyrimidin-2-ylamine; N4-(2-Amino-ethyl)-6-(4-chloro-benzyl)-N4-methyl-pyrimidine-2,4-diamine; 4-Ethyoxymethyl-6-(4-methyl-piperazin-1-yl)-pyrimidin-2-ylamine; 4-Ethoxymethyl-6-piperazin-1-yl-pyrimidin-2-ylamine; (R)-Ethoxymethyl-6-(3-methylamino-pyrrolidin-1-yl)-pyrimidin-2-ylamine; (R)-Ethoxymethyl-6-(3-amino-pyrrolidin-1-yl)-pyrimidin-2-ylamine; Isopropoxymethyl-6-((R)-3-methylamino-pyrrolidin-1-yl)-pyrimidin-2-ylamine; 4-Isopropoxymethyl-6-piperazin-1-yl-pyrimidin-2-ylamine; (R)-Isopropoxymethyl-6-(3-amino-pyrrolidin-1-yl)-pyrimidin-2-ylamine; 4-Isopropoxymethyl-6-(4-methyl-piperazin-1-yl)-pyrimidin-2-ylamine; 4-Phenethyl-6-piperazin-1-yl-pyrimidin-2-ylamine; 4-(3-Amino-azetidin-1-yl)-6-phenethyl-pyrimidin-2-ylamine; (R)-4-(3-Amino-pyrrolidin-1-yl)-6-(tetrahydro-pyran-4-yl)-pyrimidin-2-ylamine; N⁴-(2-Amino-ethyl)-6-benzyl-N4-methyl-pyrimidine-2,4-diamine; 4-Indan-2-yl-6-(octahydro-pyrrolo[3,4-b]pyridin-6-yl)-pyrimidin-2-ylamine; 4-(3-Amino-azetidin-1-yl)-7,8-dihydro-5H-pyrano[4,3-d]pyrimidin-2-ylamine; 4-(3-Amino-azetidin-1-yl)-5,6,7,8-tetrahydro-quinazolin-2-ylamine; 4-(cis-5-Methyl-hexahydro-pyrrolo[3,4-c]pyrrol-2-yl)-7,8-dihydro-5H-pyrano[4,3-d]pyrimidin-2-ylamine; (R)-4-(3-Methylamino-pyrrolidin-1-yl)-6-phenyl-cyclopropyl)-pyrimidin-2-ylamine (diastereomer 1); (R)-4-(3-Methylamino-pyrrolidin-1-yl)-6-(2-phenyl-cyclopropyl)-pyrimidin-2-ylamine (diastereomer 2); 4-Cyclopentyl-6-(cis-1,7-diaza-spiro[4.4]non-7-yl)-pyrimidin-2-ylamine (enantiomer 1); 4-Cyclopentyl-6-(cis-1,7-diaza-spiro[4.4]non-7-yl)-pyrimidin-2-ylamine (enantiomer 2); (R)-4-lsopropoxymethyl-6-(3-methyl-amino-pyrrolidin-1-yl)-pyrimidin-2-ylamine; (R)-4-(3-Amino-pyrrolidin-1-yl)-6-isopropoxymethyl-pyrimidin-2-ylamine; 4-lsopropoxymethyl-6-piperazin-1-yl-pyrimidin-2-ylamine; 4-lsopropoxymethyl-6-(4-methyl-piperazin-1-yl)-pyrimidin-2-ylamine; 4-(3-Amino-azetidin-1-yl)-6-isopropoxymethyl-pyrimidin-2-ylamine; 4-Isopropoxymethyl-6-(8-methyl-3,8-diaza-bicyclo[3.2.1]oct-3-yl)-pyrimidin-2-ylamine; (R)-4-Cyclopropoxymethyl-6-(3-methylamino-pyrrolidin-1-yl)-pyrimidin-2-ylamine; (R)-(4-Amino-pyrrolidin-1-yl)-6-cyclopropoxymethyl-pyrimidin-2-ylamine; 4-Cyclopropoxymethyl-6-piperazin-1-yl-pyrimidin-2-ylamine; 4-Cyclopropoxymethyl-6-(4-methyl-piperazin-1-yl)-pyhmidin-2-ylamine; 4-(3-Amino-azetidin-1-yl)-6-cyclopropoxymethyl-pyrimidin-2-ylamine; 4-Cyclopropoxymethyl-6-(8-methyl-3,8-diaza-bicyclo[3.2.1]oct-3-yl)-pyrimidin-2-ylamine; (R)-4-tert-Butoxymethyl-6-(3-methylamino-pyrrolidin-1-yl)-pyrimidin-2-ylamine; (R)-4-(3-Amino-pyrrolidin-1-yl)-6-tert-butoxymethyl-pyhmidin-2-ylamine; 4-tert-Butoxymethyl-6-piperazin-1-yl-pyrimidin-2-ylamine; 4-tert-Butoxymethyl-6-(4-methyl-piperazin-1-yl)-pyrimidin-2-ylamine; 4-(3-Amino-azetidin-1-yl)-6-tert-butoxymethyl-pyrimidin-2-ylamine; 4-tert-Butoxymethyl-6-(8-methyl-3,8-diaza-bicyclo[3.2.1]oct-3-yl)-pyrimidin-2-ylamine; 4-Ethyl-6-(8-methyl-3,8-diaza-bicyclo[3.2.1]oct-3-yl)-pyrimidin-2-ylamine; 4-(8-Methyl-3,8-diaza-bicyclo[3.2.1]oct-3-yl)-6-propyl-pyrimidin-2-ylamine; 4-Isopropyl-6-(8-methyl-3,8-diaza-bicyclo[3.2.1]oct-3-yl)-pyrimidin-2-ylamine; 4-Cyclopentyl-6-(8-methyl-3,8-diaza-bicyclo[3.2.1]oct-3-yl)-pyrimidin-2-ylamine; and pharmaceutically acceptable salts thereof.

In another embodiment, the Histamine H4 antagonist or selective Histamine H4 antagonists are selected from those described in the international Patent Application WO2008/008359: 8-Chloro-4-(4-methyl-piperazin-1-yl)-benzo[4,5]furo[3,2-d]pyrimidin-2-ylamine; 6,8-Dichloro-4-(octahydro-pyrrolo[3,4-b]pyridin-6-yl)-benzo[4,5]furo[3,2-d]pyrimidin-2-ylamine; 8-Chloro-4-(4-isopropyl-[1,4]diazepan-1-yl)-benzo[4,5]furo[3,2-d]pyrimidin-2-ylamine; 4-(3-Amino-pyrrolidin-1-yl)-6,8-dichloro-benzo[4,5]furo[3,2-d]pyrimidin-2-ylamine; (R)-6,8-Dichloro-4-(3-methyl-amino-pyrrolidin-1-yl)-benzo[4,5]furo[3,2-d]pyrimidin-2-ylamine; (R)-4-(3-Methylamino-pyrrolidin-1-yl)-benzo[4,5]furo[3,2-d]pyrimidin-2-ylamine; 8-Chloro-4-[1,4]diazepan-1-yl-benzo[4,5]furo[3,2-d]pyrimidin-2-ylamine; 8-Chloro-4-(octahydro-pyrido[1,2-a]pyrazin-2-yl)-benzo[4,5]furo[3,2-d]pyrimidin-2-ylamine; 8-Chloro-8-(otahydro-pyrrolo[3,4-b]pyridin-6-yl)-benzo[4,5]furo[3,2-d]pyrimidin-2-ylamine; 8-Chloro-4-(4-methyl-[1,4]diazepan-1-yl)-benzo[4,5]furo[3,2-d]pyrimidin-2-ylamine; (S,S)-8-Chloro-4-(2,5-diaza-bicyclo[2.2.1]hept-2-yl)-benzo[4,5]furo[3,2-d]pyrimidin-2-ylamine; 8-Chloro-4-(3-methylamino-pyrrolidin-1-yl)-benzo[4,5]furo[3,2-d]pyrimidin-2-ylamine; (S)-4-(3-Amino-piperidin-1-yl)-8-chloro-benzo[4,5]furo[3,2-d]pyrimidin-2-ylamine; 8-Chloro-4-piperazin-1-yl-benzo[4,5]furo[3,2-d]pyrimidin-2-ylamine; 8-Chloro-4-(3-dimethylamino-pyrrolidin-1-yl)-benzo[4,5]furo[3,2-d]pyrimidin-2-ylamine; 4-(3-Amino-pyrrolidin-1-yl)-8-chloro-benzo[4,5]furo[3,2-d]pyrimidin-2-ylamine; (S)-8-Chloro-4-(3-methylamino-pyrrolidin-1-yl)-benzo[4,5]furo[3,2-d]pyrimidin-2-ylamine; (R)-8-Chloro-4-(3-methylamino-pyrrolidin-1-yl)-benzo[4,5]furo[3,2-d]pyrimidin-2-ylamine; (R)-8-Bromo-4-(3-methylamino-pyrrolidin-1-yl)-benzo[4,5]furo[3,2-d]pyrimidin-2-ylamine; 8-Bromo-4-(hexahydro-pyrrolo[1,2-a]pyrazin-2-yl)-benzo[4,5]furo[3,2-d]pyrimidin-2-ylamine; 4-(3-Amino-pyrrolidin-1-yl)-benzo[4,5]furo[3,2-d]pyrimidin-2-ylamine; (R)-4-(3-Dimethylamino-pyrrolidin-1-yl)-benzo[4,5]furo[3,2-d]pyrimidin-2-ylamine; 4-Piperazin-1-yl-benzo[4,5]furo[3,2-d]pyrimidin-2-ylamine; (R)-8-Chloro-4-(3-dimethylamino-pyrrolidin-1-yl)-benzo[4,5]furo[3,2-d]pyrimidin-2-ylamine; (R)-4-(3-Amino-pyrrolidin-1-yl)-8-chloro-benzo[4,5]furo[3,2-d]pyrimidin-2-ylamine; (S)-4-(3-Aminomethyl-pyrrolidin-1-yl)-8-chloro-benzo[4,5]furo[3,2-d]pyrimidin-2-ylamine; 8-Chloro-4-(hexahydro-pyrrolo[3,4-c]pyrrol-2-yl)-benzo[4,5]furo[3,2-d]pyrimidin-2-ylamine; (R)-4-(3-Amino-piperidin-1-yl)-8-chloro-benzo[4,5]furo[3,2-d]

pyrimidin-2-ylamine; 4-(3-Aminomethyl-pyrrolidin-1-yl)-8-chloro-benzo[4,5]furo[3,2-d]pyrimidin-2-ylamine; (R)-4-(3-Aminomethyl-pyrrolidin-1-yl)-8-chloro-benzo[4,5]furo[3,2-d]pyrimidin-2-ylamine; 6,8-Dichloro-4-piperazin-1-yl-benzo[4,5]furo[3,2-d]pyrimidin-2-ylamine; 6,8-Dichloro-4-[1,4]diazepan-1-yl-benzo[4,5]furo[3,2-d]pyrimidin-2-ylamine; (S,S)-4-(2,5-Diaza-bicyclo[2.2.1]hept-2-yl)-benzo[4l5]furo[3,2-d]pyrimidin-2-ylamine; 8-Chloro-4-(4-isopropyl-piperazin-1-yl)-benzo[4,5]furo[3,2-d]pyrimidin-2-ylamine; 6,8-Dichloro-4-(3-dimethylamino-pyrrolidin-1-yl)-benzo[4,5]furo[3,2-d]pyrimidin-2-ylamine; 4-(Octahydro-pyrido[1,2-a]pyrazin-2-yl)-benzo[4,5]furo[3,2-d]pyrimidin-2-ylamine; 6,8-Dichloro-4-(octahydro-pyrido[1,2-a]pyrazin-2-yl)-benzo[4,5]furo[3,2-d]pyrimidin-2-ylamine; (S,S)-6,8-Dichloro-4-(2,5-diaza-bicyclo[2.2.1]hept-2-yl)-benzo[4,5]furo[3,2-d]pyrimidin-2-ylamine; (R)-8-Fluoro-4-(3-methylamino-pyrrolidin-1-yl)-benzo[4,5]furo[3,2-d]pyrimidin-2-ylamine; 8-Fluoro-4-(hexahydro-pyrrolo[1,2-a]pyrazin-2-yl)-benzo[4,5]furo[3,2-d]pyrimidin-2-ylamine; 8-Fluoro-N$^4$-methyl-N$^4$-(1-methyl-pyrrolidin-3-yl)-benzo[4,5]furo[3,2-d]pyrimidine-2,4-diamine; (R)-8-(3-Methylamino-pyrrolidin-1-yl)-9-oxa-1,5,7-triaza-fluoren-6-ylamine; 8-(Octahydro-pyrrolo[3,4-b]pyridin-6-yl)-9-oxa-1,5,7-triaza-fluoren-6-ylamine; 4-(4-Methyl-piperazin-1-yl)-benzo[4,5]thieno[3,2-d]pyrimidin-2-ylamine; 8-Bromo-4-(octahydro-pyrrolo[3,4-b]pyridin-6-yl)-benzo[4,5]thieno[3,2-d]pyrimidin-2-ylamine; 7-Bromo-4-(octahydro-pyrrolo[3,4-b]pyridin-6-yl)-benzo[4,5]thieno[3,2-d]pyrimidin-2-ylamine; (S)-8-Bromo-4-(3-methylamino-pyrrolidin-1-yl)-benzo[4,5]thieno[3,2-d]pyrimidin-2-ylamine; (R)-8-Bromo-4-(3-methylamino-pyrrolidin-1-yl)-benzo[4,5]thieno[3,2-d]pyrimidin-2-ylamine; (S,S)-8-Bromo-4-(2,5-diaza-bicyclo[2.2.1]hept-2-yl)-benzo[4,5]thieno[3,2-d]pyrimidin-2-ylamine; 8-Bromo-4-(4-methyl-piperazin-1-yl)-benzo[4,5]thieno[3,2-d]pyrimidin-2-ylamine; (S)-4-(3-Methylamino-pyrrolidin-1-yl)-7-trifluoromethyl-benzo[4,5]thieno[3,2-d]pyrimidin-2-ylamine; (R)-4-(3-Methylamino-pyrrolidin-1-yl)-7-trifluoromethyl-benzo[4,5]thieno[3,2-d]pyrimidin-2-ylamine; (S,S)-4-(2,5-Diaza-bicyclo[2.2.1]hept-2-yl)-7-trifluoromethyl-benzo[4,5]thieno[3,2-d]pyrimidin-2-ylamine; 4-(4-Methyl-piperazin-1-yl)-7-trifluoromethyl-benzo[4,5]thieno[3,2-d]pyrimidin-2-ylamine; 7-Bromo-4-(4-methyl-piperazin-1-y])-benzo[4,5]thieno[3,2-d]pyrimidin-2-ylamine; (R)-7-Bromo4-(3-methylamino-pyrrolidin-1-yl)-benzo[4,5]thieno[3,2-d]pyrimidin-2-ylamine; (S)-7-Bromo-4-(3-methylamino-pyrrolidin-1-yl)-benzo[4,5]thieno[3,2-d]pyrimidin-2-ylamine; 4-(Octahydro-pyrrolo[3,4-b]pyridin-6-yl)-7-trifluoromethyl-benzo[4,5]thieno[3,2-d]pyrimidin-2-ylamine; 7-Chloro-4-(octahydro-pyrrolo[3,4-b]pyridin-6-yl)-benzo[4,5]thieno[3,2-d]pyrimidin-2-ylamine; (R)-7-Chloro-4-(3-methylamino-pyrrolidin-1-yl)-benzo[4,5]thieno[3,2-d]pyrimidin-2-ylamine; (S)-7-Chloro-4-(3-methylamino-pyrrolidin-1-yl)-benzo[4,5]thieno[3,2-d]pyrimidin-2-ylamine; (S,S)-7-Chloro-4-(2,5-diaza-bicyclo[2.2.1]hept-2-yl)-benzo[4l5]thieno[3,2-d]pyrimidin-2-ylamine; 7-Chloro-4-(4-methyl-piperazin-1-yl)-benzo[4,5]thieno[3,2-d]pyrimidin-2-ylamine; 8-Chloro-4-(octahydro-pyrrolo[3,4-b]pyridin-6-yl)-benzo[4,5]thieno[3,2-d]pyrimidin-2-ylamine; (S)-8-Chloro-4-(3-methylamino-pyrrolidin-1-yl)-benzo[4,5]thieno[3,2-d]pyrimidin-2-ylamine; (R)-8-Chloro-4-(3-methylamino-pyrrolidin-1-yl)-benzo[4,5]thieno[3,2-d]pyrimidin-2-ylamine; 8-Chloro-4-(4-methyl-piperazin-1-yl)-benzo[4,5]thieno[3,2-d]pyrimidin-2-ylamine; (S,S)-8-Chloro-4-(2,5-diaza-bicyclo[2.2.1]hept-2-yl)-benzo[4,5]thieno[3,2-d]pyrimidin-2-ylamine; 8-Chloro-4-(hexahydro-pyrrolo[1,2-a]pyrazin-2-yl)-benzo[4,5]furo[3,2-d]pyrimidin-2-ylamine; 8-Fluoro-4-(4-methyl-piperazin-1-yl)-benzo[4,5]thieno[3,2-d]pyrimidin-2-ylamine; 8-Fluoro-4-(hexahydro-pyrrolo[3,4-b]pyrrol-5-yl)-benzo[4,5]furo[3,2-d]pyrimidin-2-ylamine; (S)-8-Chloro-4-(3-ethylamino-piperidin-1-yl)-benzo[4,5]furo[3,2-d]pyrimidin-2-ylamine; (R)-8-Chloro-4-(3-ethylamino-pyrrolidin-1-yl)-benzo[4,5]furo[3,2-d]pyrimidin-2-ylamine; (S)-8-Chloro-4-(3-methyl-amino-piperidin-1-yl)-benzo[4,5]furo[3,2-d]pyrimidin-2-ylamine; (S)-8-Chloro-4-(3-dimethylamino-piperidin-1-yl)-benzo[4,5]furo[3,2-d]pyrimidin-2-ylamine; (R)-8-Fluoro-4-(3-methylamino-pyrrolidin-1-yl)-benzo[4,5]thieno[3,2-d]pyrimidin-2-ylamine; (S,S)-7-Bromo-4-(2,5-diaza-bicyclop[2.2.1]hept-2-yl)-benzo[4,5]thieno[3,2-d]pyrimidin-2-ylamine; 4-(6-Amino-3-aza-bicyclo[3.1.0]hex-3-yl)-8-chloro-benzo[4,5]furo[3,2-d]pyrimidin-2-ylamine; (R)-4-(2-Aminomethyl-pyrrolidin-1-yl)-8-chloro-benzo[4,5]furo[3,2-d]pyrimidin-2-ylamine; 8-Chloro-4-(hexahydro-pyrrolo[3,4-b]pyrrol-5-yl)-benzo[4,5]furo[3,2-d]pyrimidin-2-ylamine; (R,R)-8-Chloro-4-(2,6-diaza-bicyclo[2.2.1]hept-2-yl)-benzo[4,5]furo[3,2-d]pyrimidin-2-ylamine; (R,R)-8-Chloro-4-(octahydro-pyrrolo[3,4-b]pyridin-6-yl)-benzo[4,5]furo[3,2-d]pyrimidin-2-ylamine; 8-Chloro-4-(octahydro-pyrrolo[3,4-b]pyridin-6-yl)-benzo[4,5]furo[3,2-d]pyrimidin-2-ylamine; (R)-4-(3-Methylamino-pyrrolidin-1-yl)-9-trifluoromethyl-benzo[4,5]furo[3,2-d]pyrimidin-2-ylamine; (S,S)-4-(2,5-Diaza-bicyclo[2.2.1]hept-2-yl)-9-methoxy-benzo[4,5]furo[3,2-d]pyrimidin-2-ylamine; 9-Methoxy-4-piperazin-1-yl-benzo[4,5]furo[3,2-d]pyrimidin-2-ylamine; (S)-4-(3-Amino-piperidin-1-yl)-9-methoxy-benzo[4,5]furo[3,2-d]pyrimidin-2-ylamine; 9-Methoxy-4-(4-methyl-piperazin-1-yl)-benzo[4,5]furo[3,2-d]pyrimidin-2-ylamine; 8-Methoxy-4-(4-methyl-piperazin-1-yl)-benzo[4,5]furo[3,2-d]pyrimidin-2-ylamine; 4-Piperazin-1-yl-9-trifluoromethyl-benzo[4,5]furo[3,2-d]pyrimidin-2-ylamine; 4-(4-Methyl-piperazin-1-yl)-9-trifluoromethyl-benzo[4,5]furo[3,2-d]pyrimidin-2-ylamine; (S)-4-(3-Amino-piperidin-1-yl)-9-trifluoromethyl-benzo[4,5]furo[3,2-d]pyrimidin-2-ylamine; (S)-4-(3-Amino-piperidin-1-yl)-8,9-dichloro-benzo[4,5]furo[3,2-d]pyrimidin-2-ylamine; (S,S)-4-(2,5-Diaza-bicyclo[2.2.1]hept-2-yl)-9-trifluoromethyl-benzo[4,5]furo[3,2-d]pyrimidin-2-ylamine; (cis)-8-Chloro-4-(hexahydro-pyrrolo[3,4-b]pyrrol-1-yl)-benzo[4,5]furo[3,2-d]pyrimidin-2-ylamine; N4-(2-Amino-ethyl)-8-chloro-N4-methyl-benzo[4,5]furo[3,2-d]pyrimidine-2,4-diamine; 8-Chloro-4-(3,8-diaza-bicyclo[3.2.1]oct-3-yl)-benzo[4,5]furo[3,2-d]pyrimidin-2-ylamine; (S,S)-8,9-Dichloro-4-(2,5-diaza-bicyclo[2.2.1]hept-2-yl)-benzo[4,5]furo[3,2-d]pyrimidin-2-ylamine; (R)-8,9-Dichloro-4(3-methylamino-pyrrolidin-1-yl)-benzo[4,5]furo[3,2-d]pyrimidin-2-ylamine; (R)-9-Methoxy-4-(3-methylamino-pyrrolidin-1-yl)-benzo[4,5]furo[3,2-d]pyrimidin-2-ylamine; 8,9-Dichloro-4-(4-methyl-piperazin-1-yl)-benzo[4,5]furo[3,2-d]pyrimidin-2-ylamine; (R)-8-Methoxy-4-(3-methylamino-pyrrolidin-1-yl)-benzo[4,5]furo[3,2-d]pyrimidin-2-ylamine; 4-(3-Aminomethyl-azetidin-1-yl)-8-chloro-benzo[4,5]furo[3,2-d]pyrimidin-2-ylamine; 8,9-Dichloro-4-piperazin-1-yl-benzo[4,5]furo[3,2-d]pyrimidin-2-ylamine; (cis)-8-Methoxy-4-(octahydro-pyrrolo[3,4-b]pyridin-6-yl-benzo[4,5]furo[3,2-d]pyrimidin-2-ylamine; (S,S)-8-Chloro-4-(5-methyl-2,5-diaza-bicyclo[2.2.1]hept-2-yl)-benzo[4,5]furo[3,2-d]pyrimidin-2-ylamine; (S)-4-(3-Amino-piperidin-1-yl)-8-methoxy-benzo[4,5]furo[3,2-d]pyrimidin-2-ylamine; (R)-4-(3-Amino-pyrrolidin-1-yl)-benzo[4,5]furo[3,2-d]pyrimidin-2-ylamine; (R)-3-Chloro-8-(3-methylamino-pyrrolidin-1-yl)-9-oxa-1,5,7-triaza-fluoren-6-ylamine; N$^4$-Azetidin-3-ylmethyl-8-chloro-benzo[4,5]furo[3,2-d]pyrimidine- 2,4-diamine; N⁴-Azetidin-3-yl-8-chloro-benzo[4,5]furo[3,2-d]pyrimidine-2,4-diamine; N⁴-(2-Amino-ethyl)-8-chloro-benzo[4,5]furo[3,2-d]pyrimidine-2,4-diamine; (S,S)-4-(2,5-Diaza-bicyclo[2.2.1]hept-2-yl)-8-methoxy-benzo[4,5]furo[3,2-d]pyrimidin-2-ylamine; (cis)-4-(Hexahydro-pyrrolo[3,4-b]pyrrol-5-yl)-8-methoxy-benzo[4,5]furo[3,2-d]pyrimidin-2-ylamine; 2-[8-Chloro-4-(4-methyl-piperazin-1-yl)-benzo[4,5]furo[3,2-d]pyrimidin-2-ylamino]-ethanol; 2-[4-(4-Methyl-piperazin-1-yl)-benzo[4,5]furo[3,2-d]pyrimidin-2-ylamino]-ethanol; (cis)-2-[8-Chloro-4-octahydro-pyrrol[3,4-b]pyridin-6-yl)-benzo[4,5]furo[3,2-d]pyrimidin-2-ylamino]-ethanol; 2-[8-Methoxy-4-(4-methyl-piperazin-1-yl)-benzo[4,5]furo[3,2-d]pyrimidin-2-ylamino]-ethanol; [8-Chloro-4-(4-methyl-piperazin-1-yl)-benzo[4,5]furo[3,2-d]pyrimidin-2-yl]-cyclopropyl-amine; [8-Chloro-4-(4-methyl-piperazin-1-yl)-benzo[4,5]furo[3,2-d]pyrimidin-2-yl]-isobutyl-amine; Allyl-[8-chloro-4-(4-methyl-piperazin-1-yl)-benzo[4,5]furo[3,2-d]pyrimidin-2-yl]-amine; N¹-[8-Chloro-4-(4-methyl-piperazin-1-yl)-benzo[4,5]furo[3,2-d]pyrimidin-2-yl]-propane-1,3-diamine; [8-Chloro-4-(4-methyl-piperazin-1-yl)-benzo[4,5]furo[3,2-d]pyrimidin-2-yl]-(2-methylsulfanyl-ethyl)-amine; [8-Chloro-4-(4-methyl-piperazin-1-yl)-benzo[4,5]furo[3,2-d]pyrimidin-2-yl]-methyl-amine; (S,S)-2-[8-Chloro-4-(2,5-diaza-bicyclo[2.2.1]hept-2-yl)-benzo[4,5]furo[3,2-d]pyrimidin-2-ylamino]-ethanol; 2-[8-Chloro-4-(3-methylamino-pyrrolidin-1-yl)-benzo[4,5]furo[3,2-d]pyrimidin-2-ylamino]-ethanol; 2-[8-Chloro-4-(4-methyl-[1,4]diazepan-1-yl)-benzo[4,5]furo[3,2-d]pyrimidin-2-ylamino]-ethanol; 8-Chloro-4-(3,5-dimethyl-piperazin-1-yl)-benzo[4,5]furo[3,2-d]pyrimidin-2-ylamine; 4-(3-Amino-azetidin-1-yl)-8-chloro-benzo[4,5]furo[3,2-d]pyrimidin-2-ylamine; (2S,5R)-8-Chloro-4-(2,5-dimethyl-piperazin-1-yl)-benzo[4,5]furo[3,2-d]pyrimidin-2-ylamine; (S)-8-Chloro-4-(2-methyl-piperazin-1-yl)-benzo[4,5]furo[3,2-d]pyrimidin-2-ylamine; (R)-8-Chloro-4-(2-methyl-piperazin-1-yl)-benzo[4,5]furo[3,2-d]pyrimidin-2-ylamine; (S)-8-Chloro-4-(5-methyl-piperazin-1-yl)-benzo[4,5]furo[3,2-d]pyrimidin-2-ylamine; (R)-8-Chloro-4-(5-methyl-piperazin-1-yl)-benzo[4,5]furo[3,2-d]pyrimidin-2-ylamine; 9-Fluoro-4-(4-methyl-piperazin-1-yl)-benzo[4,5]furo[3,2-d]pyrimidin-2-ylamine; (R)-9-Fluoro-4-(3-methylamino-pyrrolidin-1-yl)-benzo[4,5]furo[3,2-d]pyrimidin-2-ylamine; 9-Fluoro-4-piperazin-1-yl-benzo[4,5]furo[3,2-d]pyrimidin-2-ylamine; 4-(3-Amino-azetidin-1-yl)-9-fluoro-benzo[4,5]furo[3,2-d]pyrimidin-2-ylamine; 4-(4-Methyl-piperazin-1-yl)-8-trifluoromethyl-benzo[4,5]furo[3,2-d]pyrimidin-2-ylamine; (R)-4-(3-Methylamino-pyrrolidin-1-yl)-8-trifluoromethyl-benzo[4,5]furo[3,2-d]pyrimidin-2-ylamine; (S)-4-(3-Amino-piperidin-1-yl)-8-trifluoromethyl-benzo[4,5]furo[3,2-d]pyrimidin-2-ylamine; 4-Piperazin-1-yl-8-trifluoromethyl-benzo[4,5]furo[3,2-d]pyrimidin-2-ylamine; (S,S)-4,2,5-Diaza-bicyclo[2.2.1]hept-2-yl)-8-trifluoromethyl-benzo[4,5]furo[3,2-d]pyrimidin-2-ylamine; 4-(3-Amino-azetidin-1-yl)-8-trifluoromethyl-benzo[4,5]furo[3,2-d]pyrimidin-2-ylamine; 8,9-Difluoro-4-(4-methyl-piperazin-1-yl)-benzo[4,5]furo[3,2-d]pyrimidin-2-ylamine; 8,9-Difluoro-4-piperazin-1-yl-benzo[4,5]furo[3,2-d]pyrimidin-2-ylamine; (S)-4-(3-Amino-piperidin-1-yl)-8,9-difluoro-benzo[4,5]furo[3,2-d]pyrimidin-2-ylamine; (R)-8,9-Difluoro-4-(3-methylamino-pyrrolidin-1-yl)-benzo[4,5]furo[3,2-d]pyrimidin-2-ylamine; (S,S)-4-(2,5-Diaza-bicyclo[2.2.1]hept-2-yl)-8,9-difluoro-benzo[4,5]furo[3,2-d]pyrimidin-2-ylamine; 4-(3-Amino-azetidin-1-yl)-8,9-difluoro-benzo[4,5]furo[3,2-d]pyrimidin-2-ylamine; 9-Chloro-4-(4-methyl-piperazin-1-yl)-benzo[4,5]furo[3,2-d]pyrimidin-2-ylamine; (R)-9-Chloro-4-(3-methylamino-pyrrolidin-1-yl)-benzo[4,5]furo[3,2-d]pyrimidin-2-ylamine; 9-Chloro-4-piperazin-1-yl-benzo[4,5]furo[3,2-d]pyrimidin-2-ylamine; (S)-4-(3-Amino-piperidin-1-yl)-9-chloro-benzo[4,5]furo[3,2-d]pyrimidin-2-ylamine; (S,S)-9-Chloro-4-(2I5-diaza-bicyclo[2.2.1]hept-2-yl)-benzo[4,5]furo[3,2-d]pyrimidin-2-ylamine; 4-(3-Amino-azetidin-1-yl)-9-chloro-benzo[4,5]furo[3,2-d]pyrimidin-2-ylamine; (R)-7-Methoxy-4-(3-methylamino-pyrrolidin-1-yl)-benzo[4,5]furo[3,2-d]pyrimidin-2-ylamine; (S)-7-Methoxy-4-(3-methylamino-pyrrolidin-1-yl)-benzo[4,5]thieno[3,2-d]pyrimidin-2-ylamine; 7-Methoxy-(4-methyl-piperazin-1-yl)-benzo[4,5]thieno[3,2-d]pyrimidin-2-ylamine; (S)-2-[4-(3-Amino-piperidin-1-yl)-8-chloro-benzo[4,5]furo[3,2-d]pyrimidin-2-ylamino]-ethanol; 2-(8-Chloro-4-piperazin-1-yl-benzo[4,5]furo[3,2-d]pyrimidin-2-ylamino)-ethanol; 2-[4-(3-Amino-azetidin-1-yl)-8-chloro-benzo[4,5]furo[3,2-d]pyrimidin-2-ylamino]-ethanol; [8-Chloro-4-(4-methyl-piperazin-1-yl)-benzo[4,5]furo[3,2-d]pyrimidin-2-yl]-dimethyl-amine; and pharmaceutically acceptable salts thereof.

In another embodiment, the Histamine H4 antagonist or selective Histamine H4 antagonists are selected from those described in the international Patent Application WO2009077608: 4-Cyclohexyloxymethyl-6-(3-(methylamino) azetidin-1-yl)pyrimidin-2-amine; 4-Cyclohexyloxymethyl-6-((3R)-3-(methylamino)pyrrolidin-1-yl)pyrimidin-2-amine; 4-(Cyclopropylmethoxymethyl)-6-(3-(methylamino)azetidin-1-yl)pyrimidin-2-amine; 4-(Cyclopropylmethoxymethyl)-6-((3R)-3-(methylamino)pyrrolidin-1-yl)pyrimidin-2-amine; 4-Cyclobutoxymethyl-6-(3-(methylamino)azetidin-1-yl)pyrimidin-2-amine; 4-Cyclobutoxymethyl-6-((3R)-3-(methylamino)pyrrolidin-1-yl)pyrimidin-2-amine; 4-Cyclopentoxymethyl-6-(3-(methylamino) azetidin-1-yl)pyrimidin-2-annine; 4-Cyclopentoxymethyl-6-((3R)-3-(methylamino)pyrrolidin-1-yl)pyrimidin-2-amine; 4-Isopropoxymethyl-6-(3-(methylamino)azetidin-1-yl)pyrimidin-2-amine; 4-Isopropoxymethyl-6-((3R)-3-(methylamino)pyrrolidin-1-yl)pyrimidin-2-amine; 4-Isobutoxymethyl-6-(3-(methylannino) azetidin-1-yl)pyrimidin-2-amine; 4-Isobutoxymethyl-6-((3R)-3-(methylamino)pyrrolidin-1-yl)pyrimidin-2-amine; 4-(2,2-Dimethylpropoxymethyl)-6-(3-(methylamino) azetidin-1-yl)pyrimidin-2-amine; 4-(2,2-Dimethylpropoxymethyl)-6-((3R)-3-(methylannino)pyrrolidin-1-yl)pyrimidin-2-amine; 4-tert-Butoxymethyl-6-((3R)-3-(methylamino)pyrrolidin-1-yl)pyrimidin-2-amine; 4-(Cyclopentylmethoxymethyl)-6-(3-(methylamino) azetidin-1-yl)pyrimidin-2-amine; 4-(Cyclopentylmethoxymethyl)-6-((3R)-3-(methylamino)pyrrolidin-1-yl)pyrimidin-2-amine; 4-(((1S,2R,4R)-Bicyclo[2.2.1]heptan-2-yloxy)methyl)-6-(3-(methylamino)azetidin-1-yl) pyrimidin-2-amine; 4-(((1S,2R,4R)-Bicyclo[2.2.1]heptan-2-yloxy)methyl)-6-((3R)-3-(methylamino)pyrrolidin-1-yl)pyrimidine-2-amine; 4-Benzyloxymethyl-6-(3-(methylamino)azetidin-1-yl)pyrimidin-2-amine; 4-Benzyloxymethyl-6-((3R)-3-(methylamino)pyrrolidin-1-yl)pyrimidin-2-amine; 6-Methoxymethyl-4-((3R)-3-(methylamino)pyrrolidin-1-yl)pyrimidin-2-amine; 6-Methoxymethyl-4-(3-(methylamino)azetidin-1-yl)pyrimidin-2-amine; 4-(3-(Methylamino) azetidin-1-yl)-6-phenoxymethylpyrimidin-2-amine; 6-(2-Methoxyethyl)4-(3-(methylamino)azetidin-1-yl)pyrimidin-2-amine; 4-(4-Fluorophenoxymethyl)-6-(3-(methylamino)azetidin-1-yl)pyrimidin-2-amine; 4-(2,4-Difluorophenoxymethyl)-6-(3-(methylamino)azetidin-1-yl)pyrimidin-2-amine; 4-(3,4-Difluorophenoxymethyl)-6-(3-(methylamino)azetidin-1-yl)pyrimidin-2-amine; 4-(2,4-Difluorophenoxymethyl)-6-((3R)-3-(methylamino)pyrrolidin-1-yl)pyrimidin-2-amine; 4-(3,4-Difluorophenoxymethyl)-6-((3R)-3-(methylamino)pyrrolidin-1-yl)pyrimidin-2-amine; 4-(3-Aminoazetidin-1-yl)-6- isopropoxymethylpyrimidin-2-amine; 4-((3R)-3-Aminopyrrolidin-1-yl)-6-isopropoxymethylpyrimidin-2-amine; 4-(3-(Methylamino)azetidin-1-yl)-6-(tetrahydropyran-4-yl)pyrimidin-2-amine; 4-(3-(Methylamino)azetidin-1-yl)-6-((S)-tetrahydrofuran-2-yl)pyrimidin-2-amine; 4-((3R)-3-(Methylamino)pyrrolidin-1-yl)-6-((S)-tetrahydrofuran-2-yl)pyrimidin-2-amine; 4-(3-(Methylamino)azetidin-1-yl)-6-((R)-tetrahydrofuran-2-yl)pyrimidin-2-amine; 4-((3R)-3-(Methylamino)pyrrolidin-1-yl)-6-((R)-tetrahydrofuran-2-yl)pyrimidin-2-amine; 4-(2-(4-Chlorophenoxy)propan-2-yl)-6-(3-(methylamino)azetidin-1-yl)pyrimidin-2-amine; 4-(2-(4-Chlorophenoxy)propan-2-yl)-6-((3R)-3-(methylamino)pyrrolidin-1-yl)pyrimidin-2-amine; 6-((R)-1-Methoxyethyl)-4-(3-(methylamino)azetidin-1-yl)pyrimidin-2-amine; 4-(3-(Methylamino)azetidin-1-yl)-6-((R)-phenyl(methoxy)methyl)pyrimidin-2-amine; 4-((3R)-3-(Methylamino)pyrrolidin-1-yl)-6-((R)-phenyl(methoxy)methyl)pyrimidin-2-amine; 4-(3-(Methylamino)azetidin-1-yl)-6-((S)-phenyl(methoxy)methyl)pyrimidin-2-amine; 4-Cyclohexyloxymethyl-6-[3-methyl-3-(methylamino)azetidin-1-yl]pyrimidin-2-amine; 4-lsobutoxymethyl-6-[3-methyl-3-(methylamino)azetidin-1-yl]pyrimidin-2-amine; 4-lsopropoxymethyl-6-[3-methyl-3-(methylamino)azetidin-1-yl]pyrimidin-2-amine; 4-(1,1-Dimethyl-2-methoxyethyl)-6-(3-(methylamino)azetidin-1-yl)pyrimidin-2-amine; 4-(2-lsopropoxyethyl)-6-(3-(methylamino)azetidin-1-yl)pyrimidin-2-amine; 4-(1-(Methoxymethyl)cyclopentyl)-6-((3R)-3-(methylamino)pyrrolidin-1-yl)pyrimidin-2-amine; 4-[3-Methyl-3-(methylamino)azetidin-1-yl]-6-[(2S)-tetrahydrofuran-2-yl]pyrimidin-2-amine; 4-[(Dicyclopropylmethoxy)methyl]-6-(3-(methylamino)azetidin-1-yl)pyrimidin-2-amine; 4-(1-(Methoxymethyl)cyclopentyl)-6-(3-(methylamino)azetidin-1-yl)pyrimidin-2-amine; Methyl 3-(((2-amino-6-(3-(methylamino)azetidin-1-yl)pyrimidin-4-yl)methoxy)methyl)benzoate; Methyl-4-(((2-amino-6-(3-(methylamino)azetidin-1-yl)pyrimidin-4-yl)methoxy)methyl)benzoate; Methyl-2-(((2-amino-6-(3-(methylamino)azetidin-1-yl)pyrimidin-4-yl)methoxy)methyl)benzoate; 4-(3-(Methylamino)azetidin-1-yl)-6-((4-(methylsulfonyl)benzyloxy)methyl)pyrimidin-2-amine; 4-(3-(Methylamino)azetidin-1-yl)-6-((3-(methylsulfonyl)benzyloxy)methyl)pyrimidin-2-amine; 2-[3-(((2-Amino-6-(3-(methylamino)azetidin-1-yl)pyrimidin-4-yl)methoxy)methyl]phenyl]propan-2-ol; [3-(((2-Amino-6-(3-(methylamino)azetidin-1-yl)pyrimidin-4-yl)methoxy)methyl]phenyl]methanol; [4-(((2-Amino-6-(3-(methylamino)azetidin-1-yl)pyrimidin-4-yl)methoxy)methyl]phenyl]methanol; [2-(((2-Amino-6-(3-(methylamino)azetidin-1-yl)pyrimidin-4-yl)methoxy)methyl]phenyl]methanol; 3-[((2-Amino-6-(3-(methylamino)azetidin-1-yl)pyrimidin-4-yl)methoxy)methyl]benzoic acid; 3-[((2-Amino-6-(3-(methylamino)azetidin-1-yl)pyrimidin-4-yl)methoxy)methyl]benzamide; and 3-[(((2-Amino-6-(3-(methylamino)azetidin-1-yl)pyrimidin-4-yl)methoxy)methyl]-N-butylbenzamide, or a salt thereof.

In another embodiment, the Histamine H4 antagonist or selective Histamine H4 antagonists are selected from those described in the international Patent Application WO2009/056551: 4-[(3R)-3-(Methylamino)pyrrolidin-1-yl]-6,7,8,9-tetrahydrobenzofuro[3,2-d]pyrimidin-2-amine; 4-[3-(Methylamino)azetidin-1-yl]-6,7,8,9-tetrahydrobenzofuro[3,2-d]pyrimidin-2-amine; 4-[(3R)-3-Aminopyrrolidin-1-yl]-6,7,8,9-tetrahydrobenzofuro[3,2-d]pyrimidin-2-amine; 4-(3-Aminoazetidin-1-yl)-6,7,8,9-tetrahydrobenzofuro[3,2-d]pyrimidin-2-amine; 4-[(4aR,7aR)-Octahydro-6H-pyrrolo[3,4-b]pyridin-6-yl]-6,7,8,9-tetrahydrobenzofuro[3,2-d]pyrimidin-2-amine; 4-[3-Methyl-3-(Methylamino)azetidin-1-yl]-6,7,8,9-tetrahydrobenzofuro[3,2-d]pyrimidin-2-amine; 4-Piperazin-1-yl-6,7,8,9-tetrahydrobenzofuro[3,2-d]pyrimidin-2-amine; 4-(1,4-Diazepan-1-yl)-6,7,8,9-tetrahydrobenzofuro[3,2-d]pyrimidin-2-amine; 4-[(3R)-3-(Methylamino)pyrrolidin-1-yl]-6,7,8,9-tetrahydrobenzofuro[3,2-d]pyrimidine; 4-[3-(Methylamino)azetidin-1-yl]-6,7,8,9-tetrahydrobenzofuro[3,2-d]pyrimidine; 4-(1,4-Diazepan-1-yl)-6,7,8,9-tetrahydrobenzofuro[3,2-d]pyrinnidine; 4-[(3R)-3-(Methylamino)pyrrolidin-1-yl]-7,8,9,10-tetrahydro-6H-cyclohepta[4,5]furo[3,2-d]pyrimidin-2-amine; 4-[3-(Methylamino)azetidin-1-yl]-7,8,9,10-tetrahydro-6H-cyclohepta[4,5]furo[3,2-d]pyrimidin-2-amine; 4-[(3R)-3-Aminopyrrolidin-1-yl]-7,8,9,10-tetrahydro-6H-cyclohepta[4,5]furo[3,2-d]pyrimidin-2-amine; 4-[3-Methyl-3-(methylamino)azetidin-1-yl]-7,8,9,10-tetrahydro-6H-cyclohepta[4,5]furo[3,2-d]pyrimidin-2-amine; 4-[3-(Methylamino)azetidin-1-yl]-7,8-dihydro-6H-cyclopenta[4,5]furo[3,2-d]pyrimidin-2-amine; 4-[(3R)-3-(Methylamino)pyrrolidin-1-yl]-7,8-dihydro-6H-cyclopenta[4,5]furo[3,2-d]pyrimidin-2-amine; $N^4$-[(3R)-1-(Methylpyrrolidin-3-yl]amino-6,7,8,9-tetrahydrobenzofuro[3,2-d]pyrimidine-2,4-diamine; 4-(4-Methylpiperazin-1-yl)-6,7,8,9-tetrahydrobenzofuro[3,2-d]pyrimidin-2-amine; (S)-4-(3-Methylpiperazin-1-yl)-6,7,8,9-tetrahydrobenzofuro[3,2-d]pyrimidin-2-amine; and 4-(4-Methylpiperazin-1-yl)-6,7,8,9-tetrahydrobenzofuro[3,2-d]pyrimidin and salts thereof.

In another embodiment, the Histamine H4 antagonist or selective Histamine H4 antagonists are selected from those described in the international Patent Application WO2009/068512: 4-(Cyclopropylmethyl)-6-((3R)-3-(methylamino)pyrrolidin-1-yl)pyrimidin-2-amine; 4-Cyclopropylmethyl-6-(3-(methylamino)azetidin-1-yl)pyrimidin-2-amine; 4-Cyclopropylmethyl-6-((3R)-3-aminopyrrolidin-1-yl)pyrimidin-2-amine; 4-Cyclopropylmethyl-6-(piperazin-1-yl)pyrimidin-2-amine; 4-Cyclopropylmethyl-6-(3-methyl-3-(methylamino)azetidin-1-yl)pyrimidin-2-amine; 4-(3-Aminoazetidin-1-yl)-6-cyclopropylmethyl-pyrimidin-2-amine; 4-Cyclopropylmethyl-6-(1,4-diazepan-1-yl)pyrimidin-2-amine; 4-(4-Aminopiperidin-1-yl)-6-cyclopropylmethyl-pyrimidin-2-amine; 4-Cyclopropylmethyl-6-((4aR,7aR)-octahydropyrrolo[3,4-b]pyridine-6-yl)pyrimidin-2-amine; 4-Cyclopropylmethyl-6-((3S)-3-(methylamino)pyrrolidin-1-yl)pyrimidin-2-amine; (R)-4-Cyclopropylmethyl-6-[(N-methylpyrrolidin-3-yl)amine]pyrimidin-2-amine; (S)-4-Cyclopropylmethyl-6-(3-methylpiperazin-1-yl)pyrimidin-2-amine; (R)-4-Cyclopropylmethyl-6-(3-methylpiperazin-1-yl)pyrimidin-2-amine; 4-Cyclopropylmethyl-6-[3-(pyrrolidin-1-yl)azetidin-1-yl]pyrimidin-2-amine; 4-(Cyclopropylmethyl)-6-(hexahydropyrrolo[1,2-a]pyrazin-2(1H)-yl)pyrimidin-2-amine; (S)-4-(Cyclopropylmethyl)-6-(hexahydropyrrolo[1,2-a)]-2(1H)-yl)pyrimidin-2-amine; 4-Isopropyl-6-(3-(methylamino)azetidin-1-yl)pyrimidin-2-amine; 4-Isopropyl-6-((3R)-3-(methylamino)pyrrolidin-1-yl)pyrimidin-2-amine; 4-tert-Butyl-6-(3-(methylamino)azetidin-1-yl)pyrimidin-2-amine; 4-tert-Butyl-6-((3R)-3-(methylamino)pyrrolidin-1-yl)pyrimidin-2-amine; 4-(3-(Methylamino)azetidin-1-yl)-6-propylpyrimidin-2-amine; 4-((3R)-3-(Methylamino)pyrrolidin-1-yl)-6-propylpyrimidin-2-amine; 4-Cyclopropyl-6-(3-(methylamino)azetidin-1-yl)pyrimidin-2-amine; 4-Cyclopropyl-6-((3R)-3-(methylamino)pyrrolidin-1-yl)pyrimidin-2-amine; 4-Ethyl-6-(3-(methylamino)azetidin-1-yl)pyrimidin-2-amine; 4-Ethyl-6-((3R)-3-(methylamino)pyrrolidin-1-yl)pyrimidin-2-amine; 4-Butyl-6-(3-(methylamino)azetidin-1-yl)pyrimidin-2-amine; 4-Butyl-6-((3R)-3-(methylamino)pyrrolidin-1-yl)

pyrimidin-2-amine; 4-Cyclopentylmethyl-6-(3-(methylamino)azetidin-1-yl)pyrimidin-2-amine; 4-Cyclopentylmethyl-6-((3R)-3-(methylamino)pyrrolidin-1-yl)pyrimidin-2-amine; 4-Isobutyl-6-((3R)-3-(methylamino)pyrrolidin-1-yl)pyrimidin-2-amine; 4-Isobutyl-6-(3-(methylamino)azetidin-1-yl)pyrimidin-2-amine; 4-(2,2-Dimethylpropyl)-6-((3R)-3-(methylamino)pyrrolidin-1-yl)pyrimidin-2-amine; 4-(2,2-Dimethylpropyl)-6-(3-(methylamino)azetidin-1-yl)pyrimidin-2-amine; trans-4-(2-Phenylcyclopropyl)-6-((3R)-3-(methylamino)pyrrolidin-1-yl)pyrimidin-2-amine; (R)-4-tert-Butyl-6-[(N-methylpyrrolidin-3-yl)amine]pyrimidin-2-amine; 4-(2-Cyclopentylethyl)-6-((3R)-3-(methylamino)pyrrolidin-1-yl)pyrimidin-2-amine; 4-(2-Cyclopentylethyl)-6-(3-(methylamino)azetidin-1-yl)pyrimidin-2-annine; 4-(2-Cyclopropylethyl)-6-((3R)-3-(methylamino)pyrrolidin-1-yl)pyrimidin-2-amine; 4-((3R)-3-(Methylamino)pyrrolidin-1-yl)-6-(4-methylpentyl)pyrimidin-2-amine; 4-(3-(Methylamino)azetidin-1-yl)-6-(4-methylpentyl)pyrimidin-2-amine; 4-(3-Cyclopentylpropyl)-6-((3R)-3-(methylamino)pyrrolidin-1-yl)pyrimidin-2-amine; 4-(4-Cyclohexylbutyl)-6-((3R)-3-(methylamino)pyrrolidin-1-yl)pyrimidin-2-amine; 4-(4-Cyclohexylbutyl)-6-(3-(methylamino)azetidin-1-yl)pyrimidin-2-amine; (S)-4-(2-Cyclopropylethyl)-6-(3-methylpiperazin-1-yl)pyrimidin-2-amine; 4-Aminoazetidin-1-yl)-6-(cyclopentylmethyl)pyrimidin-2-amine; 4-(3-(Methylamino)azetidin-1-yl)-6-(2,2,3,3-tetramethylcyclopropyl)pyrimidin-2-amine; 4-Cyclobutyl-6-(3-(methylamino)azetidin-1-yl)pyrimidin-2-amine; 4-Cyclopentyl-6-(3-(methylamino)azetidin-1-yl)pyrimidin-2-amine; 4-((3R)-3-(Methylamino)pyrrolidin-1-yl)-6-(2,2,3,3-tetramethylcyclopropyl)pyrimidin-2-amine; 4-Isobutyl-6-(3-methyl-3-(methylamino)azetidin-1-yl)pyrimidin-2-amine; 4-(3-Methyl-3-(methylamino)azetidin-1-yl)-6-neopentylpyrimidin-2-amine; (S)-4-(3-Methylpiperazin-1-yl)-6-neopentylpyrimidin-2-amine; 4-(3-(Methylamino)azetidin-1-yl)-6-(1-methylcyclopropyl)pyrimidin-2-amine; (R)-4-(Cyclopropylmethyl)-6-(hexahydropyrrolo[1,2-a]pyrazin-2(1H)-yl)pyrimidin-2-amine; 4-Cyclopentyl-6-(3-methyl-3-(methylamino)azetidin-1-yl)pyrimidin-2-amine; 4-Cyclobutyl-6-(3-methyl-3-(methylamino)azetidin-1-yl)pyrimidin-2-amine; 4-(3-Methyl-3-(methylamino)azetidin-1-yl)-6-(2,2,3,3-tetramethylcyclopropyl)pyrimidin-2-amine; (S)-4-(3-Methylpiperazin-1-yl)-6-(2,2,3,3-tetramethylcyclopropyl)pyrimidin-2-amine; 4-(3-(Methylamino)azetidin-1-yl)-6-(pentan-3-yl)pyrimidin-2-amine; 4-((3R)-3-(Methylamino)pyrrolidin-1-yl)-6-(pentan-3-yl) pyrimidin-2-amine; 4-((1S,2S,4S)-Bicyclo[2.2.1]heptan-2-yl)-6-(3-(methylamino)azetidin-1-yl)pyrimidin-2-amine; and 4-((1S,2R,4S)-Bicyclo[2.2.1]heptan-2-yl)-6-(3-(methylamino)azetidin-1-yl)pyrimidin-2-amine and salts thereof.

In another embodiment, the Histamine H4 antagonist or selective Histamine H4 antagonists are selected from those described in the international Patent Application WO2009/080721: 2-Isobutyl-6-((3R)-3-(methylamino)pyrrolidin-1-yl)pyrimidin-4-amine; 2-Cyclohexylmethyl-6-((3R)-3-(methylamino)pyrrolidin-1-yl)pyrimidin-4-amine; 2-(4-Fluorobenzyl)-6-(3-(methylamino)azetidin-1-yl)pyrimidin-4-amine; 2-Isobutyl-6-(3-(methylamino)azetidin-1-yl)pyrimidin-4-amine; 2-Cyclopropyl-6-(3-(methylamino)azetidin-1-yl)pyrimidin-4-amine; 2-tert-Butyl-6-(3-(methylamino)azetidin-1-yl)pyrimidin-4-amine; 2-Isopropyl-6-(3-(methylamino)azetidin-1-yl)pyrimidin-4-amine; 2-(Cyclopropylmethyl)-6-(3-(methylamino)azetidin-1-yl)pyrimidin-4-amine; 6-(3-(Methylamino)azetidin-1-yl)-2-(phenoxymethyl)pyrimidin-4-amine; 2-Cyclopropyl-6-((3R)-3-(methylamino)pyrrolidin-1-yl)pyrimidin-4-amine; 2-tert-Butyl-6-((3R)-3-(methylamino)pyrrolidin-1-yl)pyrimidin-4-amine; 2-Isopropyl-6-((3R)-3-(methylamino)pyrrolidin-1-yl)pyrimidin-4-amine; 6-((3R)-3-(Methylamino)pyrrolidin-1-yl)-2-(phenoxymethyl)pyrimidin-4-amine; 6-(3-Aminoazetidin-1-yl)-2-isobutylpyrimidin-4-amine; 2-Isobutyl-6-(3-methyl-3-(methylamino)azetidin-1-yl)pyrimidin-4-amine; 6-((3R)-3-aminopyrrolidin-1-yl)-2-isobutylpyrimidin-4-amine; 2-Cyclobutyl-6-(3-(methylamino)azetidin-1-yl)pyrimidin-4-amine; 2-Cyclobutyl-6-((3R)-3-(methylamino)pyrrolidin-1-yl)pyrimidin-4-amine; 2-Cyclopentyl-6-(3-(methylamino)azetidin-1-yl)pyrimidin-4-amine; 2-Cyclopentyl-6-((3R)-3-(methylamino)pyrrolidin-1-yl)pyrimidin-4-amine; 2-(2,2-Dimethylpropyl)-6-(3-(methylamino)azetidin-1-yl)pyrimidin-4-amine; 2-(2,2-Dimethylpropyl)-6-((3R)-3-(methylamino)pyrrolidin-1-yl)pyrimidin-4-amine; 2-(2-Cyclopentylethyl)-6-((3R)-3-(methylamino)pyrrolidin-1-yl)pyrimidin-4-amine; 2-Cyclohexylmethyl-6-(3-(methylamino)azetidin-1-yl)pyrimidin-4-amine; 2-Cyclopropylmethyl-6-((3R)-3-(methylamino)pyrrolidin-1-yl)pyrimidin-4-amine; 2-Cyclohexyl-6-(3-(methylamino)azetidin-1-yl)pyrimidin-4-amine; 2-Cyclohexyl-6-((3R)-3-(methylannino)pyrrolidin-1-yl)pyrimidin-4-amine; and 2-(4-Fluorobenzyl)-6-((3R)-3-(methylamino)pyrrolidin-1-yl)pyrimidin-4-amine, or a salt thereof.

In another embodiment, the Histamine H4 antagonist or selective Histamine H4 antagonists are selected from those described in the international Patent Application WO2009/115496: 7-Cyclopropyl-4-(4-methylpiperazin-1-yl)furo[3,2-d]pyrimidin-2-amine; 7-Cyclopropyl-4-[(3S)-(3-methylpiperazin-1-yl)furo[3,2-d]pyrimidin-2-amine; 7-Ethyl-4-[4-methylpiperazin-1-yl]furo[3,2-d]pyrimidin-2-amine; 4-[4-methylpiperazin-1-yl)-7-propylfuro[3,2-d]pyrimidin-2-amine; 7-Cyclopropyl-4-(3-(methylamino)azetidin-1-yl)furo[3,2-d]pyrimidin-2-amine; 7-Cyclopropyl-4-[(3R)-3-(methylamino)pyrrolidin-1-yl)furo[3,2-d]pyrimidin-2-amine; 4-[(3R)-3-Aminopyrrolidin-1-yl)-7-cyclopropylfuro[3,2-d]pyrimidin-2-amine; 4-(3-Aminoazetidin-1-yl)-7-cyclopropylfuro[3,2-d]pyrimidin-2-amine; 7-Cyclopropyl-4-(3-methyl-3-(methylamino)azetidin-1-yl)furo[3,2-d]pyrimidin-2-amine; 7-Cyclopropyl-4-(piperazin-1-yl)furo[3,2-d]pyrimidin-2-amine; 7-Cyclopropyl-4-(1,4-diazepan-1-yl)furo[3,2-d]pyrimidin-2-amine; 7-Ethyl-4-(3-(methylamino)azetidin-1-yl)furo[3,2-d]pyrimidin-2-amine; 7-Ethyl-4-[(3R)-3-(methylamino)pyrrolidin-1-yl)furo[3,2-d]pyrimidin-2-amine; 4-[(3R)-3-Aminopyrrolidin-1-yl]-7-ethylfuro[3,2-d]pyrimidin-2-amine; 7-Ethyl-4-(3-methyl-3-(methylamino)azetidin-1-yl)furo[3,2-d]pyrimidin-2-amine; 7-Ethyl-4-(piperazin-1-yl)furo[3,2-d]pyrimidin-2-amine; 4-(3-(Methylamino)azetidin-1-yl)-7-propylfuro[3,2-d]pyrimidin-2-amine; 4-[(3R)-3-(Methylamino)pyrrolidin-1-yl]-7-propylfuro[3,2-d]pyrimidin-2-amine; 4-[(3R)-3-(Aminopyrrolidin-1-yl)-7-propylfuro[3,2-d]pyrimidin-2-amine; 4-(3-Methyl-3-(methylamino)azetidin-1-yl]-7-propylfuro[3,2-d]pyrimidin-2-amine; 4-(Piperazin-1-yl]-7-propylfuro[3,2-d]pyrimidin-2-amine; 7-Isopropyl-4-(3-(methylamino)azetidin-1-yl]furo[3,2-d]pyrimidin-2-amine; 7-Isopropyl-4-[(3R)-3-(methylamino)pyrrolidin-1-yl]furo[3,2-d]pyrimidin-2-amine; 7-Benzyl-4-(3-(methylamino)azetidin-1-yl]furo[3,2-d]pyrimidin-2-amine; 7-Benzyl-4-[(3R)-3-(methylamino)pyrrolidin-1-yl]furo[3,2-d]pyrimidin-2-amine; 7-Cyclobutyl-4-(3-(methylamino)azetidin-1-yl)furo[3,2d]pyrimidin-2-amine; 7-Cyclobutyl-4-[(3R)-3-methylamino)pyrrolidin-1-yl)furo[3,2d]pyrimidin-2-amine; 7-Cyclopentyl-4-(3-(methylamino)azetidin-1-yl)furo[3,2d]pyrimidin-2-amine; 7-Cyclopentyl-4-[(3R)-3-methylamino)pyrrolidin-1-yl)furo[3,2d]pyrimidin-2-amine; 7-Isobutyl-4-

(3-(methylamino)azetidin-1-yl)furo[3,2d]pyrimidin-2-amine; 7-Isobutyl-4-[(3R)-3-methylamino)pyrrolidin-1-yl)furo[3,2d]pyrimidin-2-amine; 4-(3-(Methylamino)azetidin-1-yl)-7-phenylfuro[3,2d]pyrimidin-2-amine; 4-[(3R)-3-(Methylamino)pyrrolidin-1-yl]-7-phenylfuro[3,2d]pyrimidin-2-amine; 7-tert-butyl-4-(3-(methylamino)azetidin-1-yl)furo[3,2d]pyrimidin-2-amine; 7-tert-butyl-4-[(3R)-3-methylamino)pyrrolidin-1-yl)furo[3,2d]pyrimidin-2-amine; 7-Cyclopropyl-4-(3-(methylamino)azetidin-1-yl)furo[3,2d]pyrimidin-2-amine; 6-Chloro-7-cyclobutyl-4-(3-(methylamino)azetidin-1-yl)furo[3,2-d]pyrimidin-2-amine; 6-Chloro-7-cyclopropyl-4-(3-(methylamino)azetidin-1-yl)furo[3,2-d]pyrimidin-2-amine; 6-Chloro-7-cyclopropyl-4-[(3R)-3-(methylamino)pyrrolidin-1-yl]furo[3,2-d]pyrimidin-2-amine; 6-Chloro-7-isopropyl-4-(3-(methylamino)azetidin-1-yl)furo[3,2-d]pyrimidin-2-amine; 6-Chloro-7-isopropyl-4-[(3R)-3-(methylamino)pyrrolidin-1-yl]furo[3,2-d]pyrimidin-2-amine; 6-Chloro-7-cyclopentyl-4-[(3R)-3-(methylamino)pyrrolidin-1-yl)furo[3,2-d]pyrimidin-2-amine; 4-(3-(Methylamino)azetidin-1-yl)-7-(tetrahydro-2H-pyran-4-yl)furo[3,2-d]pyrimidin-2-amine; 2-Amino-7-isopropyl-4-((3R)-3-(methylamino)pyrrolidin-1-yl)furo[3,2-d]pyrimidine-6-carbonitrile; 2-Amino-7-cyclopropyl-4-(3-(methylamino)azetidin-1-yl)furo[3,2-d]pyrimidine-6-carbonitrile; 7-(1-(Methoxymethyl)cyclopropyl)-4-(3-(methylamino)azetidin-1-yl)furo[3,2-d]pyrimidin-2-amine and salts thereof.

In another embodiment, the Histamine H4 antagonist or selective Histamine H4 antagonists are selected from those described in the international Patent Application WO2007/090852: [(R)-1-(2-Amino-8-chlorobenzo[4,5]furo[3,2-d]-pyrimidin-4-yl)pyrrolidin-3-yl]N-methylamine; [(S)-1-(2-Amino-8-chlorobenzo[4,5]furo[3,2-d]-pyrimidin-4-yl)pyrrolidin-3-yl]N-methylamine; [1-(2-Ethylamino-8-chlorobenzo[4,5]furo[3,2-d]-pyrimidin-4-yl)azetidin-3-yl]N-ethylamine; 4-((R)-3-Methylamino-pyrrolidin-1-yl)-benzo[4,5]furo[3,2-d]pyrimidin-2-ylamine; 8-Methyl-4-((R)-3-methylamino-pyrrolidin-1-yl)-benzo[4,5]furo[3,2-d]pyrimidin-2-ylamine; 8-Fluoro-4-((R)-3-methylamino-pyrrolidin-1-yl)-benzo[4,5]furo[3,2-d]pyrimidin-2-ylamine; 8-Bromo-4-((R)-3-methylamino-pyrrolidin-1-yl)-benzo[4,5]furo[3,2-d]pyrimidin-2-ylamine; 7-Chloro-4-((R)-3-methylamino-pyrrolidin-1-yl)-benzo[4,5]furo[3,2-d]pyrimidin-2-ylamine; N-[1-(2-Amino-8-chlorobenzo[4,5]furo[3,2-d]pyrimidin-4-yl)azetidin-3-yl]N-methylamine; 4-(3-Methylamino-azetidin-1-yl)-benzo[4,5]furo[3,2-d]pyrimidin-2-ylamine; 8-Bromo-4-(3-methylamino-azetidin-1-yl)-benzo[4,5]furo[3,2-d]pyrimidin-2-ylamine; 8-Methyl-4-(3-methylamino-azetidin-1-yl)-benzo[4,5]furo[3,2-d]pyrimidin-2-ylamine; 8-Fluoro-4-(3-methylamino-azetidin-1-yl)-benzo[4,5]furo[3,2-d]pyrimidin-2-ylamine; 8-Methoxy-4-((R)-3-methylamino-pyrrolidin-1-yl)-benzo[4,5]furo[3,2-d]pyrimidin-2-ylamine; 4-((R)-3-Methyl-amino-pyrrolidin-1-yl)-8-trifluoromethoxy-benzo[4,5]furo[3,2-d]pyrimidin-2-ylamine; 9-Fluoro-4-((R)-3-methylamino-pyrrolidin-1-yl)-benzo[4,5]furo[3,2-d]pyrimidin-2-ylamine; 9-Methyl-4-((R)-3-methylamino-pyrrolidin-1-yl)-benzo[4,5]furo[3,2-d]pyrimidin-2-ylamine; 9-Methoxy-4-((R)-3-methylamino-pyrrolidin-1-yl)-benzo[4,5]furo[3,2-d]pyrimidin-2-ylamine; 7-Methyl-4-((R)-3-methylamino-pyrrolidin-1-yl)-benzo[4,5]furo[3,2-d]pyrimidin-2-ylamine; 7-Methoxy-4-((R)-3-methylamino-pyrrolidin-1-yl)-benzo[4,5]furo[3,2-d]pyrimidin-2-ylamine; 4-((R)-3-Methylamino-pyrrolidin-1-yl)-7-trifluoromethyl-benzo[4,5]furo[3,2-d]pyrimidin-2-ylamine; 6-Chloro-4-((R)-3-methylamino-pyrrolidin-1-yl)-benzo[4,5]furo[3,2-d]pyrimidin-2-ylamine; 6-Methyl-4-((R)-3-methylamino-pyrrolidin-1-yl)-benzo[4,5]furo[3,2-d]pyrimidin-2-ylamine; 6-Methoxy-4-((R)-3-methylamino-pyrrolidin-1-yl)-benzo[4,5]furo[3,2-d]pyrimidin-2-ylamine; 8-Methoxy-4-(3-methylamino-azetidin-1-yl)-benzo[4,5]furo[3,2-d]pyrimidin-2-ylamine; 4-(3-Methylamino-azetidin-1-yl)-8-trifluoromethoxy-benzo[4,5]furo[3,2-d]pyrimidin-2-ylamine; 9-Fluoro-4-(3-methylamino-azetidin-1-yl)-benzo[4,5]furo[3,2-d]pyrimidin-2-ylamine; 9-Methyl-4-(3-methylamino-azetidin-1-yl)-benzo[4,5]furo[3,2-d]pyrimidin-2-ylamine; 9-Methoxy-4-(3-methylamino-azetidin-1-yl)-benzo[4,5]furo[3,2-d]pyrimidin-2-ylamine; 7-Methyl-4-(3-methylamino-azetidin-1-yl)-benzo[4,5]furo[3,2-d]pyrimidin-2-ylamine; 7-Methoxy-4-(3-methylamino-azetidin-1-yl)-benzo[4,5]furo[3,2-d]pyrimidin-2-ylamine; 4-(3-Methylamino-azetidin-1-yl)-7-trifluoromethyl-benzo[4,5]furo[3,2-d]pyrimidin-2-ylamine; 6-Chloro-4-(3-methylamino-azetidin-1-yl)-benzo[4,5]furo[3,2-d]pyrimidin-2-ylamine; 6-Methyl-4-(3-methylamino-azetidin-1-yl)-benzo[4,5]furo[3,2-d]pyrimidin-2-ylamine; 6-Methoxy-4-(3-methylamino-azetidin-1-yl)-benzo[4,5]furo[3,2-d]pyrimidin-2-ylamine; 8-Chloro-4-[3-(cyclopropylmethyl-amino)-pyrrolidin-1-yl]-benzo[4,5]furo[3,2-d]pyrimidin-2-ylamine; 8-Chloro-4-((R)-3-dimethylamino-pyrrolidin-1-yl)-benzo[4,5]furo[3,2-d]pyrimidin-2-ylamine; 4-((R)-3-Amino-pyrrolidin-1-yl)-8-chloro-benzo[4,5]furo[3,2-d]pyrimidin-2-ylamine; 8-Chloro-4-(4-methylamino-piperidin-1-yl)-benzo[4,5]furo[3,2-d]pyrimidin-2-ylamine; 4-(4-Amino-piperidin-1-yl)-8-chloro-benzo[4,5]furo[3,2-d]pyrimidin-2-ylamine; 4-(3-Amino-azetidin-1-yl)-8-chloro-benzo[4,5]furo[3,2-d]pyrimidin-2-ylamine; [8-Chloro-4-((R)-3-methylamino-pyrrolidin-1-yl)-benzo[4,5]furo[3,2-d]pyrimidin-2-yl]-methyl-amine; [8-Chloro-4-((R)-3-methylamino-pyrrolidin-1-yl)-benzo[4,5]furo[3,2-d]pyrimidin-2-yl]-dimethyl-amine; N-[8-Chloro-4-((R)-3-methylamino-pyrrolidin-1-yl)-benzo[4,5]furo[3,2-d]pyrimidin-2-yl]-acetamide; N-[8-Chloro-4-((R)-3-methylamino-pyrrolidin-1-yl)-benzo[4,5]furo[3,2-d]pyrimidin-2-yl]-methanesulfonamide; [8-Chloro-4-((R)-3-methylamino-pyrrolidin-1-yl)-benzo[4,5]furo[3,2-d]pyrimidin-2-yl]-cyclopropyl-amine; [8-Chloro-4-(3-methylamino-azetidin-1-yl)-benzo[4,5]furo[3,2-d]pyrimidin-2-yl]-methyl-amine; [8-Chloro-4-(3-methylamino-azetidin-1-yl)benzo[4,5]furo[3,2-d]pyrimidin-2-yl]-dimethyl-amine; N-[8-Chloro-4-(3-methylamino-azetidin-1-yl)benzo[4,5]furo[3,2-d]pyrimidin-2-yl]-acetamide; N-[8-Chloro-4-(3-methylamino-azetidin-1-yl)benzo[4,5]furo[3,2-d]pyrimidin-2-yl]-methanesulfonamide; [8-Chloro-4-(3-methylamino-azetidin-1-yl)benzo[4,5]furo[3,2-d]pyrimidin-2-yl]-cyclopropyl-amine and salts thereof.

In another embodiment, the Histamine H4 antagonist or selective Histamine H4 antagonists are selected from those described in the international Patent Application WO2007/090853: [(R)-1-(2-Amino-8-chlorobenzo[4,5]furo[3,2-d]-pyrimidin-4-yl)pyrrolidin-3-yl]N-methyl amine; 4-((R)-3-Methylamino-pyrrolidin-1-yl)-benzo[4,5]furo[3,2-d]pyrimidin-2-ylamine; 8-Methyl-4-((R)-3-methylamino-pyrrolidin-1-yl)-benzo[4,5]furo[3,2-d]pyrimidin-2-ylamine; 8-Fluoro-4-((R)-3-methylamino-pyrrolidin-1-yl)-benzo[4,5]furo[3,2-d]pyrimidin-2-ylamine; 8-Bromo-4-((R)-3-methylamino-pyrrolidin-1-yl)-benzo[4,5]furo[3,2-d]pyrimidin-2-ylamine; 7-Chloro-4-((R)-3-methylamino-pyrrolidin-1-yl)-benzo[4,5]furo[3,2-d]pyrimidin-2-ylamine; 8-Methoxy-4-((R)-3-methylamino-pyrrolidin-1-yl)-benzo[4,5]furo[3,2-d]pyrimidin-2-ylamine; 4-((R)-3-Methylamino-pyrrolidin-1-yl)-8-trifluoromethoxy-benzo[4,5]furo[3,2-d]pyrimidin-2-ylamine; 9-Fluoro-4-((R)-3-methylamino-pyrrolidin-11- yl)-benzo[4,5]furo[3,2-d]pyrimidin-2-ylamine; 9-Methyl-4-((R)-3-methylamino-pyrrolidin-1-yl)-benzo[4,5]furo[3,2-d]pyrimidin-2-ylamine; 9-Methoxy-4-((R)-3-methylamino-pyrrolidin-1-yl)-benzo[4,5]furo[3,2-d]pyrimidin-2-ylamine; 7-Methyl-4-((R)-3-methylamino-pyrrolidin-1-yl)-benzo[4,5]furo[3,2-d]pyrimidin-2-ylamine; 7-Methoxy-4-((R)-3-methylamino-pyrrolidin-1-yl)-benzo[4,5]furo[3,2-d]pyrimidin-2-ylamine; 4-((R)-3-Methylamino-pyrrolidin-1-yl)-7-trifluoromethyl-benzo[4,5]furo[3,2-d]pyrimidin-2-ylamine; 6-Chloro-4-((R)-3-methylamino-pyrrolidin-1-yl)-benzo[4,5]furo[3,2-d]pyrimidin-2-ylamine; 6-Methyl-4-((R)-3-methylamino-pyrrolidin-1-yl)-benzo[4,5]furo[3,2-d]pyrimidin-2-ylamine; 6-Methoxy-4-((R)-3-methylamino-pyrrolidin-1-yl)-benzo[4,5]furo[3,2-d]pyrimidin-2-ylamine; 8-Chloro-4-[3-(cyclopropylmethyl-amino)-pyrrolidin-1-yl]-benzo[4,5]furo[3,2-d]pyrimidin-2-ylamine; 8-Chloro-4-((R)-3-dimethyl amino-pyrrolidin-1-yl)-benzo[4,5]furo[3,2-d]pyrimidin-2-ylamine; 4-((R)-3-Amino-pyrrolidin-1-yl)-8-chloro-benzo[4,5]furo[3,2-d]pyrimidin-2-ylamine; [8-Chloro-4-((R)-3-methylamino-pyrrolidin-1-yl)-benzo[4,5]furo[3,2-d]pyrimidin-2-yl]-methyl-amine; [8-Chloro-4-((R)-3-methylamino-pyrrolidin-1-yl)-benzo[4,5]furo[3,2-d]pyrimidin-2-yl]-dimethyl-amine; N-[8-Chloro-4-((R)-3-methylamino-pyrrolidin-1-yl)-benzo[4,5]furo[3,2-d]pyrimidin-2-yl]-acetamide; N-[8-Chloro-4-((R)-3-methylamino-pyrrolidin-1-yl)-benzo[4,5]furo[3,2-d]pyrimidin-2-yl]-methanesulfonamide; [8-Chloro-4-((R)-3-methylamino-pyrrolidin-1-yl)-benzo[4,5]furo[3,2-d]pyrimidin-2-yl]-cyclopropyl-amine Some of said compounds and/or salts or esters thereof, will exist in different stereoisomeric forms. All of these forms are subjects of the invention, provided that the amino group attached to the pyrrolidine ring in 4-position of the pyrimidine ring shows R-configuration.

In another embodiment, the Histamine H4 antagonist or selective Histamine H4 antagonists are selected from those described in the international Patent Application WO2007/090854: [1-(2-Ethylamino-8-chlorobenzo[4,5]furo[3,2-d]-pyrimidin-4-yl)azetidin-3-yl]N-ethyl amine; N-[1-(2-Amino-8-chlorobenzo[4,5]furo[3,2-d]pyrimidin-4-yl) azetidin-3-yl]N-methyl amine; 4-(3-Methylamino-azetidin-1-yl)-benzo[4,5]furo[3,2-d]pyrimidin-2-ylamine; 8-Bromo-4-(3-methylamino-azetidin-1-yl)-benzo[4,5]furo[3,2-d]pyrimidin-2-ylamine; 8-Methyl-4-(3-methylamino-azetidin-1-yl)-benzo[4,5]furo[3,2-d]pyrimidin-2-ylamine; 8-Fluoro-4-(3-methylamino-azetidin-1-yl)-benzo[4,5]furo[3,2-d]pyrimidin-2-ylamine; 8-Methoxy-4-(3-methylamino-azetidin-1-yl)-benzo[4,5]furo[3,2-d]pyrimidin-2-ylamine; 4-(3-Methylamino-azetidin-1-yl)-8-trifluoromethoxy-benzo[4,5]furo[3,2-d]pyrimidin-2-ylamine; 9-Fluoro-4-(3-methylamino-azetidin-1-yl)-benzo[4,5]furo[3,2-d]pyrimidin-2-ylamine; 9-Methyl-4-(3-methylamino-azetidin-1-yl)-benzo[4,5]furo[3,2-d]pyrimidin-2-ylamine; 9-Methoxy-4-(3-methylamino-azetidin-1-yl)-benzo[4,5]furo[3,2-d]pyrimidin-2-ylamine; 7-Methyl-4-(3-methylamino-azetidin-1-yl)-benzo[4,5]furo[3,2-d]pyrimidin-2-ylamine; 7-Methoxy-4-(3-methylamino-azetidin-1-yl)-benzo[4,5]furo[3,2-d]pyrimidin-2-ylamine; 4-(3-Methylamino-azetidin-1-yl)-7-trifluoromethyl-benzo[4,5]furo[3,2-d]pyrimidin-2-ylamine; 6-Chloro-4-(3-methylamino-azetidin-1-yl)-benzo[4,5]furo[3,2-d]pyrimidin-2-ylamine; 6-Methyl-4-(3-methylamino-azetidin-1-yl)-benzo[4,5]furo[3,2-d]pyrimidin-2-ylamine; 6-Methoxy-4-(3-methylamino-azetidin-1-yl)-benzo[4,5]furo[3,2-d]pyrimidin-2-ylamine; 4-(3-Amino-azetidin-1-yl)-8-chloro-benzo[4,5]furo[3,2-d]pyrimidin-2-ylamine; [8-Chloro-4-(3-methylamino-azetidin-1-yl)-benzo[4,5]furo[3,2-d]pyrimidin-2-yl]-methyl-amine; [8-Chloro-4-(3-methylamino-azetidin-1-yl)benzo[4,5]furo[3,2-d]pyrimidin-2-yl]-dimethyl-amine; N-[8-Chloro-4-(3-methylamino-azetidin-1-yl)benzo[4,5]furo[3,2-d]pyrimidin-2-yl]-acetamide; N-[8-Chloro-4-(3-methylamino-azetidin-1-yl)benzo[4,5]furo[3,2-d]pyrimidin-2-yl]-methanesulfonamide; [8-Chloro-4-(3-methylamino-azetidin-1-yl)benzo[4,5]furo[3,2-d]pyrimidin-2-yl]-cyclopropyl-amine Some of said compounds and/or salts or esters thereof, will exist in different stereoisomeric forms In another embodiment, the Histamine H4 antagonist or selective Histamine H4 antagonists are selected from those described in the international Patent Application WO2007/039467: N—[(R,S)-1-(8-Chloro-2-methylbenzo[4,5]furo[3,2-d]-pyrimidin-4-yl)-pyrrolidin-3-yl]-N-methyl amine; N—[(R,S)-1-(8-Chlorobenzo[4,5]furo[3,2-d]-pyrimidin-4-yl)-pyrrolidin-3-yl]-N-methyl amine; [(R,S)-1-(8-Chloro-2-methylbenzo[4,5]furo[3,2-d]pyrimidin-4-yl)pyrrolidin-3-yl]dimethyl amine; N—[(R)-1-(8-chlorobenzo[4,5]furo[3,2-d]pyrimidin-4-yl)pyrrolidin-3-yl]N-methyl amine; N-[(S)-1-(8-chlorobenzo[4,5]furo[3,2-d]pyrimidin-4-yl)pyrrolidin-3-yl]N-methyl amine; N-[1-(8-chlorobenzo[4,5]furo[3,2-d]pyrimidin-4-yl)azetidin-3-yl]amine; N-[1-(8-chlorobenzo[4,5]furo[3,2-d]pyrimidin-4-yl)azetidin-3-yl]N-methyl amine; N-1-(8-Chlorobenzo[4,5]furo[3,2-d]pyrimidin-4-yl)azetidin-3-yl]N,N-dimethyl amine; N-[1-(8-Chlorobenzo[4,5]furo[3,2-d]pyrimidin-4-yl)azetidin-3-yl]N,N-dimethyl amine; [(R,S)-1-(8-chlorobenzo[4,5-d]pyrimidin-4-yl)pyrrolidin-3-yl]amine; [(R,S)-1-(8-chlorobenzo[4,5]furo[3,2-d]pyrimidin-4-yl)pyrrolidin-3-yl]dimethyl amine; [(R,S)-1-(8-methylbenzo[4,5]furo[3,2-d]pyrimidin-4-yl)pyrrolidin-3-yl]-N-methyl amine; [(R)-1-(8-chlorobenzo[4,5]furo[3,2-d]pyrimidin-4-yl)pyrrolidin-3-yl]amine; [(S)-1-(8-chlorobenzo[4,5]furo[3,2-d]pyrimidin-4-yl)pyrrolidin-3-yl]; N—[(R)-1-(8-trifluoromethylbenzo[4,5]furo[3,2-d]pyrimidin-4-yl)pyrrolidin-3-yl]N-methyl amine; N—[(S)-1-(8-trifluoromethylbenzo[4,5]furo[3,2-d]pyrimidin-4-yl)pyrrolidin-3-yl]N-methyl amine; N—[(R)-1-(8-methylbenzo[4,5]furo[3,2-d]pyrimidin-4-yl)pyrrolidin-3-yl]N-methyl amine; N—[(S)-1-(8-methylbenzo[4,5]furo[3,2-d]pyrimidin-4-yl)pyrrolidin-3-yl]N-methyl amine; N—[(R)-1-(8-chloro-2-trifluoromethylbenzo[4,5]furo[3,2-d]pyrimidin-4-yl)pyrrolidin-3-yl]N-methyl amine; N—[(S)-1-(8-chloro-2-trifluoromethylbenzo[4,5]furo[3,2-d]pyrimidin-4-yl)pyrrolidin-3-yl]N-methyl amine; N-[1-(8-chlorobenzo[4,5]furo[3,2-d]pyrimidin-4-yl)azetidin-3-yl]N-ethyl amine; [(R,S)-1-(8-chlorobenzo[4,5]furo[3,2-d]pyrimidin-4-yl)-3-methylpyrrolidin-3-yl]-N-methyl amine; N-[1-(8-chlorobenzo[4,5]furo[3,2-d]pyrimidin-4-yl)azetidin-3-yl]N-cyclopropyl amine; and [(3RS,4RS)-1-(8-chlorobenzo[4,5]furo[3,2-d]pyrimidin-4-yl)-4-fluoropyrrolidin-3-yl]N-methyl amine. Some of said compounds and/or salts or esters thereof, will exist in different stereoisomeric forms.

In another embodiment, the Histamine H4 antagonist or selective Histamine H4 antagonists are selected from those described in the international Patent Application WO2009/071625: 10-[(3R)-1-azabicyclo[2.2.2]oct-3-ylmethyl]-10H-phenothiazine (dextrorotatory enantiomer); 10-[(3S)-1-azabicyclo[2.2.2]oct-3-ylmethyl]-10H-phenothiazine (levorotatory enantiomer); the racemic mixture of the two enantiomers 10-[(3R,3S)-1-azabicyclo[2.2.2]oct-3-ylmethyl]-10H-phenothiazine.

In another embodiment, the Histamine H4 antagonist or selective Histamine H4 antagonists are selected from those described in the international Patent Application WO2009/134726: 4-piperazin-1-yl-5,6,7a,8,9,10,11,11a-octahydro[1]benzofuro[2,3-h]quinazolin-2-amine; 4-[(3R)-3-(methylamino)pyrrolidin-1-yl]-5,6,7a,8,9,10,11,11a-octahydro[1]benzofuro[2,3-h]quinazolin-2-amine; (7aS,11aS)-4-piperazin-1-yl-5,6,7a,8,9,10,11,11a-octahydro[1]benzofuro[2,3-h]quinazolin-2-amine; (7aR,11aR)-4-piperazin-1-yl-5,6,7a,8,9,10,11,11a-octahydro[1]benzofuro[2,3-h]quinazolin-2-amine; 4-(4-methyl-1,4-diazepan-1-yl)-5,6,7a,8,9,10,11,11a-octahydro[1]benzofuro[2,3-h]quinazolin-2-amine; 4-(4-methylpiperazin-1-yl)-5,6,7a,8,9,10,11,11a-octahydro[1]benzofuro[2,3-h]quinazolin-2-amine; 4-[(3R)-3-aminopyrrolidin-1-yl]-7a,8,9,10,11,11a-hexahydro[1]benzofuro[2,3-h]quinazolin-2-amine; 4-[(1R,5S)-3,6-diazabicyclo[3.2.0]hept-6-yl]-7a,8,9,10,11,11a-hexahydro[1]benzofuro[2,3-h]quinazolin-2-amine; 4-(1,4-diazepan-1-yl)-5,6,7a,8,9,10,11,11a-octahydro[1]benzofuro[2,3-h]quinazolin-2-amine; 4-(4-isopropyl-1,4-diazepan-1-yl)-5,6,7a,8,9,10,11,11a-octahydro[1]benzofuro[2,3-h]quinazolin-2-amine; 4-(4-cyclobutyl-1,4-diazepan-1-yl)-5,6,7a,8,9,10,11,11a-octahydro[1]benzofuro[2,3-h]quinazolin-2-amine; trans-4-piperazin-1-yl-5,6,6a,7,8,9,10,10a-octahydrobenzo[h]quinazolin-2-amine; cis-4-piperazin-1-yl-5,6,6a,7,8,9,10,10a-octahydrobenzo[h]quinazolin-2-amine; trans-4-[3-(methylamino)azetidin-1-yl]-5,6,6a,7,8,9,10,10a-octahydrobenzo[h]quinazolin-2-amine; trans-4-[3-(ethylamino)azetidin-1-yl]-5,6,6a,7,8,9,10,10a-octahydrobenzo[h]quinazolin-2-amine; trans-4-[(3R)-3-(methylamino)pyrrolidin-1-yl]-5,6,6a,7,8,9,10,10a-octahydrobenzo[h]quinazolin-2-amine; trans-4-[(3R)-3-aminopyrrolidin-1-yl]-5,6,6a,7,8,9,10,10a-octahydrobenzo[h]quinazolin-2-amine; trans-4-octahydro-6H-pyrrolo[3,4-b]pyridin-6-yl-5,6,6a,7,8,9,10,10a-octahydrobenzo[h]quinazolin-2-amine; cis-4-[(3R)-3-(methylamino)pyrrolidin-1-yl]-5,6,6a,7,8,9,10,10a-octahydrobenzo[h]quinazolin-2-amine; cis-4-[(3R)-3-aminopyrrolidin-1-yl]-5,6,6a,7,8,9,10,10a-octahydrobenzo[h]quinazolin-2-amine; cis-4-[cis-octahydro-6H-pyrrolo[3,4-b]pyridin-6-yl]-5,6,6a,7,8,9,10,10a-octahydrobenzo[h]quinazolin-2-amine; cis-4-[3-(methylamino)azetidin-1-yl]-5,6,6a,7,8,9,10,10a-octahydrobenzo[h]quinazolin-2-amine; cis-4-[3-(ethylamino)azetidin-1-yl]-5,6,6a,7,8,9,10,10a-octahydrobenzo[h]quinazolin-2-amine; 4-cis-octahydro-6H-pyrrolo[3,4-6]pyridin-6-yl-6,7,7a,8,11,11a-hexahydro-5H-8,11-ethanobenzo[6,7]cyclohepta[1,2-d]pyrimidin-2-amine; 4-[(3R)-3-(methylamino)pyrrolidin-1-yl]-6,7,7a,8,11,11a-hexahydro-5H-8,11-ethanobenzo[6,7]cyclohepta[1,2-d]pyrimidin-2-amine; 4-piperazin-1-yl-6,7,7a,8,11,11a-hexahydro-5H-8,11-ethanobenzo[6,7]cyclohepta[1,2-d]pyrimidin-2-amine; 4-cis-octahydro-6H-pyrrolo[3,4-b]pyridin-6-yl-6,7,7a,8,9,10,11,11a-octahydro-5H-8,11-ethanobenzo[6,7]cyclohepta[1,2-d]pyrimidin-2-amine; or 4-[(3R)-3-(methylamino)pyrrolidin-1-yl]-6,7,7a,8,9,10,11,11a-octahydro-5H-8,11-ethanobenzo[6,7]cyclohepta[1,2-d]pyrimidin-2-amine.

In another embodiment, the Histamine H4 antagonist or selective Histamine H4 antagonists are selected from those described in the international Patent Application WO2009/114575: (R)-4'-(3-(methylamino)pyrrolidin-1-yl)-6',7'-dihydro-5'H-spiro[cyclopentane-1,8'-quinazolin]-2'-amine; 4'-(piperazin-1-yl)-6',7'-dihydro-5'H-spiro[cyclopentane-1,8'-quinazolin]-2'-amine; 4'-(3-(methylamino)azetidin-1-yl)-6',7'-dihydro-5'H-spiro[cyclopentane-1,8'-quinazolin]-2'-amine; (R)-4'-(3-aminopyrrolidin-1-yl)-6'7'-dihydro-5'H-spiro[cyclopentane-1,8'-quinazolin]-2'-amine; (S)-4'-(3-aminopyrrolidin-1-yl)-6'7'-dihydro-5'H-spiro[cyclopentane-1,8'-quinazolin]-2'-amine; 4'-((3aR,6aR)-hexahydropyrrolo[3,4-b]pyrrol-1(2H)-yl)-6l,71-dihydro-5H-spiro[cyclopentane-1,8'-quinazolin]-2'-amine; 4'-((3 aS,6aS)-hexahydropyrrolo[3,4-b]pyrrol-1 (2H)-yl)-6'7'-dihydro-5'H-spiro[cyclopentane-1,8'-quinazolin]-2'-amine; 4'-(1,4-diazepan-1-yl)-6',7'-dihydro-5'H-spiro[cyclopentane-1,8'-quinazolin]-2'-amine; 4'-((4aR,7aR)-tetrahydro-1H-pyrrolo[3,4-b]pyridin-6(2H,7H,7aH)-yl)-6',7'-dihydro-5'H-spiro[cyclopentane-1,8'-quinazolin]-2'-amine; N4'-(1-methylpiperidin-4-yl)-6',7'-dihydro-5H-spiro[cyclopentane-1,8'-quinazoline]-2',4'-diamine; methyl 4-amino-1-(2'-amino-6',7'-dihydro-5'H-spiro[cyclopentane-1,8'-quinazoline]-4'-yl)piperidine-4-carboxylate; 4-amino-1-(2'-amino-6',7'-dihydro-5H-spiro[cyclopentane-1,8'-quinazoline]-4'-yl)piperidine-4-carboxylic acid; 4'-(3-aminoazetidin-1-yl)-6',7'-dihydro-5'H-spiro[cyclopentane-1,8'-quinazolin]-2'-amine; 4'-(2-(dimethylamino)ethoxy)-6',7'-dihydro-5'H-spiro[cyclopentane-1,8'-quinazolin]-2'-amine; (R)-4'-(1-methylpyrrolidin-3-yloxy)-6'7'-dihydro-5'H-spiro[cyclopentane-1,8'-quinazolin]-2'-amine; 4-(piperazin-1-yl)-5,6,7,8-tetrahydrospiro[cyclohepta[d]pyrimidine-9,1'-cyclohexan]-2-amine; (R)-4-(3-aminopyrrolidin-1-yl-5,6,7,8-tetrahydrospiro[cyclohepta[d]pyrimidine-9,1'-cyclohexan]-2-amine; 4-((4aR,7aR)-tetrahydro-1H-pyrrolo[3,4-b]pyridin-6(2H,7H,7aH)-yl)-5,6,7,8-tetrahydrospiro[cyclohepta[d]pyrimidine-9,1'-cyclohexan]-2-amine; 4-(piperazin-1-yl)-1',3',5,6,7,8-hexahydrospiro[cyclohepta[d]pyrimidine-9,2'-inden]-2-amine; and (R)-4-(3-aminopyrrolidin-1-yl)-1',3',5,6,7,8-hexahydrospiro[cyclohepta[d]pyrimidine-9,2'-inden]-2-amine.

In another embodiment, the Histamine H4 antagonist or selective Histamine H4 antagonists are selected from those described in the international Patent Application WO2008/060767: 6-Methyl-4-[(3R)-3-methylamino-pyrrolidin-1-yl]-5,6-dihydro-benzo[h]quinazolin-2-ylamine; 6-Methyl-4-(3-methylamino-azetidin-1-yl)-5,6-dihydro-benzo[h]quinazolin-2-ylamine; 4-(3-Methylamino-azetidin-1-yl)-6,7-dihydro-5H-benzo[6,7]cyclohepta[1,2-d]pyrimidin-2-ylamine; 6-Methyl-4-piperazin-1-yl-5,6-dihydro-benzo[h]quinazolin-2-ylamine; 4-(3-(R)-Methylamino-pyrrolidin-1-yl)-6,7-dihydro-5H-benzo[6,7]cyclohepta[1,2-d]pyrimidin-2-ylamine; 4-Piperazin-1-yl-6,7-dihydro-5H-benzo[6,7]cyclohepta[1,2-d]pyrimidin-2-ylamine; 1-(3-Methylamino-azetidin-1-yl)-10H-9-oxa-2,4-diaza-phenanthren-3-ylamine; 1-{3-(R)-Methylamino-pyrrolidin-1-yl)-10H-9-oxa-2,4-diaza-phenanthren-3-ylamine; 1-Piperazin-1-yl-10H-9-oxa-2,4-diaza-phenanthren-3-ylamine; 10-Fluoro-4-(3-(R)-methylamino-pyrrolidin-1-yl)-6,7-dihydro-5H-benzo[6,7]cyclohepta[1,2-d]pyrimidin-2-ylamine; 10-Fluoro-4-(3-methylamino-azetidin-1-yl)-6,7-dihydro-5H-benzo[6,7]cyclohepta[1,2-d]pyrimidin-2-ylamine; 10-Fluoro-4-piperazin-1-yl-6,7-dihydro-5H-benzo[6,7]cyclohepta[1,2-d]pyrimidin-2-ylamine; 4-[(3S)-3-Methyl-amino-pyrrolidin-1-yl]-6,7-dihydro-5H-benzo[6,7]cyclohepta[1,2-d]pyrimidin-2-ylamine; 4-((3aR,6aR)-1-Methyl-hexahydro-pyrrolo[3,4-b]pyrrol-5-yl)-6,7-dihydro-5H-benzo[6,7]cyclohepta[1,2-d]pyrimidin-2-ylamine; 4-((3R)-3-Amino-pyrrolidin-1-yl)-6,7-dihydro-5H-benzo[6,7]cyclohepta[1,2-d]pyrimidin-2-ylamine; 4-((1S,4S)-2,5-Diaza-bicyclo[2.2.1]hept-2-yl)-6,7-dihydro-5H-benzo[6,7]cyclohepta[1,2-d]pyrimidin-2-ylamine; 4-(3-Piperidin-1-yl-pyrrolidin-1-yl)-6,7-dihydro-5H-benzo[6,7]cyclohepta[1,2-d]pyrimidin-2-ylamine; 4-{(3aR,6aR)-Hexahydro-pyrrolo[3,4-b]pyrrol-1-yl)-6,7-dihydro-5H-benzo[6,7]cyclohepta[1,2-d]pyrimidin-2-ylamine; 4-Piperazin-1-yl-5,6,7,8-tetrahydro-1,3-diaza-dibenzo[a,c]cycloocten-2-ylamine; 4-Piperazin-1-yl-6,7,8,9-tetrahydro-5H-1,3-diaza-dibenzo[a,c]cyclononen-2-ylamine; 4-(Hexahydro-pyrrolo[3,4-c]pyrrol-1-yl)-6,7-dihydro-5H-benzo[6,7]cyclohepta[1,2-d]pyrimidin-2-ylamine; 4-{3-(R)-Methylamino-pyrrolidin-1-yl)-6,7,8,9-tetrahydro-5H-1,3-diaza-dibenzo[a,c]

cyclononen-2-ylamine; 4-({R}-3-Amino-pyrrolidin-1-yl)-6,7,8,9-tetrahydro-5H-1,3-diaza-dibenzo[a,c]cyclononen-2-ylamine; 4-{(S)-3'Amino-pyrrolidin-1-yl)-6,7,8,9-tetrahydro-5H-1,3-diaza-dibenzo[a,c]cyclononen-2-ylamine; 4-(3-Methylamino-azetidin-1-yl)-6,7,8,9-tetrahydro-5H-1,3-diaza-dibenzo[a,c]cyclononen-2-ylamine; 4-1(3 aS,6aS)-Hexahydro-pyrrolo[3,4-b]pyrrol-1-yl)-6,7,8,9-tetrahydro-5H-1,3-diaza-dibenzo[a,c]cyclononen-2-ylamine; 4-((1S,4S)-2,5-Diaza-bicyclo[2.2.1]hept-2-yl)-6,7,8,9-tetrahydro-5H-1,3-diaza-dibenzo[a,c]cyclononen-2-ylamine; 4-{4-Methyl-piperazin-1-yl)-5,6-dihydro-7-oxa-1,3-diaza-dibenzo[a,c]cyclohepten-2-ylamine; 4-Piperazin-1-yl-5,6-dihydro-7-oxa-1,3-diaza-dibenzo[a,c]cyclohepten-2-ylamine; 4-((R)-3-Methylamino-pyrrolidin-1-yl)-5,6-dihydro-7-oxa-1,3-diaza-dibenzo[a,c]cyclohepten-2-ylamine, 4-(3-Methylamino-azetidin-1-yl)-5,6-dihydro-7-oxa-1,3-diaza-dibenzo[a,c]cyclohepten-2-ylamine; 4-(3-Methylamino-azetidin-1-yl)-5,6-dihydro-7-thia-1,3-diaza-dibenzo[a,c]cyclohepten-2-ylamine; 4-(3-(R)-Methylamino-pyrrolidin-1-yl)-5,6-dihydro-7-thia-1,3-diaza-dibenzo[a,c]cyclohepten-2-ylamine; 4-{3-(R)-Amino-pyrrolidin-1-yl)-5,6-dihydro-7-thia-1,3-diaza-dibenzo[a,c]cyclohepten-2-ylamine; 4-Piperazin-1-yl-5,6-dihydro-7-thia-1,3-diaza-dibenzo[a,c]cyclohepten-2-ylamine; 4-(3-Methylamino-azetidin-1-yl)-7-oxo-6,7-dihydro-5H-7λ4-thia-1,3-diaza-dibenzo[a,c]cyclohepten-2-ylamine; 4-(3-Methylamino-azetidin-1-yl)-7,7-dioxo-6,7-dihydro-5H-7λ6-thia-1,3-diaza-dibenzo[a,c]cyclohepten-2-ylamine; 4-(3-(R)-Methylamino-pyrrolidin-1-yl)-5,6-dihydro-benzo[h]quinazolin-2-ylamine; 4-(3-Methylamino-azetidin-1-yl)-5t6-dihydro-benzo[h]quinazolin-2-ylamine; 4-Piperazin-1-yl-5,6-dihydro-benzo[h]quinazolin-2-ylamine; 10-chloro-4-[(3R)-3-(methylamino)pyrrolidin-1-yl]-5,6-dihydro[1]benzoxepino[5,4-d]pyrimidin-2-amine; 10-methyl-4-[(3R)-3-{methylamino)pyrrolidin-1-yl]-5,6-dihydro[1]benzoxepino[5,4-of]pyrimidin-2-amine; 10-methoxy-4-[(3R)-3-(methylamino)pyrrolidin-1-yl]-5,6-dihydro[1]benzoxepino[5,4-d]pyrimidin-2-amine; 9-chloro-4-[(3R)-3-(methylamino)pyrrolidin-1-yl]-5,6-dihydro[1]benzoxepino[5,4-d]pyrimidin-2-amine; 9-nπethyl-4-[{3R)-3-(methylamino)pyrrolidin-1-yl]-5,6'-dihydro[1]benzoxepino[5,4-d]pyrimidin-2-amine; 9-methoxy-4-[(3R)-3-{methylamino)pyrrolidin-1-yl]-5,6-dihydro[1]benzoxepino[5,4-d]pyrimidin-2-arnine; 8-chloro-4-[(3R)-3-(methylamino)pyrrolidin-1-yl]-5,6-dihydro[1]benzoxepino[5,4-d]pyrimidin-2-amine; 8-Methyl-4-((R)-3-methylamino-pyrrolidin-1-yl)-5,6-dihydro-7-oxa-1,3-diaza-dibenzo[a,c]cyclohepten-2-ylamine; 8-methoxy-4-[(3R)-3-(methylamino)pyrrolidin-1-yl]-5,6-dihydro[1]benzoxepino[5,4-d]pyrimidin-2-amine; 4-[(3R)-3-(methylamino)pyrrolidin-1-yl]-5,6,7,8-tetrahydrobenzo[7,8]cycloocta[1,2-d]pyrimidin-2-amine; 4-[(3R)-3-aminopyrrolidin-1-yl]-5,6,7,8-tetrahydrobenzo[7,8]cycloocta[1,2-d]pyrimidin-2-amine; 4-[(3S)-3-aminopyrrolidin-1-yl]-5,6,7,8-tetrahydrobenzo[7,8]cycloocta[1,2-d]pyrimidin-2-amine; 4-(3-aminoazetidin-1-yl)-5,6,7,8-tetrahydrobenzo[7,8]cycloocta[1,2-d]pyrimidin-2-amine; 4-[(3aR,6aR)-hexahydro-pyrrolo[3,4-b]pyrrol-1(2H)-yl]-5,6,7,8-tetrahydrobenzo[7,8]cycloocta[1,2-d]pyrimidin-2-amine; 4-octahydro-6H-pyrrolo[3,4-b]pyridin-6-yl-6,7-dihydro-5H-benzo[6,7]cyclohepta[1,2-d]pyrimidin-2-amine; 4-(2,8-diazaspiro[4.5]dec-8-yl)-6,7-dihydro-5H-benzo[6,7]cyclohepta[1,2-d]pyrimidin-2-amine; 4-(1,5-diazocan-1-yl)-6,7-dihydro-5H-benzo[6,7]cyclohepta[1,2-d]pyrimidin-2-amine; 4-{4-aminopiperidin-1-yl)-6,7-dihydro-5H-benzo[6,7]cyclohepta[1,2-d]pyrimidin-2-amine; N4-(2-azetidin-2-ylethyl)-6,7-dihydro-5H-benzo[6,7]cyclohepta[1,2-d]pyrimidine-2,4-diamine; N4-[(2R)-azetidin-2-ylmethyl]-6,7-dihydro-5H-benzo[6,7]cyclohepta[1,2-d]pyrimidine-2,4-diamine; N4-(1-methylpiperidin-4-yl)-6,7-dihydro-5H-benzo[6,7]cycloheptat[1,2-d]pyrimidine-2,4-diamine; N4-[(1R,5S)-8-methyl-8-azabicyclo[3.2.1]oct-3-yl]-6,7-dihydro-5H-benzo[6,7]cyclohepta[1,2-d]pyrimidine-2,4-diamine; 4-(5-methyl-1,4-diazepan-1-yl)-6,7-dihydro-5H-benzo[6,7]cyclohepta[1,2-d]pyrimidin-2-amine; 4-(1-Methyl-piperidin-4-yloxy)-6,7-dihydro-5H-benzo[6,7]cyclohepta[1,2-d]pyrimidin-2-ylamine; 4-(1-methyl-piperidin-3-yloxy)-6,7-dihydro-5H-benzo[6,7]cyclohepta[1,2-d]pyrimidin-2-ylamine; 4-((R)-1-Methyl-pyrrolidin-3-yloxy)-6,7-dihydro-5H-benzo[6,7]cyclohepta[1,2-d]pyrimidin-2-ylamine; 4-((S)-1-Methyl-pyrrolidin-3-yloxy)-6,7-dihydro-5H-benzo[6,7]cyclohepta[1,2-d]pyrimidin-2-ylamine, 4-(Piperidin-4-yloxy)-6,7-dihydro-5H-benzo[6,7]cyclohepta[1,2-d]pyrimidin-2-ylamine; 4-((S)-Pyrrolidin-3-yloxy)-6,7-dihydro-5H-benzo[6,7]cyclohepta[1,2-d]pyrimidin-2-ylamine, 4-(2-Dimethylamino-ethoxy)-6,7-dihydro-5H-benzo[6,7]cyclohepta[1,2-d]pyrimidin-2-ylamine; 4-(1,9-Diaza-spiro[5.5]undec-9-yl)-6,7-dihydro-5H-benzo[6,7]cyclohepta[1,2-d]pyrimidin-2-ylamine; 4-((R)-3-Dimethylamino-pyrrolidin-1-yl)-6,7-dihydro-5H-benzo[6,7]cyclohepta[1,2-d]pyrimidin-2-ylamine; 4-(2,6-Diaza-spiro[3.5]non-2-yl)-6,7-dihydro-5H-benzo[6,7]cyclohepta[1,2-d]pyrimidin-2-ylamine; 4-(2,5-Diaza-spiro[3.5]non-2-yl)-6,7-dihydro-5H-benzo[6,7]cyclohepta[1,2-d]pyrimidin-2-ylamine; 4-(Octahydro-pyrrolo[3,4-c]pyridin-2-yl)-6,7-dihydro-5H-benzo[6,7]cyclohepta[1,2-d]pyrimidin-2-ylamine; 4-(Octahydro-pyrrolo[1,2-a]pyrazin-2-yl)-6,7-dihydro-5H-benzo[6,7]cyclohepta[1,2-d]pyrimidin-2-ylamine; 4-(3,6-Diaza-bicyclo[3.2.1]oct-6-yl)-6,7-dihydro-5H-benzo[6,7]cyclohepta[1,2-d]pyrimidin-2-ylamine; 4-(2,6-Diaza-bicyclo[3.2.1]oct-2-yl)-6,7-dihydro-5H-benzo[6,7]cyclohepta[1,2-d]pyrimidin-2-ylamine; N-(4-Piperazin-1-yl-6,7-dihydro-5H-benzo[6,7]cyclohepta[1,2-d]pyrimidin-2-yl)-acetamide, N-(4-Piperazin-1-yl-6,7-dihydro-5H-benzo[6,7]cyclohepta[1,2-d]pyrimidin-2-yl)-benzamide, 4-(5-Methyl-octahydro-pyrrolo[3,4-c]pyridin-2-yl)-6,7-dihydro-5H-benzo[6,7]cyclohepta[1,2-d]pyrimidin-2-ylamine, 4-(3-Methyl-3,6-diaza-bicyclo[3.2.1]oct-6-yl)-6,7-dihydro-5H-benzo[6,7]cyclohepta[1,2-d]pyrimidin-2-ylamine, 2-Dimethylamino-N-(4-piperazin-1-yl-6,7-dihydro-5H-benzo[6,7]cyclohepta[1,2-d]pyrimidin-2-yl)-acetamide; 2-Methylamino-N-(4-piperazin-1-yl-6,7-dihydro-5H-benzo[6,7]cyclohepta[1,2-d]pyrimidin-2-yl)-acetamide; 2-Amino-N-(4-piperazin-1-yl-6,7-dihydro-5H-benzo[6,7]cyclohepta[1,2-d]pyrimidin-2-yl)-acetamide; 1-Methyl-3-(4-piperazin-1-yl-6,7-dihydro-5H-benzo[6,7]cyclohepta[1,2-d]pyrimidin-2-yl)-urea; 4-Amino-N-(4-piperazin-1-yl-6,7-dihydro-5H-benzo[6,7]cyclohepta[1,2-d]pyrimidin-2-yl)-butyramide; 6-{2-pyridin-3-ylmethylamino-6,7-dihydro-5H-benzo[6,7]cyclohepta[1,2-d]pyrimidin-4-yl)octahydro-1H-pyrrolo[3,4-b]pyridine; 3-Amino-N-(4-piperazin-1-yl-6,7-dihydro-5H-benzo[6,7]cyclohepta[1,2-d]pyrimidin-2-yl)-propionamide; 4-[1,4,7]Triazonan-1-yl-6,7-dihydro-5H-benzo[6,7]cyclohepta[1,2-d]pyrimidin-2-ylamine; N,N-Dimethyl-N'-(4-piperazin-1-yl-6,7-dihydro-5H-benzo[6,7]cyclohepta[1,2-d]pyrimidin-2-yl)-ethane-1,2-diamine; 4-(Octahydro-pyrrolo[3,4-b]pyridin-6-yl)-5,6-dihydro-7-thia-1,3-diaza-dibenzo[a,c]cyclohepten-2-ylamine; 4-((R)-3-Methylamino-pyrrolidin-1-yl)-6,7,9,10,11,12-hexahydro-5H-1,3-diaza-benzo[3,4]cyclohepta[1,2-b]naphthalen-2-ylamine; 4'(Octahydro-pyrrolo[3,4-b]pyridin-6-yl)-6,7,9,10,11,12-hexahydro-5H-1,3-diaza-benzo[3,4]cyclohepta[1,2-b]naphthalen-2- ylamine; 4-Piperazin-1-yl-6,7,9,10,11,12-hexahydro-5H-1,3-diaza-benzo[3,4]cyclohepta[1,2-b]naphthalen-2-ylamine; 9-Iodo-4-({R}-3-methylamino-pyrrolidin-1-yl)-5,6-dihydro-7-oxa-1,3-diaza-dibenzo[a,c]cyclohepten-2-ylamine; 9-Iodo-4-piperazin-1-yl-5,6-dihydro-7-oxa-1,3-diaza-dibenzo[a,c]cyclohepten-2-ylamine; 9-Iodo-4-octahydro-pyrrolo[3,4-b]pyridin-6-yl-5,6-dihydro-7-oxa-1,3-diaza-dibenzo[a,c]cyclohepten-2-ylamine; 2,4-Di-piperazin-1-yl-6,7-dihydro-5H-benzo[6,7]cyclohepta[1,2-d]pyrimidine; 2-Amino-4-octahydro-pyrrolo[3,4-b]pyridin-6-yl-5,6-dihydro-7-oxa-1,3-diaza-dibenzo[a,c]cycloheptene-9-carbonitrile; 4-Octahydro-pyrrolo[3,4-b]pyridin-6-yl-9-phenyl-5,6-dihydro-7-oxa-1,3-diaza-dibenzo[a,c]cyclohepten-2-ylamine; 4-Octahydro-pyrrolo[3,4-b]pyridin-6-yl-9-pyridin-3-yl-5,6-dihydro-7-oxa-1,3-diaza-dibenzo[a,c]cyclohepten-2-ylamine; 4-((R)-3-Methylamino-pyrrolidin-1-yl)-6,7-dihydro-5-thia-1,3-diaza-dibenzo[a,c]cyclohepten-2-ylamine; 2-Amino-4-octahydro-pyrrolo[3,4-b]pyridin-6-yl-5,6-dihydro-7-oxa-1,3-diaza-dibenzo[a,c]cycloheptene-9-carboxylic acid methyl ester; 4-Piperazin-1-yl-6,7-dihydro-5-thia-1,3-diaza-dibenzo[a,c]cyclohepten-2-ylamine; 4-(Octahydro-pyrrolo[3,4-b]pyridin-6-yl)-6,7-dihydro-5-thia-1,3-diaza-dibenzo[a.c]cyclohepten-2-ylamine; 4-((R)-3-Methylamino-pyrrolidin-1-yl)-5,5-dioxo-6,7-dihydro-5H-5λ6-thia-1,3-diaza-dibenzo[a,c]cyclohepten-2-ylamine; 4-((R)-3-Methylamino-pyrrolidin-1-yl)-5-oxo-6,7-dihydro-5-thia-1,3-diaza-dibenzo[a,c]cyclohepten-2-ylamine; N4-(3-Piperidin-1-yl-propyl)-6,7-dihydro-5H-benzo[6,7]cyclohepta[1,2-]pyrimidine-2,4-diamine; 4-(4-Dimethylamino-piperidin-1-yl)-6,7-dihydro-5H-benzo[6,7]cyclohepta[1,2-d]pyrimidin-2-ylamine; 10-fluoro-4-octahydro-6H-pyrrolo[3,4-b]pyridin-6-yl-6,7-dihydro-5H-benzo[6,7]cyclohepta[1,2-d]pyrimidin-2-amine; 4-[1,4]Diazepan-1-yl-6,7-dihydro-5H-benzo[6,7]cyclohepta[1,2-d]pyrimidin-2-ylamine; (1R,5S)-4-(3,6-Diaza-bicyclo[3.2.0]hept-6-yl-6,7-dihydro-5H-benzo[6,7]cyclohepta[1,2-d]pyrimidin-2-ylamine; 4-Piperazin-1-yl-6,7-dihydro-5H-benzo[6,7]cyclohepta[1,2-d]pyrimidine; (3 aS,6aS)-4-(Hexahydro-pyrrolo[3,4-b]pyrrol-1-yl)-6,7-dihydro-5H-benzo[6,7]cyclohepta[1,2-d]pyrimidin-2-ylamine; {1S,5S)-4-(3,6-Diaza-bicyclo[3.2.0]hept-3-yl)-6,7-dihydro-5H-benzo[6,7]cyclohepta[1,2-d]pyrimidin-2-ylamine; N4-Piperidin-3-yl-6,7-dihydro-5H-benzo[6,7]cyclohepta[1,2-d]pyrimidine-2,4-diamine; N4-(Octahydro-isoindol-4-yl)-6,7-dihydro-5H-benzo[6,7]cyclohepta[1,2-d]pyrimidine-2,4-diamine; Methyl-{4-piperazin-1-yl-6,7-dihydro-5H-benzo[6,7]cyclohepta[1,2-d]pyrimidin-2-yl)-amine; 4-{3-(R)-Methylamino-pyrrolidin-1-yl)-6,7-dihydro-5H-benzo[6,7]cyclohepta[1,2-d]pyrimidine; [1-(6,7-Dihydro-5H-benzo[6,7]cyclohepta[1,2-d]pyrimidin-4-yl)-azetidin-3-yl]-amine; 8,10-Dimethyl-piperazin-1-yl-6,7-dihydro-5H-benzo[6,7]cyclohepta[1,2-d]pyrimidin-2-ylamine; 6-{2-(1H-imidazol-4-yl)ethylamino-6,7-dihydro-5H-benzo[6,7]cyclohepta[1,2-d]pyrimidin-4-yl)octahydro-1H-pyrrolo[3,4-b]pyridine; (2-Amino-4-piperazin-1-yl-6,7-dihydro-5H-benzo[6,7]cyclohepta[1,2-d]pyrimidin-10-yl)-methyl-carbannic acid methyl ester; 10-N-Methyl-4-piperazin-1-yl-6,7-dihydro-5H-benzo[6,7]cyclohepta[1,2-d]pyrimidine-2,10-diamine; (2-Amino-4-octahydro-pyrrolo[3,4-b]pyridin-6-yl-6,7-dihydro-5H-benzo[6,7]cyclohepta[1,2-d]pyrimidin-10-yl)-methyl-carbamic acid methyl ester; 10-N-methyl-4-[(4aR,7aR)-octahydro-6H-pyrrolo[3,4-b]pyridin-6-yl]-6,7-dihydro-5H-benzo[6,7]cyclohepta[1,2-d]pyrimidine-2,10-diamine; N-{2-Amino-4-piperazin-1-yl-6,7-dihydro-5H-benzo[6,7]cyclohepta[1,2-d]pyrimidin-11-yl)-acetamide; 4-(Octahydro-pyrrolo[3,4-b]pyridin-6-yl)-6,7-dihydro-5H-benzo[6,7]cyclohepta[1,2-d]pyrimidine-2-carboxylic acid methyl ester; 4-(Octahydro-pyrrolo[3,4-b]pyridin-6-yl)-6,7-dihydro-5H-benzo[6,7]cyclohepta[1,2-d]pyrimidine-2-carboxylic acid.

In another embodiment, the Histamine H4 antagonist or selective Histamine H4 antagonists are selected from those described in the international Patent Application WO2009137492: 4-octahydro-6H-pyrrolo[3,4-b]pyridin-6-yl-6,7-dihydro-5H-thieno[2',3':6,7]cyclohepta[1,2-d]pyrimidin-2-amine; 4-[(3R)-3-aminopyrrolidin-1-yl]-6,7-dihydro-5H-thieno[2',3':6,7]cyclohepta[1,2-d]pyrimidin-2-amine; 4-[(3R)-3-(methylamino)pyrrolidin-1-yl]-6,7-dihydro-5H-thieno[2',3':6,7]cyclohepta[1,2-d]pyrimidin-2-amine; 4-octahydro-6H-pyrrolo[3,4-b]pyridin-6-yl-6,7-dihydro-5H-furo[2',3':6,7]cyclohepta[1,2-d]pyrimidin-2-amine; 9-methyl-4-octahydro-6H-pyrrolo[3,4-b]pyridin-6-yl-6,7-dihydro-5H-furo[2',3':6,7]cyclohepta[1,2-d]pyrimidin-2-amine; 4-[(3R)-3-aminopyrrolidin-1-yl]-9-methyl-6,7-dihydro-5H-furo[2',3':6,7]cyclohepta[1,2-d]pyrimidin-2-amine; 4-octahydro-6H-pyrrolo[3,4-b]pyridin-6-yl-6,7-dihydro-5H-furo[3',2':6,7]cyclohepta[1,2-d]pyrimidin-2-amine; 4-[(3R)-3-aminopyrrolidin-1-yl]-8-methyl-5,6,7,8-tetrahydropyrazolo[3',4':6,7]cyclohepta[1,2-d]pyrimidin-2-amine; 8-tert-butyl-4-octahydro-6H-pyrrolo[3,4-b]pyridin-6-yl-5,6,7,8-tetrahydropyrazolo[3',4':6,7]cyclohepta[1,2-d]pyrimidin-2-amine; 4-[(3R)-3-(methylamino)pyrrolidin-1-yl]-8-phenyl-5,6,7,8-tetrahydropyrazolo[3',4':6,7]cyclohepta[1,2-d]pyrimidin-2-amine; 9-bromo-4-octahydro-6H-pyrrolo[3,4-b]pyridin-6-yl-6,7-dihydro-5H-thieno[2',3':6,7]cyclohepta[1,2-d]pyrimidin-2-amine; 4-octahydro-6H-pyrrolo[3,4-b]pyridin-6-yl-9-phenyl-6,7-dihydro-5H-thieno[2',3':6,7]cyclohepta[1,2-d]pyrimidin-2-amine; 4-[(3R)-3-aminopyrrolidin-1-yl]-6,7-dihydro-5H-pyrido[3',2':6,7]cyclohepta[1,2-d]pyrimidin-2-amine; 4-[(3R)-3-aminopyrrolidin-1-yl]-10-methyl-6,7-dihydro-5H-isoxazolo[5',4':6,7]cyclohepta[1,2-d]pyrimidin-2-amine; 4-[(4aR,7aR)-octahydro-6H-pyrrolo[3,4-b]pyridin-6-yl]-6,7-dihydro-5H-thieno[2',3':6,7]cyclohepta[1,2-d]pyrimidin-2-amine; or a pharmaceutically acceptable salt thereof.

In another embodiment, the Histamine H4 antagonist or selective Histamine H4 antagonists are selected from those described in the international Patent Application WO2009123967: (R)-4-(3-aminopyrrolidin-1-yl)-9,9-dimethyl-6,7.8.9-tetrahydro-5H-cyclohepta[d]pyrimidin-2-amine; 9,9-dimethyl-4-(piperazin-1-yl)-6,7,8,9-tetrahydro-5H-cyclohepta[d]pyrimidin-52-amine; (R)-4-(3-aminopyrrolidin-1-yl)-9,9-diethyl-6,7,8,9-tetrahydro-5H-cyclohepta[d]pyrimidin-2-amine; (R)-4-(3-aminopyrrolidin-1-yl)-9,9-dibenzyl-6,7,8,9-tetrahydro-5H-cyclohepta[d]pyrimidin-2-amine; 8-phenyl-4-(piperazin-1-yl)-6,7,8,9-tetrahydro-5H-cyclohepta[d]pyrimidin-2-amine; 8-phenyl-4-(tetrahydro-1H-pyrrolo[3,4-b]pyridine-692H,7H,7aH0-yl)-6,7,8,9-tetrahydro-5H-cyclohepta[d]pyrimidin-2-amine; 4-((R)-3-(methylamino)pyrrolidin-1-yl)-8-phenyl-6,7,8,9-tetrahydro-5H-5-cyclohepta[d]pyrimidin-2-amine; 4-(3-aminoazetidin-1-yl)-8-phenyl-6,7,8,9-tetrahydro-5H-cyclohepta[d]pyrimidin-2-amine; 8-phenyl-4-(piperazine-1-yl)-5,6,7,8-tetrahydroquinazolin-2-amine; 8-phenyl-4-((4aR,7aR)-tetrahydro-1H-pyrrolo[3,4-b]pyridin-6(2H,7H,7aH)-yl)-5,6,7,8-tetrahydroquinazolin-2-amine; 4-((R)-3-(methylamino)pyrrolidin-1-yl)-8-phenyl-5,6,7,8-tetrahydroquinazolin-2-amine; 8,8-dimethoxy-4-(piperazin-1-yl)-5,6,7,8-tetrahydroquinazolin-2-amine; 4-(piperazin-1-yl)-6,7,8,9-tetrahydro-5H-cyclohepta[d]pyrimidin-2-amine; 9-(2-methylpyridin-4-yl)-4-(piperazin-1-yl)-6,7,8,9-tetrahydro-5H-cyclohepta[d]pyrimidin-2-amine; methyl 5-(2-amino-4-(piperazin-1-yl)-6,7,8,9-tetrahydro- 5H-cyclohepta[d]pyrimidin-9-yl)nicotinate; 5-(2-amino-4-(piperazin-1-yl)-6,7,8,9-tetrahydro-5H-cyclohepta[d]pyrimidin-9-yl)nicotinic acid; 4-((R)-3-(methylamino) pyrrolidin-1-yl)-9-phenyl-6,7,8,9-tetrahydro-5H-cyclohepta [d]pyrimidin-2-amine; 4-(3-(methylamino)azetidin-1-yl)-9-phenyl-6,7,8,9-tetrahydro-5H-cyclohepta[d]pyrimidin-2-amine; 9-phenyl-4-(piperazin-1-yl)-6,7,8,9-tetrahydro-5H-cyclohepta[d]pyrimidin-2-amine; 9-phenyl-4-tetrahydro-1H-pyrrolo[3,4-b]pyridine-6(2H, 7H, 7 aH)-6,7,8,9-tetrahydro-5H-cyclohepta[d]pyrimidin-2-amine; or 5,9-phenyl-4-((4aR,7aR)-tetrahydro-1H-pyrrolo[3,4-b]pyridin-6(2H, 7H, 7aH)-yl)-6,7,8,9-tetrahydro-5H-cyclohepta[d]pyrimidin-2-amine.

In another embodiment, the Histamine H4 antagonist or selective Histamine H4 antagonists are selected from those described in the international Patent Application WO2005/054239: 4-[octahydro-6H-pyrrolo[3,4-b]pyridin-6-yl]-6-phenylpyrimidin-2-amine; 4-(3-methoxyphenyl)-6-[octahydro-6H-pyrrolo[3,4-b]pyridin-6-yl]pyrimidin-2-amine; 3-{2-amino-6-[octahydro-6H-pyrrolo[3,4-b]pyridin-6-yl] pyrimidin-4-yl}benzonitrile; 4-(1-naphthyl)-6-[octahydro-6H-pyrrolo[3,4-b]pyridin-6-yl]pyrimidin-2-amine; 4-(3-methylphenyl)-6-[octahydro-6H-pyrrolo[3,4-b]pyridin-6-yl]pyrimidin-2-amine; 4-(3-chlorophenyl)-6-[octahydro-6H-pyrrolo[3,4-b]pyridin-6-yl]pyrimidin-2-amine, 4-[octahydro-6H-pyrrolo[3,4-b]pyridin-6-yl]-6-[3-(trifluoromethyl)phenyl]pyrimidin-2-amine; 1-(3-{2-amino-6-[octahydro-6H-pyrrolo[3,4-b]pyridin-6-yl]pyrimidin-4-yl}phenyl) ethanone; 4-(3-nitrophenyl)-6-[octahydro-6H-pyrrolo[3,4-b]pyridin-6-yl]pyrimidin-2-amine; (3-{2-amino-6-[octahydro-6H-pyrrolo[3,4-b]pyridin-6-yl] pyrimidin-4-yl}phenyl)methanol; 4-(3,4-dichlorophenyl)-6-[octahydro-6H-pyrrolo[3,4-b]pyridin-6-yl]pyrimidin-2-amine; 4-(4-nitrophenyl)-6-[octahydro-6H-pyrrolo[3,4-b] pyridin-6-yl]pyrimidin-2-amine; 4-(3-fluorophenyl)-6-[octahydro-6H-pyrrolo[3,4-b]pyridin-6-yl]pyrimidin-2-amine; 5-methyl-4-[octahydro-6H-pyrrolo[3,4-b]pyridin-6-yl]-6-phenylpyrimidin-2-amine; 4-[octahydro-6H-pyrrolo[3,4-b]pyridin-6-yl]-6-(3-thienyl)pyrimidin-2-amine; 4-(3-chlorophenyl)-5-methyl-6-[octahydro-6H-pyrrolo[3,4-b] pyridin-6-yl]pyrimidin-2-amine; 5-methyl-4-(3-methylphenyl)-6-[octahydro-6H-pyrrolo[3,4-b]pyridin-6-yl]pyrimidin-2-amine; 4-(3-fluorophenyl)-5-methyl-6-[octahydro-6H-pyrrolo[3,4-b]pyridin-6-yl]pyrimidin-2-amine; 4-(3-aminopyrrolidin-1-yl)-6-phenylpyrimidin-2-amine; 4-[3-(methylamino) azetidin-1-yl]-6-phenylpyrimidin-2-amine; 4-[3-(dimethylamino)azetidin-1-yl]-6-phenylpyrimidin-2-amine; 4-(3-chlorophenyl)-6-[3-(methylamino) azetidin-1-yl]pyrimidin-2-amine; 4-[3-(methylamino)azetidin-1-yl]-6-(3-methylphenyl) pyrimidin-2-amine; 4-(3-fluorophenyl)-6-[3-(methylamino) azetidin-1-yl]pyrimidin-2-amine; 4-(3-methoxyphenyl)-6-[3-(methylamino)azetidin-1-yl]pyrimidin-2-amine; 3-{2-amino-6-[3-(methylamino)azetidin-1-yl]pyrimidin-4-yl}benzonitrile; 1-(3-{2-amino-6-[3-(methylamino) azetidin-1-yl]pyrimidin-4-yl}phenyl)ethanone; 4-[3-(methylamino) azetidin-1-yl]-6-(3-nitrophenyl)pyrimidin-2-amine; 3-{2-amino-6-[3-(methylamino) azetidin-1-yl] pyrimidin-4-yl}phenol; 4-(3-aminophenyl)-6-[3-(methylamino)azetidin-1-yl]pyrimidin-2-amine; 5-fluoro-4-[3-(methylamino)azetidin-1-yl]-6-phenylpyrimidin-2-amine; 5-methyl-4-[3-(methylamino)azetidin-1-yl]-6-phenylpyrimidin-2-amine; 4-[3-(methylamino)azetidin-1-yl]-6-[3-(trifluoromethyl)phenyl]pyrimidin-2-amine; 4-[3-(dimethylamino)phenyl]-6-[3-(methylamino)azetidin-1-yl] pyrimidin-2-amine; 4-[3-(methylamino)azetidin-1-yl]-6-(1-naphthyl)pyrimidin-2-amine; 4-[3-(methylamino)azetidin-1-yl]-6-(4-methylphenyl)pyrimidin-2-amine; 4-(4-chlorophenyl)-6-[3-(methylamino)azetidin-1-yl]pyrimidin-2-amine; 4-(4-fluorophenyl)-6-[3-(methylamino)azetidin-1-yl]pyrimidin-2-amine; 4-(4-methoxyphenyl)-6-[3-(methylamino)azetidin-1-yl]pyrimidin-2-amine; 4-{2-amino-6-[3-(methylamino)azetidin-1-yl]pyrimidin-4-yl}benzonitrile; 4-[3-(methylamino)azetidin-1-yl]-6-(4-nitrophenyl)pyrimidin-2-amine; and 4-{2-amino-6-[3-(methylamino)azetidin-1-yl]pyrimidin-4-yl}phenol;

4-[(4aR,7aR)-octahydro-6H-pyrrolo[3,4-b]pyridin-6-yl]-6-phenylpyrimidin-2-amine trihydrochloride; 4-(3-methoxyphenyl)-6-[(4aR,7aR)-octahydro-6H-pyrrolo[3,4-b]pyridin-6-yl]pyrimidin-2-amine trihydrochloride; 3-{2-amino-6-[(4aR,7aR)-octahydro-6H-pyrrolo[3,4-b]pyridin-6-yl] pyrimidin-4-yl}benzonitrile trihydrochloride; 4-(1-naphthyl)-6-[(4aR,7aR)-octahydro-6H-pyrrolo[3,4-b] pyridin-6-yl]pyrimidin-2-amine trihydrochloride; 4-(3-methylphenyl)-6-[(4aR,7aR)-octahydro-6H-pyrrolo[3,4-b] pyridin-6-yl]pyrimidin-2-amine trihydrochloride; 4-(3-chlorophenyl)-6-[(4aR,7aR)-octahydro-6H-pyrrolo[3,4-b] pyridin-6-yl]pyrimidin-2-amine trihydrochloride; 4-[(4aR,7aR)-octahydro-6H-pyrrolo[3,4-b]pyridin-6-yl]-6-[3-(trifluoromethyl)phenyl]pyrimidin-2-amine trihydrochloride; 1-(3-{2-amino-6-[(4aR,7aR)-octahydro-6H-pyrrolo[3,4-b]pyridin-6-yl]pyrimidin-4-yl}phenyl)ethanone trihydrochloride; 4-(3-nitrophenyl)-6-[(4aR,7aR)-octahydro-6H-pyrrolo[3,4-b]pyridin-6-yl]pyrimidin-2-amine trihydrochloride; (3-{2-amino-6-[(4aR,7aR)-octahydro-6H-pyrrolo[3,4-b]pyridin-6-yl]pyrimidin-4-yl}phenyl)methanol trihydrochloride; 4-(3,4-dichlorophenyl)-6-[(4aR,7aR)-octahydro-6H-pyrrolo[3,4-b]pyridin-6-yl]pyrimidin-2-amine dihydrochloride; 4-(4-nitrophenyl)-6-[(4aR,7aR)-octahydro-6H-pyrrolo[3,4-b]pyridin-6-yl]pyrimidin-2-amine dihydrochloride; 4-(3-fluorophenyl)-6-[(4aR,7aR)-octahydro-6H-pyrrolo[3,4-b]pyridin-6-yl]pyrimidin-2-amine dihydrochloride; 5-methyl-4-[(4aR,7aR)-octahydro-6H-pyrrolo[3,4-b]pyridin-6-yl]-6-phenylpyrimidin-2-amine dihydrochloride; 4-[(4aR,7aR)-octahydro-6H-pyrrolo[3,4-b]pyridin-6-yl]-6-(3-thienyl)pyrimidin-2-amine dihydrochloride; 4-(3-chlorophenyl)-5-methyl-6-[(4aR,7aR)-octahydro-6H-pyrrolo[3,4-b]pyridin-6-yl]pyrimidin-2-amine dihydrochloride; 5-methyl-4-(3-methylphenyl)-6-[(4aR,7aR)-octahydro-6H-pyrrolo[3,4-b]pyridin-6-yl] pyrimidin-2-amine dihydrochloride; and 4-(3-fluorophenyl)-5-methyl-6-[(4aR,7aR)-6octahydro-6H-pyrrolo[3,4-b]pyridin-6-yl]pyrimidin-2-amine dihydrochloride.

In another embodiment, the Histamine H4 antagonist or selective Histamine H4 antagonists are selected from those described in the international Patent Application WO2005/014556: 4-(3-aminopyrrolidin-1-yl)-6-phenylpyrimidin-2-amine trihydrochloride; 4-[3-(dimethylamino) pyrrolidin-1-yl]-6-phenylpyrimidin-2-amine trihydrochloride; 4-[3-(methylamino) pyrrolidin-1-yl]-6-phenylpyrimidin-2-amine trihydrochloride; 4-[3-(methylamino) pyrrolidin-1-yl]-6-(3-nitrophenyl)pyrimidin-2-amine trihydrochloride; 4-[(3R)-3-(methylamino)pyrrolidin-1-yl]-6-(3-nitrophenyl)pyrimidin-2-amine trihydrochloride; 4-[(3S)-3-(methylamino) pyrrolidin-1-yl]-6-(3-nitrophenyl)pyrimidin-2-amine trihydrochloride; 4-[(3S)-3-(methylamino)pyrrolidin-1-yl]-6-phenylpyrimidin-2-amine trihydrochloride; 4-[(3R)-3-(methylamino)pyrrolidin-1-yl]-6-phenylpyrimidin-2-amine trihydrochloride; 4-[3-(methylamino)pyrrolidin-1-yl]-6-(3-methylphenyl)pyrimidin-2-amine trihydrochloride; 1-(3-{2-amino-6-[3-(methylamino)pyrrolidin-1-yl]pyrimidin-4-yl}phenyl) ethanone trihydrochloride; 3-{2-amino-6-[3-(methylamino)pyrrolidin-1-yl]pyrimidin-4-yl}phenol trihydrochloride; (3-{2-amino-6-[3-(methylamino)pyrrolidin-1-yl]pyrimidin-4-yl}phenyl)methanol trihydrochloride; and 3-{2-amino-6-[3-(methylamino)pyrrolidin-1-yl]pyrimidin-4-yl}benzonitrile trihydrochloride; 3-[2-amino-6-(4-methylpiperazin-1-yl)pyrimidin-4-yl]phenol; 1-{3-[2-amino-6-(4-methylpiperazin-1-yl)pyrimidin-4-yl]phenyl}ethanone, {3-[2-amino-6-(4-methylpiperazin-1-yl)pyrimidin-4-yl]phenyl}methanol; 4-(4-methylpiperazin-1-yl)-6-[3-(trifluoromethyl)phenyl]pyrimidin-2-amine; 4-biphenyl-3-yl-6-(4-methylpiperazin-1-yl)pyrimidin-2-amine trihydrochloride; 4-[3-(dimethylamino)phenyl]-6-(4-methylpiperazin-1-yl)pyrimidin-2-amine; 4-(4-methylpiperazin-1-yl)-6-(1-naphthyl)pyrimidin-2-amine; and 3-[2-amino-6-(4-methylpiperazin-1-yl) pyrimidin-4-yl] benzonitrile.

In another embodiment, the Histamine H4 antagonist or selective Histamine H4 antagonists are selected from those described in the international Patent Application WO2006/056848: (5-chloro-1H-indol-2-yl)-(4-methyl-piperazin-1-yl)-methanone; in WO02/072548: 6-bromo-4-methyl-2-{[(3aR,6aS)-5-methylhexahydropyrrolo[3,4-c]pyrrol-2 (1H)-yl]carbonyl}-1H-benzimidazole and 6-fluoro-4-methyl-2-{[(3aR,6aS)-5-methylhexahydropyrrolo[3,4-c]pyrrol-2(1H)-yl]carbonyl}-1H-benzimidazole.

In another embodiment, the Histamine H4 antagonist or selective Histamine H4 antagonists are selected from those described in the international Patent Application WO2007/072163: $N^4$-(Cyclopropylmethyl)-6-[(3R)-3-(methylamino)pyrrolidin-1-yl]pyrimidine-2,4-diamine, $N^4$-(Cyclopropylmethyl)-6-[(3R)-3-(methylamino)pyrrolidin-1-yl]pyrimidine-2,4-diamine tartrate, $N^4$-Isobutyl-6-[(3R)-3-(methylamino)pyrrolidin-1-yl]pyrimidine-2,4-diamine, $N^4$-(2,2-Dimethylpropyl)-6-[(3R)-3-(methylamino)pyrrolidin-1-yl]pyrimidine-2,4-diamine-N-lsobutyl-6-[(3R)-3-(methylamino)pyrrolidin-1-yl]pyrimidin-4-amine, N-(Cyclopropylmethyl)-6-[(3R)-3-(methylamino)pyrrolidin-1-yl]pyrimidin-4-amine, $N^4$-(2,2-Dimethylpropyl)-6-[(4aR*,7aR*)-octahydro-6H-pyrrolo[3,4-b]pyridin-6-yl]pyrimidine-2,4-diamine, $N^4$-Cyclopropyl-6-[(4aR*,7aR*)-octahydro-6H-pyrrolo[3,4-b]pyridin-6-yl]pyrimidine-2,4-diamine, $N^4$-Cyclobutyl-6-[(4aR*,7aR*)-octahydro-6H-pyrrolo[3,4-b]pyridin-6-yl]pyrimidine-2,4-diamine, $N^4$-(2,2-Dimethylpropyl)-6-[3-(methylamino)azetidin-1-yl]pyrimidine-2,4-diamine, 6-(3-Methylamino-azetidin-1-yl)-$N^4$-(3,3,3-trifluoro-propyl)-pyrimidine-2,4-diamine, $N^4$-Cyclopropylmethyl-6-(3-methylamino-azetidin-1-yl)-pyrimidine-2,4-diamine, $N^4$-(3,3-Dimethyl-butyl)-6-(3-methylamino-azetidin-1-yl)-pyrimidine-2,4-diamine, $N^4$-(3-Fluoro-benzyl)-6-(3-methylamino-azetidin-1-yl)-pyrimidine-2,4-diamine, $N^4$-Cyclopentylmethyl-6-(3-methylamino-azetidin-1-yl)-pyrimidine-2,4-diamine, $N^4$-lsobutyl-6-[3-(methylamino)azetidin-1-yl]pyrimidine-2,4-diamine, 6-[3-(Methylamino)azetidin-1-yl]-$N^4$-propylpyrimidine-2,4-diamine, $N^4$-(2-Methoxybenzyl)-6-[3-(methylamino)azetidin-1-yl]pyrimidine-2,4-diamine, $N^4$-(2,2-Dimethylpropyl)-6-[(3R)-3-methylpiperazin-1-yl]pyrimidine-2,4-diamine, N4-Ethyl-6-(4-methylpiperazin-1-yl)pyrimidine-2,4-diamine, $N^4$-(Cyclopropylmethyl)-6-(4-methylpiperazin-1-yl)pyrimidine-2,4-diamine, 6-[3-(Methylamino)azetidin-1-yl]-$N^4$-(2-methylbutyl) pyrimidine-2,4-diamine, $N^4$-(2,5-Difluorobenzyl)-6-[3-(methylamino)azetidin-1-yl]pyrimidine-2,4-diamine, $N^4$-(2,3-Difluorobenzyl)-6-[3-(methylamino)azetidin-1-yl] pyrimidine-2,4-diamine, $N^4$-Butyl-6-[3-(methylamino) azetidin-1-yl]pyrimidine-2,4-diamine, 6-[(3R)-3-(Methylamino)pyrrolidin-1-yl]-$N^4$-(2-methylcyclopropyl) pyrimidine-2,4-diamine, $N^4$-lsobutyl-6-(4-methyl-1,4-diazepan-1-yl)pyrimidine-2,4-diamine, $N^4$-(Cyclopropylmethyl)-6-(3-pyrrolidin-1-ylazetidin-1-yl)pyrimidine-2,4-diamine, $N^4$-Bicyclo[1.1.1]pent-1-yl-6-[(3R)-3-(methylamino)pyrrolidin-1-yl]pyrimidine-2,4-diamine, 6-[3-Methyl-3-(methylamino)azetidin-1-yl]-$N^4$-propylpyrimidine-2,4-diamine, $N^4$-(2,2-Dimethylpropyl)-6-(hexahydropyrrolo[1,2-a]pyrazin-2(1H)-yl)pyrimidine-2,4-diamine, $N^4$-(2,2-Dimethylpropyl)-6-(3-pyrrolidin-1-ylazetidin-1-yl)pyrimidine-2,4-diamine, N4-(2,2-Dimethylpropyl)-6-[3-(isopropylamino)azetidin-1-yl] pyrimidine-2,4-diamine, N4-(tert-Butyl)-6-[(3R)-3-(methylamino)pyrrolidin-1-yl]pyrimidine-2,4-diamine, 6-[(3R)-3-(Methylamino)pyrrolidin-1-yl]-$N^4$-(1-methylcyclopropyl)pyrimidine-2,4-diamine, $N^4$-(tert-Butyl)-6-[(4aS*,7aS*)-octahydro-6H-pyrrolo[3,4-b]pyridine-2,4-diamine, $N^4$-(2,2-Dimethylpropyl)-6-piperazin-1-ylpyrimidine-2,4-diamine, $N^4$-(2,2-Dimethylpropyl)-6-[3-(methylamino)azetidin-1-yl] pyrimidine-2,4-diamine hydrochloride, $N^4$-(2,2-Dimethylpropyl)-6-[(3aR*,7aS*)-octahydro-5H-pyrrolo[3,2-c]pyridin-5-yl]pyrimidine-2,4-diamine, 6-Piperazin-1-yl-$N^4$-propylpyrimidine-2,4-diamine, $N^4$-(Cyclopropylmethyl)-6-[4aR,7aR]-octahydro-6H-pyrrolo[3,4-b]pyridin-6-yl]pyrimidine-2,4-diamine, $N^4$-(2,2-Dimethylpropyl)-6-[(4 aS,7aS)-octahydro-6H-pyrrolo[3,4-b]pyridin-6-yl]pyrimidine-2,4-diamine $N^4$-(Cyclopropylmethyl)-6-[(3R)-3-(methylamino)pyrrolidin-1-yl]pyrimidine-2,4-diamine, $N^4$-lsopropyl-6-[(4aS,7aS)-octahydro-6H-pyrrolo[3,4-b]pyridin-6-yl]pyrimidine-2,4-diamine, 4-[3-(Methylamino)azetidin-1-yl]-6-(4-methylpiperidin-1-yl)pyrimidin-2-amine, $N^4$-(Cyclopentylmethyl)-6-[(3R)-3-(methylamino)pyrrolidin-1-yl]pyrimidine-2,4-diamine, $N^4$-Cyclobutyl-6-[(4aS,7aS)-octahydro-6H-pyrrolo[3,4-b]pyridin-6-yl]pyrimidine-2,4-diamine, 6-[(3R)-3-(Methylamino)pyrrolidin-1-yl]-$N^4$-propylpyrimidine-2,4-diamine, and, N4-Ethyl-6-(4-methyl-1,4-diazepan-1-yl)pyrimidine-2,4-diamine.

In another embodiment, the Histamine H4 antagonist or selective Histamine H4 antagonists are selected from those described in the international Patent Application WO2008/074445: 4-(4-Methyl-piperazin-1-yl)-benzo[4,5]furo[3,2-d]pyrimidin-2-ylamine; 8-Chloro-4-(4-methyl-piperazin-1-yl)-benzo[4,5]furo[3,2-d]pyrimidin-2-ylamine; 4-(4-Methylpiperazin-1-yl)pyrido[3',2':4,5]furo[3,2-d]pyrimidin-2-amine; 8-Chloro-4-(4-methylpiperazin-1-yl)[1]benzofuro[3,2-d]pyrimidin-2-amine; 8-Chloro-4-[(3S)-3-methylpiperazin-1-yl][1]benzofuro[3,2-d]pyrimidin-2-amine; 8-Methoxy-4-piperazin-1-yl[1]benzofuro[3,2-d]pyrimidin-2-amine, bis acetate salt; $N^4$-1-Azabicyclo[2.2.2] oct-3-yl-8-chloro[1]benzofuro[3,2-d]pyrimidine-2,4-diamine; 4-(3-Aminopyrrolidin-1-yl)-8-methoxy[1]benzofuro[3,2-d]pyrimidin-2-amine; 4-(3-Aminopyrrolidin-1-yl)-7-chloro[1]benzofuro[3,2-d]pyrimidin-2-amine; 7-Chloro-4-piperazin-1-yl[1]benzofuro[3,2-αf]pyrimidin-2-amine; 8-Chloro-4-piperazin-1-yl[1]benzofuro[3,2-d]pyrimidin-2-amine, dihydrochloride; 8-(2-Methoxyethoxy)-4-piperazin-1-yl[1]benzofuro[3,2-d]pyrimidin-2-amine; 8-Ethoxy-4-piperazin-1-yl[1]benzofuro[3,2-d]pyrimidin-2-amine; 8-Chloro-4-(3-ethylpiperazin-1-yl)[1]benzofuro[3,2-d]pyrimidin-2-amine; 8-Chloro-4-[(3S)-3-isopropylpiperazin-1-yl][1]benzofuro[3,2-d]pyrimidin-2-amine; 8-Chloro-4-piperazin-1-yl[1]benzofuro[3,2-d]pyrimidin-2-amine; 8-Chloro-4-(1,4-diazepan-1-yl)[1]benzofuro[3,2-d]pyrimidin-2-amine; 8-Chloro-4-[(3aR,6aS)-hexahydropyrrolo[3,4-c]pyrrol-2(1H)-yl][1]benzofuro[3,2-d]pyrimidin-2-amine; 8-Chloro-[(3S)-3-methyl-1,4-diazepan-1-yl][1]benzofuro[3,2-d]pyrimidin-2-amine; (8-Chloro-N4-[2-(methylamino)

ethyl][1]benzofuro[3I2-c0pyrimidine-2,4-diamine; 8-Chloro-N⁴-pyrrolidin-3-yl[1]benzofuro[3,2-d]pyrimidine-2,4-diamine; (7-Chloro-4-(4-methylpiperazin-1-yl)[1]benzofuro[3,2-d]pyrimidin-2-amine, formate salt; 2-Amino-4-(3-aminopyrrolidin-1-yl)[1]benzofuro[3,2-d]pyrimidin-8-ol; 4-(4-Methyl-piperazin-1-yl)-5H-indeno[1,2-d]pyrimidin-2-ylamine; 8-Chloro-4-(4-methyl-piperazin-1-yl)-5H-indeno[1,2-d]pyrimidin-2-ylamine; 8-Bromo-4-[(3S)-3-methylpiperazin-1-yl][1]benzofuro[3,2-d]pyrimidin-2-amine); 8-Bromo-4-piperazin-1-yl[1]benzofuro[3,2-d]pyrimidin-2-amine; 8-Bromo-4-(1,4-diazepan-1-yl)[1]benzofuro[3,2-d]pyrimidin-2-amine; Methyl-2-amino-4-[(3S)-3-methylpiperazin-1-yl][1]benzofuro[3,2-d]pyrimidine-8-carboxylate; Methyl-2-amino-4-(1,4-diazepan-1-yl)[1]benzofuro[3,2-d]pyrimidine-8-carboxylate; 2-Amino-4-[(3S)-3-methylpiperazin-1-yl][1]benzofuro[3,2-d]pyrimidine-8-carboxylic acid; 4-(4-Methylpiperazin-1-yl)[1]benzofuro[3,2-d]pyrimidin-2-amine; 8-Chloro-4-(4-methylpiperazin-1-yl)[1]benzofuro[3,2-d]pyrimidin-2-amine; 4-(4-Methylpiperazin-1-yl)-5H-indeno[1,2-d]pyrimidin-2-amine; 8-Chloro-4-[(3R)-3-methylpiperazin-1-yl][1]benzofuro[3,2-d]pyrimidin-2-amine; 4-(3-Aminopyrrolidin-1-yl)-7-chloro[1]benzofuro[3,2-d]pyrimidin-2-amine; 7-Chloro-4-piperazin-1-yl[1]benzofuro[3,2-d]pyrimidin-2-amine; 7-Chloro-4-(4-methylpiperazin-1-yl)[1]benzofuro[3,2-d]pyrimidin-2-amine, formic acid salt; 4-(4-Methylpiperazin-1-yl)pyrido[3',2':4,5]furo[3,2-d]pyrimidin-2-amine; 8-Chloro-4-[(3aR,6aS)-hexahydropyrrolo[3,4-c]pyrrol-2(1H)-yl][1]benzofuro[3,2-d]pyrimidin-2-amine; 8-Chloro-4-(4-methylpiperazin-1-yl)-5H-indeno[1,2-d]pyrimidin-2-amine; 8-Chloro-4-[(3S)-3-methyl-1,4-diazepan-1-yl][1]benzofuro[3,2-d]pyrimidin-2-amine; 4-(3-Aminopyrrolidin-1-yl)-8-methoxy[1]benzofuro[3,2-d]pyrimidin-2-amine; 8-Chloro-4-piperazin-1-yl[1]benzofuro[3,2-d]pyrimidin-2-amine; 2-Amino-4-(3-aminopyrrolidin-1-yl)[1]benzofuro[3,2-d]pyrimidin-8-ol; 8-Chloro-N⁴-[2-(methylamino)ethyl][1]benzofuro[3,2-d]pyrimidine-2,4-diamine; 8-Chloro-4-(1,4-diazepan-1-yl)[1]benzofuro[3,2-d]pyrimidin-2-amine; 8-Methoxy-4-piperazin-1-yl[1]benzofuro[3,2-d]pyrimidin-2-amine, diacetate; 8-Chloro-4-[(3S)-3-methylpiperazin-1-yl][1]benzofuro[3,2-d]pyrimidin-2-amine; 8-Chloro-4-piperazin-1-yl[1]benzofuro[3,2-d]pyrimidin-2-amine, dihydrochloride; 8-Bromo-4-[(3S)-3-methylpiperazin-1-yl][1]benzofuro[3,2-d]pyrimidin-2-amine; 8-Bromo-4-piperazin-1-yl[1]benzofuro[3,2-d]pyrimidin-2-amine; 8-Bromo-4-(1,4-diazepan-1-yl)[1]benzofuro[3,2-d]pyrimidin-2-amine; Methyl-2-amino-4-[(3S)-3-methylpiperazin-1-yl][1]benzofuro[3,2-d]pyrimidine-8-carboxylate; Methyl-2-amino-4-(1,4-diazepan-1-yl)[1]benzofuro[3,2-d]pyrimidine-8-carboxylate; 2-Amino-4-[(3S)-3-methylpiperazin-1-yl][1]benzofuro[3,2-d]pyrimidine-8-carboxylic acid; 8-Ethoxy-4-piperazin-1-yl[1]benzofuro[3,2-d]pyrimidin-2-amine; 8-Chloro-4-[(3S)-3-methyl-1,4-diazepan-1-yl][1]benzofuro[3,2-d]pyrimidin-2-amine; 4-(3-Aminopyrrolidin-1-yl)-8-methoxy[1]benzofuro[3,2-d]pyrimidin-2-amine; 8-Chloro-4-piperazin-1-yl[1]benzofuro[3,2-d]pyrimidin-2-amine; 2-Amino-4-(3-aminopyrrolidin-1-yl)[1]benzofuro[3,2-d]pyrimidin-8-ol; 8-Chloro-N⁴-[2-(methylamino)ethyl][1]benzofurol[3,2-d]pyrimidine-2,4-diamine; 8-Chloro-4-(1,4-diazepan-1-yl)[1]benzofuro[3,2-d]pyrimidin-2-amine; 8-Methoxy-4-piperazin-1-yl[1]benzofuro[3,2-d]pyrimidin-2-amine, diacetate; 8-Chloro-4-[(3S)-3-methylpiperazin-1-yl][1]benzofuro[3,2-d]pyrimidin-2-amine; 8-Chloro-4-piperazin-1-yl[1]benzofuro[3,2-cy]pyrimidin-2-amine, dihydrochloride; 8-Bromo-4-[(3S)-3-methylpiperazin-1-yl][1]benzofuro[3,2-d]pyrimidin-2-amine; 8-Bromo-4-piperazin-1-yl[1]benzofuro[3,2-d]pyrimidin-2-amine; 8-Bromo-4-(1,4-diazepan-1-yl)[1]benzofuro[3,2-d]pyrimidin-2-amine.

In another embodiment, the Histamine H4 antagonist or selective Histamine H4 antagonists are selected from those described in the international Patent Application WO2008/031556: 4-(4-methylpiperazin-1-yl)-6-piperidin-1-ylpyrimidin-2-amine; 4-(1,3-dihydro-2H-isoindol-2-yl)-6-(4-methylpiperazin-1-yl)pyrimidin-2-amine; 4-(4-methylpiperazin-1-yl)-6-(4-methylpiperidin-1-yl)pyrimidin-2-amine; 4-[4-(2-methoxyphenyl)piperidin-1-yl]-6-(4-methylpiperazin-1-yl)pyrimidin-2-amine; 4-(3,4-dihydroisoquinolin-2(1H)-yl)-6-(4-methylpiperazin-1-yl)pyrimidin-2-amine; 4-(5-fluoro-1,3-dihydro-2H-isoindol-2-yl)-6-(4-methylpiperazin-1-yl)pyrimidin-2-amine; 4-(3-aminopyrrolidin-1-yl)-6-(1,3-dihydro-2H-isoindol-2-yl)pyrimidin-2-amine; 4-(4-methylpiperazin-1-yl)-6-(2-methylpyrrolidin-1-yl)pyrimidin-2-amine; 4-(2-ethylpiperidin-1-yl)-6-(4-methylpiperazin-1-yl)pyrimidin-2-amine; 4-[3-(2-methoxyphenyl)pyrrolidin-1-yl]-6-(4-methylpiperazin-1-yl)pyrimidin-2-amine; 4-[3-(4-chlorophenyl)pyrrolidin-1-yl]-6-(4-methylpiperazin-1-yl)pyrimidin-2-amine; 4-(2-methylpyrrolidin-1-yl)-6-piperidin-1-ylpyrimidin-2-amine; 4-(4-methylpiperazin-1-yl)-6-[(2R)-2-methylpyrrolidin-1-yl]pyrimidin-2-amine; 4-(4-methylpiperazin-1-yl)-6-[(2S)-2-methylpyrrolidin-1-yl]pyrimidin-2-amine; 4-(2,6-dimethylpiperidin-1-yl)-6-(4-methylpiperazin-1-yl)pyrimidin-2-amine; 4-(6-azabicyclo[3.2.1]oct-6-yl)-6-(4-methylpiperazin-1-yl)pyrimidin-2-amine; 4-azepan-1-yl-6-(4-methylpiperazin-1-yl)pyrimidin-2-amine; 1-[2-amino-6-(4-methylpiperazin-1-yl)pyrimidin-4-yl]-4-(4-chlorophenyl)piperidin-4-ol; 4-(4-methylpiperazin-1-yl)-6-(3-phenylpiperidin-1-yl)pyrimidin-2-amine; N⁴-cyclohexyl-6-(hexahydropyrrolo[1,2-a]pyrazin-2(1H)-yl)pyrimidine-2,4-diamine; N⁴-adamantan-1-yl-6-(4-methylpiperazin-1-yl)pyrimidine-2,4-diamine; 6-(4-methylpiperazin-1-yl)-N⁴-(1,3,3-trimethylbicyclo[2.2.1]hept-2-yl)pyrimidine-2,4-diamine; N4-adamantan-2-yl-6-(4-methylpiperazin-1-yl)pyrimidine-2,4-diamine; 6-(4-methylpiperazin-1-yl)-N⁴(1R;4R)(1,7,7-trimethylbicyclo[2.2.1]hept-2-yl)pyrimidine-2,4-diamine; N⁴-cyclohexyl-N⁴-methyl-6-(4-methylpiperazin-1-yl)pyrimidine-2,4-cliamine; 4-(7-azabicyclo[2.2.1]hept-7-yl)-6-(4-methylpiperazin-1-yl)pyrimidin-2-amine; 4-(3-aminopyrrolidin-1-yl)-6-(5-fluoro-1,3-dihydro-2H-isoindol-2-yl)pyrimidin-2-amine; 4-(hexahydropyrrolo[1,2-a]pyrazin-2(1H)-yl)-6-(2-methylpyrrolidin-1-yl)pyrimidin-2-amine; N⁴-1-azabicyclo[2.2.2]oct-3-yl-6-(1,3-dihydro-2H-isoindol-2-yl)pyrimidine-2,4-diamine; 4-(3-methyl-3,4-dihydroisoquinolin-2(1H)-yl)-6-(4-methylpiperazin-1-yl)pyrimidin-2-amine; N⁴-1-azabicyclo[2.2.2]oct-3-yl-6-(2-methylpyrrolidin-1-yl)pyrimidine-2,4-diamine; 6-(2-methylpyrrolidin-1-yl)-N⁴-pyrrolidin-3-ylpyrimidine-2,4-diamine; 4-[4-(methylamino)piperidin-1-yl]-6-(2-methylpyrrolidin-1-yl)pyrimidin-2-amine; 4-(1,3-dihydro-2H-isoindol-2-yl)-6-[4-(methylamino)piperidin-1-yl]pyrimidin-2-amine; 4-(1,3-dihydro-2H-isoindol-2-yl)-6-(4-methyl-1,4-diazepan-1-yl)pyrimidin-2-amine; 6-[(3R)-3-aminopyrrolidin-1-yl]-N⁴-cyclohexylpyrimidine-2,4-diamine triacetate salt; 4(R)-(3-methyl-3,4-dihydroisoquinolin-2(1H)-yl)-6-(4-methylpiperazin-1-yl)pyrimidin-2-amine; 4(S)-(3-methyl-3,4-dihydroisoquinolin-2(1H)-yl)-6-(4-methylpiperazin-1-yl)pyrimidin-2-amine; N⁴-cyclohexyl-N⁶-[2-(dimethylamino)ethyl]pyrimidine-2,4,6-triamine; N4-cyclohexyl-6-[4-(methylamino)piperidin-1-yl]pyrimidine-2,4-diamine; 6-[(3S)-3-aminopyrrolidin-1-yl]-N⁴-cyclohexylpyrimidine-2,4-diamine; N⁴-cyclopentyl-6-(4-methylpiperazin-1-yl)pyrimidine-2,4-diamine;

N$^4$-cyclopentyl-N4-methyl-6-(4-methylpiperazin-1-yl)pyrimidine-2,4-diamine; N$^4$-cycloheptyl-6-(4-methylpiperazin-1-yl)pyrimidine-2,4-diamine; 4-[(1R*,5S*)-8-azabicyclo[3.2.1]oct-8-yl]-6-(4-methylpiperazin-1-yl)pyrimidin-2-amine; N$^4$-[(1R*,2S*,4S*)-bicyclo[2.2.1]hept-2-yl]-6-(4-methylpiperazin-1-yl)pyrimidine-2,4-diamine; N$^4$-bicyclo[2.2.1]hept-2-yl-6-(4-methylpiperazin-1-yl)pyrimidine-2,4-diamine; N$^4$-[(1R*,2S*,4S*)-bicyclo[2.2.1]hept-2-yl]-N$^6$-dimethylaminoJethyllpyrimidine-2,4-triamine; N$^4$-[(1R*,2S*,4S*)-bicyclo[2.2.1]hept-2-yl]-6-[(3aR*,6aS*)-hexahydropyrrolo[3,4-c]pyrrol-2 (1H)-yl]pyrimidine-2,4-diamine; 4-cyclohexyl-6-(4-methylpiperazin-1-yl)pyrimidin-2-amine; 4-adamantan-2-yl-6-(4-methylpiperazin-1-yl)pyrimidin-2-amine; 4-Isopropyl-6-(4-methylpiperazin-1-yl)pyrimidin-2-amine; 4-(1-methylpentyl)-6-(4-methylpiperazin-1-yl)pyrimidin-2-amine; 4-cyclopentyl-6-(4-methylpiperazin-1-yl)pyrimidin-2-amine; 4-(1-ethylpropyl)-6-(4-methylpiperazin-1-yl)pyrimidin-2-amine; 4-cyclohexyl-6-(hexahydropyrrolo[1,2-a]pyrazin-2(1H)-yl)pyrimidin-2-amine; 4-cyclohexyl-6-(4-methyl-1,4-diazepan-1-yl)pyrimidin-2-amine; 4-cyclohexyl-6-(4-ethylpiperazin-1-yl)pyrimidin-2-amine; 4-cyclohexyl-6-[3-(dimethylamino)pyrrolidin-1-yl]pyrimidin-2-amine; 6-cyclohexyl-N$^4$-methyl-N$^4$-(1-methylpyrrolidin-3-yl)pyrimidine-2,4-diamine; 6-cyclohexyl-N$^4$-(1-methylpiperidin-4-yl)pyrimidine-2,4-diamine; 4(R)-(4-methylpiperazin-1-yl)-6-(1-phenylethyl)pyrimidin-2-amine; 4(S)-(4-methylpiperazin-1-yl)-6-(1-phenylethyl)pyrimidin-2-amine, 4-(3-aminopyrrolidin-1-yl)-6-cyclopropylpyrimidin-2-amine; 4-cyclopropyl-6-[3-(methylamino)pyrrolidin-1-yl]pyrimidin-2-amine; 4-(3-aminopyrrolidin-1-yl)-6-(4-methylcyclohex-1-en-1-yl)pyrimidin-2-amine di-trifluoroacetic acid salt; 6-cyclohex-1-en-1-yl-N$^4$-[2-(dimethylamino)ethyl]pyrimidine-2,4-diamine; 4-tert-butyl-6-(4-methylpiperazin-1-yl)pyrimidin-2-amine acetate salt; 4-tert-butyl-6-[3-(methylamino)pyrrolidin-1-yl]pyrimidin-2-amine acetate salt; 4-[adamantan-2-yl]-6-[(3S)-3-aminopyrrolidin-1-yl]pyrimidin-2-amine; 4-[adamantan-2-yl]-6-[(3S)-3-(methylamino)pyrrolidin-1-yl]pyrimidin-2-amine; 4-cyclohept-1-en-1-yl-6-(4-methylpiperazin-1-yl)pyrimidin-2-amine; 4-cyclopentyl-6-(3-methylpiperazin-1-yl)pyrimidin-2-amine; 4-(3-aminoazetidin-1-yl)-6-cyclohex-1-en-1-ylpyrimidin-2-amine; 4-cyclohexyl-6-(3-methylpiperazin-1-yl)pyrimidin-2-amine; 4-(3-aminoazetidin-1-yl)-6-cyclohexylpyrimidin-2-amine; 4-(4-methylpiperazin-1-yl)-6-(1,2,3,4-tetrahydronaphthalen-2-yl)pyrimidin-2-amine; 4-[3-(methylamino)pyrrolidin-1-yl]-6-(1,2,3,4-tetrahydronaphthalen-2-yl)pyrimidin-2-amine; 4-(3-aminopyrrolidin-1-yl)-6-(1,2,3,4-tetrahydronaphthalen-2-yl)pyrimidin-2-amine; 4-cyclopentyl-6-[(3S)-3-methylpiperazin-1-yl]pyrimidin-2-amine; 4-cyclopentyl-6-[(3R)-3-methylpiperazin-1-yl]pyrimidin-2-amine; 4-cyclohexyl-6-[(2S)-2-methylpiperazin-1-yl]pyrimidin-2-amine; 4-[(3R)-3-aminopyrrolidin-1-yl]-6-[(1E)-3,3-dimethylbut-1-en-1-yl]pyrimidin-2-amine; 4-[3-(aminomethyl)azetidin-1-yl]-6-cyclohexylpyrimidin-2-amine; 4-(3-aminoazetidin-1-yl)-6-cyclopentylpyrimidin-2-amine, 4-cyclopentyl-6-(3-ethylpiperazin-1-yl)pyrimidin-2-amine; 4-cyclopentyl-6-[(3S)-3-isopropylpiperazin-1-yl]pyrimidin-2-amine; 4-cyclopentyl-6-(3,8-diazabicyclo[3.2.1]oct-3-yl)pyrimidin-2-amine; N$^4$-(2,3-dihydro-1H-inden-2-yl)-6-[3-methylamino)pyrrolidin-1-yl]pyrimidine-2,4-diamine; 4-cyclopentyl-6-[(3S)-3-isobutylpiperazin-1-yl]pyrimidin-2-amine; 4-cyclopentyl-6-[3-(ethylamino)azetidin-1-yl]pyrimidin-2-amine; 6-(4-methylpiperazin-1-yl)-N$^4$-(tetrahydro-2H-pyran-4-yl)pyrimidine-2,4-diamine; 6-(4-methylpiperazin-1-yl)-N$^4$-(tetrahydro-2H-pyran-4-yl)pyrimidine-2,4-diamine acetate; N$^4$-cyclohexyl-6-(4-methylpiperazin-1-yl)pyrimidine-2,4-diamine; 4-(1,3-dihydro-2H-isoindol-2-yl)-6-piperazin-1-ylpyrimidin-2-amine; 4-(3-aminopyrrolidin-1-yl)-6-(2-methylpyrrolidin-1-yl)pyrimidin-2-amine; 4-[3-(methylamino)pyrrolidin-1-yl]-6-(2-methylpyrrolidin-1-yl)pyrimidin-2-amine; 6-(3-aminopyrrolidin-1-yl)-N$^4$-[(1R*,2S*,4S*)-bicyclo[2.2.1]hept-2-yl]pyrimidine-2,4-diamine; N$^4$-[(1R*,2S*,4S*)-bicyclo[2.2.1]hept-2-yl]-6-[3-(methylamino)pyrrolidin-1-yl]pyrimidine-2,4-diamine; 6-[(3S)-3-aminopyrrolidin-1-yl]-N$^4$-[(1R*,2S*,4S*)-bicyclo[2.2.1]hept-2-yl]pyrimidine-2,4-diamine; 6-[(3R)-3-aminopyrrolidin-1-yl]-N$^4$-[(1R*,2S*,4S*)-bicyclo[2.2.1]hept-2-yl]pyrimidine-2,4-diamine; 6-[(3S)-3-aminopyrrolidin-1-yl]-N$^4$-[(1R*,2R*,4S*)-bicyclo[2.2.1]hept-2-yl]pyrimidine-2,4-diamine; 6-[(3R)-3-aminopyrrolidin-1-yl]-N$^4$-[(1R*,2R*,4S*)-bicyclo[2.2.1]hept-2-yl]pyrimidine-2,4-diamine; N4-[exo-bicyclo[2.2.1]hept-2-yl]-6-[(3S)-3-(methylamino)pyrrolidin-1-yl]pyrimidine-2,4-diamine; N$^4$-[(1R*,2S*,4S*)-bicyclo[2.2.1]hept-2-yl]-6-[3R]-3-(methylamino)pyrrolidin-1-yl]pyrimidine-2,4-diamine; N$^4$-[(1R*,2S*,4S*)-bicyclo[2.2.1]hept-2-yl]-6-[(3S)-3-(methylamino)pyrrolidin-1-yl]pyrimidine-2,4-diamine; N$^4$-[(1R*,2S*,4S*)-bicyclo[2.2.1]hept-2-yl]-6-[(3R)-3-(methylamino)pyrrolidin-1-yl]pyrimidine-2,4-diamine; N$^4$-[(1R*,2S*,4S*)-bicyclo[2.2.1]hept-2-yl]-6-(3-methylpiperazin-1-yl)pyrimidine-2,4-diamine; N$^4$-[(1R*,2R*,4S*)-bicyclo[2.2.1]hept-2-yl]-6-(1,4-diazepan-1-yl)pyrimidine-2,4-diamine; N$^4$-[(1R*,2R*,4S*)-bicyclo[2.2.1]hept-2-yl]-6-((4aR*,7aR*)-octahydro-6H-pyrrolo[3,4-b]pyridin-6-yl)pyrimidine-2,4-diamine; N$^4$-[(1R*,2R*,4S*)-bicyclo[2.2.1]hept-2-yl]-6-(hexahydropyrrolo[1,2-a]pyrazin-2 (1H)-yl)pyrimidine-2,4-diamine; N$^4$-[(1R*,2R*,4S*)-bicyclo[2.2.1]hept-2-yl]-6-piperazin-1-yl-pyrimidine-2,4-diamine; 4-(3-aminopyrrolidin-1-yl)-6-cyclopentylpyrimidin-2-amine; 4-adamantan-2-yl-6-(3-aminopyrrolidin-1-yl)pyrimidin-2-amine; 4-cyclopentyl-6-[3-(methylamino)pyrrolidin-1-yl]pyrimidin-2-amine; 4-[(3S)-3-aminopyrrolidin-1-yl]-6-cyclohexylpyrimidin-2-amine; 4-[(3R)-3-aminopyrrolidin-1-yl]-6-cyclohexylpyrimidin-2-amine; 4-(3-aminopyrrolidin-1-yl)-6-(cyclohexylmethyl)pyrimidin-2-amine; 4-cyclopentyl-6-piperazin-1-ylpyrimidin-2-amine; 4-[adamantan-2-yl]-6-[(3R)-3-(methylamino)pyrrolidin-1-yl]pyrimidin-2-amine; 4-[adamantan-2-yl]-6-[(3R)-3-aminopyrrolidin-1-yl]pyrimidin-2-amine; 4-(cyclopentylmethyl)-6-(3-methylpiperazin-1-yl)pyrimidin-2-amine; 4-(3-aminopyrrolidin-1-yl)-6-(cyclopentylmethyl)pyrimidin-2-amine; 4-cyclohexyl-6-[3-(methylamino)azetidin-1-yl]pyrimidin-2-amine; 4-cyclopentyl-6-[(4aR*,7aR*)-octahydro-6H-pyrrolo[3,4-b]pyridin-6-yl]pyrimidin-2-amine; 4-cyclohexyl-6-(1,4-diazepan-1-yl)pyrimidin-2-amine; 4-cyclopentyl-6-(1,4-diazepan-1-yl)pyrimidin-2-amine; 6-cyclopentyl-N$^4$-[2-(methylamino)ethyl]pyrimidine-2,4-diamine; 4-[(3R)-3-aminopyrrolidin-1-yl]-6-cyclohex-1-en-1-ylpyrimidin-2-amine; N$^4$-cyclohexyl-6-(4-methylpiperazin-1-yl)pyrimidine-2,4-diamine; 4-(1,3-dihydro-2H-isoindol-2-yl)-6-piperazin-1-ylpyrimidin-2-amine; 4-(3-aminopyrrolidin-1-yl)-6-(2-methylpyrrolidin-1-yl)pyrimidin-2-amine; 4-[3-(methylamino)pyrrolidin-1-yl]-6-(2-methylpyrrolidin-1-yl)pyrimidin-2-amine; 6-(3-aminopyrrolidin-1-yl)-N$^4$-[(1R*,2S*,4S*)-bicyclo[2.2.1]hept-2-yl]pyrimidine-2,4-diamine; N4-[(1R*,2S*,4S*)-bicyclo[2.2.1]hept-2-yl]-6-[3-(methylamino)pyrrolidin-1-yl]pyrimidine-2,4-diamine; 6-[(3S)-3-aminopyrrolidin-1-yl]-N$^4$-[(1R*,2S*,4S*)-bicyclo[2.2.1]hept-2-yl]pyrimidine-2,4-diamine; 6-[(3R)-3-aminopyrrolidin-1-yl]-N$^4$-[(1R*,2S*,4S*)-bicyclo[2.2.1]hept-2-yl]pyrimidine-2,4-diamine; 6-[(3S)-3- aminopyrrolidin-1-yl]-N⁴-[(1R*,2R*,4S*)-bicyclo[2.2.1]hept-2-yl]pyrimidine-2,4-diamine; 6-[(3R)-3-aminopyrrolidin-1-yl]-N⁴-[(1R*,2R*,4S*)-bicyclo[2.2.1]hept-2-yl]pyrimidine-2,4-diamine; N⁴-[exo-bicyclo[2.2.1]hept-2-yl]-6-[(3S)-3-(methylamino)pyrrolidin-1-yl]pyrimidine-2,4-diamine; N⁴-[(1R*,2R*,4S*)-bicyclo[2.2.1]hept-2-yl]-6-[(3R)-3-(methylamino)pyrrolidin-1-yl]pyrimidine-2,4-diamine; N⁴-[(1R*,2S*,4S*)-bicyclo[2.2.1]hept-2-yl]-6-[(3S)-3-(methylamino)pyrrolidin-1-yl]pyrimidine-2,4-diamine; N⁴-[(1R,2S*,4S*)-bicyclo[2.2.1]hept-2-yl]-6-[(3R)-3-(methylamino)pyrrolidin-1-yl]pyrimidine-2,4-diamine; N⁴-[(1R*,2R*,4S*)-bicyclo[2.2.1]hept-2-yl]-6-(3-methylpiperazin-1-yl)pyrimidine-2,4-diamine; N⁴-[(1R*,2R*,4S*)-bicyclo[2.2.1]hept-2-yl]-6-(1,4-diazepan-1-yl)pyrimidine-2,4-diamine; N⁴-[(1R*,2R*,4S*)-bicyclo[2.2.1]hept-2-yl]-6-((4aR*,7aR*)-octahydro-6H-pyrrolo[3,4-b]pyridin-6-yl)pyrimidine-2,4-diamine; N⁴-[(1R*,2R*,4S*)-bicyclo[2.2.1]hept-2-yl]-6-(hexahydropyrrolo[1,2-a]pyrazin-2 (1H)-yl)pyrimidine-2,4-diamine; N⁴-[(1R*,2R*,4S*)-bicyclo[2.2.1]hept-2-yl]-6-piperazin-1-ylpyrimidine-2,4-diamine; 4-(3-aminopyrrolidin-1-yl)-6-cyclopentylpyrimidin-2-amine; 4-adamantan-2-yl-6-(3-aminopyrrolidin-1-yl)pyrimidin-2-amine; 4-cyclopentyl-6-[3-(methylamino)pyrrolidin-1-yl]pyrimidin-2-amine; 4-[(3S)-3-aminopyrrolidin-1-yl]-6-cyclohexylpyrimidin-2-amine; 4-[(3R)-3-aminopyrrolidin-1-yl]-6-cyclohexylpyrimidin-2-amine; 4-(3-aminopyrrolidin-1-yl)-6-(cyclohexylmethyl)pyrimidin-2-amine; 4-cyclopentyl-6-piperazin-1-ylpyrimidin-2-amine; 4-[adamantan-2-yl]-6-[(3R)-3-(methylamino)pyrrolidin-1-yl]pyrimidin-2-amine; 4-[adamantan-2-yl]-6-[(3R)-3-aminopyrrolidin-1-yl]pyrimidin-2-amine; 4-(cyclopentylmethyl)-6-(3-methylpiperazin-1-yl)pyrimidin-2-amine; 4-(3-aminopyrrolidin-1-yl)-6-(cyclopentylmethyl)pyrimidin-2-amine; 4-cyclohexyl-6-[3-(methylamino)azetidin-1-yl]pyrimidin-2-amine; 4-cyclopentyl-6-[(4aR*,7aR*)-octahydro-6H-pyrrolo[3,4-b]pyridin-6-yl]pyrimidin-2-amine; 4-cyclohexyl-6-(1,4-diazepan-1-yl)pyrimidin-2-amine; 4-cyclopentyl-6-(1,4-diazepan-1-yl)pyrimidin-2-amine; 6-cyclopentyl-N⁴-(methylamino)ethyl]pyrimidine-2,4-diamine; 4-[(3R)-3-aminopyrrolidin-1-yl]-6-cyclohex-1-en-1-ylpyrimidin-2-amine.

In another embodiment, the Histamine H4 antagonist or selective Histamine H4 antagonists are selected from those described in the international Patent Application WO2008122378: 6-cyclohex-1-en-1-yl-4-[3-(methylamino)pyrrolidin-1-yl]pyridin-2-amine; 6-(4-chlorophenyl)-4-(4-methylpiperazin-1-yl)pyridin-2-amine; 6-(4-methylcyclohex-1-en-1-yl)-4-(4-methylpiperazin-1-yl)pyridin-2-amine; 6-adamantan-2-yl-4-(4-methylpiperazin-1-yl)pyridin-2-amine; 4-(3-aminopyrrolidin-1-yl)-6-cyclohex-1-en-1-ylpyridin-2-amine; 6-(3-methylphenyl)-4-(4-methylpiperazin-1-yl)pyridin-2-amine; 4-[(3R)-3-aminopyrrolidin-1-yl]-6-(4-chlorophenyl)pyridin-2-amine; 4-(4-methylpiperazin-1-yl)-6-(4-methylpiperidin-1-yl)pyridin-2-amine; N-cycloheptyl-4-(4-methylpiperazin-1-yl)pyridine-2,6-diamine; 4-[3-(methylamino)pyrrolidin-1-yl]-6-(2-methylpyrrolidin-1-yl)pyridin-2-amine; 4-(4-methylpiperazin-1-yl)-6-(2-methylpyrrolidin-1-yl)pyridin-2-amine; 4-[3-(methylamino)pyrrolidin-1-yl]-6-(4-methylpiperidin-1-yl)pyridin-2-amine; 4-[(3-methylamino)pyrrolidin-1-yl]-6-(4-trifluoromethylphenyl)pyridin-2-amine; 4-[(3-methylamino)pyrrolidin-1-yl]-6-(4-trifluoromethoxyphenyl)pyridin-2-amine; 6-(4-chlorophenyl)-4-[(3-methylamino)pyrrolidin-1-yl]pyridin-2-amine; 4-[(3-methylamino)pyrrolidin-1-yl]-6-(3-methylphenyl)pyridin-2-amine; N-cycloheptyl-4-(4-methylpiperazin-1-yl)pyridine-2,6-diamine; 4-[3-(methylamino)pyrrolidin-1-yl]-6-(2-methylpyrrolidin-1-yl)pyridin-2-amine; 4-[(3-methylamino)pyrrolidin-1-yl]-6-(3-methylphenyl)pyridin-2-amine; 6-cyclohex-1-en-1-yl-4-[3-(methylamino)pyrrolidin-1-yl]pyridin-2-amine; 6-(4-chlorophenyl)-4-[(3-methylamino)pyrrolidin-1-yl]pyridin-2-amine.

In another embodiment, the Histamine H4 antagonist or selective Histamine H4 antagonists are selected from those described in the international Patent Application WO2009047255: 4-(4-methylpiperazin-1-yl)-7-phenyl-5,6,7,8-tetrahydroquinazolin-2-amine; 4-(3-aminoazetidin-1-yl)-7-phenyl-5,6,7,8-tetrahydroquinazolin-2-amine; 4-(3-aminopyrrolidin-1-yl)-7-phenyl-5,6,7,8-tetrahydroquinazolin-2-amine; 4-[(4aR*,7aR*)-octahydro-6H-pyrrolo[3,4-b]pyridin-6-yl]-7-phenyl-5,6,7,8-tetrahydroquinazolin-2-amine; 4-(3-methylpiperazin-1-yl)-7-phenyl-5,6,7,8-tetrahydroquinazolin-2-amine; 7-(3-chlorophenyl)-4-(4-methylpiperazin-1-yl)-5,6,7,8-tetrahydroquinazolin-2-amine; 7-(3-chlorophenyl)-4-(1,4-diazepan-1-yl)-5,6,7,8-tetrahydroquinazolin-2-amine; 7-(3-chlorophenyl)-4-[(4aR*,7aR*)-octahydro-6H-pyrrolo[3,4-b]pyridin-6-yl]-5,6,7,8-tetrahydroquinazolin-2-amine; 7,7-dimethyl-4-(4-methylpiperazin-1-yl)-5,6,7,8-tetrahydroquinazolin-2-amine; 4-(1,4-diazepan-1-yl)-7,7-dimethyl-5,6,7,8-tetrahydroquinazolin-2-amine; 4-(3-aminopyrrolidin-1-yl)-7,7-dimethyl-5,6,7,8-tetrahydroquinazolin-2-amine; 7,7-dimethyl-4-[(4aR*,7aR*)-octahydro-6H-pyrrolo[3,4-b]pyridin-6-yl]-5,6,7,8-tetrahydroquinazolin-2-amine; 4-(3-aminopyrrolidin-1-yl)-7-(3-chlorophenyl)-5,6,7,8-tetrahydroquinazolin-2-amine; 7,7-dimethyl-4-(3-methylpiperazin-1-yl)-5,6,7,8-tetrahydroquinazolin-2-amine; 7,7-dimethyl-4-piperazin-1-yl-5,6,7,8-tetrahydroquinazolin-2-amine; 7-(2-chlorophenyl)-4-(4-methylpiperazin-1-yl)-5,6,7,8-tetrahydroquinazolin-2-amine; 7-(2-chlorophenyl)-4-(1,4-diazepan-1-yl)-5,6,7,8-tetrahydroquinazolin-2-amine; 4-(3-aminopyrrolidin-1-yl)-7-(2-chlorophenyl)-5,6,7,8-tetrahydroquinazolin-2-amine; 4-(1,4-diazepan-1-yl)-7-(4-fluorophenyl)-5,6,7,8-tetrahydroquinazolin-2-amine; 7-(4-fluorophenyl)-4-(4-methylpiperazin-1-yl)-5,6,7,8-tetrahydroquinazolin-2-amine; 4-piperazin-1-yl-7-pyridin-2-yl-5,6,7,8-tetrahydroquinazolin-2-amine; 4-(4-methylpiperazin-1-yl)-7-pyridin-2-yl-5,6,7,8-tetrahydroquinazolin-2-amine; 4-(1,4-diazepan-1-yl)-7-pyridin-2-yl-5,6,7,8-tetrahydroquinazolin-2-amine; 7-(5-chloro-2-thienyl)-4-piperazin-1-yl-5,6,7,8-tetrahydroquinazolin-2-amine; 5-(5-chloro-2-thienyl)-4-piperazin-1-yl-5,6,7,8-tetrahydroquinazolin-2-amine; 5-(5-chloro-2-thienyl)-4-(4-methylpiperazin-1-yl)-5,6,7,8-tetrahydroquinazolin-2-amine; 7-(5-chloro-2-thienyl)-4-(4-methylpiperazin-1-yl)-5,6,7,8-tetrahydroquinazolin-2-amine; 5-(5-chloro-2-thienyl)-4-(1,4-diazepan-1-yl)-5,6,7,8-tetrahydroquinazolin-2-amine; 7-(5-chloro-2-thienyl)-4-(1,4-diazepan-1-yl)-5,6,7,8-tetrahydroquinazolin-2-amine; 7-(4-fluorophenyl)-4-[(4aR*,7aR*)-octahydro-6H-pyrrolo[3,4-b]pyridin-6-yl]-5,6,7,8-tetrahydroquinazolin-2-amine trifluoroacetic acid salt; 7-(4-fluorophenyl)-N-4-[2-(methylamino)ethyl]-5,6,7,8-tetrahydroquinazoline-2,4-diamine; 7,7-dimethyl-N-4-[2-(methylamino)ethyl]-5,6,7,8-tetrahydroquinazoline-2,4-diamine; 4-(hexahydropyrrolo[3,4-c]pyrrol-2(1H)-yl)-7,7-dimethyl-5,6,7,8-tetrahydroquinazolin-2-amine; 7,7-dimethyl-4-[(3S)-3-methyl-1,4-diazepan-1-yl]-5,6,7,8-tetrahydroquinazolin-2-amine; 8,8-dimethyl-4-(3-methylpiperazin-1-yl)-5,6,7,8-tetrahydroquinazolin-2-amine; 4-(3-aminoazetidin-1-yl)-8,8-dimethyl-5,6,7,8-tetrahydroquinazolin-2-amine; 8,8-dimethyl-N-4-piperidin-4-yl-5,6,7,8-tetrahydroquinazoline-2,4-diamine; 8,8- dimethyl-N-4-pyrrolidin-3-yl-5,6,7,8-tetrahydroquinazoline-2,4-diamine; 8,8-dimethyl-4-[(3S)-3-methylpiperazin-1-yl]-5,6,7,8-tetrahydroquinazolin-2-amine; 6,6-dimethyl-4-(4-methylpiperazin-1-yl)-6,7-dihydro-5H-cyclopenta[d]pyrimidin-2-amine; 4-(4-methylpiperazin-1-yl)-7-[4-(trifluoromethyl)pyrimidin-2-yl]-5,6,7,8-tetrahydropyrido[3,4-d]pyrimidin-2-amine; 7,7-dimethyl-4-(4-methylpiperazin-1-yl)-5,6,7,8-tetrahydroquinazolin-2-amine; 4-(1,4-diazepan-1-yl)-7,7-dimethyl-5,6,7,8-tetrahydroquinazolin-2-amine; 4-(3-aminopyrrolidin-1-yl)-7,7-dimethyl-5,6,7,8-tetrahydroquinazolin-2-amine; 7,7-dimethyl-4-[(4aR*,7aR*)-octahydro-6H-pyrrolo[3,4-b]pyridin-6-yl]-5,6,7,8-tetrahydroquinazolin-2-amine; 7,7-dimethyl-4-(3-methylpiperazin-1-yl)-5,6,7,8-tetrahydroquinazolin-2-amine; 7,7-dimethyl-4-piperazin-1-yl-5,6,7,8-tetrahydroquinazolin-2-amine; 7-(5-chloro-2-thienyl)-4-piperazin-1-yl-5,6,7,8-tetrahydroquinazolin-2-amine; 7-(5-chloro-2-thienyl)-4-(1,4-diazepan-1-yl)-5,6,7,8-tetrahydroquinazolin-2-amine; 4-(3-aminoazetidin-1-yl)-7,7-dimethyl-5,6,7,8-tetrahydroquinazolin-2-amine; 7-isobutyl-4-piperazin-1-yl-5,6,7,8-tetrahydroquinazolin-2-amine; 8,8-dimethyl-4-(4-methylpiperazin-1-yl)-5,6,7,8-tetrahydroquinazolin-2-amine; 4-(1,4-diazepan-1-yl)-8,8-dimethyl-5,6,7,8-tetrahydroquinazolin-2-amine bis acetic acid salt; 7,7-dimethyl-4-[3-(methylamino)pyrrolidin-1-yl]-5,6,7,8-tetrahydroquinazolin-2-amine; 7,7-dimethyl-4-[(3S)-3-methylpiperazin-1-yl]-5,6,7,8-tetrahydroquinazolin-2-amine; 4-(1,4-diazepan-1-yl)-7-isobutyl-5,6,7,8-tetrahydroquinazolin-2-amine acetic acid salt; 7-isobutyl-4-(4-methylpiperazin-1-yl)-5,6,7,8-tetrahydroquinazolin-2-amine acetic acid salt; 7,7-dimethyl-4-[3-(methylamino)azetidin-1-yl]-5,6,7,8-tetrahydroquinazolin-2-amine; 8,8-dimethyl-4-[(4aR*,7aR*)-octahydro-6H-pyrrolo[3,4-b]pyridin-6-yl]-5,6,7,8-tetrahydroquinazolin-2-amine; 4'-(4-methylpiperazin-1-yl)-5'8'-dihydro-6'H-spiro[cyclohexane-1,7'-quinazolin]-2'-amine; 4'-[(4aR*,7aR*)-octahydro-6H-pyrrolo[3,4-b]pyridin-6-yl]-5',8'-dihydro-6'H-spiro[cyclohexane-1,7'-quinazolin]-2'-amine; 4'-[(3S)-3-methylpiperazin-1-yl]-5'8'-dihydro-6'H-spiro[cyclohexane-1,7'-quinazolin]-2'-amine bis acetic acid salt; 4'-(1,4-diazepan-1-yl)-5'8'-dihydro-6'H-spiro[cyclohexane-1,7'-quinazolin]-2'-amine bis acetic acid salt; 4'-piperazin-1-yl-5'8'-dihydro-6'H-spiro[cyclohexane-1,7'-quinazolin]-2'-amine bis acetic acid salt; 4'-[3-(methylamino)azetidin-1-yl]-5'8'-dihydro-6'H-spiro[cyclohexane-1,7'-quinazolin]-2'-amine bis acetate salt; 4-(3-aminopyrrolidin-1-yl)-7-isobutyl-5,6,7,8-tetrahydroquinazolin-2-amine bis acetate salt; 7-isopropyl-4-(4-methylpiperazin-1-yl)-5,6,7,8-tetrahydroquinazolin-2-amine; 7-isopropyl-4-[(3S)-3-methylpiperazin-1-yl]-5,6,7,8-tetrahydroquinazolin-2-amine bis acetic acid salt; 7-isopropyl-4-[(4aR*,7aR*)-octahydro-6H-pyrrolo[3,4-b]pyridin-6-yl]-5,6,7,8-tetrahydroquinazolin-2-amine; 7-isopropyl-4-[3-(methylamino)azetidin-1-yl]-5,6,7,8-tetrahydroquinazolin-2-amine; tert-butyl-4-(2-amino-7,7-dimethyl-5,6,7,8-tetrahydroquinazolin-4-yl)-1,4-diazepane-1-carboxylate.

In another embodiment, the Histamine H4 antagonist or selective Histamine H4 antagonists are selected from those described in the international Patent Application WO2008/003702: 4-amino-6-chloro-2-(4-methylpiperazinyl)-quinazoline, 2-(4-methylpiperazinyl)-4-phenoxyquinazoline, 4-(benzyloxy)-2-(4-methylpiperazinyl)-quinazoline, 2-(4-methylpiperazinyl)-quinoline, 2-(4-methylpiperazinyl)-quinoxaline, 6-chloro-2-(4-methyl-piperazinyl)-quinoline, 6-chloro-2-(4-methylpiperazinyl)-quinoxaline, 2-(4-methylpiperazinyl)-quinazoline, 3-(4-methylpiperazinyl)-isoquinoline, 1-(4-methylpiperazinyl)-isoquinoline, 3-benzyl-2-(4-methylpiperazinyl)-quinoxaline, 6,7-dichloro-2-methoxy-3-(4-methylpiperazinyl)-quinoxaline and 7-chloro-2-methoxy-3-(4-methylpiperazinyl)-quinoxaline.

In another embodiment, the Histamine H4 antagonist or selective Histamine H4 antagonists are selected from those described in the international Patent Application WO2006/050965: 8-chloro-2-methyl-4-(4-methylpiperazin-1-yl)benzo[4,5]furo[3,2-d]pyrimidine; 8-chloro-4-(4-methylpiperazin-1-yl)benzo[4,5]furo[3,2-d]pyrimidine; 4-(4-methylpiperazin-1-yl)benzo[4,5]furo[3,2-d]pyrimidine; 6-chloro-1-(4-methylpiperazin-1-yl)-9H-2,4,9-triazafluorene; 4-(Piperazin-1-yl)benzo[4,5]furo[3,2-d]pyrimidine; 4-(piperazin-1-yl)benzo[4,5]thieno[3,2-d]pyrimidine; 8-Chloro-4-(1,4-diazepan-1-yl)benzo[4,5]thieno[3,2-d]pyrimidine; 8-Chloro-2-cyclopropyl-4-(4-methylpiperazin-1-yl)benzo[4,5]furo[3,2-d]pyrimidine; 8-Chloro-4-(4-methylpiperazin-1-yl)-2-trifluoromethylbenzo[4,5]furo[3,2-d]pyrimidine; 8-Chloro-4-(1-methylpiperidin-4-yl)benzo[4,5]furo[3,2-d]pyrimidine; 8-Chloro-4-[(1S,4S)-2,5-diazabicyclo[2.2.1]hept-2-yl]benzo[4,5]furo[3,2-d]pyrimidine; 8-Chloro-4-(3-methylpiperazin-1-yl)benzo[4,5]furo[3,2-d]pyrimidine; 8-Chloro-4-[(1S,4S)-5-methyl-2,5-diazabicyclo[2.2.1]hept-2-yl]benzo[4,5]furo[3,2-d]pyrimidine; 8-Chloro-4-(3,4-dimethylpiperazin-1-yl)benzo[4,5]furo[3,2-d]pyrimidine; 8-Cloro-4-(1-metylpyrrolidin-3-yl)benzo[4,5]furo[3,2-d]pyrimidine; 8-Chloro-4-(8-methyl-3,8-diazabicyclo[3.2.1]oct-3-yl)benzo[4,5]furo[3,2-d]pyrimidine; 8-Chloro-4-[(1R,4R)-5-methyl-2,5-diazabicyclo[2.2.1]hept-2-yl]benzo[4,5]furo[3,2-d]pyrimidine; 8-Chloro-4-[5-methyl-2,5-diazabicyclo[2.2.2]oct-2-yl]benzo[4,5]furo[3,2-d]pyrimidine; and 8-Chloro-4-[5-methyl-2,5-diazabicyclo[3.2.1]oct-2-yl]benzo[4,5]furo[3,2-d]pyrimidine.

In another embodiment, the Histamine H4 antagonist or selective Histamine H4 antagonists are selected from those described in the international Patent Application WO2005/014579: 4-(1H-Imidazol-4-ylmethoxy)-1-(1-oxo-3-phenyl-butyl)-piperidine; 4-(1H-Imidazol-4-ylmethoxy)-1-[[4-(trifluoromethyl)phenyl]acetyl]-piperidine; 1-[2-(4-Hydroxyphenyl)-1-oxopropyl]-4-[(5-methyl-1H-imidazol-4-yl)methoxy]-piperidine; 1-[(4-fluorophenyl)acetyl]-4-(1H-imidazol-4-ylmethoxy)-piperidine; 1-[(2-chlorophenyl)acetyl]-4-(1H-imidazol-4-ylmethoxy)-piperidine; 1-[(4-chlorophenyl)acetyl]-4-(1H-imidazol-4-ylmethoxy)-piperidine; 4-(H-imidazol-4-ylmethoxy)-1-(phenylacetyl)-piperidine; 1-(4-cyclohexylbenzoyl)-4-(1H-imidazol-4-ylmethoxy)-piperidine; 1-[(3,4-dichlorophenyl)acetyl]-4-(H-imidazol-4-ylmethoxy)-piperidine; 4-(1H-imidazol-4-ylmethoxy)-1-[(4-methylphenyl)acetyl]-piperidine; 1-[(3,4-difluorophenyl)acetyl]-4-(1H-imidazol-4-ylmethoxy)-piperidine; 1-[(2,4-difluorophenyl)acetyl]-4-(1H-imidazol-4-ylmethoxy)-piperidine; 4-(1H-imidazol-4-ylmethoxy)-1-[(4'-propyl[1,1'-biphenyl]-4-yl)carbonyl]-piperine; 1-[2-(4-hydroxyphenyl)-1-oxopropyl]-4-(1H-imidazol-4-ylmethoxy)-piperidine; 1-[(2E)-3-(3,4-dichlorophenyl)-1-oxo-2-propenyl]-4-(1H-imidazol-4-ylmethoxy)-piperidine; 1-[3-(2,4-dichlorophenyl)-1-oxopropyl]-4-(1H-imidazol-4-ylmethoxy)-piperidine; 1-[(2,4-dichlorophenyl)acetyl]-4-(1H-imidazol-4-ylmethoxy)-piperidine; 1-[(2-Bromophenyl)methyl]-4-(1H-imidazol-4-ylmethoxy)-piperidine; 1-[(3-Bromo-2-thienyl)methyl]-4-[(5-methyl-1H-imidazol-4-yl)methoxy]-piperidine; 1-[(3-bromo-2-thienyl)methyl]-4-(1H-imidazol-4-ylmethoxy)-piperidine; 1-[(4-ethynylphenyl)methyl]-4-(1H-imidazol-4-ylmethoxy)-piperidine; 4-(1H-imidazol-4-ylmethoxy)-1-[[3-(4-methylphenoxy)phenyl]methyl]-piperidine; 4-(1H-imidazol-4-ylmethoxy)-1-[[4-(2-propenyloxy)phenyl]methyl]-piperidine; 4-[[4-

(1H-imidazol-4-ylmethoxy)-1-piperidinyl]methyl]-phenol; 4-(1H-imidazol-4-ylmethoxy)-1-[(2-methoxyphenyl)methyl]-piperidine; 4-(1H-imidazol-4-ylmethoxy)-1-[[3-(4-methoxyphenoxy)phenyl]methyl]-piperidine; 1-[(2,3-dichlorophenyl)methyl]-4-(1H-imidazol-4-ylmethoxy)-piperidine; 1-[(2-chloro-4-fluorophenyl)methyl]-4-(1H-imidazol-4-ylmethoxy)-piperidine; 1-(2-dibenzofuranylmethyl)-4-(1H-imidazol-4-ylmethoxy)-piperidine; 4-(1H-imidazol-4-ylmethoxy)-1-[[2-(methylthio)phenyl]methyl]-piperidine; 4-(1H-imidazol-4-ylmethoxy)-1-(thieno[2,3-b][1]benzothien-2-ylmethyl)-piperidine; 1-[(2-chloro-5-nitrophenyl)methyl]-4-(1H-imidazol-4-ylmethoxy)-piperidine; 1H-pyrrole,2-[[4-(1H-imidazol-4-ylmethoxy)-1-piperidinyl]methyl]-1-[(4-methylphenyl)sulfonyl]-; 2-ethoxy-6-[[4-(1H-imidazol-4-ylmethoxy)-1-piperidinyl]methyl]-phenol; 1-(1,3-benzoidoxol-5-ylmethyl)-4-(1H-imidazol-4-ylmethoxy)-piperidine; 4-(1H-imidazol-4-ylmethoxy)-1-[[4-(phenylmethoxy)phenyl]methyl]-piperidine; 1-[[2-fluoro-4-(trifluoromethyl)phenyl]methyl]-4-(1H-imidazol-4-ylmethoxy)-piperidine; 1-[(4-bromophenyl)methyl]-4-(1H-imidazol-4-ylmethoxy)-piperidine; 4-(1H-imidazol-4-ylmethoxy)-1-[(4-methylphenyl)methyl]-piperidine; 4-(H-imidazol-4-ylmethoxy)-1-(2-thienylmethyl)-piperidine; 1-[(4-chlorophenyl)methyl]-4-(1H-imidazol-4-ylmethoxy)-piperidine; 1-[(2-chloro-6-fluorophenyl)methyl]-4-(1H-imidazol-4-ylmethoxy)-piperidine; 4-(1H-imidazol-4-ylmethoxy)-1-[(3-methyl-2-thienyl)methyl]-piperidine; 4-(1H-imidazol-4-ylmethoxy)-1-(2-naphthalenylmethyl)-piperidine; 4-(1H-imidazol-4-ylmethoxy)-1-(1-naphthalenylmethyl)-piperidine; 4-(1H-imidazol-4-ylmethoxy)-1-[(2-nitrophenyl)methyl]-piperidine; 4-(1H-imidazol-4-ylmethoxy)-1-(3-thienylmethyl)-piperidine; 1-([1,1'-biphenyl]-4-ylmethyl)-4-(1H-imidazol-4-ylmethoxy)-piperidine; 1-[(2,5-difluorophenyl)methyl]-4-(1H-imidazol-4-ylmethoxy)-piperidine; 4-(1H-imidazol-4-ylmethoxy)-1-[(3-phenoxyphenyl)methyl]-piperidine; 4-(1H-imidazol-4-ylmethoxy)-1-[(3-methylphenyl)methyl]-piperidine; 1-(2-furanylmethyl)-4-(1H-imidazol-4-ylmethoxy)-piperidine; 1-[(2,6-dichlorophenyl)methyl]-4-(1H-imidazol-4-ylmethoxy)-piperidine; 1-[(4-fluorophenyl)methyl]-4-(1H-imidazol-4-ylmethoxy)-piperidine; 1-[(3-fluorophenyl)methyl]-4-(1H-imidazol-4-ylmethoxy)-piperidine; 1-(3-furanylmethyl)-4-(1H-imidazol-4-ylmethoxy)-piperidine; 1-[(4-ethylphenyl)methyl]-4-(1H-imidazol-4-ylmethoxy)-piperidine; 4-(1H-imidazol-4-ylmethoxy)-1-[(2-methylphenyl)methyl]-piperidine; 1-[(3-chlorophenyl)methyl]-4-(1H-imidazol-4-ylmethoxy)-piperidine; 4-(1H-imidazol-4-ylmethoxy)-1-[(5-methyl-2-thienyl)methyl]-piperidine; 1-[(4-bromo-2-thienyl)methyl]-4-(1H-imidazol-4-ylmethoxy)-piperidine; 1-([2,2'-bithiophen]-5-ylmethyl)-4-(1H-imidazol-4-ylmethoxy)-piperidine; 3,5-dichloro-2-[[4-(1H-imidazol-4-ylmethoxy)-1-piperidinyl]methyl]-phenol; 1-[(3,4-difluorophenyl)methyl]-4-(1H-imidazol-4-ylmethoxy)-piperidine; 1-[(3,5-difluorophenyl)methyl]-4-(1H-imidazol-4-ylmethoxy)-piperidine; 1-[(6-chloro-1,3-benzodioxol-5-yl)methyl]-4-(1H-imidazol-4-ylmethoxy)-piperidine; 1-[[4-[4-(1,1-dimethylethyl)-2-thiazolyl]phenyl]methyl]-4-(1H-imidazol-4-ylmethoxy)-piperidine; 4-(1H-imidazol-4-ylmethoxy)-1-[(1-methyl-1H-pyrrol-2-yl)methyl]-piperidine; 1H-indole,3-[[4-(1H-imidazol-4-ylmethoxy)-1-piperidinyl]methyl]-1-(phenylmethyl)-; 1-[(5-chloro-2-thienyl)methyl]-4-(1H-imidazol-4-ylmethoxy)-piperidine; 1-(1,3-benzodioxol-4-ylmethyl)-4-(1H-imidazol-4-ylmethoxy)-piperidine; 2-thiophenecarbonitrile, 3-[[4-[[4-(1H-imidazol-4-ylmethoxy)-1-piperidinyl]methyl]phenoxy]methyl]-piperidine; 4-(1H-imidazol-4-ylmethoxy)-1-[[5-(phenylethynyl)-2-thienyl]methyl]-piperidine; 4-(1H-imidazol-4-ylmethoxy)-1-[[5-(4-nitrophenyl)-2-furanyl]methyl]-piperidine; 4-(1H-imidazol-4-ylmethoxy)-1-[[5-(3-nitrophenyl)-2-furanyl]methyl]-piperidine; 1-[(4-chloro-1H-pyrazol-3-yl)methyl]-4-(1H-imidazol-4-ylmethoxy)-piperidine; 1-[(4-bromo-1-methyl-1H-pyrazol-3-yl)methyl]-4-(1H-imidazol-4-ylmethoxy)-piperidine; 1-[(4-bromo-1H-pyrazol-3-yl)methyl]-4-(1H-imidazol-4-ylmethoxy)-piperidine; 2-[[4-(1H-imidazol-4-ylmethoxy)-1-piperidinyl]methyl]-benzonitrile; 4-(1H-imidazol-4-ylmethoxy)-1-[(4-iodophenyl)methyl]-piperidine; 1-[(5-ethyl-2-thienyl)methyl]-4-(1H-imidazol-4-ylmethoxy)-piperidine; 4-(1H-imidazol-4-ylmethoxy)-1-[[5-(methylthio)-2-thienyl]methyl]-piperidine; 1-[[1-(3,5-dichlorophenyl)-1H-pyrrol-2-yl]methyl]-4-(1H-imidazol-4-ylmethoxy)-piperidine; 1-[[1-(4-chlorophenyl)-1H-pyrrol-2-yl]methyl]-4-(1H-imidazol-4-ylmethoxy)-piperidine; 4-(1H-imidazol-4-ylmethoxy)-1-[[4-(phenylethynyl)-2-thienyl]methyl]-piperidine; 4-(1H-imidazol-4-ylmethoxy)-1-[(3-phenoxy-2-thienyl)methyl]-piperidine; 1-[[2-chloro-5-(trifluoromethyl)phenyl]methyl]-4-(1H-imidazol-4-ylmethoxy)-piperidine; 4-(1H-imidazol-4-ylmethoxy)-1-[(4-propoxyphenyl)methyl]-piperidine; 2-[[4-(1H-imidazol-4-ylmethoxy)-1-piperidinyl]methyl]-phenol; 1-[(2,4-difluorophenyl)methyl]-4-(1H-imidazol-4-ylmethoxy)-piperidine; 3-[[4-(1H-imidazol-4-ylmethoxy)-1-piperidinyl]methyl]-2-thiophenecarbonitrile; 1-(benzolb]thien-3-ylmethyl)-4-(1H-imidazol-4-ylmethoxy)-piperidine; 2-chloro-3-[[4-(1H-imidazol-4-ylmethoxy)-1-piperidinyl]methyl]-pyridine; 3-[[4-(1H-imidazol-4-ylmethoxy)-1-piperidinyl]methyl]-2-(2-propenyl)-phenol; 1-[(4-chloro-3-fluorophenyl)methyl]-4-(1H-imidazol-4-ylmethoxy)-piperidine; 4-(1H-imidazol-4-ylmethoxy)-1-[[4-(trifluoromethoxy)phenyl]methyl]-piperidine; 1-[(2,6-difluorophenyl)methyl]-4-(1H-imidazol-4-ylmethoxy)-piperidine; 1-[(4-bromo-2-fluorophenyl)methyl]-4-(1H-imidazol-4-ylmethoxy)-piperidine; 1-[(2,2-difluoro-1,3-benzodioxol-5-yl)methyl]-4-(1H-imidazol-4-ylmethoxy)-piperidine; 1-[(4-butoxyphenyl)methyl]-4-(1H-imidazol-4-ylmethoxy)-piperidine; 4-(1H-imidazol-4-ylmethoxy)-1-[(2,3,5-trichlorophenyl)methyl]-piperidine; 1-[(2,5-dichlorophenyl)methyl]-4-(1H-imidazol-4-ylmethoxy)-piperidine; 4-(H-imidazol-4-ylmethoxy)-1-[[2-(trifluoromethyl)phenyl]methyl]-piperidine, or 1-[(4-chloro-2-nitrophenyl)methyl]-4-(1H-imidazol-4-ylmethoxy)-piperidine or pharmaceutically acceptable salts or solvates thereof.

In another embodiment, the Histamine H4 antagonist or selective Histamine H4 antagonists are selected from those described in the international Patent Application WO2009107767.

In another embodiment, the Histamine H4 antagonist or selective Histamine H4 antagonists are benzazole derivatives, such as described in the Patent Application WO2012041860: 2-[(1-methylpiperidin-4-yloxy)phenylmethyl]benzothiazole; 2-[(1-methylpyrrolidin-3-yloxy)phenylmethyl]benzothiazole; 2-[(4-fluorophenyl)(1-methylpiperidin-4-yloxy)methyl]benzothiazole; 2-[(4-chlorophenyl)(1-methylpiperidin-4-yloxy)methyl]benzothiazole; 2-[(3-fluorophenyl)(1-methylpiperidin-4-yloxymethyl]benzothiazole; 2-[(2-fluorophenyl)(1-methylpiperidin-4-yloxy)methyl]benzothiazole; 2-[(1-methylpiperidin-4-yloxy)-p-tolylmethyl]benzothiazole; 2-[(1-methylpiperidin-4-yloxy)(m-tolyl)methyl]benzothiazole; (benzothiazol-2-yl)phenylmethyl)(1-methylpiperidin-4-yl)amine; 2-[(2,3-dihydrobenzo[1,4]dioxin-6-yl)(1-methylpiperidin-4-yloxy)methyl]benzothiazole; 2-[(3-methoxyphenyl)(1- methylpiperidin-4-yloxy)methyl]benzothiazole; 2-[(2,4-difluorophenyl)(1-methylpiperidin-4-yloxy)methyl]benzothiazole; 2-[(1-methylpiperidin-4-yloxy)thiophen-2-ylmethyl]benzothiazole; 2-[(4-methoxyphenyl)(1-methylpiperidin-4-yloxy)methyl]benzothiazole; 2-[(3,5-difluorophenyl)(1-methylpiperidin-4-yloxy)methyl]benzothiazole; 2-[(1-methylpiperidin-4-yloxy)thiophen-3-ylmethyl]benzothiazole; 2-[(1-methylpiperidin-4-yloxy)naphthalen-1-ylmethyl]benzothiazole; 2-[(1-methylpiperidin-4-yloxy)naphthalen-2-ylmethyl]benzothiazole; 2-[(1-methylpiperidin-4-yloxy)(5-methylthiophen-2-yl)methyl]benzothiazole; 2-[benzo[1,3]dioxol-5-yl(1-methylpiperidin-4-yloxy)methyl]benzothiazole; [(benzothiazol-2-yl)(m-tolyl)methyl](1-methylpiperidin-4-yl)amine; 2-[(3-allyloxyphenyl)(1-methylpiperidin-4-yloxy)methyl]benzothiazole; 2-[(1-methylpiperidin-4-yloxy)(3-trifluoromethoxyphenyl)methyl]benzothiazole; 2-[(1-methylpiperidin-4-yloxy)(4-trifluoromethoxyphenyl)methyl]benzothiazole; [benzothiazol-2-yl(3-methoxyphenyl)methyl](1-methylpiperidin-4-yl)amine; 2-[(1-methylpiperidin-4-yloxy)(3-propoxy-phenyl)methyl]benzothiazole; 2-[(3-bromo-phenyl)(1-methylpiperidin-4-yloxy)methyl]benzothiazole; 2-[(1-methylpiperidin-4-yloxy)(3-phenoxy-phenyl)methyl]benzothiazole; 5-methyl-2-[(1-methylpiperidin-4-yloxy)phenylmethyl]benzothiazole; 2-[(1-methylpiperidin-4-yloxy)phenylmethyl]-1H-benzimidazole; 2-[(1-methylpiperidin-4-yloxy)(3-trifluoromethylphenyl)methyl]benzothiazole; 2-[(2,3-dihydrobenzo furan-5-yl)(1-methylpiperidin-4-yloxy)methyl]benzothiazole; 5-fluoro-2-[(1-methylpiperidin-4-yloxy)phenylmethyl]benzothiazole; 2-[(4-fluoro-3-methylphenyl)(1-methylpiperidin-4-yloxy)methyl]benzothiazole; [benzothiazol-2-yl(4-fluoro-3-methyl-phenyl)methyl](1-methylpiperidin-4-yl)amine; (benzothiazol-2-yl-p-tolylmethyl)(1-methylpiperidin-4-yl)amine; [(benzofuran-2-yl)(benzothiazol-2-yl)methyl](1-methylpiperidin-4-yl)amine; 2-[(3-fluoro-5-methylphenyl)(1-methylpiperidin-4-yloxy)methyl]benzothiazole; [(1H-benzimidazol-2-yl)phenylmethyl](1-methylpiperidin-4-yl)amine; 2-[(3-fluoro-5-methoxyphenyl)(1-methylpiperidin-4-yloxy)methyl]benzothiazole; 2-[(3-iodophenyl)(1-methylpiperidin-4-yloxy)methyl]benzothiazole; [benzothiazol-2-yl(3-propoxyphenyl)methyl](1-methylpiperidin-4-yl)amine; [benzothiazol-2-yl(3-fluoro-5-methoxyphenyl)methyl](1-methylpiperidin-4-yl)amine; [benzothiazol-2-yl(3-fluoro-5-methylphenyl)methyl](1-methylpiperidin-4-yl)amine; 2-[(3-benzyloxyphenyl)(1-methylpiperidin-4-yloxy)methyl]benzothiazole; 2-[benzofuran-5-yl(1-methylpiperidin-4-yloxy)methyl]benzothiazole; 2-[(3-ethoxyphenyl)(1-methylpiperidin-4-yloxy)methyl]benzothiazole; [benzothiazol-2-yl(3-iodophenyl)methyl](1-methylpiperidin-4-yl)amine; 2-[(1-methylpiperidin-4-yloxy)(3-propoxyphenyl)methyl]-1H-benzimidazole; [(1H-benzimidazol-2-yl)(3-propoxyphenyl)methyl](1-methylpiperidin-4-yl)amine; 2-[(3-iodophenyl)(1-methylpiperidin-4-yloxy)methyl]-1H-benzimidazole; (benzothiazol-2-ylpyridin-3-ylmethyl)(1-methylpiperidin-4-yl)amine; 2-[biphenyl-3-yl(1-methylpiperidin-4-yloxy)methyl]benzothiazole; {3'-[benzothiazol-2-yl(1-methylpiperidin-4-yloxymethyl]biphenyl-3-yl}methanol; 2-[(3-isopropoxyphenyl)(1-methylpiperidin-4-yloxy)methyl]benzothiazole; [benzothiazol-2-yl(3-propoxyphenyl)methyl](1-methylpiperidin-4-yl)amine; [benzothiazol-2-yl(3-propoxyphenyl)methyl](1-methylpiperidin-4-yl)amine [benzothiazol-2-yl(3-pyrrol-2-yl)methyl](1-methylpiperidin-4-yl)amine; [(1H-benzimidazol-2-yl)(3-trifluoromethylphenyl)methyl](1-methylpiperidin-4-yl)amine; [(1H-benz imidazol-2-yl)(3-trifluoromethoxyphenyl)methyl](1-methylpiperidin-4-yl)amine; [(1H-benzimidazol-2-yl)(3-ethylphenyl)methyl](1-methylpiperidin-4-yl)amine; 3-[benzothiazol-2-yl(1-methylpiperidin-4-yloxy)methyl]phenol; 2-[(1-methylpiperidin-4-yloxy)(3-pyridin-3-ylphenyl)methyl]benzothiazole; [(1H-benzimidazol-2-yl)(3-bromophenyl)methyl](1-methylpiperidin-4-yl)amine; [(1H-benzimidazol-2-yl)(3-benzyloxyphenyl)methyl](1-methylpiperidin-4-yl)amine; [(1H-benzimidazol-2-yl)(3-isopropylphenyl)methyl](1-methylpiperidin-4-yl)amine; [(1H-benzimidazol-2-yl)(3-isobutoxyphenyl)methyl](1-methylpiperidin-4-yl)amine; {(1H-benzimidazol-2-yl)[3-(3-methylbutoxy)phenyl]methyl}(1-methylpiperidin-4-yl)amine; [(1H-benzimidazol-2-yl)(3-butoxyphenyl)methyl](1-methylpiperidin-4-yl)amine; [(1H-benzimidazol-2-yl)(3-methoxyphenyl)methyl](1-methylpiperidin-4-yl)amine; trifluoromethanesulfonic acid 3-[benzothiazol-2-yl(1-methylpiperidin-4-yloxy)methyl]phenyl ester; trifluoromethanesulfonic acid 3-[benzothiazol-2-yl(1-methylpiperidin-4-yloxy)methyl]phenyl ester; [(1H-benzimidazol-2-yl)(3-cyclohexylmethoxyphenyl)methyl](1-methylpiperidin-4-yl)amine; [(1H-benzimidazol-2-yl)(3-fluorophenyl)methyl](1-methylpiperidin-4-yl)amine; [(1H-benzimidazol-2-yl)(3-methylsulfanylphenyl)methyl](1-methylpiperidin-4-yl)amine; [(1H-benzimidazol-2-yl)(3-hexylphenyl)methyl](1-methylpiperidin-4-yl)amine; [(1H-benzimidazol-2-yl)(3-isopropoxyphenyl)methyl](1-methylpiperidin-4-yl)amine; 2-[(3-bromophenyl)(1-methylpiperidin-4-yloxy)methyl]-1H-benzimidazole; 3'-[benzothiazol-2-yl(1-methylpiperidin-4-yloxy)methyl]biphenyl-3-ylamine; 2-[(3-butylphenyl)(1-methylpiperidin-4-yloxy)methyl]benzothiazole; 2-[biphenyl-3-yl(1-methylpiperidin-4-yloxy)methyl]-1H-benzimidazole; [benzothiazol-2-yl(3-bromophenyl)methyl](1-methylpiperidin-4-yl)amine [(1H-benzimidazol-2-yl)(3-ethoxyphenyl)methyl](1-methylpiperidin-4-yl)amine; [(1H-benzimidazol-2-yl)(m-tolyl)methyl](1-methylpiperidin-4-yl)amine; [(1H-benzimidazol-2-yl)(3-phenoxyphenyl)methyl](1-methylpiperidin-4-yl)amine; {3'-[(1H-benzimidazol-2-yl)(1-methylpiperidin-4-yloxy)methyl]biphenyl-3-yl}methanol; 3'-[(1H-benzimidazol-2-yl)(1-methylpiperidin-4-yloxy)methyl]biphenyl-3-ylamine; [benzothiazol-2-yl(3-isopropoxyphenyl)methyl](1-methylpiperidin-4-yl)amine; 2-[(1-methylpiperidin-4-yloxy)(3-pyridin-3-ylphenyl)methyl]-1H-benzimidazole; 1-{3-[(1H-benzimidazol-2-yl)(1-methylpiperidin-4-ylamino)methyl]phenyl}ethanone; [benzothiazol-2-yl(3-butoxyphenyl)methyl](1-methylpiperidin-4-yl)amine; 2-[(3-butoxyphenyl)(1-methylpiperidin-4-yloxy)methyl]benzothiazole; [benzothiazol-2-yl(3-cyclohexylmethoxyphenyl)methyl](1-methylpiperidin-4-yl)amine; [(1H-benzimidazol-2-yl)biphenyl-3-ylmethyl](1-methylpiperidin-4-yl)amine; [(1H-benzimidazol-2-yl)(3-pentyloxyphenyl)methyl](1-methylpiperidin-4-yl)amine; 2-[(2'-methoxybiphenyl-3-yl)(1-methylpiperidin-4-yloxy)methyl]benzothiazole; 2-[(1-methylpiperidin-4-yloxy)(3'-nitrobiphenyl-3-yl)methyl]benzothiazole; {3'-[benzothiazol-2-yl(1-methylpiperidin-4-yloxy)methyl]biphenyl-3-yl}acetonitrile; 2-[(3'-methoxybiphenyl-3-yl)(1-methylpiperidin-4-yloxy)methyl]benzothiazole; 2-[(4'-methoxybiphenyl-3-yl)(1-methylpiperidin-4-yloxy)methyl]benzothiazole; [benzothiazol-2-yl(3-benzyloxyphenyl)methyl](1-methylpiperidin-4-yl)amine; (benzothiazol-2-ylbiphenyl-3-ylmethyl)(1-methylpiperidin-4-yl)amine; {(1H-benzimidazol-2-yl)[3-(4-fluorobenzyloxyl)phenyl]methyl}(1-methylpiperidin-4-yl)amine; [(1H-benzimidazol-2-yl)(3-benzylsulfanylphenyl)methyl](1-methylpiperidin-4-yl)amine; {(1H-benzimidazol-2-yl)[3-(3-fluorobenzyloxyl)

phenyl]methyl}(1-methylpiperidin-4-yl)amine; {(1H-benzimidazol-2-yl)[3-(2-phenoxyethoxy)phenyl]methyl}(1-methylpiperidin-4-yl)amine; [benzothiazol-2-yl(3-benzylsulfanylphenyl)methyl](1-methylpiperidin-4-yl)amine; 1-{3'-[(1H-benzimidazol-2-yl)(1-methylpiperidin-4-yloxy)methyl]biphenyl-4-yl}ethanone; 2-[(3'-fluoro-biphenyl-3-yl)(1-methylpiperidin-4-yloxy)methyl]-1H-benzimidazole; 1-{3'-[(1H-benzimidazol-2-yl)(1-methylpiperidin-4-yloxy)methyl]biphenyl-3-yl}ethanone; [benzothiazol-2-yl(3-methylsulfanylphenyl)methyl](1-methylpiperidin-4-yl)amine; [(3-allyloxyphenyl)(1H-benzimidazol-2-yl)methyl](1-methylpiperidin-4-yl)amine; {(1H-benzimidazol-2-yl)[3-(2-fluorobenzyloxyl)phenyl]methyl}(1-methylpiperidin-4-yl)amine; 2-[(1-methylpiperidin-4-yloxy)(2'-methylsulfanylbiphenyl-3-yl)methyl]-1H benzimidazole; 2-[(4'-fluorobiphenyl-3-yl)(1-methylpiperidin-4-yloxy)methyl]-1H-benzimidazole; 2-[(1-methylpiperidin-4-yloxy)(3'-methylsulfanylbiphenyl-3-yl)methyl]-1H-benzimidazole; 2-[(3-iodophenyl)(1-methylpiperidin-4-yloxy)methyl]benzothiazole; 2-[(3-iodophenyl)(1-methylpiperidin-4-yloxy)methyl]benzothiazole; 2-[(1-methylpiperidin-4-yloxy)(4'-trifluoromethylbiphenyl-3-yl)methyl]-1H-benzimidazole; {(1H-benzimidazol-2-yl)[3-(tetrahydropyran-2-yloxy)phenyl]methyl}(1-methylpiperidin-4-yl)amine; 2-[(2'-chlorobiphenyl-3-yl)(1-methylpiperidin-4-yloxy)methyl]-1H-benzimidazole; 2-[(3',4'-dichlorobiphenyl-3-yl)(1-methylpiperidin-4-yloxy)methyl]-1H-benzimidazole; {3'-[(1H-benzimidazol-2-yl)(1-methylpiperidin-4-yloxy)methyl]biphenyl-2-yl}methanol; {(1H-benzimidazol-2-yl)[3-(4-methoxybenzyloxyl)phenyl]methyl}(1-methylpiperidin-4-yl)amine; {(1H-benzimidazol-2-yl)[3-(3-methoxybenzyloxyl)phenyl]methyl}(1-methylpiperidin-4-yl)amine; 3-[(1H-benzimidazol-2-yl)(1-methylpiperidin-4-ylamino)methyl]phenol; {3'-[benzothiazol-2-yl(1-methylpiperidin-4-yloxy)methyl]biphenyl-2-yl}methanol; 2-[(1-methylpiperidin-4-yloxy)(3'-methylsulfanylbiphenyl-3-yl)methyl]benzothiazole; {(1H-benzimidazol-2-yl)[3-(2-methylbenzyloxy)phenyl]methyl}(1-methylpiperidin-4-yl)amine; {(1H-benzimidazol-2-yl)[3-(4-methylbenzyloxy)phenyl]methyl}(1-methylpiperidin-4-yl)amine; [(1H-benzimidazol-2-yl)(3-nitrophenyl)methyl](1-methylpiperidin-4-yl)amine; [(3-azidophenyl)(1H-benzimidazol-2-yl)methyl](1-methylpiperidin-4-yl)amine; 2-[(3',4'-dichlorobiphenyl-3-yl)(1-methylpiperidin-4-yloxy)methyl]benzothiazole; {(1H-benzimidazol-2-yl)[3-(2-ethoxyethoxy)phenyl]methyl}(1-methylpiperidin-4-yl)amine; [(1H-benzimidazol-2-yl)(3-pent-4-enyloxyphenyl)methyl](1-methylpiperidin-4-yl)amine; 2-[(4'-fluorobiphenyl-3-yl)(1-methylpiperidin-4-yloxy)methyl]benzothiazole; 2-[(2'-fluorobiphenyl-3-yl)(1-methylpiperidin-4-yloxy)methyl]benzothiazole; {3'-[(1H-benzimidazol-2-yl)(1-methylpiperidin-4-yloxy)methyl]biphenyl-4-yl}carbamic acid tert-butyl ester; 2-[(3'-fluorobiphenyl-3-yl)(1-methylpiperidin-4-yloxy)methyl]benzothiazole; 2-[(1-methylpiperidin-4-yloxy)(4'-trifluoromethylbiphenyl-3-yl)methyl]benzothiazole; 2-[(1-methylpiperidin-4-yloxy)(2',3',4'-trifluorobiphenyl-3-yl)methyl]benzothiazole; 2-[(2'-fluorobiphenyl-3-yl)(1-methylpiperidin-4-yloxy)methyl]-1H-benzimidazole; {3'-[benzothiazol-2-yl(1-methylpiperidin-4-yloxy)methyl]biphenyl-4-yl}carbamic acid tert-butyl ester; [(1H-benzimidazol-2-yl)(3-furan-2-ylphenyl)methyl](1-methylpiperidin-4-yl)amine; [(1H-benzimidazol-2-yl)(3-but-3-enyloxyphenyl)methyl](1-methylpiperidin-4-yl)amine; {(1H-benzimidazol-2-yl)[3-(4-methylpentyloxy)phenyl]methyl}(1-methylpiperidin-4-yl)amine; 2-[(1-methylpiperidin-4-yloxy)(3-pyrazol-1-ylphenyl)methyl]benzothiazole; 2-[(3-benzylsulfanylphenyl)(1-methylpiperidin-4-yloxy)methyl]benzothiazole; {(1H-benzimidazol-2-yl)[3-(2,5-difluoro-benzyloxy)phenyl]methyl}(1-methylpiperidin-4-yl)amine; 2-[(3-benzylsulfanylphenyl)(1-methylpiperidin-4-yloxy)methyl]-1H-benzimidazole; 2-[(2-chlorophenyl)(1-methylpiperidin-4-yloxy)methyl]-1H-benzimidazole; 2-[(3-ethylphenyl)(1-methylpiperidin-4-yloxy)methyl]benzothiazole; 2-[(3-ethylsulfanylphenyl)(1-methylpiperidin-4-yloxy)methyl]-1H-benzimidazole; {3-[(1H-benzimidazol-2-yl)(1-methylpiperidin-4-yloxy)methyl]phenylsulfanyl}acetic acid methyl ester; 2-[(3-fluorophenyl)(1-methylpiperidin-4-yloxy)methyl]-1H-benzimidazole; 2-[[3-(2,5-difluorobenzyloxyl)phenyl](1-methylpiperidin-4-yloxy)methyl]benzothiazole; 2-{3-[(1H-benzimidazol-2-yl)(1-methylpiperidin-4-yloxy)methyl]phenylsulfanyl}ethanol; 2-{3-[benzothiazol-2-yl(1-methylpiperidin-4-yloxy)methyl]phenylsulfanyl}ethanol; 2-[(3-ethylsulfanylphenyl)(1-methylpiperidin-4-yloxy)methyl]benzothiazole; {3-[benzothiazol-2-yl(1-methylpiperidin-4-yloxy)methyl]phenylsulfanyl}acetic acid methyl ester; 2-[[3-(2,3-difluorobenzyloxyl)phenyl](1-methylpiperidin-4-yloxy)methyl]benzothiazole; {(1H-benzimidazol-2-yl)[3-(2,3-difluoro-benzyloxy)phenyl]methyl}(1-methylpiperidin-4-yl)amine; 2-[[3-(2-fluoroethoxy)phenyl](1-methylpiperidin-4-yloxy)methyl]benzothiazole; 2-[(1-methylpiperidin-4-yloxy)(m-tolyl)methyl]-1H-benzimidazole; 5,6-dichloro-2-[(1-methylpiperidin-4-yloxy)phenyl-methyl]-1H-benzimidazole; 5-fluoro-2-[(1-methylpiperidin-4-yloxy)phenyl-methyl]-1H-benzimidazole; 2-[(2-fluorophenyl)(1-methylpiperidin-4-yloxy)methyl]-1H-benzimidazole; 2-[(1-methylpiperidin-4-yloxy)(3-pent-4-enyloxy-phenyl)methyl]benzothiazole; 2-{(1-methylpiperidin-4-yloxy)[3-(4,4,4-trifluoro-butoxy)phenyl]methyl}benzothiazole; 5-bromo-2-[(1-methylpiperidin-4-yloxy)phenyl-methyl]-1H-benzimidazole; 2-[[3-(3-fluorobenzyloxyl)phenyl](1-methylpiperidin-4-yloxy)methyl]benzothiazole; 3-[(1H-benzimidazol-2-yl)(1-methylpiperidin-4-yloxy)methyl]benzonitrile; 2-[[3-(furan-2-ylmethylsulfanyl)phenyl](1-methylpiperidin-4-yloxy)methyl]-1H-benzimidazole; ((1H-benzimidazol-2-yl)-{3-[3-(2-methyl-[1,3]dioxolan-2-yl)-propoxy]phenyl}methyl)(1-methylpiperidin-4-yl)amine; {(1H-benzimidazol-2-yl)[3-(4,4,4-trifluoro-butoxy)phenyl]methyl}(1-methylpiperidin-4-yl)amine; 2-[[3-(3-fluoropropoxy)phenyl](1-methylpiperidin-4-yloxy)methyl]benzothiazole; 2-[(1-methylpiperidin-4-yloxy)-p-tolyl-methyl]-1H-benzimidazole; 2-{(1-methylpiperidin-4-yloxy)[3-(3,3,3-trifluoropropoxy)phenyl]methyl}benzothiazole; 2-[(4'-fluorophenyl)(1-methylpiperidin-4-yloxy)methyl]-1H-benzimidazole; {(1H-benzimidazol-2-yl)[3-(2-fluoro-ethoxy)phenyl]methyl}(1-methylpiperidin-4-yl)amine; ((1H-benzimidazol-2-yl)-{3-[2-(6,6-dimethyl-bicyclo[3.1.1]hept-2-en-2-yl)ethoxy]phenyl}methyl)(1-methylpiperidin-4-yl)amine; 2-[(1-methylpiperidin-4-yloxy)(4'-trifluoromethoxy-biphenyl-3-yl)methyl]-1H-benzimidazole; 2-[(4'-methoxybiphenyl-3-yl)(1-methylpiperidin-4-yloxy)methyl]-1H-benzimidazole; 2-[(3-benzo[1,3]dioxol-5-yl-phenyl)(1-methylpiperidin-4-yloxy)methyl]-1H-benzimidazole; 2-[[3-(3-methoxybenzyloxyl)phenyl](1-methylpiperidin-4-yloxy)methyl]benzothiazole; 5-{3-[benzothiazol-2-yl(1-methylpiperidin-4-yloxy)methyl]phenoxy}pentan-2-one; 2-{(1-methylpiperidin-4-yloxy)[3-(3-trifluoromethylbenzyloxy)phenyl]methyl}benzothiazole; 4-[benzothiazol-2-yl(3-bromo-phenyl)methoxy]-1,1-dimethylpiperidinium; 2-(3-{3-[(1H-benzimidazol-2-yl)(1-methylpiperidin-4-yloxy)methyl]phenyl}prop-2-ynyl)isoindole-1,3-dione; 3-{3-[(1H-benzimidazol-2-yl)(1- methylpiperidin-4-yloxy)methyl]phenyl}prop-2-yn-1-ol; 4-{3-[(1H-benzimidazol-2-yl)(1-methylpiperidin-4-yloxy)methyl]phenyl}but-3-yn-1-ol; 5-{3-[(1H-benzimidazol-2-yl)(1-methylpiperidin-4-yloxy)methyl]phenyl}pent-4-yn-1-ol; 2-[(1-methylpiperidin-4-yloxy)-o-tolyl-methyl]-1H-benzimidazole; 3-{3-[(1H-benzimidazol-2-yl)(1-methylpiperidin-4-yloxy)methyl]phenyl}prop-2-ynylamine; 2-[(3-ethynylphenyl)(1-methylpiperidin-4-yloxy)methyl]-1H-benzimidazole; 2-{(1-methylpiperidin-4-yloxy)[3-(3-nitro-benzyloxy)phenyl]methyl}benzothiazole; 3-[benzothiazol-2-yl(1-methylpiperidin-4-yloxy)methyl]benzonitrile; 2-{(1-methylpiperidin-4-yloxy)[3-(1H-[1,2,3]triazol-4-yl)phenyl]methyl}-1H-benzimidazole; 3-[benzothiazol-2-yl(1-methylpiperidin-4-yloxy)methyl]benzoic acid methyl ester; 2-[(1-methylpiperidin-4-yloxy)phenyl-methyl]-3H-benzimidazol-4-ylamine; 2-[(1-methylpiperidin-4-yloxy)(3-methylsulfanyl-phenyl)methyl]benzothiazole; 2-[(1-methyl-piperidin-4-yloxy)(3-methylsulfanyl-phenyl)methyl]-1H-benzimidazole; 2-[(3-methanesulfonylphenyl)(1-methylpiperidin-4-yloxy)methyl]benzothiazole; 2-[(4-bromophenyl)(1-methylpiperidin-4-yloxy)methyl]-1H-benzimidazole; 3-{3-[benzothiazol-2-yl(1-methylpiperidin-4-yloxy)methyl]phenyl}acrylic acid tert-butyl ester; 3-[benzothiazol-2-yl(1-methylpiperidin-4-yloxy)methyl] benzoic acid ethyl ester; {3-[benzothiazol-2-yl(1-methylpiperidin-4-yloxy)methyl]phenyl}methanol; 3-{3-[benzothiazol-2-yl(1-methylpiperidin-4-yloxy)methyl] phenyl}propionic acid tert-butyl ester; 2-[[3-(2-benzenesulfonylvinyl)phenyl](1-methylpiperidin-4-yloxy)methyl]benzothiazole; 2-[(1-methylpiperidin-4-yloxy) phenyl-methyl]-3H-benzimidazol-4-ol; [benzothiazol-2-yl(4'-methoxy-biphenyl-3-yl)methyl](1-methylpiperidin-4-yl)amine; 2-[[3-(2-methanesulfonylvinyl)phenyl](1-methylpiperidin-4-yloxy)methyl]benzothiazole; 2-[(2-chloro-4-methylphenyl)(1-methylpiperidin-4-yloxy)methyl]-1H-benzimidazole; 5-{3-[benzothiazol-2-yl(1-methylpiperidin-4-yloxy)methyl]phenyl}pyrimidin-2-ol; 2-[(3-tert-butylsulfanylphenyl)(1-methylpiperidin-4-yloxy)methyl]-1H-benzimidazole; 2-[(1-methylpiperidin-4-yloxy)(3-pyrimidin-5-yl-phenyl)methyl]benzothiazole; 3-{3-[benzothiazol-2-yl(1-methylpiperidin-4-yloxy)methyl]phenyl}acrylonitrile; 2-[(1-methylpiperidin-4-yloxy)(3-vinyl-phenyl)methyl]benzothiazole; 3-[benzothiazol-2-yl(1-methylpiperidin-4-yloxy)methyl]-N-benzyl-N-methylbenzamide; 3-[benzothiazol-2-yl(1-methylpiperidin-4-yloxy)methyl]-N-propylbenzamide; 2-[(2,4-difluorophenyl)(1-methylpiperidin-4-yloxy)methyl]-1H-benzimidazole; [(1H-benzimidazol-2-yl)(4'-methoxy-biphenyl-3-yl)methyl](1-methylpiperidin-4-yl)amine; 3-[benzothiazol-2-yl(1-methylpiperidin-4-yloxy)methyl]-N-methyl-N-phenylbenzamide; 3-[(1H-benzimidazol-2-yl)(1-methylpiperidin-4-yloxy)methyl]phenylamine; 2-[(3-chlorophenyl)(1-methylpiperidin-4-yloxy)methyl]-1H-benzimidazole; 2-[(4-chlorophenyl)(1-methylpiperidin-4-yloxy)methyl]-1H-benzimidazole; 3-{3-[benzothiazol-2-yl(1-methylpiperidin-4-yloxy)methyl]phenyl}prop-2-yn-1-ol; 3-{3-[benzothiazol-2-yl(1-methylpiperidin-4-yloxy)methyl]phenoxymethyl}-phenylamine; 2-{3-[benzothiazol-2-yl(1-methylpiperidin-4-yloxy)methyl]phenylsulfanyl}ethanol; 2-{3-[benzothiazol-2-yl(1-methylpiperidin-4-yloxy)methyl]phenylsulfanyl}ethanol; 2-[(3-azidophenyl)(1-methylpiperidin-4-yloxy)methyl]-1H-benzimidazole; 2-{(1-methylpiperidin-4-yloxy)[3-(2-pyrazin-2-yl-ethylsulfanyl)phenyl]methyl}-1H-benzimidazole; 2-{(1-methylpiperidin-4-yloxy)[3-(2-pyrazin-2-yl-ethylsulfanyl)phenyl]methyl}benzothiazole; {3-[benzothiazol-2-yl(1-methylpiperidin-4-yloxy)methyl]phenyl}benzyl-amine; 3-{3-[(1H-benzimidazol-2-yl)(1-methylpiperidin-4-yloxy)methyl]phenylsulfanyl}-3-methyl-butan-1-ol; 4-{3-[benzothiazol-2-yl(1-methylpiperidin-4-yloxy)methyl]phenyl}but-3-yn-1-ol; 5-{3-[benzothiazol-2-yl(1-methylpiperidin-4-yloxy)methyl]phenyl}pent-4-yn-1-ol; 4-{3-[benzothiazol-2-yl(1-methylpiperidin-4-yloxy)methyl]phenyl}butan-1-ol; (1-{3-[benzothiazol-2-yl(1-methylpiperidin-4-yloxy)methyl]phenylsulfanylmethyl}-cyclopropyl)acetic acid methyl ester; 2-{(1-methylpiperidin-4-yloxy)[3-(2-[1,2,3]triazol-2-yl-ethylsulfanyl)phenyl]methyl}benzothiazole; 2-{(1-methylpiperidin-4-yloxy)[3-(2-[1,2,3]triazol-1-yl-ethylsulfanyl)phenyl]methyl}benzothiazole; 3-{3-[benzothiazol-2-yl(1-methylpiperidin-4-yloxy)methyl]phenylsulfanyl}-3-methyl-butan-1-ol; 2-[(1-methylpiperidin-4-yloxy)(3-morpholin-4-yl-phenyl)methyl]benzothiazole; 2-{3-[benzothiazol-2-yl(1-methylpiperidin-4-yloxy)methyl]phenoxy}ethanol; 2-[(1-methylpiperidin-4-yloxy)(3-vinyl-phenyl)methyl]-1H-benzimidazole; 3-{3-[(1H-benzimidazol-2-yl)(1-methylpiperidin-4-yloxy)methyl]phenylsulfanyl}propan-1-ol; 1-{3-[(1H-benzimidazol-2-yl)(1-methylpiperidin-4-yloxy)methyl]phenylsulfanyl}propan-2-ol; 4-{3-[(1H-benzimidazol-2-yl)(1-methylpiperidin-4-yloxy)methyl]phenylsulfanyl}butan-1-ol; 2-{3-[(1H-benzimidazol-2-yl)(1-methylpiperidin-4-yloxy)methyl]phenylsulfanyl}ethylamine; 2-{(1-methylpiperidin-4-yloxy)[3-(2-methylsulfanylethoxy)phenyl]methyl}benzothiazole, 2-[(1-methylpiperidin-4-yloxy)(2-trifluoromethoxy-phenyl)methyl]-1H-benzimidazole; 2-[(1-methylpiperidin-4-yloxy)-p-tolylmethyl]-1H-benzimidazole; 2-[(1-methylpiperidin-4-yloxy)-p-tolyl-methyl]-1H-benzimidazole; 3-{3-[benzothiazol-2-yl(1-methylpiperidin-4-yloxy)methyl]phenylsulfanyl}propan-1-ol; 1-{3-[benzothiazol-2-yl(1-methylpiperidin-4-yloxy)methyl]phenylsulfanyl}propan-2-ol; 4-{3-[benzothiazol-2-yl(1-methylpiperidin-4-yloxy)methyl]phenylsulfanyl}butan-1-ol; 2-(1-{3-[(1H-benzimidazol-2-yl)(1-methylpiperidin-4-yloxy)methyl]phenylsulfanylmethyl}-cyclopropyl)ethanol; 3-{3-[benzothiazol-2-yl(1-methylpiperidin-4-yloxy)methyl]phenoxy}propan-1-ol; 2-{3-[benzothiazol-2-yl(1-methylpiperidin-4-yloxy)methyl]phenylsulfanyl}-N-methylacetamide; 2-{(1-methylpiperidin-4-yloxy)[3-(2H-pyrazol-3-yl)phenyl]methyl}benzothiazole; 2-[(3-bromo-4-methylphenyl)(1-methylpiperidin-4-yloxy)methyl]-1H-benzimidazole; 2-[(2-bromophenyl)(1-methylpiperidin-4-yloxy)methyl]-1H-benzimidazole; 2-{3-[benzothiazol-2-yl(1-methylpiperidin-4-yloxy)methyl]phenylsulfanyl}acetamide; {3-[benzothiazol-2-yl(1-methylpiperidin-4-yloxy)methyl]phenylsulfanyl}acetic acid hydrazide; 2-{(1-methylpiperidin-4-yloxy)[3-(pyridin-4-ylmethoxy)phenyl]methyl}benzothiazole; 4-{3-[benzothiazol-2-yl(1-methylpiperidin-4-yloxy)methyl]phenoxy}butan-1-ol; 2-[[3-(furan-2-ylmethoxy)phenyl](1-methylpiperidin-4-yloxy)methyl]benzothiazole; 2-(1-{3-[benzothiazol-2-yl(1-methylpiperidin-4-yloxy)methyl]phenylsulfanylmethyl}-cyclopropyl)ethanol; 2-{3-[benzothiazol-2-yl(1-methylpiperidin-4-yloxy)methyl]phenylsulfanyl}ethylamine; 1-{3-[benzothiazol-2-yl(1-methylpiperidin-4-yloxy)methyl]benzyloxy}propan-2-one; 2-{3-[benzothiazol-2-yl(1-methylpiperidin-4-yloxy)methyl]phenoxy}ethylamine; 2-[(1-methylpyrrolidin-3-yloxy)phenyl-methyl]-1H-benzimidazole; [(1H-benzimidazol-2-yl)-p-tolyl-methyl](1-methylpiperidin-4-yl)amine; 2-[(3-ethylsulfanyl-4-methylphenyl)(1-methylpiperidin-4-yloxy)methyl]-1H-benzimidazole; 1-(3-{3-[benzothiazol-2-yl(1-methylpiperidin-4-yloxy)methyl]phenyl}prop-2-ynyloxy)-propan-2-one; 1-(3-{3-[benzothiazol-2-yl(1-methylpiperidin-4-yloxy)methyl]phenyl}prop-2-ynyloxy)- propan-2-ol; 2-[[3-(2-methoxyethoxy)phenyl](1-methylpiperidin-4-yloxy)methyl]benzothiazole; N-(2-{3-[(1H-benzimidazol-2-yl)(1-methylpiperidin-4-yloxy)methyl]phenylsulfanyl}ethyl)guanidine; (2-{3-[benzothiazol-2-yl(1-methylpiperidin-4-yloxy)methyl]phenoxy}ethyl)methylamine; 2-[(1-methylpiperidin-4-yloxy)(3-trifluoromethoxy-phenyl)methyl]-1H-benzimidazole; 2-[(2-chlorophenyl)(1-methylpiperidin-4-yloxy)methyl]benzothiazole; 4-{3-[benzothiazol-2-yl(1-methylpiperidin-4-yloxy)methyl]phenyl}but-3-ynylamine; 2-{(1-methylpiperidin-4-yloxy)[3-(pyridin-2-ylmethoxy)phenyl]methyl}benzothiazole; 2-{(1-methylpiperidin-4-yloxy)[3-(pyridin-3-ylmethoxy)phenyl]methyl}benzothiazole; 2-[(3-Cyclohexylmethoxyphenyl)(1-methylpiperidin-4-yloxy)methyl]benzothiazole; 4-{3-[(1H-benzimidazol-2-yl)(1-methylpiperidin-4-yloxy)methyl]phenyl}but-3-ynylamine; 5-{3-[benzothiazol-2-yl(1-methylpiperidin-4-yloxy)methyl]phenyl}pent-4-ynylamine; 3-{3-[(1H-benzimidazol-2-yl)(1-methylpiperidin-4-yloxy)methyl]phenylsulfanyl}propane-1,2-diol; 5-{3-[benzothiazol-2-yl(1-methylpiperidin-4-yloxy)methyl]phenyl}pentylamine; 2-{3-[benzothiazol-2-yl(1-ethyl-piperidin-4-yloxy)methyl]phenoxy}ethylamine; 2-{3-[(1H-benzimidazol-2-yl)(1-methylpiperidin-4-yloxy)methyl]phenoxy}ethylamine; 6-{3-[benzothiazol-2-yl(1-methylpiperidin-4-yloxy)methyl]phenylsulfanyl}hexan-1-ol; 4-{3-[(1H-benzimidazol-2-yl)(1-methylpiperidin-4-yloxy)methyl]phenyl}butylamine; 5-{3-[(1H-benzimidazol-2-yl)(1-methylpiperidin-4-yloxy)methyl]phenyl}pent-4-ynylamine; 6-{3-[(1H-benzimidazol-2-yl)(1-methylpiperidin-4-yloxy)methyl]phenylsulfanyl}hexan-1-ol; 3-{3-[benzothiazol-2-yl(1-methylpiperidin-4-yloxy)methyl]phenyl}prop-2-ynylamine; 2-[benzo[1,3]dioxol-5-yl(1-methylpiperidin-4-yloxy)methyl]-1H-benzimidazole; (2-{3-[(1H-benzimidazol-2-yl)(1-methylpiperidin-4-yloxy)methyl]phenylsulfanyl}ethyl)-urea; (2-{3-[(1H-benzimidazol-2-yl)(1-methylpiperidin-4-yloxy)methyl]phenylsulfanyl}ethyl)(4,5-dihydro-thiazol-2-yl)amine; 2-[(2,3-dihydrobenzo[1,4]dioxin-6-yl)(1-methylpiperidin-4-yloxy)methyl]-1H-benzimidazole; 4-{3-[benzothiazol-2-yl(1-methylpiperidin-4-yloxy)methyl]phenoxy}butylamine; N-(2-{3-[benzothiazol-2-yl(1-methylpiperidin-4-yloxy)methyl]phenylsulfanyl}ethyl)guanidine; 3-{3-[(1H-benzimidazol-2-yl)(1-methylpiperidin-4-yloxy)methyl]phenyl}propylamine; N-tert-butoxycarbonyl-N-(2-{3-[(benzothiazol-2-yl)(1-methylpiperidin-4-yloxy)methyl]phenylsulfanyl}ethyl)guanidine; 5-{3-[benzothiazol-2-yl(1-methylpiperidin-4-yloxy)methyl]phenylsulfanyl}pentylamine; 2-[{3-[2-(1-methyl-1H-imidazol4-yl)ethyl]phenyl}(1-methylpiperidin-4-yloxy)methyl]benzothiazole; N-tert-butoxycarbonyl-N'-(4-{3-[(1H-benzimidazol-2-yl)(1-methylpiperidin-4-yloxy)methyl]phenyl}but-3-ynyl)guanidine; N-(4-{3-[(1H-benzimidazol-2-yl)(1-methylpiperidin-4-yloxy)methyl]phenyl}butyl)guanidine; N-tert-butoxycarbonyl-N-(4-{3-[(1H-benzimidazol-2-yl)(1-methylpiperidin-4-yloxy)methyl]phenyl}butyl)guanidine; 2-{(1-methylpiperidin-4-yloxy)[3-(pyridin-2-ylmethoxy)phenyl]methyl}-1H-benzimidazole; 3-{3-[benzothiazol-2-yl(1-methylpiperidin-4-yloxy)methyl]phenoxy}propylamine; 5-{3-[(1H-benzimidazol-2-yl)(1-methylpiperidin-4-yloxy)methyl]phenyl}pentylamine; N-tert-butoxycarbonyl-N'-(3-{3-[(1H-benzimidazol-2-yl)(1-methylpiperidin-4-yloxy)methyl]phenyl}propyl)guanidine; 3-{3-[benzothiazol-2-yl(1-methylpiperidin-4-yloxy)methyl]phenylsulfanyl}propylamine; 2-{(1-methylpiperidin-4-yloxy)[3-(4-[1,2,3]triazol-2-yl-butoxy)phenyl]methyl}benzothiazole; 2-{(1-methylpiperidin-4-yloxy)[3-(4-[1,2,4]triazol-1-yl-butoxy)phenyl]methyl}benzothiazole; (2-{3-[(1H-benzimidazol-2-yl)(1-methylpiperidin-4-yloxy)methyl]phenylsulfanyl}ethyl)(4,5-dihydro-1H-imidazol-2-yl)amine; N-(2-{3-[(1H-benzimidazol-2-yl)(1-methylpiperidin-4-yloxy)methyl]phenylsulfanyl}ethyl)-N'-cyanoguanidine; 6-{3-[benzothiazol-2-yl(1-methylpiperidin-4-yloxy)methyl]phenyl}hex-5-ynylamine; N-(3-{3-[(1H-benzimidazol-2-yl)(1-methylpiperidin-4-yloxy)methyl]phenyl}propyl)guanidine; N-(3-{3-[(1H-benzimidazol-2-yl)(1-methylpiperidin-4-yloxy)methyl]phenyl}propyl)guanidine; 2-{(1-methylpiperidin-4-yloxy)[3-(4-morpholin-4-yl-butoxy)phenyl]methyl}benzothiazole; (1-{3-[benzothiazol-2-yl(1-methylpiperidin-4-yloxy)methyl]phenyl}pyrrolidin-2-yl)methanol; (1-{3-[benzothiazol-2-yl(1-methylpiperidin-4-yloxy)methyl]phenyl}pyrrolidin-2-yl)methanol; 6-{3-[benzothiazol-2-yl(1-methylpiperidin-4-yloxy)methyl]phenyl}hexylamine; 4-{3-[(1H-benzimidazol-2-yl)(1-methylpiperidin-4-yloxy)methyl]phenylsulfanyl}butylamine; 3-{3-[(1H-benzimidazol-2-yl)(1-methylpiperidin-4-yloxy)methyl]phenoxy}propylamine; 4-(2-{3-[benzothiazol-2-yl(1-methylpiperidin-4-yloxy)methyl]phenoxy}ethyl)piperazine-1-carboxylic acid tert-butyl ester; 4-(2-{3-[benzothiazol-2-yl(1-methylpiperidin-4-yloxy)methyl]phenoxy}ethyl)piperazine-1-carboxylic acid tert-butyl ester; 2-{(1-methylpiperidin-4-yloxy)[3-(2-piperazin-1-yl-ethoxy)phenyl]methyl}benzothiazole; 4-{3-[(1H-benzimidazol-2-yl)(1-methylpiperidin-4-yloxy)methyl]phenoxy}butylamine; 2-{(1-methylpiperidin-4-yloxy)[3-(4-morpholin-4-yl-butoxy)phenyl]methyl}-1H-benzimidazole; 2-{(1-methylpiperidin-4-yloxy)[3-(4-piperidin-1-yl-butoxy)phenyl]methyl}-1H-benzimidazole; 2-[(2-fluoro-3-iodophenyl)(1-methylpiperidin-4-yloxy)methyl]-1H-benzimidazole; N-tert-butoxycarbonyl-N'-(-{3-[(1H-benzimidazol-2-yl)(1-methylpiperidin-4-yloxy)methyl]phenyl}pentyl)guanidine; N-tert-butoxycarbonyl-N'-(3-{3-[1H-benzimidazol-2-yl)(1-methylpiperidin-4-yloxy)methyl]phenyl}prop-2-ynyl)guanidine; 6-{3-[(1H-benzimidazol-2-yl)(1-methylpiperidin-4-yloxy)methyl]phenyl}hex-5-ynylamine; 2-{(1-methylpiperidin-4-yloxy)[3-(1,2,3,6-tetrahydro-pyridin-4-yl)phenyl]methyl}-1H-benzimidazole; N-tert-butoxycarbonyl-N'-(5-{3-[(benzothiazol-2-yl)(1-methylpiperidin-4-yloxy)methyl]phenyl}pent-5-ynyl)guanidine; N-(5-{3-[benzothiazol-2-yl(1-methylpiperidin-4-yloxy)methyl]phenyl}pent-4-ynyl)guanidine; N-tert-butoxycarbonyl-N'-(6-{3-[(benzothiazol-2-yl)(1-methylpiperidin-4-yloxy)methyl]phenyl}hex-5-ynyl)guanidine N-(6-{3-[benzothiazol-2-yl(1-methylpiperidin-4-yloxy)methyl]phenyl}hex-5-ynyl)guanidine; 4-(4-{3-[(1H-benzimidazol-2-yl)(1-methylpiperidin-4-yloxy)methyl]phenoxy}butyl)piperazine-1-carboxylic acid tert-butyl ester; 6-{3-[(1H-benzimidazol-2-yl)(1-methylpiperidin-4-yloxy)methyl]phenyl}hexylamine; N-tert-butoxycarbonyl-N'-(6-{3-[(1H-benzimidazol-2-yl)(1-methylpiperidin-4-yloxy)methyl]phenyl}hex-5-ynyl)guanidine; N-(6-{3-[(1H-benzimidazol-2-yl)(1-methylpiperidin-4-yloxy)methyl]phenyl}hex-5-ynyl)guanidine; 1-(2-{3-[(1H-benzimidazol-2-yl)(1-methylpiperidin-4-yloxy)methyl]phenylsulfanyl}ethyl)-3-isopropyl-thiourea; 2-{(1-methylpiperidin-4-yloxy)[3-(3-[1,2,4]triazol-1-yl-propoxy)phenyl]methyl}benzothiazole; 2-{(1-methylpiperidin-4-yloxy)[3-(3-[1,2,3]triazol-2-yl-propoxy)phenyl]methyl}benzothiazole; 2-{(1-methylpiperidin-4-yloxy)[3-(3-morpholin-4-yl-propoxy)phenyl]methyl}benzothiazole; 4-(3-{3-[benzothiazol-2-yl(1-methylpiperidin-4-yloxy)methyl]phenoxy}propyl)piperazine-1-carboxylic acid tert-butyl ester; 2-{3-[(1H-benzimidazol-2-yl)(1-methylpiperidin-4-yloxy)methyl]-2-fluoro-phenylsulfanyl}ethylamine; 4-{3-[(1H-benzimidazol-2-yl)(1-methylpiperidin-4-yloxy) methyl]phenyl}-3,6-dihydro-2H-pyridine-1-carboxamidine; 2-[[3-(2-chloroethoxyl)phenyl](1-methylpiperidin-4-yloxy) methyl]benzothiazole; N-(6-{3-[(1H-benzimidazol-2-yl)(1-methylpiperidin-4-yloxy)methyl]phenyl}hexyl)guanidine; 2-{(1-methylpiperidin-4-yloxy)[3-(2-piperidin-1-yl-ethoxy) phenyl]methyl}-1H-benzimidazole; N-tert-butoxycarbonyl-N'-(5-{3-[(1H-benzimidazol-2-yl)(1-methylpiperidin-4-yloxy)methyl]phenyl}pent-4-ynyl)guanidine; N-(5-{3-[(1H-benzimidazol-2-yl)(1-methylpiperidin-4-yloxy) methyl]phenyl}pent-4-ynyl)guanidine; 4-{3-[benzothiazol-2-yl(1-methylpiperidin-4-yloxy)methyl] phenylsulfanyl}butylamine; 4-(3-{3-[(1H-benzimidazol-2-yl)(1-methylpiperidin-4-yloxy)methyl]phenoxy}propyl) piperazine-1-carboxylic acid tert-butyl ester; (2-{3-[(1H-benzimidazol-2-yl)(1-methylpiperidin-4-yloxy)methyl] phenoxy}ethylamino)acetic acid tert-butyl ester; 4-(5-{3-[benzothiazol-2-yl(1-methylpiperidin-4-yloxy)methyl] phenoxy}pentyl)piperazine-1-carboxylic acid tert-butyl ester; N-(6-{3-[benzothiazol-2-yl(1-methylpiperidin-4-yloxy)methyl]phenyl}hexyl)guanidine; N-tert-butoxycarbonyl-N'-(6-{3-[(1H-benzimidazol-2-yl)(1-methylpiperidin-4-yloxy)methyl]phenyl}hexyl)guanidine; N-(5-{3-[benzothiazol-2-yl(1-methylpiperidin-4-yloxy)methyl] phenyl}pentyl)guanidine; 4-{3-[benzothiazol-2-yl(1-methylpiperidin-4-yloxy)methyl]phenyl}butylamine; [[3-(4-aminobutoxy)phenyl](1H-benzimidazol-2-yl)methyl](1-methylpiperidin-4-yl)amine; 3-{3-[(1H-benzimidazol-2-yl)(1-methylpiperidin-4-yloxy)methyl] phenylsulfanyl}propylamine; 4-(2-{3-[(1H-benzimidazol-2-yl)(1-methylpiperidin-4-yloxy)methyl]phenoxy}ethyl) piperazine-1-carboxylic acid tert-butyl ester; (2-{3-[benzothiazol-2-yl(1-methylpiperidin-4-yloxy)methyl] phenoxy}ethylamino)acetic acid tert-butyl ester; 5-{3-[benzothiazol-2-yl(1-methylpiperidin-4-yloxy)methyl] phenoxy}pentylamine; N-(4-{3-[benzothiazol-2-yl(1-methylpiperidin-4-yloxy)methyl]phenyl}but-3-ynyl) guanidine; N-(3-{3-[benzothiazol-2-yl(1-methylpiperidin-4-yloxy)methyl]phenyl}prop-2-ynyl)guanidine; N-(4-{3-[benzothiazol-2-yl(1-methylpiperidin-4-yloxy)methyl] phenyl}butyl)guanidine; (5-{3-[benzothiazol-2-yl(1-methylpiperidin-4-yloxy)methyl]phenoxy}pentylamino) acetic acid tert-butyl ester; 2-[(1-methylpiperidin-4-yloxy)(3-piperidin-4-ylethynyl-phenyl)methyl]-1H-benzimidazole; 2-{(1-methylpiperidin-4-yloxy) [3-(piperidin-4-ylmethoxy)phenyl]methyl}benzothiazole; 2-{(1-methylpiperidin-4-yloxy)[3-(piperidin-3-ylmethoxy) phenyl]methyl}benzothiazole; 2-[[3-(1-methylpiperidin-3-ylmethoxy)phenyl](1-methylpiperidin-4-yloxy)methyl]benzothiazole; 2-[(1-methylpiperidin-4-yloxy)(3-piperidin-3-ylethynyl-phenyl)methyl]-1H-benzimidazole; 5-{3-[(1H-benzimidazol-2-yl)(1-methylpiperidin-4-yloxy)methyl] phenylsulfanyl}pentylamine; 2-{(1-methylpiperidin-4-yloxy)[3-(pyrrolidin-3-yloxy)phenyl] methyl}benzothiazole; 2-{(1-methylpiperidin-4-yloxy)[3-(pyrrolidin-3-yloxy)phenyl]methyl}benzothiazole; 5-{3-[benzothiazol-2-yl(1-methylpiperidin-4-yloxy)methyl] phenyl}pent-4-en-1-ol; 3-amino-4-(2-{3-[(1H-benzimidazol-2-yl)(1-methylpiperidin-4-yloxy)methyl] phenylsulfanyl}ethylamino)-cyclobut-3-ene-1,2-dione; [[3-(6-aminohex-1-ynyl)phenyl](1H-benzimidazol-2-yl) methyl](1-methylpiperidin-4-yl)amine; {[3-(4-aminobutoxy)phenyl]benzothiazol-2-yl-methyl}(1-methylpiperidin-4-yl)amine; 2-[(3-azetidin-3-ylethynylphenyl)(1-methylpiperidin-4-yloxy)methyl]-1H-benzimidazole; 5-{3-[(1H-benzimidazol-2-yl)(1-methylpiperidin-4-yloxy)methyl]phenyl}pent-4-en-1-ol; 5-{3-[benzothiazol-2-yl(1-methylpiperidin-4-yloxy)methyl] phenyl}pent-4-en-1-ol; 4-(5-{3-[1H-benzimidazol-2-yl)(1-methylpiperidin-4-yloxy)methyl]phenoxy}pentyl)piperazine-1-carboxylic acid tert-butyl ester; 2-[[3-(2-azetidin-3-ylethyl)phenyl](1-methylpiperidin-4-yloxy)methyl]-1H-benzimidazole; N-(4-{3-[(1H-benzimidazol-2-yl)(1-methylpiperidin-4-yloxy)methyl]phenyl}but-3-ynyl) guanidine; 4-{3-[(1H-benzimidazol-2-yl)(1-methylpiperidin-4-yloxy)methyl]phenyl}piperidine-1-carboxamidine; 2-{(1-methylpiperidin-4-yloxy)[3-(2-piperidin-2-yl-ethylsulfanyl)phenyl]methyl}-1H-benzimidazole; 2-{(1-methylpiperidin-4-yloxy)[3-(2-piperidin-4-yl-ethyl)phenyl]methyl}-1H-benzimidazole; N-(5-{3-[(1H-benzimidazol-2-yl)(1-methylpiperidin-4-yloxy)methyl]phenyl}pentyl)guanidine; 2-[{3-[3-(3H-imidazol-4-yl)propylsulfanyl]phenyl}(1-methylpiperidin-4-yloxy)methyl]-1H-benzimidazole; N-tert-butoxycarbonyl-N'-(4-{3-[(benzothiazol-2-yl)(1-methylpiperidin-4-yloxy) methyl]phenyl}but-3-ynyl)guanidine; 5-{3-[(1H-benzimidazol-2-yl)(1-methylpiperidin-4-yloxy)methyl] phenoxy}pentylamine; N-acetyl-N'-(2-{3-[(1H-benzimidazol-2-yl)(1-methylpiperidin-4-yloxy)methyl] phenylsulfanyl}ethyl)guanidine; 2-[[3-(azetidin-3-yloxy) phenyl](1-methylpiperidin-4-yloxy)methyl]benzothiazole; 1-{3-[benzothiazol-2-yl(1-methylpiperidin-4-yloxy)methyl] phenyl}azetidin-3-ol; (1-{3-[benzothiazol-2-yl(1-methylpiperidin-4-yloxy)methyl]phenyl}pyrrolidin-3-yl)methanol; 1-{3-[benzothiazol-2-yl(1-methylpiperidin-4-yloxy)methyl] phenyl}piperidin-4-ylamine; 1-{3-[benzothiazol-2-yl(1-methylpiperidin-4-yloxy)methyl]phenyl}pyrrolidin-3-ol; 1-{3-[benzothiazol-2-yl(1-methylpiperidin-4-yloxy)methyl] phenyl}pyrrolidin-3-ol; N-(1-{3-[benzothiazol-2-yl(1-methylpiperidin-4-yloxy)methyl]phenyl}pyrrolidin-3-yl)acetamide; 2-[[3-(5-imidazol-1-ylpent-1-ynyl)phenyl](1-methylpiperidin-4-yloxy)methyl]-1H-benzimidazole; 2-{(1-methylpiperidin-4-yloxy)[3-(5-pyrazol-1-yl-pent-1-ynyl) phenyl]methyl}-1H-benzimidazole; 1-{3-[benzothiazol-2-yl(1-methylpiperidin-4-yloxy)methyl]phenyl}piperidin-4-ol; 2-[{3-[2-(1H-imidazol-4-yl)ethyl]phenyl}(1-methylpiperidin-4-yloxy)methyl]-1H-benzimidazole; acetic acid 1-{3-[benzothiazol-2-yl(1-methylpiperidin-4-yloxy) methyl]phenyl}piperidin-4-yl ester; 2-[(3-bromo-phenyl)(1-methyl-pyrrolidin-3-ylmethoxy)methyl]-1H-benzimidazole; 2-{(1-methylpiperidin-4-yloxy)[3-(piperidin-4-yloxy)phenyl]methyl}benzothiazole; 2-{(1-methylpiperidin-4-yloxy) [3-(5-[1,2,3]triazol-2-yl-pent-1-ynyl)phenyl]methyl}-1H-benzimidazole; 2-{(1-methylpiperidin-4-yloxy)[3-(5-[1,2,3] triazol-1-yl-pent-1-ynyl)phenyl]methyl}-1H-benzimidazole; N-(3-{3-[(1H-benzimidazol-2-yl)(1-methylpiperidin-4-yloxy)methyl]phenyl}prop-2-ynyl) guanidine; N1-(5-{3-[(1H-benzimidazol-2-yl)(1-methylpiperidin-4-yloxy)methyl]phenoxy}pentyl)butane-1,4-diamine; {[3-(6-aminohex-1-ynyl)phenyl]benzothiazol-2-yl-methyl}(1-methylpiperidin-4-yl)amine; 5-{3-[(1H-benzimidazol-2-yl)(1-methylpiperidin-4-yloxy)methyl] phenyl}pent-4-enylamine; 4-{3-[benzothiazol-2-yl(1-methylpiperidin-4-yloxy)methyl]phenoxy}but-2-en-1-ol-1-{3-[benzothiazol2-yl(1-methylpiperidin-4-yloxy)methyl] phenyl}pyrrolidin-3-ylamine; 2-[(2,5-difluorophenyl)(1-methylpiperidin-4-yloxy)methyl]-1H-benzimidazole; 2-[(2-fluoro-5-iodo-phenyl)(1-methylpiperidin-4-yloxy)methyl]-1H-benzimidazole; 3-{3-[(1H-benzimidazol-2-yl)(1-methylpiperidin-4-yloxy)methyl]phenylethynyl}azetidine-1-carboxamidine; 4-{3-[(5-fluoro-1H-benzimidazol-2-yl) (1-methylpiperidin-4-yloxy)methyl]phenylsulfanyl}butan-1-ol; 2-{3-[(5-fluoro-1H-benzimidazol-2-yl)(1- methylpiperidin-4-yloxy)methyl]phenylsulfanyl}ethylamine; 1-{3-[benzothiazol-2-yl(1-methylpiperidin-4-yloxy)methyl]phenyl}pyrrolidin-3-ylamine; 2-[[3-(3-fluoropyrrolidin-1-yl)phenyl](1-methylpiperidin-4-yloxy)methyl]benzothiazole; 4-{3-[benzothiazol-2-yl(1-methylpiperidin-4-yloxy)methyl]phenoxy}but-2-enylamine; 2-[(2-fluoro-5-trifluoromethoxyphenyl)(1-methylpiperidin-4-yloxy)methyl]-1H-benzimidazole; 2-[(2-fluoro-5-trifluoromethoxyphenyl)(1-methylpiperidin-4-yloxy)methyl]-1H-benzimidazole (enantiomer A); 2-[(2-fluoro-5-trifluoromethoxyphenyl)(1-methylpiperidin-4-yloxy)methyl]-1H-benzimidazole (enantiomer B) as well as their enantiomers, diastereomers, mixtures thereof and pharmaceutically acceptable salts, free forms, hydrates and solvates.

In another embodiment, the Histamine H4 antagonist or selective Histamine H4 antagonists are quinazoline sulfonamide derivatives, such as described in the International Patent Application: 2-(6-chloro-2-(4-methylpiperazin-1-yl)quinazoline-4-amino)-N-methyl-N-phenylethanesulfonamide; 2-(6-chloro-2-(4-methylpiperazin-1-yl)quinazoline-4-amino)-/N-phenylethanesulfonamide; 2-(6-chloro-2-(4-methylpiperazin-1-yl)quinazoline-4-amino)-N,N-diethylethanesulfonamide; 2-(6-chloro-2-(4-methylpiperazin-1-yl)quinazoline-4-amino)-N,N/-dimethylethanesulfonamide; 2-(6-chloro-2-(4-methylpiperazin-1-yl)quinazoline-4-amino)-/N-methylethanesulfonamide; 2-(6-chloro-2-(4-methylpiperazin-1-yl)quinazoline-4-amino)-ethanesulfonamide; 6-chloro-2-(4-methylpiperazin-1-yl)-N-(2-(morpholinosulfonyl)ethyl)quinazolin-4-amine; 2-(6-chloro-2-(4-methylpiperazin-1-yl)quinazoline-4-amino)-N-(4-iodophenyl)ethanesulfonamide; 2-(6-chloro-2-(4-methylpiperazin-1-yl)quinazoline-4-amino)-S-methylethanesulfone; 3-(6-chloro-2-(4-methylpiperazin-1-yl)quinazoline-4-amino)-N-methylpropanesulfonamide; 2-(5-trifluoromethyl-2-(4-methylpiperazin-1-yl)quinazoline-4-amino)-N-phenylethanesulfonamide; 2-(6,7-dichloro-2-(4-methylpiperazin-1-yl)quinazoline-4-amino)-N-phenylethanesulfonamide; 2-(6-bromo-7-chloro-2-(4-methylpiperazin-1-yl)quinazoline-4-amino)-N-phenylethanesulfonamide; 2-(6,7-dichloro-2-(4-methylpiperazin-1-yl)quinazoline-4-amino)-N-phenylethanesulfonamide; 2-(6-iodo-2-(4-methylpiperazin-1-yl)quinazoline-4-amino)-N-phenylethanesulfonamide; 2-(7,8-dichloro-2-(4-methylpiperazin-1-yl)quinazoline-4-amino)-N-phenylethanesulfonamide; 2-(5,7-dichloro-2-(4-methylpiperazin-1-yl)quinazoline-4-amino)-N-phenylethanesulfonamide.

In another embodiment, selective Histamine H4 antagonists are indolecarboxamides derivatives, such as described by Engelhardt et al. (2012 Eur J Med Chem. 54:660-668) and that comprise the formula:

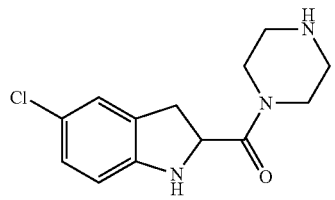

In another embodiment, the Histamine H4 antagonist or selective Histamine H4 antagonists are pyridopyrimidines derivatives, such as described by Engelhardt et al. (2012 Eur J Med Chem. 54:660-668) and in the Patent Application WO2013/060881: 7-ethyl-4-(4-methylpiperazin-1-yl)pyrido[3,2-d]pyrimidin-2-amine; 2-amino-4-(3-(methylamino)azetidin-1-yl)pyrido[3,2-d]pyrimidine-7-carbonitrile; 7-isopropyl-4-(3-(methylamino)azetidin-1-yl)pyrido[3,2-d]pyrimidin-2-amine; (R)-7-isopropyl-4-(3-(methylamino)pyrrolidin-1-yl)pyrido[3,2-d]pyrimidin-2-amine; 7-ethyl-4-(3-(methylamino)azetidin-1-yl)pyrido[3,2-d]pyrimidin-2-amine; (R)-7-ethyl-4-(3-(methylamino)pyrrolidin-1-yl)pyrido[3,2-d]pyrimidin-2-amine; 7-cyclopropyl-4-(3-(methylamino)azetidin-1-yl)pyrido[3,2-d]pyrimidin-2-amine; (R)-7-cyclopropyl-4-(3-(methylamino)pyrrolidin-1-yl)pyrido[3,2-d]pyrimidin-2-amine; 7-cyclopentyl-4-(3-(methylamino)azetidin-1-yl)pyrido[3,2-d]pyrimidin-2-amine; (R)-7-cyclopentyl-4-(3-(methylamino)pyrrolidin-1-yl)pyrido[3,2-d]pyrimidin-2-amine, or a pharmaceutically acceptable salt or ester thereof.

In another embodiment, the Histamine H4 antagonist or selective Histamine H4 antagonists are aminopyrimidine derivatives, such as described by Engelhardt et al. (2012 Eur J Med Chem. 54:660-668) and in the International Patent Application WO2010/146173: 7-methyl-4-(4-methylpiperazin-1-yl)quinazolin-2-amine; 8-methyl-4-(4-methylpiperazin-1-yl)quinazolin-2-amine; 7-bromo-4-(4-methylpiperazin-1-yl)quinazolin-2-amine; 8-bromo-4-(4-methylpiperazin-1-yl)quinazolin-2-amine; 4-(4-methylpiperazin-1-yl)-7-phenylquinazolin-2-amine; 7-(2,6-dimethylphenyl)-4-(4-methylpiperazin-1-yl)quinazolin-2-amine; 4-(2-amino-4-(4-methylpiperazin-1-yl)quinazolin-7-yl)benzonitrile; 7-(4-methoxyphenyl)-4-(4-methylpiperazin-1-yl)quinazolin-2-amine; 7-(furan-3-yl)-4-(4-methylpiperazin-1-yl)quinazolin-2-amine; 4-(4-methylpiperazin-1-yl)-8-phenylquinazolin-2-amine; 8-(2,6-dimethylphenyl)-4-(4-methylpiperazin-1-yl)quinazolin-2-amine; 4-(2-amino-4-(4-methylpiperazin-1-yl)quinazolin-8-yl)benzonitrile; 8-(4-methoxyphenyl)-4-(4-methylpiperazin-1-yl)quinazolin-2-amine; 8-(furan-3-yl)-4-(4-methylpiperazin-1-yl)quinazolin-2-amine; 7-(furan-2-yl)-4-(4-methylpiperazin-1-yl)quinazolin-2-amine and 4-(4-methylpiperazin-1-yl)-7-(thiophen-3-yl)quinazolin-2-amine.

In another embodiment, the Histamine H4 antagonist or selective Histamine H4 antagonists are pyrido[3,2-d]pyrimidine derivatives, such as described in Andaloussi et al. 2013 Bioorg Med Chem Lett. 2013 May 1; 23(9):2663-70 and comprising the following formula:

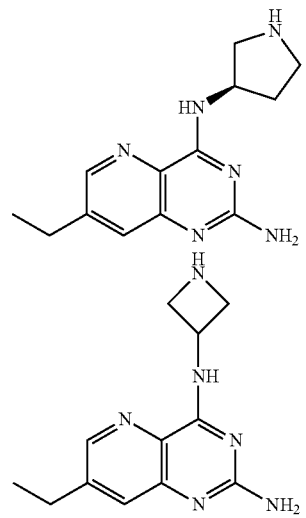

-continued

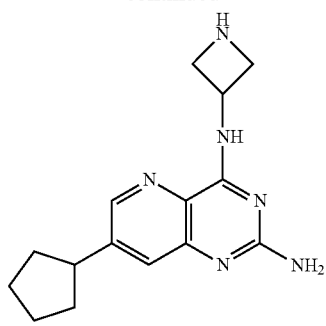

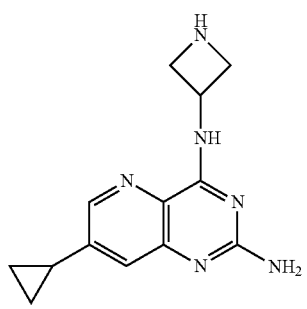

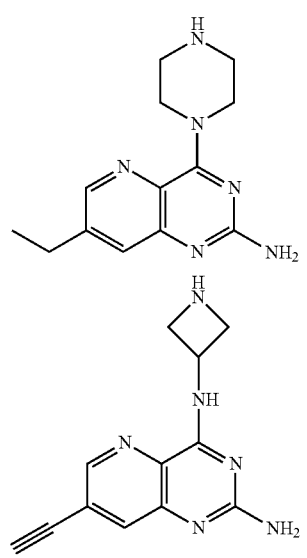

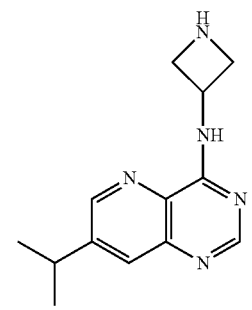

-continued

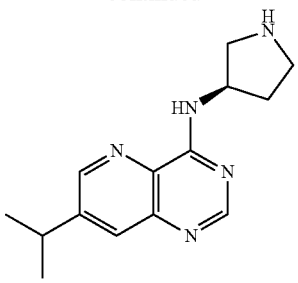

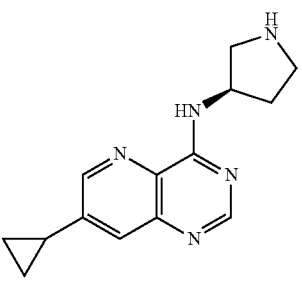

In another embodiment, the Histamine H4 antagonist or selective Histamine H4 antagonists are diamino pyrimidine derivatives such as described by Sander K et al. Inflamm. Res. (2010) 59 (Suppl 2):S249-S251.

In another embodiment, the Histamine H4 antagonist or selective Histamine H4 antagonists are pyrrolo[2,3-d]pyrimidine scaffold such as described by Gao L J et al. Bioorganic & Medicinal Chemistry Letters 23 (2013) 132-137.

In a particular embodiment, the Histamine H4 receptor antagonist is 1-[(5-chloro-1H-benzimidazol-2-yl)carbonyl]-4-methylpiperazine (also named JNJ 10191584 or VUF 6002) described by Herman D. et al. (2005). This selective antagonist binds with high affinity the human Histamine H4 receptor (Ki=26 nM). This affinity is 540-fold more selective over the H3 receptor (Ki=14.1 µM) (Zhang M. et al. 2007).

In a particular embodiment, the selective Histamine H4 receptor antagonist is 1-[(5-chloro-1H-indol-2-yl)carbonyl]-4-methylpiperazine (also named JNJ 7777120) described by Robin L. et al. (2004).

In a particular embodiment, the Histamine H4 receptor antagonist is JNJ 39758979 and comprises the formula:

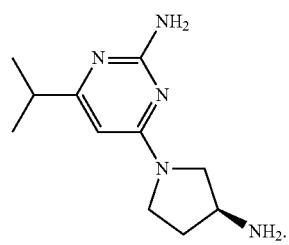 [SMILES: CC(C)c1cc(N2CC[C@H](N)C2)nc(N)n1]

In a particular embodiment, the Histamine H4 receptor antagonist is JNJ 39594906 and comprises the formula:

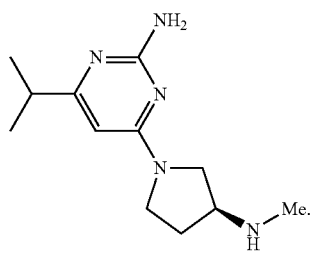 [SMILES: CN[C@H]1CCN(c2cc(C(C)C)nc(N)n2)C1]

In a particular embodiment, the Histamine H4 receptor antagonist is JNJ 28307474 and comprises the formula:

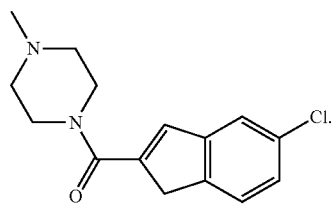 [SMILES: CN1CCN(C(=O)C2=Cc3cc(Cl)ccc3C2)CC1]

In a particular embodiment, the Histamine H4 receptor antagonist is 2-(1-Methylpiperidin-4-ylidene)-4,7-diazatricyclo[8.4.0.0$^{(3,7)}$]tetradeca-1(14),3,5,10,12-pentaene-6-carbaldehyde (also named as Alcaftadine) as described in WO/2009022551.

In a particular embodiment, the Histamine H4 receptor antagonist is JNJ 39760409 and comprises the formula:

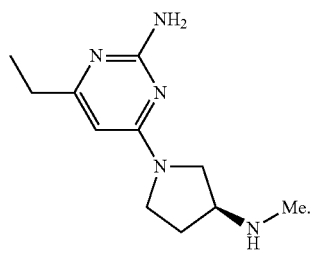 [SMILES: CCc1cc(N2CC[C@H](NC)C2)nc(N)n1]

In a particular embodiment, the selective Histamine H4 receptor antagonist is 1-[(5-Chloro-1H-benzimidazol-2-yl)carbonyl]-4-methylpiperazine maleate (also named JNJ 10191584).

In a particular embodiment, the selective Histamine H4 receptor antagonist is 4-((3R)-3-Aminopyrrolidin-1-yl)-6,7-dihydro-5H-benzo[6,7]cyclohepta[1,2-d]pyrimidin-2-ylamine (also named A-943931) described by Cowart M D. et al. (2008).

In a particular embodiment, the selective Histamine H4 receptor antagonist is cis-4-(Piperazin-1-yl)-5,6,7a,8,9,10,11,11a-octahydrobenzofuro[2,3-h]quinazolin-2-amine (also named A-987306) described by Liu H et al. (2008).

In a particular embodiment, the Histamine H4 receptor antagonist is 7-(furan-2-yl)-4-(piperazin-1-yl)quinazolin-2-amine (also named VUF11489):

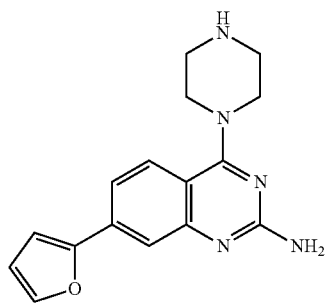 [SMILES: Nc1nc(N2CCNCC2)c2ccc(-c3ccco3)cc2n1]

In a particular embodiment, the Histamine H4 receptor antagonist is PF-3893787:

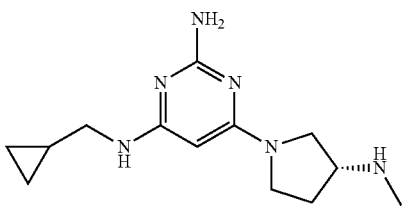 [SMILES: CN[C@@H]1CCN(c2cc(NCC3CC3)nc(N)n2)C1]

In a particular embodiment, the Histamine H4 receptor antagonist is PF-3893787-18:

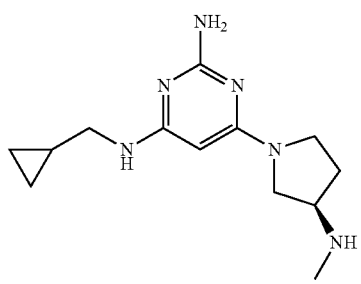 [SMILES: CN[C@@H]1CCN(c2cc(NCC3CC3)nc(N)n2)C1]

In a particular embodiment, the Histamine H4 receptor antagonist is named UR-60427.

In a particular embodiment, the Histamine H4 receptor antagonist is named UR-63325:

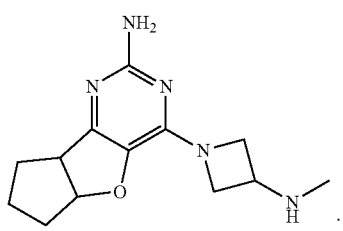 [SMILES: CNC1CN(c2nc(N)nc3c2OC2CCCC32)C1]

In a particular embodiment, the Histamine H4 receptor antagonist is 1-(7-(2-amino-6-(4-methylpiperazin-1-yl)pyrimidin-4-yl)-3,4-dihdroisoquinolin-2(1H)-yl)-2-cyclopentylethanone (also named INCB38579).

In a particular embodiment, the Histamine H4 receptor antagonist is described in Engelhardt et al. 2012 J. Med. Chem. May 28 and their formula are the following:

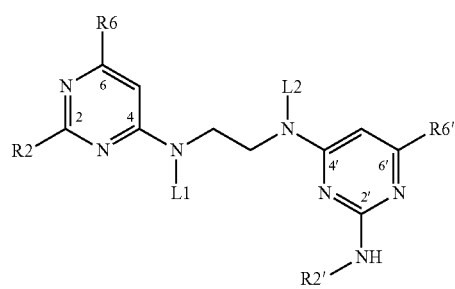

wherein

| # | R6 | R2 | L1 | L2 | R6' | R2' |
|---|----|----|----|----|-----|-----|
| 22 | H | NH$_2$ | H | H | H | H |
| 23 | H | NH$_2$ | H | H | isobutyl-NH- | H |
| 24 | H | NH$_2$ | H | H | isopentyl | H |
| 5 | H | NH$_2$ | H | H | phenyl | H |
| 25 | H | NH$_2$ | H | H | 3-chlorophenyl | H |
| 26 | phenyl | NH$_2$ | H | H | phenyl | H |
| 27 | isopentyl | NH$_2$ | H | H | phenyl | H |
| 28 | isobutyl-NH- | NH$_2$ | H | H | phenyl | H |
| 29 | H | H | H | H | phenyl | H |
| 30 | H | Me | H | H | phenyl | H |
| 31 | Cl | NH$_2$ | H | H | phenyl | H |
| 32 | Cl | NH$_2$ | H | H | isopentyl | H |
| 33 | H | NH$_2$ | H | H | phenyl | isobutyl |
| 34 | H | NH$_2$ | H | H | isobutyl-NH- | phenyl | H |
| 35 | H | NH$_2$ | H | H | isobutyl-NH- | 3-chlorophenyl | H |
| 36 | H | NH$_2$ | H | H | isobutyl-NH- | H | H |
| 37 | isobutyl-NH- | H | H | H | H | H |
| 38 | isobutyl-NH- | H | H | H | phenyl | H |
| 39 | H | NH$_2$ | H | Me | phenyl | H |
| 40 | H | NH$_2$ | H | Me | isobutyl-NH- | 3-chlorophenyl | H |
| 41 | H | NH$_2$ | H | Me | isobutyl-NH- | H |

-continued

| # | R6 | R2 | L1 | L2 | R6' | R2' |
|---|----|----|----|----|-----|-----|
| 42 | H | NH$_2$ | H | Me | 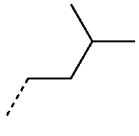 | H |
| 43 | H | 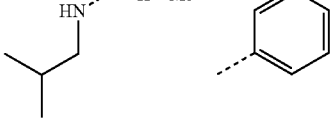 | H | Me |  | H |
| 44 | H | NH$_2$ | Me | H | 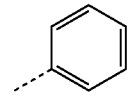 | H |

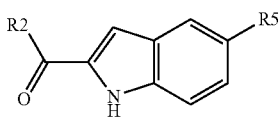

wherein

| # | R2 | R5 |
|---|----|----|
| 1a |  | Cl |
| 1b |  | H |
| 45 | 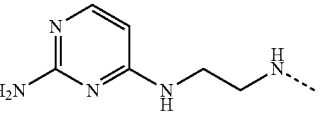 | H |
| 46 | 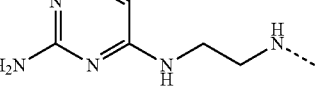 | Cl |
| 47 | 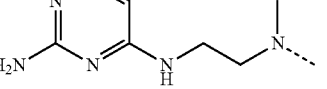 | Cl |
| 48 | 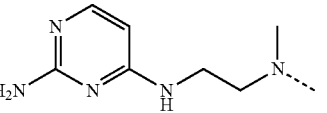 | H |

In one embodiment of the invention, the H4 antagonist is 4-N-[2-[(2-Aminopyrimidin-4-yl)amino]ethyl]pyrimidine-2,4-diamine.

In one embodiment of the invention, the H4 antagonist is 4-N-[2-[(2-Aminopyrimidin-4-yl)amino]ethyl]-6-N-(2-methylpropyl)pyrimidine-2,4,6-triamine.

In one embodiment of the invention, the H4 antagonist is 4-N-[2-[(2-Aminopyrimidin-4-yl)amino]ethyl]-6-(3-methylbutyl) pyrimidine-2,4-diamine.

In one embodiment of the invention, the H4 antagonist is 4-N-[2-[(2-Amino-6-chloropryrimidin-4-yl)amino]ethyl]-6-phenylpyrimidine-2,4-diamine.

In one embodiment of the invention, the H4 antagonist is 4-N-[2-[(2-Aminopyrimidin-4-yl)amino]ethyl]-2-N-(2-methylpropyl)-6-phenylpyrimidine-2,4-diamine.

In one embodiment of the invention, the H4 antagonist is 4-N-[2-[[6-(2-Methylpropylamino)pyrimidin-4-yl]amino]-ethyl]-6-phenylpyrimidine-2,4-diamine.

In one embodiment of the invention, the H4 antagonist is 4-N-[2-[(2-Aminopyrimidin-4-yl)amino]ethyl]-4-N-methyl-6-N-(2-methylpropyl)pyrimidine-2,4,6-triamine.

In one embodiment of the invention, the H4 antagonist is 4-N-[2-[(2-Aminopyrimidin-4-yl)amino]ethyl]-6-phenylpyrimidine-2,4-diamine.

In one embodiment of the invention, the H4 antagonist is 4-N-[2-[(2-Aminopyrimidin-4-yl)amino]ethyl]-1H-indole-2-carboxamide.

The present invention relates to dual H1-H4 and/or H3-H4 receptor antagonists for treating or for use in treating tinnitus.

In a particular embodiment, the Histamine H4 receptor antagonist is the inverse agonist ST-1012 as described in Werner at al. 2010 ChemBioChem 11:1850-1855 and that comprises formula:

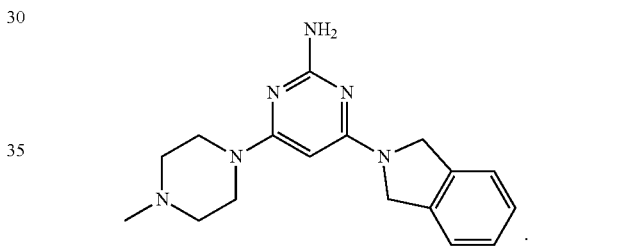

In one embodiment of the invention, the dual antagonists are as described in WO2004/066960 and Jablonowski J A et al. (2003) J Med Chem. September 11; 46(19):3957-600, compound 6, 10e, 10l from and that comprise the following formula:

compound 6

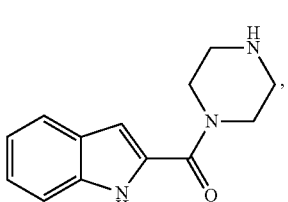

compound 10e

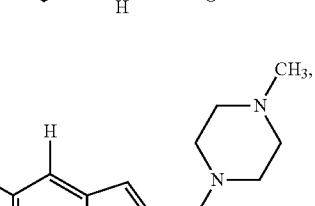

compound 101
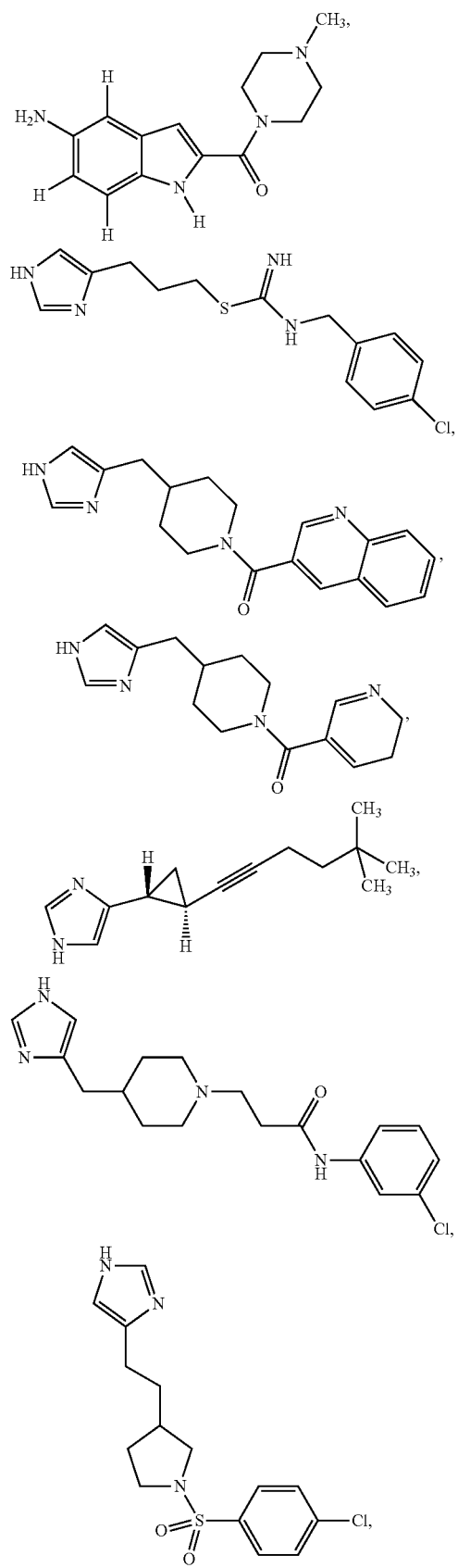
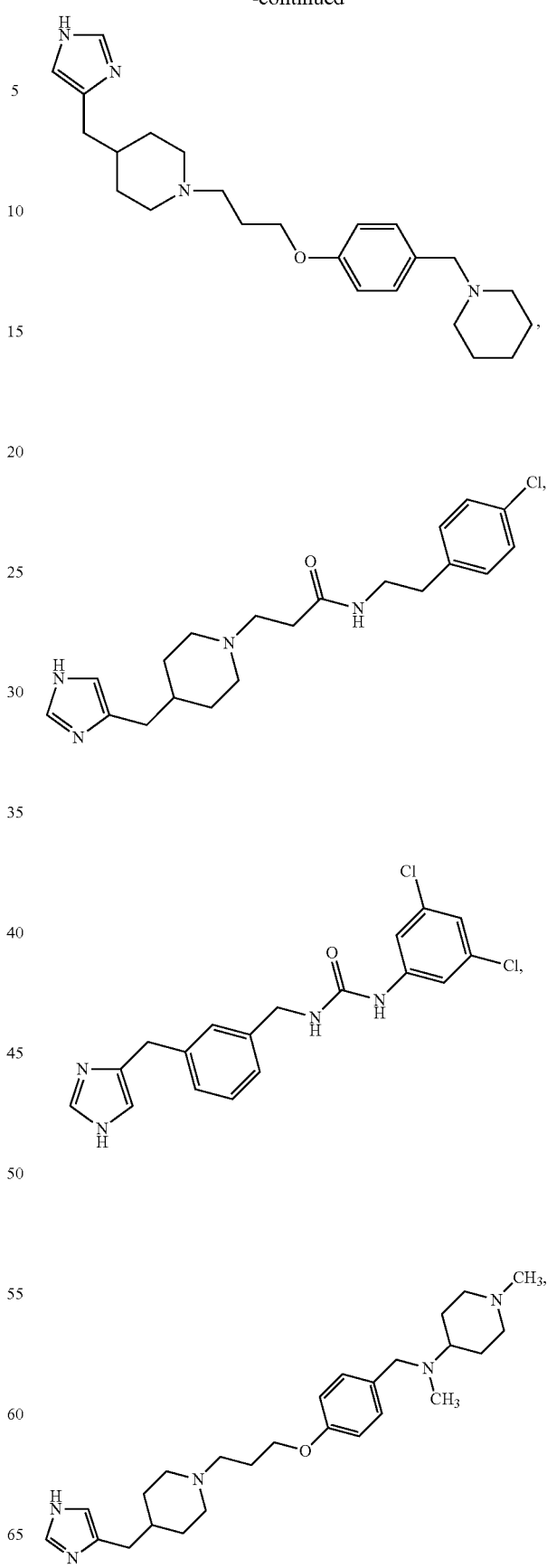

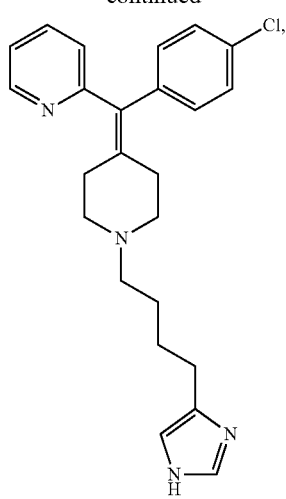

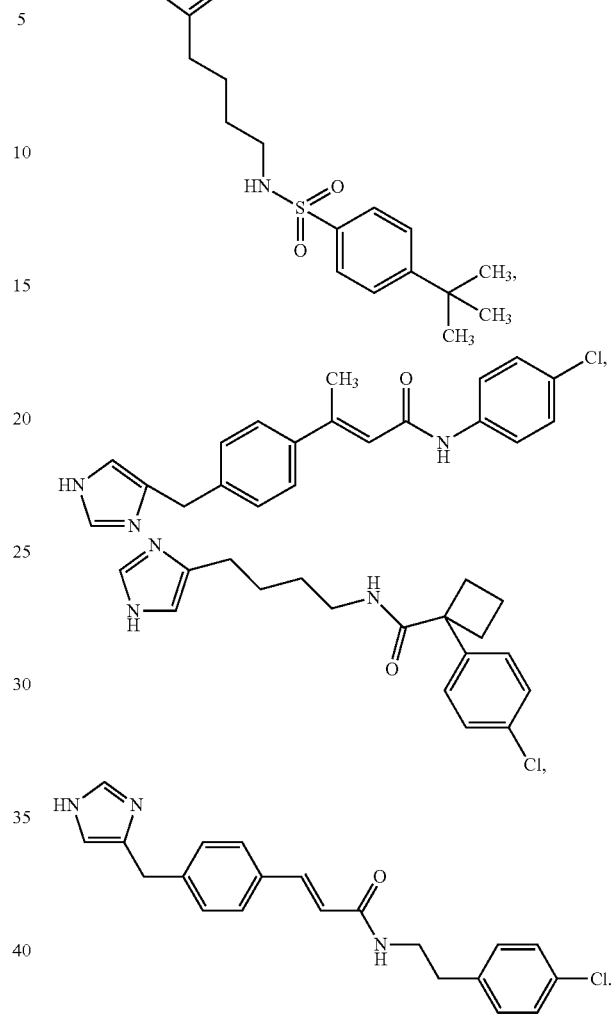

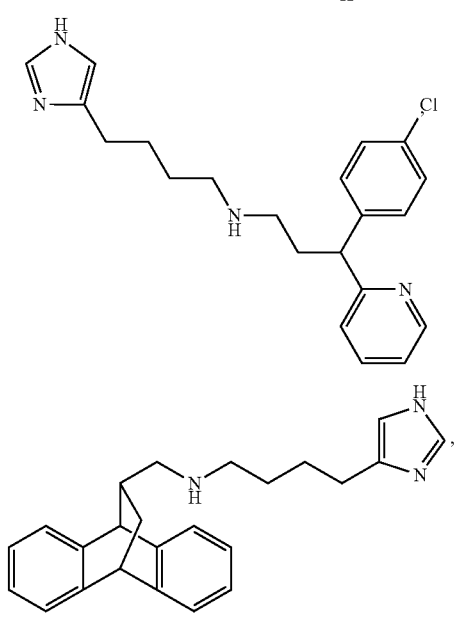

In one embodiment of the invention, the dual antagonists are as described in Wijtmans et al. 2011 J Med Chem 54:1693-1703 and are: 1-(3-(1H-Imidazol-4-yl)propyl)-4-(cyclohexylmethyl)-1H-1,2,3-triazole; 1-(3-(1H-Imidazol-4-yl)propyl)-4-(cyclopentylmethyl)-1H-1,2,3-triazole.

Examples of H1-H4 dual receptor antagonists include but are not limited to: doxepin hydrochloride and astemizole.

In one embodiment of the invention, the dual antagonists are as described in WO 02/56871 that include: thioperamide maleate, clobenpropit dihydrobromide and iodophenpropit.

Examples of H3-H4 dual receptor antagonists include but are not limited to: N-Alkenyl and cycloalkyl carbamates, Imetit dihydrobromide, Immepip dihydrobromide, Immethridine dihydrobromide, thioperamide maleate, 3-(1H-imidazol-4-yl)propyl(cyclohexylmethyl)carbamate or 4-(3-(3-phenylpropylthio)propyl)-1H-imidazole.

In another embodiment the selective Histamine H4 receptor antagonist may consist in an antibody (the term including antibody fragment) that can block Histamine H4 receptor activation.

In particular, the selective Histamine H4 receptor antagonist may consist in an antibody directed against the Histamine H4 receptor or a ligand of the Histamine H4 receptor, in such a way that said antibody impairs the binding of a H4 ligand to said receptor.

Antibodies directed against the Histamine H4 receptor can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against Histamine H4 receptor or ligands of Histamine H4 receptors can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see, e.g., U.S. Pat. No. 4,946,778) can be adapted to produce anti-H4, or anti-H4 ligands single chain antibodies. Histamine H4 receptor antagonists useful in practicing the present invention also include anti-H4, or anti-H4 ligands antibody fragments including but not limited to F(ab')$_2$ fragments, which can be generated by pepsin digestion of an intact antibody molecule, and Fab fragments, which can be generated by reducing the disulfide bridges of the F(ab')$_2$ fragments. Alternatively, Fab and/or scFv expression libraries can be constructed to allow rapid identification of fragments having the desired specificity to Histamine H4 receptor.

Humanized anti-Histamine H4 receptor or anti-H4 ligands antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

Then after raising antibodies directed against the Histamine H4 receptor as above described, the skilled man in the art can easily select those blocking Histamine H4 receptor activation.

In another embodiment the selective Histamine H4 receptor antagonist is an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

Then after raising aptamers directed against the Histamine H4 receptor as above described, the skilled man in the art can easily select those blocking Histamine H4 receptor activation.

Another aspect of the invention relates to the use of an inhibitor of Histamine H4 receptor gene expression.

Histamine receptor (H1, H2, H3 or H4) sequences showing low sequence identity, the inhibitors of Histamine H4 receptor gene expression which may be used according to the invention advantageously provides selective inhibition of Histamine H4 receptor gene expression, by comparison with the other histamine receptors (H1, H2, or H3) expression.

Inhibitors of Histamine H4 receptor gene expression for use in the present invention may be based on anti-sense oligonucleotide constructs. Anti-sense oligonucleotides, including anti-sense RNA molecules and anti-sense DNA molecules, would act to directly block the translation of Histamine H4 receptor mRNA by binding thereto and thus preventing protein translation or increasing mRNA degradation, thus decreasing the level of Histamine H4 receptors, and thus activity, in a cell. For example, antisense oligonucleotides of at least about 15 bases and complementary to unique regions of the mRNA transcript sequence encoding Histamine H4 receptor can be synthesized, e.g., by conventional phosphodiester techniques and administered by e.g., intravenous injection or infusion. Methods for using anti-sense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of Histamine H4 receptor gene expression for use in the present invention. Histamine H4 receptor gene expression can be reduced by contacting a subject or cell with a small double stranded RNA (dsRNA), or a vector or construct causing the production of a small double stranded RNA, such that Histamine H4 receptor gene expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of Histamine H4 receptor gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of Histamine H4 receptor mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of Histamine H4 receptor gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing Histamine H4 receptor. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

Another object of the invention relates to a method for treating tinnitus comprising administering a subject in need thereof with a selective Histamine H4 receptor antagonist or an inhibitor of Histamine H4 receptor gene expression.

The compound of the invention can be administered prior to, during or after tinnitus has been induced.

Selective Histamine H4 receptor antagonists or inhibitors of Histamine H4 receptor gene expression may be administered in the form of a pharmaceutical composition, as defined below.

Preferably, said antagonists or inhibitors are administered in a therapeutically effective amount.

By a "therapeutically effective amount" is meant a sufficient amount of the selective Histamine H4 receptor antagonist or inhibitor of Histamine H4 receptor gene expression to treat tinnitus at a reasonable benefit/risk ratio applicable to any medical treatment.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The selective Histamine H4 receptor antagonists or inhibitors of Histamine H4 receptor gene expression may be combined with pharmaceutically acceptable excipients, and optionally sustained-release matrices, such as biodegradable polymers, to form therapeutic compositions.

In the pharmaceutical compositions of the present invention, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The selective Histamine H4 receptor antagonists or inhibitors of Histamine H4 receptor gene expression of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with one or several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The selective Histamine H4 receptor antagonists or inhibitors of Histamine H4 receptor gene expression of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

In a particular embodiment, the selective Histamine H4 receptor antagonists or inhibitors of Histamine H4 receptor gene expression are administered directly in the inner ear. This administration route may be preferred for introducing a direct and long term effect on the vestibule. Said administration can be accomplished by various delivery techniques, including the use of devices or drug carriers to transport and/or deliver the H4 receptor antagonists or inhibitors of Histamine H4 receptor gene expression to the membranes of the round or oval window, where it diffuses into the inner ear or is actively infused. Examples include, but are not limited to, otowicks, round window catheters, various types of gels, foams, fibrins or other drug carriers, which are placed in the round window niche or on the oval window, and loaded with the compound of the invention for sustained release. It also includes devices that are inserted into the cochlear duct or any other part of the cochlea. The compound of the invention may also be administered to the inner ear by transtympanic or intratympanic injection.

EXAMPLES

Example 1: Expression of H4R mRNA in Postnatal (P) 9-11 Rat Cochlea

H4R mRNA Expression-RT-PCR

Cochlea of postnatal (P) 9-12 Wistar rats were dissected from the temporal bone and were flash frozen in liquid nitrogen immediately after dissection from adult rats. In a single experiment, at least 4-6 cochlea and 1 spleen (used a tissue (positive) control to test H4R mRNA expression) were used to extract the total RNA using a standard protocol with TRIzol (RiboPure, Ambion) and chloroform. First-strand cDNA synthesis (reverse transcription, RT) was performed with 0.5-1 µg of total RNA DNAse treated and Oligo(dT) primers (Kit Quantitect reverse transcription, Qiagen). Reaction was done at 42° C. for 30 min. followed by 95° C. for 3 min. PCR was performed with 1-2 µl of RT reactions. Amplification was for 30 cycles for spleen and cochlear ganglia with 30 s at 95° C., 30 sec at the primer-specific annealing temperature (58-60° C.) and 1 min at 72° C. A final extension was done at 72° C. for 7 min. For $H_4R$, RT was preferentially done using sequence specific primer and PCR products (1 µl) were resolved on 2% agarose gels containing ethidium bromide (10%). Results were obtained in 3 different (independents) experiments and PCR products were systematically sequenced to attest the nature of the amplified product as from H4R sequence. To avoid genomic cDNA contaminations a reverse transcription without the reverse transcriptase enzyme was performed. Additionally, primer sets were designed across intron-exon boundaries as determined from H4R rat sequence (SEQ ID NO: 1) and GAPDH rat sequence (SEQ ID NO: 6) using the free NCBI/Primer-Blast software (FIG. 1) and nested PCR were performed using the first PCR products. GAPDH primers (SEQ ID NO: 7 and SEQ ID NO: 8) were used as a positive control and for $H_4R$; primers (SEQ ID NO: 2 to SEQ ID NO: 5) were systematically tested for quality on spleen tissue.

Figure 1:
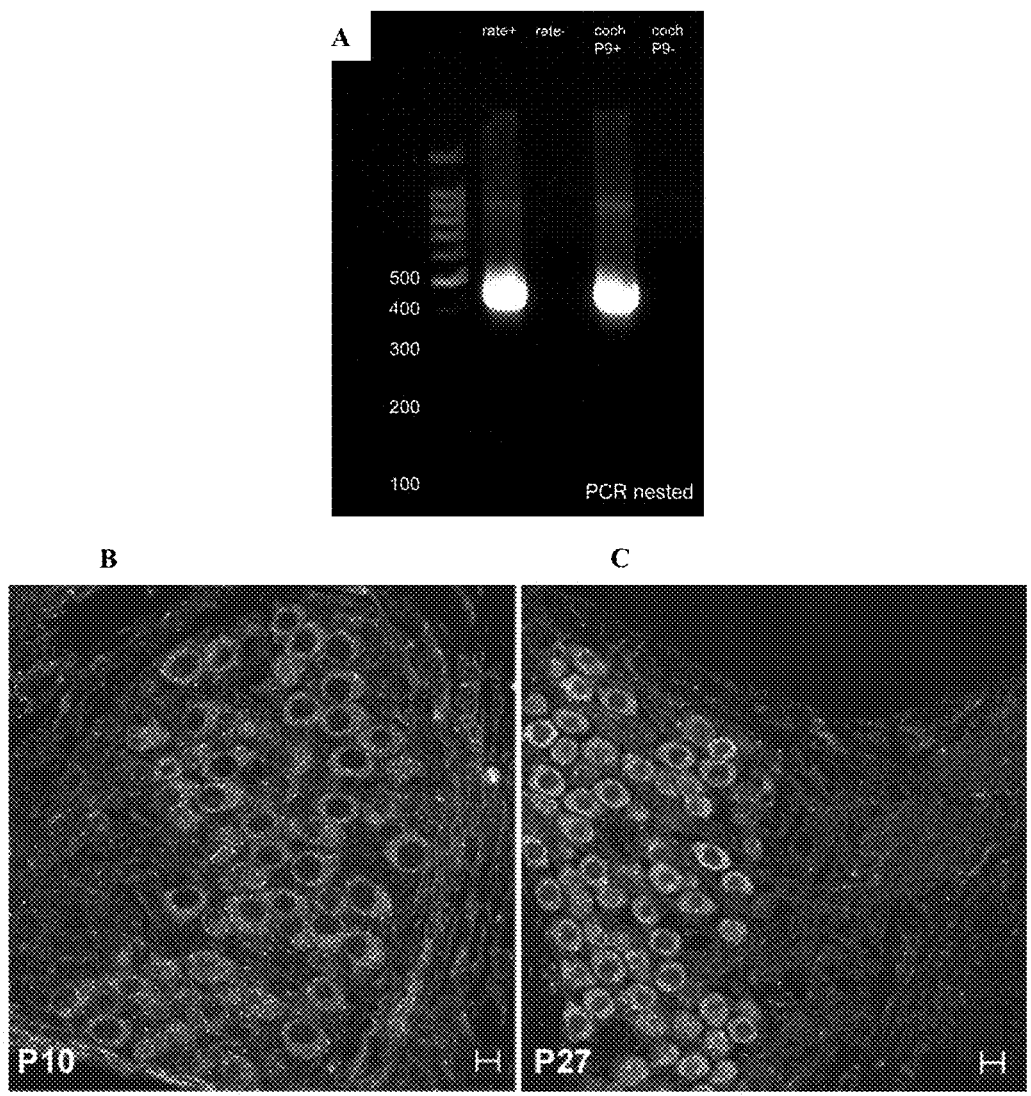
FIG. 1 represents the localization of H4R in the cochlea. Panel (A) shows expression of H4R mRNA in P9 cochlea. Panel (B) shows the localization of H4R protein in P10 rat spiral ganglion neurons (SGNs). Panel (C) shows localization of H4R protein in P27 rat spiral ganglion neurons (SGNs).

For both the cochlea and the tissue control (spleen) samples, the size of the bands observed in gels corresponded to the predicted sizes of the amplified products: 477 bp for H₄R and 502 bp for GAPDH (not shown) used as a positive control for the PCR reaction (FIG. 1A). As expected, no bands were seen in our negative controls (RT−) confirming the purity of our RNA samples. Since H4R expression was low with a single PCR experiments a second amplification of the first PCR product using nested primers (refereed as H4R-F2 and H4R-R2 in FIG. 1) was systematically necessary to increase chances to reveal the expression of H₄R. In this case, H4R mRNA expression has been tested and found in 3 independent experiments. Direct sequencing performed on all PCR products confirmed the nature of the amplified product as H4R mRNA.

H4R Localization-Immunofluorescence

To further confirm the presence of H4R in spiral ganglion neurons at all ages, we checked the localization of the receptor at the protein level using a (polyclonal) anti-H4R antibody. These tests have been conducted using postnatal "mature" (P) 10, (P) 27 and adult rat cochlea (i.e. here mature cochlea is in the sense of post onset of hearing cochlea). Postnatal (P)10-27 and adult (12 weeks) Wistar rats were deeply anesthetized with Pentobarbital (0.4%), then perfused transcardially with heparin PBS (0.01 M) followed by a fixative solution (4% paraformaldehyde, 1% picric acid, with 5% sucrose). Temporal bones were postfixed in the same solution before the cochlea was dissected in PBS. Vestibular endorgans were embedded in 4% agarose, and 40 μm thick sections were cut with a vibratome (HM650V, Microm). The free-floating sections were first permeabilized with 4% Triton X-100, non-specific binding was prevented by a pre-incubation step in a blocking solution of 0.5% fish gelatin, 0.5% Triton X-100 and 1% BSA. Samples were then incubated with primary antibodies: polyclonal rat anti-H4R (0.5 ug/ml; Gift from P. Chazot Laboratory) diluted in the blocking solution. For control experiments, the investigated primary antibody was omitted, while the following procedures were unchanged. Specific labeling was revealed with Alexa 594-fluorescent secondary antibodies (1:700) in the blocking solution combined to neurofilament staining with Alexa 488-conjugated phalloidin (Fisher Scientific). Samples were observed with a laser scanning confocal microscope (LSM 5 LIVE DUO, Zeiss). Final image processing was done with Adobe Photoshop software (San Jose, Calif.). Control reactions were observed and processed with the parameters used for the stained sections. All immunofluorescence experiments have been performed at least 3 times (3 independent experiments).

H4R have been localized in SGNs (double labeled with anti-Neurofilament) in all turns of the cochlea (apical, middle and basal) with an increasing gradient of expression during the development: P10 rat cochlear neurons expressed H4R in low density (correlating with our RT-PCR data at this age) (FIG. 1B) while P27 cochlea showed a higher expression of H4R in these neurons (FIG. 1C). H4R were expressed as well in SGNs from adult cochlea (data not shown). Interestingly, the co-labeling with the anti-neurofilament antibody revealed that H4R was localized in a large majority of SGNs, although a small population did not express the receptor. At the cellular level, H4R were found to be localized preferentially in the membranous and sub membranous regions.

Example 2: H4R Antagonists are Modulators of Spiral Ganglion Excitability

Cell Culture

The head of 5-8 days old Wistar rats (CERJ, Le Genest, Berthevin, France) was hemi-sectioned aseptically and the cochlea dissected from the temporal bone. In L15 (Leibovitz) medium (Gibco) medium, the cochlear bone was gently removed using fine forceps to isolate the sensorineural tissue. The spiral ganglion was separated from the organ of Corti just before the habenula perforata, and enzymatically (collagenase 0.75 mg·mL⁻¹, dispase 1 mg·mL⁻¹ and DNAse 0.75 mg·mL⁻¹) dissociated for 15 min at 25° C. After washing thoroughly with a Tyrode's solution (Sigma), a transfer pipette was used to gently dissociate the ganglion neurons in culture medium (DMEM/F-12 medium 1:1, 2% N2 nutrient, 28 mM Glc, 1.5 mM Gln, 15 mM HEPES, 2 μM AraC, 10 ng mL-1 BDNF and 1% penicillin/streptomycin). The spiral ganglion neurons were plated onto culture dishes previously coated with 10 ug·mL-1 laminin (Sigma). These low density cultures were maintained at 37° C. in 5% CO2 for 3 to 5 days prior whole cell patch-clamp experiments.

Semi-Intact Cochlea Preparation

For this preparation postnatal day (P) 10-14 Wistar rats were used. First steps of the protocol were similar to the cell culture one until the cochlea was freed from the cochlear bone. Cochlear turns (apical and middle) were dissected and isolated in sterile-filtered L-15 (Leibovitz) Medium. Explants were plated upside down (spiral ganglion neurons on top) on 10 μl of growth factor-reduced Matrigel (BD biosciences) and laminin (10 μg/ml)-coated glass coverslips. These preparations were first incubated for 30 min at 37° C. in a 95%/5% O2/CO2 atmosphere and then cultured for 2 to 5 days in vitro in (50%) F12/(50%) DMEM (Invitrogen) supplemented with (2%) N2 nutrient (Fisher Scientific). The medium was renewed once, 3 days after plating the explants.

In Vitro. Electrophysiology

Efficacy of H4R antagonist has been tested using two patch clamp technics: whole-cell current-clamp recordings with dissociated spiral ganglion neurons (SGNs) and loose-patch recordings for SGNs in semi-intact cochlea preparations. For these experiments postnatal day (P) 10-14 Wistar rats were used at DIV2-5.

All experiments were performed using an Axopatch 200B amplifier. Traces were low-pass filtered at 10-20 kHz, and digitized at 100 kHz with a Digidata 1440A board. Data were stored with PClamp10.2 software (Axon Instruments; Molecular Devices Corp., USA) and were analyzed off-line using Clampfit 10.2 (Molecular Devices) and Origin 8 (OriginLab) softwares.

The recording solution contained (in mM): NaCl 135, HEPES 10, glucose 10, MgCl₂ 1, KCl 5, and CaCl₂ 2.5, (pH 7.35). For whole-cell patch clamp recordings, recording glass pipettes (4-6 MΩ) were coated with Wax to reduce pipette capacitance and were filled with (in mM): KCl 135, HEPES 10, glucose 10, NaCl 5, EGTA 5, Mg-ATP 3, GTP-Na 1, pH 7.35. For these solutions a minor 3.7 mV liquid junction potential could be measured but membrane voltages were not corrected for it. The osmolarity of all solutions was adjusted to 300 mOsm/L. The control and test solutions were applied using a multiple capillary perfusion system (flow rate~500 μl/min). After each application of the tested drug, the cells were washed with control buffer.

Recordings were performed at room temperature (RT; 22-25° C.). In dissociated neurons, a 150-200 pA DC square current (1 s duration) was applied every 6 s in order to elicit trains of action potentials. The pharmacological tests were conducted only when recordings presented the following criteria: series resistance (<10 MΩ on average) no more than 3 times the pipette resistance, stable resting membrane potential (R.M.P) negative to −40 mV, overshooting action potentials (magnitude >60 mV for the first action potential), stable firing for up to a minute in control condition.

Electrodes for loose-patch SGN recordings had a tip resistance of 1.0-1.5 MΩ and filled with the recording solution. In these semi-intact cochlea preparations, spontaneous discharges of action potential were directly recorded. For each test, the compound was applied for at least 2 minutes. To verify the response reversibility, neurons were washed with control medium after each drug test. In vitro results were expressed as means±S.E.M.

To assess the efficacy of H4R antagonists (JNJ7777120 and JNJ10191584) to modulate SGNs hyperexcitability, we measured the percentage of inhibition of action potential (A.P) firing of the two compounds. Two concentrations have been tested: 100 μM and 100 nM.

Figure 2:
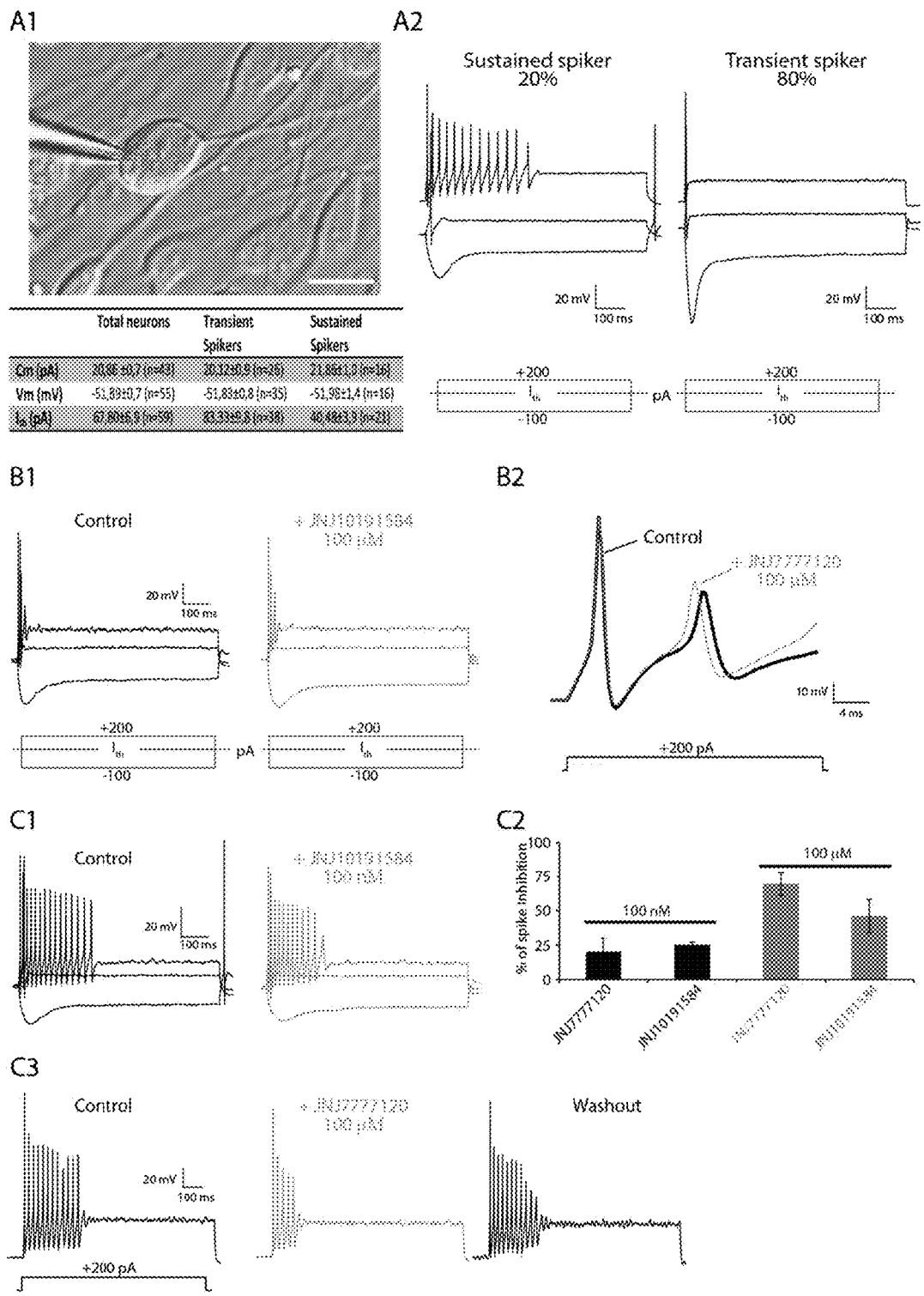
FIG. 2 represents H4R antagonist modulation of spiral ganglion neurons excitability in vitro. Panel (A1) shows an example of cultured SGNs for 3 DIV. Typically cultures contained neurons (10-20 µm diameter) that were either monopolar, bipolar or pseudomonopolar. In most cultures, these neurons were still covered with myelin. In Panel (A2) distinctive traces of transient and sustained neurons highlight the (fast and slowly adapting) A.P firing pattern in these neurons. Panel (B1) shows an example of step-induced action potentials in a control condition (black) and in presence of 1000 µM JNJ10191584 in a transient neuron (gray). Panel (B2) shows a distinctive trace of the first action potential in a transient neuron in a control condition (black), in presence of 100 µM JNJ7777120 (gray). Neither the frequency nor the amplitude of spikes was affected by H4R antagonists as summarized in the bar plots (panel C2). Panel (C1) shows an example of step-induced action potentials in control and in presence of JNJ10191584 100 nM in a sustained neuron. Panel (C2) summarize the percentage of inhibition obtained in sustained neurons treated with the H4R antagonists a 100 nM or 100 µM. Panel (C3) shows an example of step-induced action potentials in control and in presence of JNJ7777120 100 µM in a sustained neuron.

Typically, in dissociated SGNs, (FIG. $2A_1$) small depolarizing current steps (0.1 nA-0.4 nA) evoked two types of action potential discharge: transient (no more than 1-2 spikes-rapidly adapting neurons) and sustained firing (number of spikes increasing linearly above threshold-slowly adapting neurons) (FIG. $2A_2$). Transient spikers SGNs represented the majority of neurons in our cell cultures (80% versus 20% of sustained spikers neurons). The percentage of both type of neurons and their membrane properties (capacitance, input resistance, R.M.P, spike threshold) are comparable to previous studies (see summary in table-FIG. 2). Tests of inhibitory action of JNJ10191584 and JNJ777120 were performed on both sustained and transient SGNs (FIG. 2B, 2C).

For transient spikers SGNs, neither JNJ10191584 nor JNJ7777120 had an effect on the only spike at all concentration tested. Frequency of spikes (1-3 spikes) and the amplitude of the first spike were unaffected by the two specific antagonists (85.6±4.1 mV (n=4) versus 83.7±5.2 mV for respectively the control and 100 μM JNJ10191584 and 77±5.6 mV (n=7) versus 73.3±6.1 mV for respectively the control and 100 μM JNJ7777120) (FIG. $2B_1$-$B_2$).

On the contrary, JNJ7777120 and JNJ10191584 reduced the mean evoked number of step-evoked action potentials in a dose-dependent manner (FIG. 2C). At 100 nM concentration, frequency of A.P firing was slightly inhibited by 25.2±2.0% (n=3) and 21.6±1.7% (n=2) respectively for JNJ10191584 and JNJ7777120 (FIG. $2C_1$-$C_2$). Resting membrane potential of SGNs was not affected by H4R antagonists (in average −0.13±0.4 mV difference with JNJ10191584 and 0.55±0.2 mV (n=2) in average in presence of JNJ7777120 versus control). Likewise, the action potential threshold did not significantly varied in presence of H4R antagonists (data not shown). At a concentration of 100 μM, both JNJ10191584 and JNJ7777120 had a larger inhibitory effect on the frequency of A.P. JNJ10191584 and JNJ7777120 (100 μM) inhibited the frequency by respectively 46.2±12% (n=3) and by 69.05±8% (n=3) (FIG. $2C_2$-$C_3$). After a period of washout, the frequency of action potential increased up to 70% of the frequency measured in the control condition. Additionally, in presence of high concentration of H4R antagonist JNJ10191584, the resting membrane potential was not affected (1.5±1 mV increase versus control). Nonetheless, although the number of A.P decreased in presence of either H4R antagonists, the first spike remained unaffected; this is coherent with a modulatory action of the compounds on SGNs excitability rather than a pure blocking effect.

Figure 3:
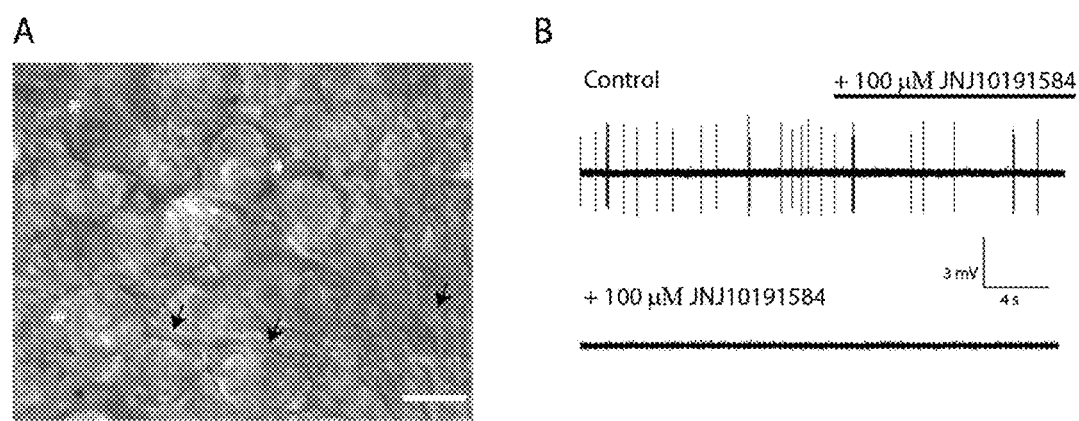
FIG. 3 represents H4R antagonist modulation of synaptically-driven spontaneous A.P firing in a semi-intact cochlear preparation. Panel (A) shows an example of a cultured semi-intact cochlea preparation at the level of the SGNs. Stars highlight the presence of myelin around cell bodies and black arrows show intact SGNs fibers going toward the sensory hair cells of the organ of Corti. Panel (B) show a distinctive recording from a SGN with spontaneous (synaptically-driven) action potentials in control condition and in presence of JNJ10191584 (100 µM).

Using the (ex vivo) semi-intact cochlear preparations, we tested the efficacy of JNJ10191584 to decrease spontaneous (synaptically driven) action potential discharge recorded from SGNs with a loose-patch configuration. In our conditions, few SGN have shown spontaneous activity (9 out of 41 SGNs recorded). Recordings from the SGNs cytoplasmic membrane in presence of a large myelin sheath enwrapping not only their neurites but the cell bodies as well (FIG. 3A) limited the number of successful recordings. Frequency of spontaneous A.P was ranging from 0.1 to a maximum of 3 Hz (in average 1.08±0.3 Hz, n=9). In two experiments the low frequency spontaneous action potential discharge was fully abolished within two minutes following the beginning of a bath application of 100 μM of JNJ10191584 (FIG. 3B).

To check whether H4R antagonists are able to modulate SGNs excitability in a "pathological" condition (similar to hyperexcited SGNs in tinnitus models), we are testing the efficacy of these compounds on SGNs with increased A.P discharge. Such SGNs hyperexcitability can be induced for instance by 3-5 mM sodium salicylate, known to strongly enhance synaptically-induced A.P in rodent. The positive outcome of this experiment reinforce the modulatory efficacy of H4R antagonists in sustained spikers SGNs or any type of SGNs that would have an increased A.P discharge activity.

Example 3: Efficacy of H4R Antagonists to Decrease Behavioral Model of Tinnitus

The aim of these in vivo tests is to measure the efficacy of H4R antagonists to decrease (transient and permanent) tinnitus symptoms induced either by sodium salicylate or by high level noise exposure. Evaluation of efficacy is performed in adult rats using the tinnitus test developed by Turner et al. 2006: the Gap-Prepulse Inhibition of Acoustic Startle (GPIAS) behavioral model. This model uses a gap in a constant acoustic background as a pre-stimulus that reduces the acoustic startle reflex amplitude. Rats perceiving tinnitus in a specific frequency have decreased detection of gap embedded in bands similar to the tinnitus frequency. Reduction of the gating efficiency of the gap produces a larger acoustic startle (reduced GPIAS).

The level of GPIAS is measured in baseline condition in a cohort of 6 to 8 adult rats. Tinnitus is induced by an i.p administration of sodium salicylate (250 mg/kg) and GPIAS is measured at T1h post-induction to measure the reduction in GPIAS (attesting presence of tinnitus). Rats are treated with H4R antagonists (single i.p. administration) or with the vehicle the same day and GPIAS is measured at different time points according to the PK profile of the compounds Alternatively, tinnitus is induced by a unilateral exposure to a 12 kHz narrow band noise presented at 120-126 dB SPL (the contralateral ear is protected with an ear plug) for 2h. Two types of noise are used for this form of tinnitus induction: 120 dB noise to induce a transient tinnitus (lasting up to 2 days) and 126 dB to induce a permanent tinnitus (lasting ≥10 days). For these "noise exposure" experiments, all rats are anesthetized with Isoflurane gas and placed on a temperature controlled heating pad. A 120-126 dB exposure is used to induce tinnitus and GPIAS is measured 24 h after the exposure to assess the reduction in GPIAS (attesting presence of noise induced transient tinnitus); and up to 10 days to attest the presence of a (noise-induced) permanent tinnitus. Animals with transient tinnitus are treated with H4R antagonists (single i.p. administration) T24h post tinnitus induction and changes in GPIAS are measured at different time points according to the PK profile of the H4R antagonists. Similarly animals with permanent tinnitus (≥10 days) are treated with H4R antagonists (single i.p. administration) at day 11 after tinnitus induction and changes in GPIAS are measured at different time points.

Increase in GPIAS values in rats treated with H4R antagonists (JNJ7777120 and JNJ10191584) compared to the pre-treatment condition (salicylate alone) or sham treatment (vehicle alone) will show an improvement of tinnitus in these models.

Material
Drugs/Chemicals:
The 1-[(5-Chloro-1H-benzimidazol-2-yl)carbonyl]-4-methyl piperazine (JNJ 10191584) and the 1-[(5-chloro-1H-indol-2-yl)carbonyl]-4-methyl piperazine maleate (JNJ 7777120) was purchase from Axon Medchem BV (Groningen, The Netherlands). Stock solutions were prepared at 60 mM in 100% dimethyl sulfoxide as recommended by the suppliers. Drugs were then diluted the day of experiment in the recording solution accordingly to get 100 nM and 100 µM concentrations for both compounds.

The invention claimed is:

1. A method for treating tinnitus in a subject, comprising administering to the subject an inhibitor of Histamine type 4 receptor (H4R), wherein said inhibitor of Histamine type 4 receptor (H4R) has a Ki(H3)/Ki(H4) ratio above 10, and wherein said inhibitor of Histamine type 4 receptor (H4R) is selected from the group consisting of 2-aminopyrimidine derivatives, pyrimidine derivatives, quinazoline derivatives, quinazoline sulfonamide compounds, bicyclic heteroaryl-substituted imidazole compounds, thieno-pyrimidine compounds, furo-pyrimidine compounds and mequitazine compounds.

2. The method according to claim 1, wherein said inhibitor inhibits H4R protein expression and/or activity and/or gene expression.

3. The method according to claim 1, wherein said inhibitor is a selective inhibitor of H4R.

4. The method according to claim 1, wherein said inhibitor is a dual antagonist for H1R and H4R or H3R and H4R.

5. The method according to claim 1, wherein said inhibitor is 1-[(5-chloro-1H-indol-2-yl)carbonyl]-4-methylpiperazine or 4-((3R)-3-Aminopyrrolidin-1-yl)-6,7-dihydro-5H-benzo[6,7]cyclohepta[1,2-d]pyrimidin-2-ylamine or cis-4-(Piperazin-1-yl)-5,6,7a,8,9,10,11,11a-octahydrobenzofuro[2,3-h]quinazolin-2-amine or 7-(furan-2-yl)-4-(piperazin-1-yl)quinazolin-2-amine or 1-(7-(2-amino-6-(4-methylpiperazin-1-yl) pyrimidin-4-yl)-3,4-dihdroisoquinolin-2(1H)-yl)-2-cyclopentylethanone or 1-[(5-Chloro-1H-benzimidazol-2-yl) carbonyl]-4-methylpiperazine maleate or PF-3893787 or PF-3893787-18 or JNJ39758979 or UR-63325 or 2-isobutyl-6-(3-(methylamino)azetidin-1-yl)pyrimidin-4-amine, or N4-(Cyclopropylmethyl)-6-[(3R)-3-(methylamino)pyrrolidin-1-yl]pyrimidine-2,4-diamine or (R)-4-(3-Amino-pyrrolidin-1-yl)-6-isopropyl-pyrimidin-2-ylamine.

* * * * *

SEQUENCE LISTING

<160> NUMBER OF SEQ ID NOS: 8

<210> SEQ ID NO 1
<211> LENGTH: 1593
<212> TYPE: DNA
<213> ORGANISM: Rattus norvegicus
<220> FEATURE:
<221> NAME/KEY: source
<222> LOCATION: 1..1593
<223> OTHER INFORMATION: /mol_type="unassigned DNA"
      /note="Histamine 4 Receptor sequence"
      /organism="Rattus norvegicus"

<400> SEQUENCE: 1

```
agtggaactt ctgtagtggc ccattattta atgtgatgtc ggagtctaac ggcactgacg      60
tcttgccact gactgctcaa gtcccttgg cattttaat gtccctgctt gcttttgcta      120
taacgatagg caatgctgtg gtcattttag cctttgtagc agacagaaac cttagacatc      180
gaagtaatta ttttttcctt aatttggcta tttctgactt cttcgtgggt gtcatctcca      240
ttcctctgta catccctcac acgctgttta actggaattt tggaagtgga atctgcatgt      300
tttggctcat tactgactat cttttgtgca cagcatccgt ctacagtatt gtcctcatta      360
gctacgatcg ataccagtca gtttcaaacg ctgtgcgtta tagagcacag cacactggca      420
tcctgaaaat tgttgctcaa atggtggctg tttggatact ggctttcttg gtcaatggcc      480
caatgattct ggcttcggat tcttggaaga acagcaccaa cacagaggag tgcgagcctg      540
gctttgttac tgagtggtac atcctcgcca ttacagcatt cttggaattc ctgctccctg      600
tctccttggt ggtctatttc agtgtacaga tttactggag cctgtggaag cgtgggagtc      660
tcagtaggtg ccctagccac gctggattca tcgctacctc ttccaggggc actggacact      720
cacgcagaac tgggttggct tgtaggacaa gtcttcctgg attaaaggaa ccagccgcat      780
cccttcattc agaaagtcca cgaggaaaga gcagtctcct ggtgtcctta aggactcaca      840
tgagcggtag tatcatcgcc ttcaaagtgg gttccttctg ccgatcagaa agcccagtgc      900
ttcaccagag agagcacgtg gagcttctca gaggcaggaa gctagccagg tcgctagctg      960
tcctcctgag tgcttttgcc atttgctggg ctccgtattg cctgttcaca attgttcttt      1020
caacttatcg cagaggggag cgccccaaat cgatttggta cagcatagcc ttttggctac      1080
agtggttcaa ttcacttatt aatcccttc tataccctt gtgccacaga cgtttccaga      1140
aggctttctg gaagatactc tgtgtgacaa agcaaccagc accttcacag acccagtcag      1200
tatcttcttg aggagaagct tcatgtgtgc cagcttctgt ctctgtcccc tgaacggatc      1260
taagcttcca tcttgctctg tccactcgag caaacaatgc acaaaatgta atgttcgaca      1320
attttaataa aaaccctcca cattcaagtc agtggaacac gagccaacag cagtttaagg      1380
aacgtgacaa actgacagct gcaaaaatac taatattttc ctcagtgctc tctgtctctt      1440
```

-continued

```
ttttgataca acattgattg tgttaccccct gtcttctttc tgtctcagtg tttctccaa      1500 tagcattagt ttctttgtgt gtatatgtgt gcgtgtgtgc atgtgtacat ctatgtggtg      1560
tgtacatgta tctatgtgtg tgcatgtgta tct                                   1593

<210> SEQ ID NO 2
<211> LENGTH: 20
<212> TYPE: DNA
<213> ORGANISM: Artificial sequence
<220> FEATURE:
<221> NAME/KEY: source
<222> LOCATION: 1..20
<223> OTHER INFORMATION: /mol_type="unassigned DNA"
      /note="H4R Forward primer 1"
      /organism="Artificial sequence"

<400> SEQUENCE: 2
tgtgatgtcg gagtctaacg                                                  20

<210> SEQ ID NO 3
<211> LENGTH: 20
<212> TYPE: DNA
<213> ORGANISM: Artificial sequence
<220> FEATURE:
<221> NAME/KEY: source
<222> LOCATION: 1..20
<223> OTHER INFORMATION: /mol_type="unassigned DNA"
      /note="H4R Reverse primer 1"
      /organism="Artificial sequence"

<400> SEQUENCE: 3
cgaggatgta ccactcagta                                                  20

<210> SEQ ID NO 4
<211> LENGTH: 23
<212> TYPE: DNA
<213> ORGANISM: Artificial sequence
<220> FEATURE:
<221> NAME/KEY: source
<222> LOCATION: 1..23
<223> OTHER INFORMATION: /mol_type="unassigned DNA"
      /note="H4R Forward primer 2"
      /organism="Artificial sequence"

<400> SEQUENCE: 4
gccactgact gctcaagttc cct                                              23

<210> SEQ ID NO 5
<211> LENGTH: 22
<212> TYPE: DNA
<213> ORGANISM: Artificial sequence
<220> FEATURE:
<221> NAME/KEY: source
<222> LOCATION: 1..22
<223> OTHER INFORMATION: /mol_type="unassigned DNA"
      /note="H4R Reverse primer 2"
      /organism="Artificial sequence"

<400> SEQUENCE: 5
ccaggctcgc actcctctgt gt                                               22

<210> SEQ ID NO 6
<211> LENGTH: 1306
<212> TYPE: DNA
<213> ORGANISM: Rattus norvegicus
<220> FEATURE:
<221> NAME/KEY: source
<222> LOCATION: 1..1306
<223> OTHER INFORMATION: /mol_type="unassigned DNA"
```

/note="GAPDH sequence"
/organism="Rattus norvegicus"

<400> SEQUENCE: 6

| | | | | | |
|---|---|---|---|---|---|
| ggggctctct | gctcctccct | gttctagaga | cagccgcatc | ttcttgtgca | gtgccagcct | 60 |
| cgtctcatag | acaagatggt | gaaggtcggt | gtgaacggat | ttggccgtat | cggacgcctg | 120 |
| gttaccaggg | ctgccttctc | ttgtgacaaa | gtggacattg | ttgccatcaa | cgaccccttc | 180 |
| attgacctca | actacatggt | ctacatgttc | cagtatgact | ctacccacgg | caagttcaac | 240 |
| ggcacagtca | aggctgagaa | tgggaagctg | gtcatcaacg | gaaacccat | caccatcttc | 300 |
| caggagcgag | atcccgctaa | catcaaatgg | ggtgatgctg | gtgctgagta | tgtcgtggag | 360 |
| tctactggcg | tcttcaccac | catggagaag | gctgggctc | acctgaaggg | tggggccaaa | 420 |
| agggtcatca | tctccgcccc | ttccgctgat | gcccccatgt | ttgtgatggg | tgtgaaccac | 480 |
| gagaaatatg | acaactccct | caagattgtc | agcaatgcat | cctgcaccac | caactgctta | 540 |
| gccccctgg | ccaaggtcat | ccatgacaac | tttggcatcg | tggaagggct | catgaccaca | 600 |
| gtccatgcca | tcactgccac | tcagaagact | gtggatggcc | cctctggaaa | gctgtggcgt | 660 |
| gatggccgtg | gggcagccca | gaacatcatc | cctgcatcca | ctggtgctgc | caaggctgtg | 720 |
| ggcaaggtca | tcccagagct | gaacgggaag | ctcactggca | tggccttccg | tgttcctacc | 780 |
| cccaatgtat | ccgttgtgga | tctgacatgc | cgcctggaga | aacctgccaa | gtatgatgac | 840 |
| atcaagaagg | tggtgaagca | ggcggccgag | ggcccactaa | agggcatcct | gggctacact | 900 |
| gaggaccagg | ttgtctcctg | tgacttcaac | agcaactccc | attcttccac | ctttgatgct | 960 |
| ggggctggca | ttgctctcaa | tgacaacttt | gtgaagctca | tttcctggta | tgacaatgaa | 1020 |
| tatggctaca | gcaacagggt | ggtggacctc | atggcctaca | tggcctccaa | ggagtaagaa | 1080 |
| accctggacc | acccagccca | gcaaggatac | tgagagcaag | agagaggccc | tcagttgctg | 1140 |
| aggagtcccc | atcccaactc | agcccccaac | actgagcatc | tccctcacaa | ttccatccca | 1200 |
| gaccccataa | caacaggagg | ggcctgggga | gccctccctt | ctctcgaata | ccatcaataa | 1260 |
| agttcgctgc | accctcaaaa | aaaaaaaaaa | aaaaaaaaaa | aaaaaa | | 1306 |

<210> SEQ ID NO 7
<211> LENGTH: 25
<212> TYPE: DNA
<213> ORGANISM: Artificial sequence
<220> FEATURE:
<221> NAME/KEY: source
<222> LOCATION: 1..25
<223> OTHER INFORMATION: /mol_type="unassigned DNA"
    /note="GAPDH Forward primer"
    /organism="Artificial sequence"

<400> SEQUENCE: 7
ggtgaaggtc ggtgtgaacg gattt                                25

<210> SEQ ID NO 8
<211> LENGTH: 25
<212> TYPE: DNA
<213> ORGANISM: Artificial sequence
<220> FEATURE:
<221> NAME/KEY: source
<222> LOCATION: 1..25

```
<223> OTHER INFORMATION: /mol_type="unassigned DNA"
     /note="GAPDH Reverse primer"
     /organism="Artificial sequence"

<400> SEQUENCE: 8
gatgccaaag ttgtcatgga tgacc                                              25
```